United States Patent
Cowens et al.

(10) Patent No.: US 9,551,034 B2
(45) Date of Patent: Jan. 24, 2017

(54) METHOD TO USE GENE EXPRESSION TO DETERMINE LIKELIHOOD OF CLINICAL OUTCOME OF RENAL CANCER

(75) Inventors: Wayne Cowens, Tiburon, CA (US); Steven Shak, Hillsborough, CA (US); Audrey Goddard, San Francisco, CA (US); Dejan Knezevic, Palo Alto, CA (US); Joffre Baker, Montara, CA (US); Michael C. Kiefer, Clayton, CA (US); Tara Maddala, Sunnyvale, CA (US); Frederick L. Baehner, San Francisco, CA (US)

(73) Assignee: Genomic Health, Inc., Redwood City, CA (US)

(*) Notice: Subject to any disclaimer, the term of this patent is extended or adjusted under 35 U.S.C. 154(b) by 0 days.

(21) Appl. No.: 12/987,023

(22) Filed: Jan. 7, 2011

(65) Prior Publication Data

US 2011/0171633 A1    Jul. 14, 2011

Related U.S. Application Data

(60) Provisional application No. 61/294,038, filed on Jan. 11, 2010, provisional application No. 61/346,230, filed on May 19, 2010.

(51) Int. Cl.
*C12Q 1/68* (2006.01)
*G01N 33/574* (2006.01)

(52) U.S. Cl.
CPC ....... *C12Q 1/6886* (2013.01); *G01N 33/57438* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,135,314 B1 | 11/2006 | Leung et al. | |
| 7,611,839 B2 | 11/2009 | Twine et al. | |
| 2002/0173461 A1* | 11/2002 | Pennica et al. | 514/12 |
| 2003/0180770 A1 | 9/2003 | Damokosh et al. | |
| 2003/0224374 A1 | 12/2003 | Dai et al. | |
| 2004/0088746 A1 | 5/2004 | Grimm et al. | |
| 2004/0110197 A1* | 6/2004 | Skinner | C12Q 1/6886 435/6.11 |
| 2005/0002904 A1* | 1/2005 | Wary | A01K 67/0271 424/93.2 |
| 2005/0048542 A1 | 3/2005 | Baker et al. | |
| 2006/0088823 A1 | 4/2006 | Haab et al. | |
| 2006/0183120 A1 | 8/2006 | Teh et al. | |
| 2006/0281122 A1 | 12/2006 | Bryant et al. | |
| 2007/0037186 A1* | 2/2007 | Jiang et al. | 435/6 |
| 2007/0099209 A1 | 5/2007 | Clarke et al. | |
| 2007/0105133 A1 | 5/2007 | Clarke et al. | |
| 2008/0032299 A1 | 2/2008 | Burczynski | |
| 2008/0064055 A1 | 3/2008 | Bryant et al. | |
| 2008/0182255 A1 | 7/2008 | Baker et al. | |
| 2008/0286273 A1 | 11/2008 | Starmans et al. | |
| 2009/0023149 A1 | 1/2009 | Knudsen | |
| 2009/0035312 A1 | 2/2009 | Griffioen et al. | |
| 2009/0186924 A1 | 7/2009 | Billen et al. | |
| 2009/0258002 A1 | 10/2009 | Barrett et al. | |
| 2010/0152055 A1 | 6/2010 | Kozono et al. | |

FOREIGN PATENT DOCUMENTS

| | | |
|---|---|---|
| JP | 2005211023 | 8/2005 |
| WO | WO 02079411 A2 * | 10/2002 |
| WO | WO2004048933 A2 | 6/2004 |
| WO | WO2004097052 A2 | 11/2004 |
| WO | WO 2005117943 A2 * | 12/2005 |
| WO | 2006/089185 A2 | 8/2006 |
| WO | 2006/124022 | 11/2006 |
| WO | WO2006124836 A1 | 11/2006 |
| WO | 2007/026896 A1 | 3/2007 |
| WO | WO2007072225 A2 | 6/2007 |
| WO | WO2008021115 A2 | 2/2008 |
| WO | WO2008138579 A1 | 11/2008 |
| WO | WO2009105640 A1 | 8/2009 |

OTHER PUBLICATIONS

Whitehead. Genome Biology. 2005. 6(2): Article R13.*
Anders. Molecular Carcninogenesis. 2011.*
Yao. Int. J. Cancer. 2008. 123: 1126-1132.*
Chan. G&P magazine. 2006. 6(3): 20-26.*
Hoshikawa. Physical Genomics. 2003. 12: 209-219. 2003.*
Sengupta. Cancer. 2005. 104: 511-520.*
Tan. Int. J. Cancer. 2008. 123: 1080-1088.*
Takahashi. PNAS. (2001) 98(17): 9754-9759, p. 9755.*
GenBank: AB385541.1 (Oct. 3, 2008).*
GenBank: AF043329.1 (Jan. 5, 1999).*
NCBI Reference Sequence: NM_003713.3 (Oct. 22, 2008).*
Hata et al. Immunology Letters. 2009. 126:29-36.*
Tomsig et al. Biochem. J. 2009. 419:611-618.*
Yang, et al. (2004) "Caffeine Suppresses Metastasis in a Transgenic Mouse Model: A Prototype Molecule for Prophylaxis of Metastasis" Clin. Exp. Metastasis 21(8):719-735.
De Kok et al., "Normalization of Gene Expression Measurements in Tumor Tissues: Comparison of 13 Endogenous Control Genes," *Laboratory Investigation* 85:154-159 (2005).
International Search Report and Written Opinion in PCT Application No. PCT/US2011/020596, 10 pages (mailed Nov. 25, 2011).
Search Report and Written Opinion for Singapore Patent Application No. 201204514-2 dated Jul. 29, 2013.
Zhao, H. at al., "Gene Expression Profiling Predicts Survival in Conventional Renal Cell Carcinoma", Plos Medicine, www.plosmedicine.org. 2006, vol. 3. Issue 1, e13. pp. 1-11.
Annual Meeting of the Japanese Cancer Association, 2006, vol. 65, pp. 367, P-888.
Unwin et al., "Proteomic changes in renal cancer and co-ordinate demonstration of both the glycolytic and mitochondrial aspects of the Warburg effect", Proteomics, 2003, vol. 3, pp. 1620-1632.
Partial European Search Report dated Apr. 11 2016; for European Application No. 15203193.6, 7 pages.
Extended European Search Report dated Jul. 28 2016, for European Application No. 15203193.6, 12 pages.

* cited by examiner

Primary Examiner — Joseph G Dauner
(74) Attorney, Agent, or Firm — McNeill Baur PLLC

(57) ABSTRACT

The present disclosure provides gene and gene sets, the expression of which is important in the classification and/or prognosis of cancer, in particular of renal cell carcinoma.

12 Claims, 9 Drawing Sheets

Performance of Mayo[1] Prognostic Tool Applied to CCF Data

"5-year recurrence-free risk" means proportion without recurrence at 5 years

Example of Using 1 Gene to Improve Prediction: EMCN in addition to Mayo Criteria (Leibovich et. al.)

- Cutpoint for EMCN derived by looking at quartiles of EMCN expression and their KM curves for RFI
- EMCN gives good separation beyond clinical/pathology covariates
- Similar results with other key genes named earlier

Example of Using 1 Gene to Improve Prediction: AQP1 in addition to Mayo Criteria (Leibovich et. al.)

Cutpoint for AQP1 derived by looking at quartiles of AQP1 expression and their KM curves for RFI

Example of Using 1 Gene to Improve Prediction: PPAP2B in addition to Mayo Criteria (Leibovich et. al.)

Cutpoint for PPAP2B derived by looking at quartiles of PPAP2B expression and their KM curves for RFI

METHOD TO USE GENE EXPRESSION TO DETERMINE LIKELIHOOD OF CLINICAL OUTCOME OF RENAL CANCER

CROSS-REFERENCE TO RELATED APPLICATIONS

The present application claims priority benefit of U.S. provisional application Ser. No. 61/294,038, filed Jan. 11, 2010 and priority benefit of U.S. provisional application Ser. No. 61/346,230, filed May 19, 2010, each of which applications are incorporated herein in their entireties.

TECHNICAL FIELD

The present disclosure relates to molecular diagnostic assays that provide information concerning prognosis in renal cancer patients.

INTRODUCTION

Each year in the United States there are approximately 51,000 cases of renal cell carcinoma (kidney cancer) and upper urinary tract cancer, resulting in more than 12,900 deaths. These tumors account for approximately 3% of adult malignancies. Renal cell carcinoma (RCC) represents about 3 percent of all cancers in the United States. Predictions for the United States for the year 2007 were that 40,000 new patients would be diagnosed with RCC and that 13,000 would die from this disease.

The clinical outcome for a renal cell carcinoma patient depends largely on the aggressiveness of their particular cancer. Surgical resection is the most common treatment for this disease as systemic therapy has demonstrated only limited effectiveness. However, approximately 30% of patients with localized tumors will experience a relapse following surgery, and only 40% of all patients with renal cell carcinoma survive for 5 years.

In the US, the number of adjuvant treatment decisions that will be made by patients with early stage renal cell carcinoma in 2005 exceeded 25,000. The rates in the European Union are expected to be similar. Physicians require prognostic information to help them make informed treatment decisions for patients with renal cell carcinoma and recruit appropriate high-risk patients for clinical trials. Surgeons must decide how much kidney and surrounding tissue to remove based, in part, on predicting the aggressiveness of a particular tumor. Today, cancer tumors are generally classified based on clinical and pathological features, such as stage, grade, and the presence of necrosis. These designations are made by applying standardized criteria, the subjectivity of which has been demonstrated by a lack of concordance amongst pathology laboratories.

SUMMARY

The present disclosure provides biomarkers, the expression of which has prognostic value in renal cancer.

DETAILED DESCRIPTION

Definitions

Figure 1A:
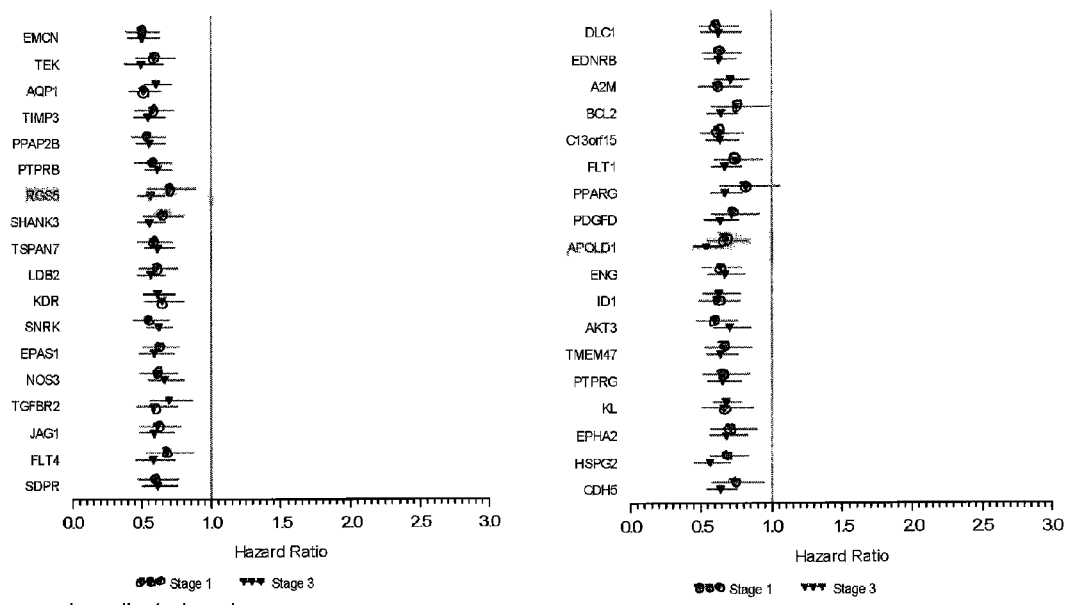
FIGS. 1a-1c: Consistency between Stage I and III for exemplary genes associated with RFI

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "tumor" is used herein to refer to all neoplastic cell growth and proliferation, and all pre-cancerous and cancerous cells and tissues. The term "primary tumor" is used herein to refer to a tumor that is at the original site where it first arose. For example, a primary renal cell carcinoma tumor is one that arose in the kidney. The term "metastatic tumor" is used herein to refer to a tumor that develops away from the site of origin. For example, renal cell carcinoma metastasis most commonly affects the spine, ribs, pelvis, and proximal long bones.

The terms "cancer" and "carcinoma" refer to or describe the physiological condition in mammals that is typically characterized by unregulated cell growth. The pathology of cancer includes, for example, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, blood vessels, etc.

As used herein, the terms "renal cancer" or "renal cell carcinoma" refer to cancer that has arisen from the kidney.

The terms "renal cell cancer" or "renal cell carcinoma" (RCC), as used herein, refer to cancer which originates in the lining of the proximal convoluted tubule. More specifically, RCC encompasses several relatively common histologic subtypes: clear cell renal cell carcinoma, papillary (chromophil), chromophobe, collecting duct carcinoma, and medullary carcinoma. Further information about renal cell carcinoma may be found in Y. Thyavihally, et al., *Int Semin Surg Oncol* 2:18 (2005), the contents of which are incorporated by reference herein. Clear cell renal cell carcinoma (ccRCC) is the most common subtype of RCC. Incidence of ccRCC is increasing, comprising 80% of localized disease and more than 90% of metastatic disease.

The staging system for renal cell carcinoma is based on the degree of tumor spread beyond the kidney. According to the tumor, node, metastasis (TNM) staging system of the American Joint Committee on Cancer (AJCC) (Greene, et al., AJCC Cancer Staging Manual, pp. 323-325 (6th Ed. 2002), the various stages of renal cell carcinoma are provided below. "Increased stage" as used herein refers to classification of a tumor at a stage that is more advanced, e.g., Stage 4 is an increased stage relative to Stages 1, 2, and 3.

Description of RCC Stages

Stages for Renal Cell Carcinoma

Stage 1: T1, N0, M0
Stage 2: T2, N0, M0
Stage 3: T1-T2, N1, M0; T3, N0-1, M0; T3a, N0-1, M0; T3b, N0-1, M0; and T3c, N0-1, M0
Stage 4: T4, N0-1, M0; Any T, N2, M0; and Any T, any N, M1
Primary tumor (T)

TX: Primary tumor cannot be assessed
T0: No evidence of primary tumor
T1: Tumor 7 cm or less in greatest dimension and limited to the kidney
T1a: Tumor 4 cm or less in greatest dimension and limited to the kidney
T1b: Tumor larger than 4 cm but 7 cm or less in greatest dimension and limited to the kidney
T2: Tumor larger than 7 cm in greatest dimension and limited to the kidney
T3: Tumor extends into major veins or invades adrenal gland or perinephric tissues but not beyond Gerota fascia
T3a: Tumor directly invades adrenal gland or perirenal and/or renal sinus fat but not beyond Gerota fascia
T3b: Tumor grossly extends into the renal vein or its segmental (i.e., muscle-containing) branches, or it extends into the vena cava below the diaphragm
T3c: Tumor grossly extends into the vena cava above the diaphragm or invades the wall of the vena cava
T4: Tumor invades beyond Gerota fascia
Regional lymph nodes (N)

NX: Regional lymph nodes cannot be assessed
N0: No regional lymph node metastasis
N1: Metastasis in a single regional lymph node
N2: Metastasis in more than one regional lymph node
Distant metastasis (M)

MX: Distant metastasis cannot be assessed
M0: No distant metastasis
M1: Distant metastasis The term "early stage renal cancer", as used herein, refers to Stages 1-3, as defined in the American Joint Committee on Cancer (AJCC) Cancer Staging Manual, pp. 323-325 (6th Ed. 2002).

Reference to tumor "grade" for renal cell carcinoma as used herein refers to a grading system based on microscopic appearance of tumor cells. According to the TNM staging system of the AJCC, the various grades of renal cell carcinoma are:
 GX (grade of differentiation cannot be assessed);
 G1 (well differentiated);
 G2 (moderately differentiated); and
 G3-G4 (poorly differentiated/undifferentiated).
"Increased grade" as used herein refers to classification of a tumor at a grade that is more advanced, e.g., Grade 4 (G4) 4 is an increased grade relative to Grades 1, 2, and 3. Tumor grading is an important prognostic factor in renal cell carcinoma. H. Rauschmeier, et al., World J Urol 2:103-108 (1984).

The terms "necrosis" or "histologic necrosis" as used herein refer to the death of living cells or tissues. The presence of necrosis may be a prognostic factor in cancer. For example, necrosis is commonly seen in renal cell carcinoma (RCC) and has been shown to be an adverse prognostic factor in certain RCC subtypes. V. Foria, et al., J Clin Pathol 58(1):39-43 (2005).

The terms "nodal invasion" or "node-positive (N+)" as used herein refer to the presence of cancer cells in one or more lymph nodes associated with the organ (e.g., drain the organ) containing a primary tumor. Nodal invasion is part of tumor staging for most cancers, including renal cell carcinoma.

The term "prognostic gene," when used in the single or plural, refers to a gene, the expression level of which is correlated with a good or bad prognosis for a cancer patient. A gene may be both a prognostic and predictive gene, depending on the association of the gene expression level with the corresponding endpoint.

The terms "correlated" and "associated" are used interchangeably herein to refer to the strength of association between two measurements (or measured entities). The disclosure provides genes and gene subsets, the expression levels of which are associated with a particular outcome measure, such as between the expression level of a gene and the likelihood of a recurrence event or relapse. For example, the increased expression level of a gene may be positively correlated (positively associated) with an increased likelihood of good clinical outcome for the patient, such as a decreased likelihood of recurrence of cancer. Such a positive correlation may be demonstrated statistically in various ways, e.g. by a hazard ratio less than 1.0. In another example, the increased expression level of a gene may be negatively correlated (negatively associated) with an increased likelihood of good clinical outcome for the patient. In that case, for example, a patient with a high expression level of a gene may have an increased likelihood of recurrence of the cancer. Such a negative correlation could indicate that the patient with a high expression level of a gene likely has a poor prognosis, or might respond poorly to a chemotherapy, and this may be demonstrated statistically in various ways, e.g., a hazard ratio greater than 1.0.

"Co-expression" is used herein to refer to strength of association between the expression levels of two different genes that are biologically similar, such that expression level of a first gene may be substituted with an expression level of a second gene in a given analysis in view of their correlation of expression. Such co-expressed genes (or correlated expression) indicates that these two genes are substitutable in an expression algorithm, for example, if a first gene is highly correlated, positively or negatively, with increased likelihood of a good clinical outcome for renal cell carcinoma, then the second co-expressed gene also correlates, in the same direction as the first gene, with the same outcome. Pairwise co-expression may be calculated by various methods known in the art, e.g., by calculating Pearson correlation coefficients or Spearman correlation coefficients or by clustering methods. The methods described herein may incorporate one or more genes that co-express, with a Pearson correlation co-efficient of at least 0.5. Co-expressed gene cliques may also be identified using graph theory. An analysis of co-expression may be calculated using normalized or standardized and normalized expression data.

The terms "prognosis" and "clinical outcome" are used interchangeably herein to refer to an estimate of the likelihood of cancer-attributable death or progression, including recurrence, and metastatic spread of a neoplastic disease, such as renal cell carcinoma. The terms "good prognosis" or "positive clinical outcome" mean a desired clinical outcome. For example, in the context of renal cell carcinoma, a good prognosis may be an expectation of no local recurrences or metastasis within two, three, four, five or more years of the initial diagnosis of renal cell carcinoma. The terms "poor prognosis" or "negative clinical outcome" are used herein interchangeably to mean an undesired clinical outcome. For example, in the context of renal cell carcinoma, a poor prognosis may be an expectation of a local recurrence or metastasis within two, three, four, five or more years of the initial diagnosis of renal cell carcinoma.

The term "predictive gene" is used herein to refer to a gene, the expression of which is correlated, positively or negatively, with likelihood of beneficial response to treatment.

A "clinical outcome" can be assessed using any endpoint, including, without limitation, (1) aggressiveness of tumor growth (e.g., movement to higher stage); (2) metastasis; (3) local recurrence; (4) increase in the length of survival following treatment; and/or (5) decreased mortality at a given point of time following treatment. Clinical response may also be expressed in terms of various measures of clinical outcome. Clinical outcome can also be considered in the context of an individual's outcome relative to an outcome of a population of patients having a comparable clinical diagnosis, and can be assessed using various endpoints such as an increase in the duration of Recurrence-Free interval (RFI), an increase in the duration of Overall Survival (OS) in a population, an increase in the duration of Disease-Free Survival (DFS), an increase in the duration of Distant Recurrence-Free Interval (DRFI), and the like.

The term "treatment", as used herein, refers to therapeutic compounds administered to patients to cease or reduce proliferation of cancer cells, shrink the tumor, avoid progression and metastasis, or cause primary tumor or metastases regression. Examples of treatment include, for example, cytokine therapy, progestational agents, anti-angiogenic therapy, hormonal therapy, and chemotherapy (including small molecules and biologics).

The terms "surgery" or "surgical resection" are used herein to refer to surgical removal of some or all of a tumor, and usually some of the surrounding tissue. Examples of surgical techniques include laproscopic procedures, biopsy, or tumor ablation, such as cryotherapy, radio frequency ablation, and high intensity ultrasound. In cancer patients, the extent of tissue removed during surgery depends on the state of the tumor as observed by a surgeon. For example, a partial nephrectomy indicates that part of one kidney is removed; a simple nephrectomy entails removal of all of one kidney; a radical nephrectomy, all of one kidney and neighboring tissue (e.g., adrenal gland, lymph nodes) removed; and bilateral nephrectomy, both kidneys removed.

The terms "recurrence" and "relapse" are used herein, in the context of potential clinical outcomes of cancer, to refer to a local or distant metastases. Identification of a recurrence could be done by, for example, CT imaging, ultrasound, arteriogram, or X-ray, biopsy, urine or blood test, physical exam, or research center tumor registry.

The term "recurrence-free interval" as used herein refers to the time from surgery to first recurrence or death due to recurrence of renal cancer. Losses to follow-up, second primary cancers, other primary cancers, and deaths prior to recurrence are considered censoring events.

The term "overall survival" is defined as the time from surgery to death from any cause. Losses to follow-up are considered censoring events. Recurrences are ignored for the purposes of calculating overall survival (OS).

The term "disease-free survival" is defined as the time from surgery to first recurrence or death from any cause, whichever occurs first. Losses to follow-up are considered censoring events.

The term "Hazard Ratio (HR)" as used herein refers to the effect of an explanatory variable on the hazard or risk of an event (i.e. recurrence or death). In proportional hazards regression models, the HR is the ratio of the predicted hazard for two groups (e.g. patients with or without necrosis) or for a unit change in a continuous variable (e.g. one standard deviation change in gene expression).

The term "Odds Ratio (OR)" as used herein refers to the effect of an explanatory variable on the odds of an event (e.g. presence of necrosis). In logistic regression models, the OR is the ratio of the predicted odds for a unit change in a continuous variable (e.g. one standard deviation change in gene expression).

The term "prognostic clinical and/or pathologic covariate" as used herein refers to clinical and/or prognostic covariates that are significantly associated ($p \leq 0.05$) with clinical outcome. For example, prognostic clinical and pathologic covariates in renal cell carcinoma include tumor stage (e.g. size, nodal invasion, etc.), and grade (e.g., Fuhrman grade), histologic necrosis, and gender.

The term "proxy gene" refers to a gene, the expression of which is correlated (positively or negatively) with one or more prognostic clinical and/or pathologic covariates. The expression level(s) of one or more proxy genes may be used instead of, or in addition to, classification of a tumor by physical or mechanical examination in a pathology laboratory.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs (e.g., cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "expression level" as applied to a gene refers to the normalized level of a gene product.

The terms "gene product" or "expression product" are used herein interchangeably to refer to the RNA transcription products (RNA transcript) of a gene, including mRNA, and the polypeptide translation product of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, (Wiley Interscience, 1995).

"Stringent conditions" or "high stringency conditions", as defined herein, typically: (1) employ low ionic strength solutions and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual* (Cold Spring Harbor Press, 1989), and include the use of washing solution and hybridization conditions (e.g., temperature, ionic strength and % SDS) less stringent that those described above. An example of moderately stringent condition is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in a mature RNA product (B. Lewin, *Genes IV* (Cell Press, 1990)). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and usually having GT and AG splice consensus sequences at their 5' and 3' boundaries.

A "computer-based system" refers to a system of hardware, software, and data storage medium used to analyze information. The minimum hardware of a patient computer-based system comprises a central processing unit (CPU), and hardware for data input, data output (e.g., display), and data storage. An ordinarily skilled artisan can readily appreciate that any currently available computer-based systems and/or components thereof are suitable for use in connection with the methods of the present disclosure. The data storage medium may comprise any manufacture comprising a recording of the present information as described above, or a memory access device that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, a suitable processor may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

The present disclosure provides methods for assessing a patient's risk of recurrence of cancer, which methods comprise assaying an expression level of at least one gene, or its gene product, in a biological sample obtained from the patient. In some embodiments, the biological sample can be a tumor sample obtained from the kidney, or surrounding tissues, of the patient. In other embodiments, the biological sample is obtained from a bodily fluid, such as blood or urine.

The present disclosure provides genes useful in the methods disclosed herein. The genes are listed in Tables 3a and 3b, wherein increased expression of genes listed in Table 3a is significantly associated with a lower risk of cancer recurrence, and increased expression of genes listed in Table 3b is significantly associated with a higher risk of cancer recurrence. In some embodiments, a co-expressed gene may be used in conjunction with, or substituted for, a gene listed in Tables 3a or 3b with which it co-expresses.

The present disclosure further provides genes significantly associated, positively or negatively, with renal cancer recurrence after adjusting for clinical/pathologic covariates (stage, tumor grade, tumor size, nodal status, and presence of necrosis). For example, Table 8a lists genes wherein increased expression is significantly associated with lower risk of renal cancer recurrence after adjusting for clinical/pathologic covariates, and Table 8b lists genes wherein increased expression is significantly associated with a higher risk of renal cancer recurrence after adjusting for clinical/pathologic covariates. Of those genes listed in Tables 8a and 8b, 16 genes with significant association, positively or negatively, with good prognosis after adjusting for clinical/pathologic covariates and controlling the false discovery rate at 10% are listed in Table 9. One or more of these genes may be used separately, or in addition to, at least one of the genes listed in Tables 3a and 3b, to provide information concerning a patient's prognosis.

The present disclosure also provides proxy genes that are useful for assessing the status of clinical and/or pathologic covariates for a cancer patient. Proxy genes for tumor stage are listed in Tables 4a and 4b, wherein increased expression of genes listed in Table 4a is significantly associated with higher tumor stage, and increased expression of genes listed in Table 4b is significantly associated with lower tumor stage. Proxy genes for tumor grade are listed in Tables 5a and 5b wherein increased expression of genes listed in Table 5a is significantly associated with higher tumor grade, and increased expression of genes listed in Table 5b is significantly associated with lower tumor grade. Proxy genes for the presence of necrosis are listed in Tables 6a and 6b, wherein expression of genes listed in Table 6a is significantly associated with the presence of necrosis, and increased expression of genes listed in Table 6b is significantly associated with the absence of necrosis. Proxy genes for nodal involvement are listed in Tables 7a and 7b wherein higher expression of genes listed in Table 7a are significantly associated with the presence of nodal invasion, and increased expression of genes listed in Table 7b are significantly associated with the absence of nodal invasion. One or more proxy genes may be used separately, or in addition to, at least one of the genes listed in Tables 3a and 3b, to provide information concerning a patient's prognosis. In some embodiments, at least two of the following proxy genes are used to provide information concerning the patient's prognosis: TSPAN7, TEK, LDB2, TIMP3, SHANK3, RGS5, KDR, SDPR, EPAS1, ID1, TGFBR2, FLT4, SDPR, ENDRB, JAG1, DLC1, and KL. In some embodiments, a co-expressed gene may be used in conjunction with, or substituted for, a proxy gene with which it co-expresses.

The present disclosure also provides sets of genes in biological pathways that are useful for assessing the likelihood that a cancer patient is likely to have a positive clinical outcome, which sets of genes are referred to herein as "gene subsets". The gene subsets include angiogenesis, immune response, cell adhesion/extracellular matrix, cell cycle, transport, and apoptosis. In some embodiments, the angiogenesis gene subset includes ADD1, ANGPTL3, APOLD1, CEACAM1, EDNRB, EMCN, ENG, EPAS1, FLT1, JAG1, KDR, KL, LDB2, NOS3, NUDT6, PPAP2B, PRKCH, PTPRB, RGS5, SHANK3, SNRK, TEK, ICAM2, and VCAM1; the immune response gene subset includes CCL5, CCR7, CD8A, CX3CL1, CXCL10, CXCL9, HLA-DPB1, IL6, IL8, and SPP1, and; the transport gene subset includes AQP1 and SGK1; the cell adhesion/extracellular matrix gene subset includes ITGB1, A2M, ITGB5, LAMB1, LOX, MMP14, TGFBR2, TIMP3, and TSPAN7; the cell cycle gene subset includes BUB1, C13orf15, CCNB1, PTTG1, TPX2, LMNB1, and TUBB2A; the apoptosis gene subset includes CASP10; the early response gene subset includes EGR1 and CYR61; the metabolic signaling gene subset includes CA12, ENO2, UGCG, and SDPR; and the signaling gene subset includes ID1 and MAP2K3.

The present disclosure also provides genes in biological pathways targeted by chemotherapy that are correlated, positively or negatively, to a risk of cancer recurrence. These genes include KIT, PDGFA, PDGFB, PDGFC, PDGFD, PDGFRb, KRAS, RAF1, MTOR, HIF1AN, VEGFA, VEGFB, and FLT4. In some embodiments, the chemotherapy is cytokine and/or anti-angiogenic therapy. In other embodiments, the chemotherapy is sunitinib, sorafenib, temsirolimus, bevacizumab, everolimus, and/or pazopanib.

In some embodiments, a co-expressed gene may be used in conjunction with, or substituted for, a gene with which it co-expresses.

In some embodiments, the cancer is renal cell carcinoma. In other embodiments, the cancer is clear cell renal cell carcinoma (ccRCC), papillary, chromophobe, collecting duct carcinoma, and/or medullary carcinoma.

Various technological approaches for determination of expression levels of the disclosed genes are set forth in this specification, including, without limitation, reverse-transciption polymerase chain reaction (RT-PCR), microarrays, high-throughput sequencing, serial analysis of gene expression (SAGE), and Digital Gene Expression (DGE), which will be discussed in detail below. In particular aspects, the expression level of each gene may be determined in relation to various features of the expression products of the gene, including exons, introns, protein epitopes, and protein activity.

The expression levels of genes identified herein may be measured in tumor tissue. For example, the tumor tissue may be obtained upon surgical resection of the tumor, or by tumor biopsy. The expression level of the identified genes may also be measured in tumor cells recovered from sites distant from the tumor, including circulating tumor cells or body fluid (e.g., urine, blood, blood fraction, etc.).

The expression product that is assayed can be, for example, RNA or a polypeptide. The expression product may be fragmented. For example, the assay may use primers that are complementary to target sequences of an expression product and could thus measure full transcripts as well as those fragmented expression products containing the target sequence. Further information is provided in Tables A and B, which provide examples of sequences of forward primers, reverse primers, probes and amplicons generated by use of the primers.

The RNA expression product may be assayed directly or by detection of a cDNA product resulting from a PCR-based amplification method, e.g., quantitative reverse transcription polymerase chain reaction (qRT-PCR). (See e.g., U.S. Pub. No. US2006-0008809A1.) Polypeptide expression product may be assayed using immunohistochemistry (IHC). Further, both RNA and polypeptide expression products may also be is assayed using microarrays.

Clinical Utility

Currently, of the expected clinical outcome for RCC patients is based on subjective determinations of a tumor's clinical and pathologic features. For example, physicians make decisions about the appropriate surgical procedures and adjuvant therapy based on a renal tumor's stage, grade, and the presence of necrosis. Although there are standardized measures to guide pathologists in making these decisions, the level of concordance between pathology laboratories is low. (See Al-Ayanti M et al. (2003) Arch Pathol Lab Med 127, 593-596) It would be useful to have a reproducible molecular assay for determining and/or confirming these tumor characteristics.

In addition, standard clinical criteria, by themselves, have limited ability to accurately estimate a patient's prognosis. It would be useful to have a reproducible molecular assay to assess a patient's prognosis based on the biology of his or her tumor. Such information could be used for the purposes of patient counseling, selecting patients for clinical trials (e.g., adjuvant trials), and understanding the biology of renal cell carcinoma. In addition, such a test would assist physicians in making surgical and treatment recommendations based on the biology of each patient's tumor. For example, a genomic test could stratify RCC patients based on risk of recurrence and/or likelihood of long-term survival without recurrence (relapse, metastasis, etc.). There are several ongoing and planned clinical trials for RCC therapies, including adjuvant radiation and chemotherapies. It would be useful to have a genomic test able to identify high-risk patients more accurately than standard clinical criteria, thereby further enriching an adjuvant RCC population for study. This would reduce the number of patients needed for an adjuvant trial and the time needed for definitive testing of these new agents in the adjuvant setting.

Finally, it would be useful to have a molecular assay that could predict a patient's likelihood to respond to treatment, such as chemotherapy. Again, this would facilitate individual treatment decisions and recruiting patients for clinical trials, and increase physician and patient confidence in making healthcare decisions after being diagnosed with cancer.

Reporting Results

The methods of the present disclosure are suited for the preparation of reports summarizing the expected clinical outcome resulting from the methods of the present disclosure. A "report," as described herein, is an electronic or tangible document that includes report elements that provide information of interest relating to a likelihood assessment and its results. A subject report includes at least a likelihood assessment, e.g., an indication as to the risk of recurrence for a subject with renal cell carcinoma. A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, where test data can include a normalized level of one or more genes of interest, and 6) other features.

The present disclosure thus provides for methods of creating reports and the reports resulting therefrom. The report may include a summary of the expression levels of the RNA transcripts, or the expression products of such RNA transcripts, for certain genes in the cells obtained from the patient's tumor. The report can include information relating to prognostic covariates of the patient. The report may include an estimate that the patient has an increased risk of recurrence. That estimate may be in the form of a score or patient stratifier scheme (e.g., low, intermediate, or high risk of recurrence). The report may include information relevant to assist with decisions about the appropriate surgery (e.g., partial or total nephrectomy) or treatment for the patient.

Thus, in some embodiments, the methods of the present disclosure further include generating a report that includes information regarding the patient's likely clinical outcome, e.g. risk of recurrence. For example, the methods disclosed herein can further include a step of generating or outputting a report providing the results of a subject risk assessment, which report can be provided in the form of an electronic medium (e.g., an electronic display on a computer monitor), or in the form of a tangible medium (e.g., a report printed on paper or other tangible medium).

A report that includes information regarding the patient's likely prognosis (e.g., the likelihood that a patient having renal cell carcinoma will have a good prognosis or positive clinical outcome in response to surgery and/or treatment) is provided to a user. An assessment as to the likelihood is referred to below as a "risk report" or, simply, "risk score." A person or entity that prepares a report ("report generator") may also perform the likelihood assessment. The report generator may also perform one or more of sample gathering, sample processing, and data generation, e.g., the report generator may also perform one or more of: a) sample gathering; b) sample processing; c) measuring a level of a risk gene; d) measuring a level of a reference gene; and e) determining a normalized level of a risk gene. Alternatively, an entity other than the report generator can perform one or more sample gathering, sample processing, and data generation.

For clarity, it should be noted that the term "user," which is used interchangeably with "client," is meant to refer to a person or entity to whom a report is transmitted, and may be the same person or entity who does one or more of the following: a) collects a sample; b) processes a sample; c) provides a sample or a processed sample; and d) generates data (e.g., level of a risk gene; level of a reference gene product(s); normalized level of a risk gene for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., an oncologist, surgeon, pathologist), etc.).

In embodiments where the user only executes a portion of the method, the individual who, after computerized data processing according to the methods of the present disclosure, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice, or liability insurance), all results, whether generated wholly or partially electronically, are subjected to a quality control routine prior to release to the user.

Methods of Assaying Expression Levels of a Gene Product

Numerous assay methods for measuring an expression level of a gene product are known in the art, including assay methods for measuring an expression level of a nucleic acid gene product (e.g., an mRNA), and assay methods for measuring an expression level of a polypeptide gene product.

Measuring a Level of a Nucleic Acid Gene Product

In general, methods of measuring a level of a nucleic acid gene product (e.g., an mRNA) include methods involving hybridization analysis of polynucleotides, and methods involving amplification of polynucleotides. Commonly used methods known in the art for the quantification of mRNA expression in a sample include northern blotting and in situ hybridization (See for example, Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Expression Methods Based on Hybridization

The level of a target nucleic acid can be measured using a probe that hybridizes to the target nucleic acid. The target nucleic acid could be, for example, a RNA expression product of a response indicator gene associated with response to a VEGF/VEGFR Inhibitor, or a RNA expression product of a reference gene. In some embodiments, the target nucleic acid is first amplified, for example using a polymerase chain reaction (PCR) method.

A number of methods are available for analyzing nucleic acid mixtures for the presence and/or level of a specific nucleic acid. mRNA may be assayed directly or reverse transcribed into cDNA for analysis.

In some embodiments, the method involves contacting a sample (e.g., a sample derived from a cancer cell) under stringent hybridization conditions with a nucleic acid probe and detecting binding, if any, of the probe to a nucleic acid in the sample. A variety of nucleic acid hybridization methods are well known to those skilled in the art, and any known method can be used. In some embodiments, the nucleic acid probe will be detectably labeled.

Expression Methods Based on Target Amplification

Methods of amplifying (e.g., by PCR) nucleic acid, methods of performing primers extension, and methods of assessing nucleic acids are generally well known in the art. (See e.g., Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.)

A target mRNA can be amplified by reverse transcribing the mRNA into cDNA, and then performing PCR (reverse transcription-PCR or RT-PCR). Alternatively, a single enzyme may be used for both steps as described in U.S. Pat. No. 5,322,770.

The fluorogenic 5' nuclease assay, known as the Taq-Man® assay (Roche Molecular Systems, Inc.), is a powerful and versatile PCR-based detection system for nucleic acid targets. For a detailed description of the TaqMan assay, reagents and conditions for use therein, see, e.g., Holland et al., Proc. Natl. Acad. Sci., U.S.A. (1991) 88:7276-7280; U.S. Pat. Nos. 5,538,848, 5,723,591, and 5,876,930, all incorporated herein by reference in their entireties. Hence, primers and probes derived from regions of a target nucleic acid as described herein can be used in TaqMan analyses to detect a level of target mRNA in a biological sample. Analysis is performed in conjunction with thermal cycling by monitoring the generation of fluorescence signals. (Taq-Man is a registered trademark of Roche Molecular Systems.)

The fluorogenic 5' nuclease assay is conveniently performed using, for example, AmpliTaq Gold® DNA polymerase, which has endogenous 5' nuclease activity, to digest an internal oligonucleotide probe labeled with both a fluorescent reporter dye and a quencher (see, Holland et al., Proc Nat Acad Sci USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid. (AmpliTaq Gold is a registered trademark of Roche Molecular Systems.)

The amplification products can be detected in solution or using solid supports. In this method, the TaqMan probe is designed to hybridize to a target sequence within the desired PCR product. The 5' end of the TaqMan probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence that can be detected.

The first step for gene expression analysis is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, head and neck, etc., tumor, or tumor cell lines, with pooled DNA from healthy donors. If the source of mRNA is a primary tumor, mRNA can be extracted, for example, from frozen or archived paraffin-embedded and fixed (e.g., formalin-fixed) tissue samples.

General methods for mRNA extraction are well known in the art and are disclosed in standard textbooks of molecular biology, including Ausubel et al., *Current Protocols of Molecular Biology* (Wiley and Sons, 1997). Methods for RNA extraction from paraffin embedded tissues are disclosed, for example, M. Cronin, Am J. Pathol 164(1):35-42 (2004), the contents of which are incorporated herein. In particular, RNA isolation can be performed using kits and reagents from commercial manufacturers according to the manufacturer's instructions. For example, total RNA from cells in culture can be isolated using RNeasy® mini-columns (Qiagen GmbH Corp.). Other commercially available RNA isolation kits include MasterPure™ Complete DNA and RNA Purification Kit (EPICENTRE® Biotechnologies, Madison, Wis.), mirVana (Applied Biosystems, Inc.), and Paraffin Block RNA Isolation Kit (Ambion, Inc.). Total RNA from tissue samples can be isolated using RNA STAT-60™ (IsoTex Diagnostics, Inc., Friendswood Tex.). RNA prepared from tumor can be isolated, for example, by cesium chloride density gradient centrifugation. (RNeasy is a registered trademark of Qiagen GmbH Corp.; MasterPure is a trademark of EPICENTRE Biotechnologies; RNA STAT-60 is a trademark of Tel-Test Inc.)

As RNA cannot serve as a template for PCR, the first step in gene expression profiling by RT-PCR is the reverse transcription of the RNA template into cDNA, followed by its exponential amplification in a PCR reaction. The two most commonly used reverse transcriptase enzymes are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp® RNA PCR kit (Applied Biosystems Inc., Foster City, Calif.) according to the manufacturer's instructions. The derived cDNA can then be used as a template in a subsequent PCR reaction. (GeneAmp is a registered trademark of Applied Biosystems Inc.)

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data. (TaqMan is a registered mark of Applied Biosystems.)

TaqMan RT-PCR can be performed using commercially available equipment, such as, for example, the ABI PRISM 7700® Sequence Detection System (Applied Biosystems, Foster City, Calif., USA), or the Lightcycler® (Roche Molecular Biochemicals, Mannheim, Germany). In a preferred embodiment, the 5' nuclease procedure is run on a real-time quantitative PCR device such as the ABI PRISM 7900™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data. (PRISM 7700 is a registered trademark of Applied Biosystems; Lightcycler is a registered trademark of Roche Diagnostics GmbH LLC.)

5'-Nuclease assay data are initially expressed as $C_t$, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize the effect of sample-to-sample variation, quantitative RT-PCR is usually performed using an internal standard, or one or more reference genes. The ideal internal standard is expressed at a constant level among different tissues, and is unaffected by the experimental treatment. RNAs that can be used to normalize patterns of gene expression include, e.g., mRNAs for the reference genes glyceraldehyde-3-phosphate-dehydrogenase (GAPDH) and β-actin.

A more recent variation of the RT-PCR technique is the real time quantitative PCR, which measures PCR product accumulation through a dual-labeled fluorogenic probe (i.e., TaqMan® probe). Real time PCR is compatible both with quantitative competitive PCR, where internal competitor for each target sequence is used for normalization, and with quantitative comparative PCR using a normalization gene contained within the sample, or a reference gene for RT-PCR. For further details see, e.g., Held et al., Genome Research 6:986-994 (1996).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g., about 50 to 70° C. can be used.

For further guidelines for PCR primer and probe design see, e.g., Dieffenbach, C. W. et al., "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. PrimerSelect: Primer and probe design. *Methods Mol. Biol.* 70:520-527 (1997), the entire disclosures of which are hereby expressly incorporated by reference.

Other suitable methods for assaying a level of a nucleic acid gene product include, e.g., microarrays; serial analysis of gene expression (SAGE); MassARRAY® analysis; digital gene expression (DGE) (J. Marioni, Genome Research 18(9):1509-1517 (2008), gene expression by massively parallel signature sequencing (see, e.g., Ding and Cantor, Proc. Nat'l Acad Sci 100:3059-3064 (2003); differential display (Liang and Pardee, Science 257:967-971 (1992)); amplified fragment length polymorphism (iAFLP) (Kawamoto et al., Genome Res. 12:1305-1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888-1898 (2001)); and high coverage expression profiling (HiCEP) analysis (Fukumura et al., Nucl. Acids. Res. 31(16) e94 (2003)).

Introns

Assays to measure the amount of an RNA gene expression product can be targeted to intron sequences or exon sequences of the primary transcript. The amount of a spliced intron that is measured in human tissue samples is generally indicative of the amount of a corresponding exon (i.e. an exon from the same gene) present in the samples. Polynucleotides that consist of or are complementary to intron sequences can be used, e.g., in hybridization methods or amplification methods to assay the expression level of response indicator genes.

Measuring Levels of a Polypeptide Gene Product

Methods of measuring a level of a polypeptide gene product are known in the art and include antibody-based methods such as enzyme-linked immunoabsorbent assay (ELISA), radioimmunoassay (RIA), protein blot analysis, immunohistochemical analysis and the like. The measure of a polypeptide gene product may also be measured in vivo in the subject using an antibody that specifically binds a target polypeptide, coupled to a paramagnetic label or other label used for in vivo imaging, and visualizing the distribution of the labeled antibody within the subject using an appropriate in vivo imaging method, such as magnetic resonance imaging. Such methods also include proteomics methods such as mass spectrometric methods, which are known in the art.

Methods of Isolating RNA from Body Fluids

Methods of isolating RNA for expression analysis from blood, plasma and serum (See for example, Tsui N B et al. (2002) 48, 1647-53 and references cited therein) and from urine (See for example, Boom R et al. (1990) J Clin Microbiol. 28, 495-503 and reference cited therein) have been described.

Methods of Isolating RNA from Paraffin-Embedded Tissue

The steps of a representative protocol for profiling gene expression using fixed, paraffin-embedded tissues as the RNA source, including mRNA isolation, purification primer extension and amplification are provided in various published journal articles. (See, e.g., T. E. Godfrey et al., J. Molec. Diagnostics 2: 84-91 (2000); K. Specht et al., Am. J. Pathol. 158: 419-29 (2001), M. Cronin, et al., Am J Pathol 164:35-42 (2004)).

Manual and Computer-Assisted Methods and Products

The methods and systems described herein can be implemented in numerous ways. In one embodiment of particular interest, the methods involve use of a communications infrastructure, for example the Internet. Several embodiments are discussed below. It is also to be understood that the present disclosure may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "risk score," where the score is transmitted as processed or partially processed responses to the reviewer's computing environment in the form of test code for subsequent execution of one or more algorithms to provide a results and/or generate a report in the reviewer's computing environment. The risk score can be a numerical score (representative of a numerical value) or a non-numerical score representative of a numerical value or range of numerical values (e.g., low, intermediate, or high).

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) that is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a risk gene, level of a reference gene product(s); normalized level of a gene; and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present disclosure.

Where used, the database(s) is usually connected to the database server component and can be any device that will hold data. For example, the database can be a any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The present disclosure also contemplates a computer-readable storage medium (e.g. CD-ROM, memory key, flash memory card, diskette, etc.) having stored thereon a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program that provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the present disclosure can be packaged with instructions (e.g., for program installation, use, etc.) recorded on a suitable substrate or a web address where such instructions may be obtained. The computer-readable storage medium can also be provided in combination with one or more reagents for carrying out response likelihood assessment (e.g., primers, probes, arrays, or other such kit components).

Methods of Data Analysis

Reference Normalization

In order to minimize expression measurement variations due to non-biological variations in samples, e.g., the amount and quality of expression product to be measured, raw expression level data measured for a gene product (e.g., cycle threshold ($C_t$) measurements obtained by qRT-PCR) may be normalized relative to the mean expression level data obtained for one or more reference genes. In one approach to normalization, a small number of genes are used as reference genes; the genes chosen for reference genes typically show a minimal amount of variation in expression from sample to sample and the expression level of other genes is compared to the relatively stable expression of the reference genes. In the global normalization approach, the expression level of each gene in a sample is compared to an average expression level in the sample of all genes in order to compare the expression of a particular gene to the total amount of material.

Unprocessed data from qRT-PCR is expressed as cycle threshold ($C_t$), the number of amplification cycles required for the detectable signal to exceed a defined threshold. High $C_t$ is indicative of low expression since more cycles are required to detect the amplification product. Normalization may be carried out such that a one-unit increase in normalized expression level of a gene product generally reflects a 2-fold increase in quantity of expression product present in the sample. For further information on normalization techniques applicable to qRT-PCR data from tumor tissue, see, e.g., Silva S et al. (2006) *BMC Cancer* 6, 200; de Kok J et al. (2005) Laboratory Investigation 85, 154-159. Gene expression may then be standardized by dividing the normalized gene expression by the standard deviation of expression across all patients for that particular gene. By standardizing normalized gene expression the hazard ratios across genes are comparable and reflect the relative risk for each standard deviation of gene expression.

Statistical Analysis

One skilled in the art will recognize that variety of statistical methods are available that are suitable for comparing the expression level of a gene (or other variable) in two groups and determining the statistical significance of expression level differences that are found. (See e.g., H. Motulsky, *Intuitive Biostatistics*(Oxford University Press, 1995); D. Freedman, *Statistics* (W.W. Norton & Co, 4$^{th}$ Ed., 2007). For example, a Cox proportional hazards regression model may be fit to a particular clinical time-to-event endpoint (e.g., RFI, OS). One assumption of the Cox proportional hazards regression model is the proportional hazards assumption, i.e. the assumption that model effects multiply the underlying hazard. Assessments of model adequacy may be performed including, but not limited to, examination of the cumulative sum of martingale residuals. One skilled in the art would recognize that there are numerous statistical methods that may be used (e.g., Royston and Parmer (2002), smoothing spline, etc.) to fit a flexible parametric model using the hazard scale and the Weibull distribution with natural spline smoothing of the log cumulative hazards function, with effects allowed to be time-dependent. (See, P. Royston, M. Parmer, *Statistics in Medicine* 21(15:2175-2197 (2002).) The relationship between recurrence risk and (1) recurrence risk groups; and (2) clinical/pathologic covariates (e.g., tumor stage, tumor grade, presence of necrosis, lymphatic or vascular invasion, etc.) may also be tested for significance. Additional examples of models include logistic or ordinal logistic regression models in which the association between gene expression and dichotomous (for logistic) or ordinal (for ordinal logistic) clinical endpoints (i.e. stage, necrosis, grade) may be evaluated. (See e.g., D. Hosmer and S. Lemeshow, *Applied Logistic Regression* (John Wiley and Sons, 1989).

In an exemplary embodiment, results were adjusted for multiple hypothesis tests, and allowed for a 10% false discovery rate (FDR), using Storey's procedure, and using TDRAS with separate classes (M. Crager, Gene identification using true discovery rate degree of association sets and estimates corrected for regression to the mean, *Statistics in Medicine* (published online December 2009). In another embodiment, genes with significant association with RFI were identified through cross-validation techniques in which forward stepwise Cox PH regression was employed using a subset of factors identified through Principal Component Analysis (PCA).

Methods for calculating correlation coefficients, particularly the Pearson product-moment correlation coefficient are known in the art. (See e.g., J. Rodgers and W. Nicewander, The American Statistician, 42, 59-66 (1988); H. Motulsky, H., Intuitive Biostatistics (Oxford University Press, 1995). To perform particular biological processes, genes often work together in a concerted way, i.e. they are co-expressed. Co-expressed gene groups identified for a disease process like cancer can serve as biomarkers for disease progression and response to treatment. Such co-expressed genes can be assayed in lieu of, or in addition to, assaying of the prognostic and/or predictive gene with which they are co-expressed.

One skilled in the art will recognize that many co-expression analysis methods now known or later developed will fall within the scope and spirit of the present invention. These methods may incorporate, for example, correlation coefficients, co-expression network analysis, clique analysis, etc., and may be based on expression data from RT-PCR, microarrays, sequencing, and other similar technologies. For example, gene expression clusters can be identified using pair-wise analysis of correlation based on Pearson or Spearman correlation coefficients. (See, e.g., Pearson K. and Lee A., Biometrika 2, 357 (1902); C. Spearman, Amer. J. Psychol 15:72-101 (1904); J. Myers, A. Well, *Research Design and Statistical Analysis*, p. 508 (2nd Ed., 2003).) In general, a correlation coefficient of equal to or greater than 0.3 is considered to be statistically significant in a sample size of at least 20. (See, e.g., G. Norman, D. Streiner, *Biostatistics: The Bare Essentials,* 137-138 (3rd Ed. 2007).)

All aspects of the present disclosure may also be practiced such that a limited number of additional genes that are co-expressed with the disclosed genes, for example as evidenced by high Pearson correlation coefficients, are included in a prognostic or predictive test in addition to and/or in place of disclosed genes.

Having described the invention, the same will be more readily understood through reference to the following Examples, which are provided by way of illustration, and are not intended to limit the invention in any way. All citations throughout the disclosure are hereby expressly incorporated by reference.

Examples

Two studies were performed to demonstrate the feasibility of gene expression profiling from renal tumors obtained from renal cell carcinoma patients. (See Abstract by M. Zhou, et al., Optimized RNA extraction and RT-PCR assays provide successful molecular analysis on a wide variety of archival fixed tissues, AACR Annual Meeting (2007)).

Study Design

Renal tumor tissue was obtained from approximately 1200 patients from the Cleveland Clinic Foundation (CCF) database. This database consists of patients who were diagnosed with renal carcinoma, clear cell type, stage I, II and III between the years of 1985 and 2003, who had available paraffin-embedded tumor (PET) blocks and adequate clinical follow-up, and who were not treated with adjuvant/neo-adjuvant systemic therapy. Patients with inherited VHL disease or bilateral tumors were also excluded. Tumors were graded using (1) Fuhrman grading system as noted in the World Health Organization Classification of Tumours: Pathology and Genetics: Tumours of the Urinary System and Male Genital Organs; and (2) the modified Fuhrman grading system (Table 1). In general, if no nodal involvement is expected or observed for patients, inspection of nodal involvement is not conducted and Nx is noted. In this study, Nx was treated as N0 for purposes of stage classification. The expression of 732 genes was quantitatively assessed for each patient tissue sample.

TABLE 1

Fuhrman Grading Systems

| Fuhrman Grade (Modified) | Fuhrman Grade (WHO) |
|---|---|
| 1 Nuclei small as lymphocyte with condensed chromatin | Small, round, uniform nuclei (~10 um); nucleoli absent or inconspicuous (at 400x) |

TABLE 1-continued

Fuhrman Grading Systems

| Fuhrman Grade (Modified) | Fuhrman Grade (WHO) |
|---|---|
| 2 Nuclei both small as lymphocytes with condensed chromatin and other nuclei demonstrating enlarged, open chromatin | Larger nuclei (~15 um) with irregular outline; small nucleoli present (at 400x) |
| 3 All nuclei enlarged with open chromatin | Larger nuclei (approaching 20 um) with more irregular outline; prominent nucleoli present (at 100x) |
| 4 Large bizarre nuclei | Grade 3 features with pleomorphic or multilobed nuclei, with or without spindle cells |

Inclusion Criteria (1) Patients who underwent nephrectomy at CCF and who have a minimum of 6 months clinical follow-up or have recurrent RCC, documented in the clinical chart, database or registry.

(2) Diagnosed with RCC, clear cell type, stage I, II, or III.

(3) Renal blocks fixed in Formalin, Hollandes fluid or Zenkers fixative.

Exclusion Criteria (1) No tumor block available from initial diagnosis in the Cleveland Clinic archive.

(2) No tumor or very little tumor (<5% of invasive cancer cell area) in block as assessed by examination of the Hollandes and/or hematoxylin and eosin stained (H&E) slide.

(3) High cycle threshold ($C_t$) values of reference genes. All samples regardless of their RNA amount will be tested by RT-qPCR, but only plates where the average Ct of reference genes is less than 35 will be analyzed.

(4) Patients with inherited VHL disease and/or bilateral tumors (5) Patients who received neo-adjuvant or adjuvant systemic therapy Concordance for Clinical and Pathologic Factors Two separate pathology laboratories conducted analyses of several clinical and pathologic factors using the same standardized measures. The level of concordance, by covariate, is provided in Table 2, below. For purposes of the statistical analysis, the determination of only one of the central laboratories was used.

TABLE 2

Concordance between two central laboratories for clinical/pathologic covariates

| Covariate | Method of analysis | Concordance |
|---|---|---|
| Presence of necrosis | Microscopic technique per Leibovich BC et al. (2003) Cancer 97(3), 1663-1671. | 47% |
| Tumor grade | Fuhrman | 65% |

Expression Profile Gene Panel

The RNA from paraffin embedded tissue (PET) samples obtained from 942 patients who met all inclusion/exclusion criteria was extracted using protocols optimized for fixed renal tissue and perform molecular assays of quantitative gene expression using TaqMan® RT-PCR. RT-PCR was performed with RNA input at 1.0 ng per 5 μL-reaction volume using two 384 well plates.

RT-PCR analysis of PET samples was conducted using 732 genes. These genes were evaluated for association with the primary and secondary endpoints, recurrence-free interval (RFI), disease-free survival (DFS) and overall survival (OS).

All primary and secondary analyses were conducted on reference normalized gene expression levels using the mean of the reference genes for normalization. Three normalization schemes were tested using AAMP, ARF1, ATP5E, EEF1A1, GPX1, RPS23, SDHA, UBB, and RPLP1. Some or all of the other genes in the test panel were used in analyses of alternative normalization schemes.

Of the 732 genes, 647 were deemed evaluable for further consideration. The outcome analyses of the 647 evaluable genes were adjusted for multiple hypothesis tests, by allowing for a 10% false discovery rate (FDR), using Storey's procedure, and using True Discovery Rate Degree of Association Sets (TDRDAS) with separate classes (M. Crager, Gene identification using true discovery rate degree of association sets and estimates corrected for regression to the mean, *Statistics in Medicine* 29:33-45 (2009)). Unadjusted for baseline covariates and without controlling the FDR, a subset of 448 (69%) of genes were identified as significantly associated with RFI ($p \leq 0.05$). Additional analysis was conducted using a supervised principal component analysis (PCA) on a subset of 188 genes that have maximum lower bound (MLB) >1.2 using TDRDAS analysis, controlling the FDR but not taking into account the separate classes. The top 10 factors were modified by keeping the genes with high factor loadings (loading/max loading >0.7) were kept. The modified top 10 factors were put into a 5-fold cross validation to assess performance of the gene groups and identify factors that were appearing most frequently.

Genes that had a significant association ($p \leq 0.05$) with risk of recurrence are listed in Tables 3a and 3b, wherein genes that are positively associated with a good prognosis (i.e., increased expression indicates a lower risk of recurrence) are listed in Table 3a. Genes that are negatively associated with a good prognosis (i.e., increased expression indicates a higher risk of recurrence) are listed in Table 3b. Genes that were associated, positively or negatively, with a good prognosis but not associated with clinical/pathologic covariates are BBC3, CCR7, CCR4, and VCAN. In addition, genes associated positively with a good prognosis after adjusting for clinical and pathological covariates (stage, tumor grade, tumor size, nodal status, and presence of necrosis) are listed in Table 8a. Genes associated negatively with a good prognosis after adjusting for clinical/pathologic covariates are listed in Table 8b. Of those genes listed in Tables 8a and 8b, 16 genes with significant association, positively or negatively, with a good prognosis after adjusting for clinical and pathologic covariates and controlling the false discovery rate at 10% are listed in Table 9.

Figure 1B:
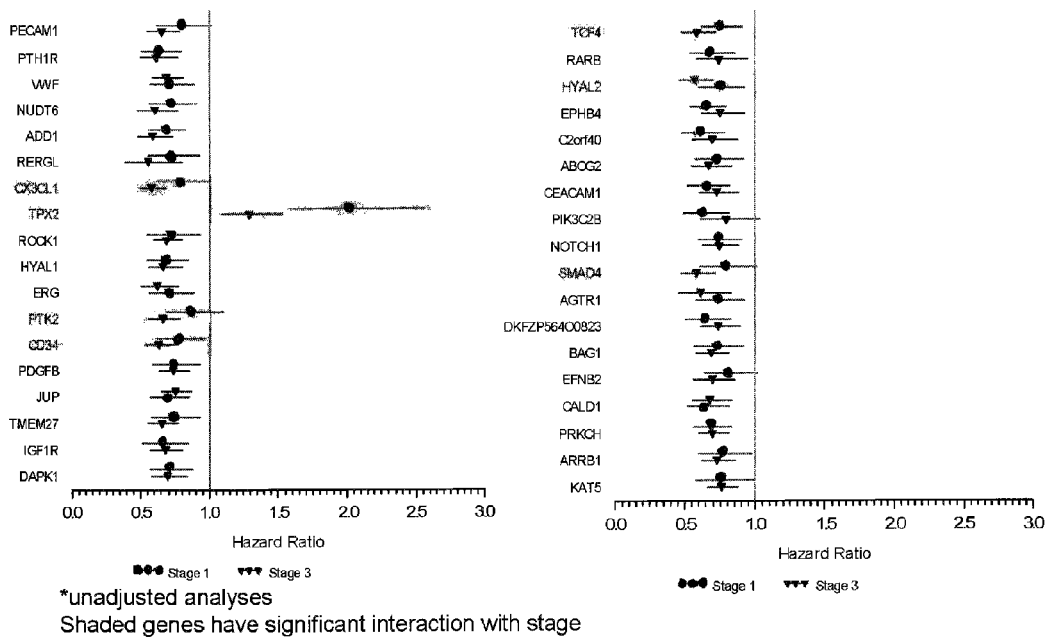
Figure 1C:
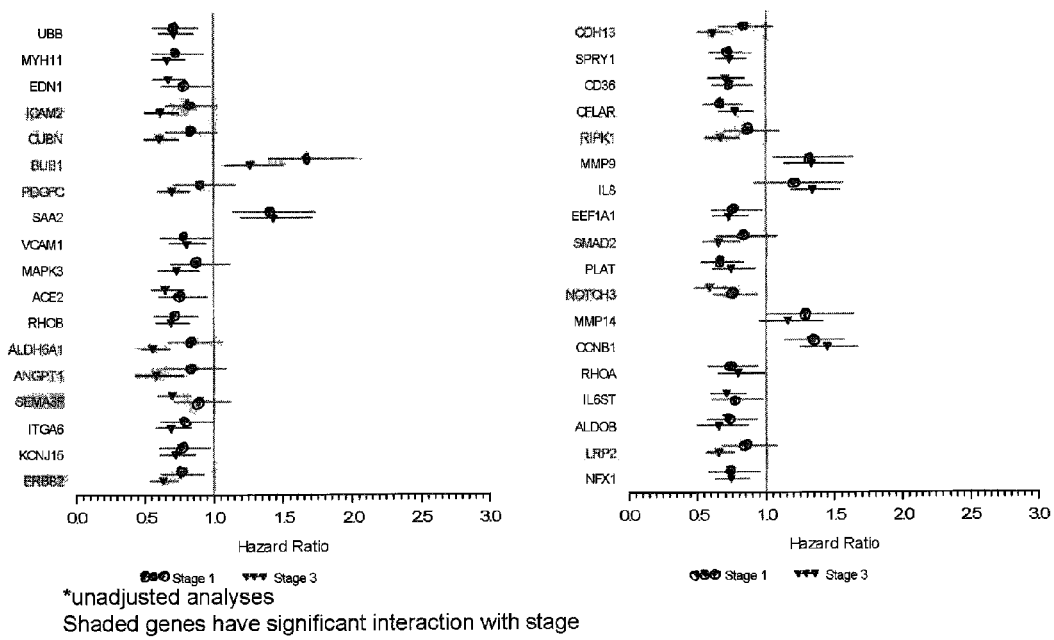
Figure 2:
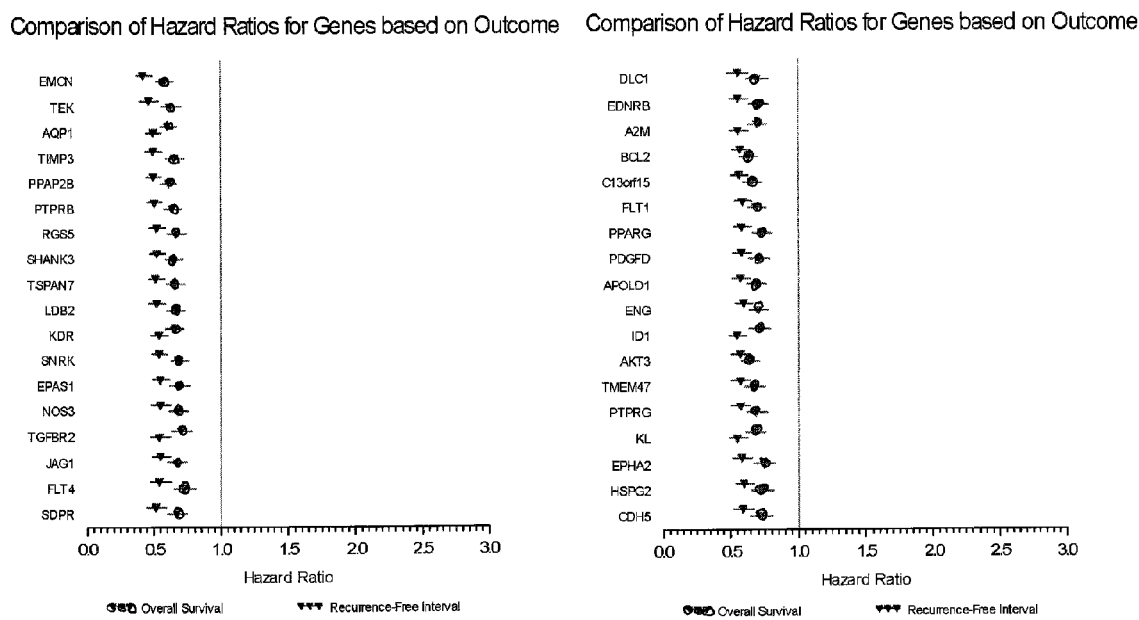
FIG. 2: Consistent results across endpoints (OS and RFI) for exemplary genes

For the majority of these genes significantly associated with RFI ($p \leq 0.05$) (82%), increased expression is associated with a good prognosis. Most of the genes significantly associated with RFI showed consistency between (1) between stages (I-III); (2) primary and secondary endpoints (RFI and OS). See, e.g., FIGS. 1 and 2, respectively.

From this analysis, certain gene subsets emerged as significantly associated with recurrence and overall survival. For example, increased expression of angiogenesis genes (e.g., EMCN, PPAP2B, NOS3, NUDT6, PTPRB, SNRK, APOLD1, PRKCH, and CEACAM1), cell adhesion/extracellular matrix genes (e.g., ITGB5, ITGB1, A2M, TIMP3), immune response genes (e.g., CCL5, CCXL9, CCR7, IL8, IL6, and CX3CL1), cell cycle (e.g., BUB1, TPX2), apoptosis (e.g., CASP10), and transport genes (AQP1) were strongly associated, positively or negatively, with RFI.

Also, certain genes that are associated with pathway targets for renal cancer drugs (sunitinib, sorafenib, temsirolimus, bevacizumab, everolimus, pazopanib) were identified as having a significant association with outcome, including: KIT, PDGFA, PDGFB, PDGFC, PDGFD, PDGFRb, KRAS, RAF1, MTOR, HIF1AN, VEGFA, VEGFB, and FLT4.

Figure 3:
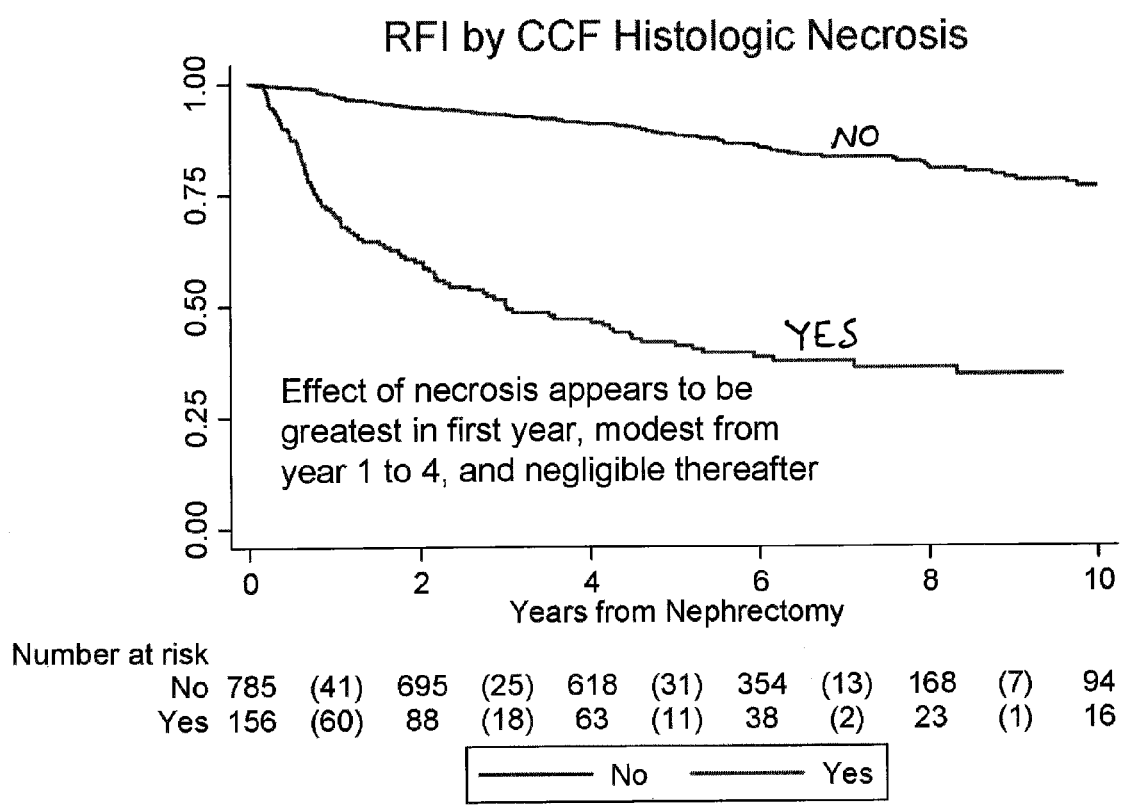
FIG. 3: Kaplan-Meier curve: Recurrence Free Internal (RFI) by Cleveland Clinic Foundation (CCF) histologic necrosis

It was determined that the presence of necrosis in these tumors was associated with a higher risk of recurrence, at least in the first 4 years after surgery. See FIG. 3. However, the prognostic effect of necrosis after year 4 was negligible.

It was also determined that expression of certain genes was correlated, positively or negatively, with pathologic and/or clinical factors ("proxy genes"). For example, increased expression of the proxy genes listed in Tables 4a-7b correlate, positively or negatively, with tumor stage, tumor grade, presence of necrosis, and nodal invasion, respectively. In Tables 4a-7b, gene expression was normalized and then standardized such that the odds ratio (OR) reflects a one standard deviation change in gene expression.

From these, key genes were identified as good proxies for baseline covariates (stage, grade, necrosis), including TSPAN7, TEK, LDB2, TIMP3, SHANK3, RGS5, KDR, SDPR, EPAS1, ID1, TGFBR2, FLT4, SDPR, ENDRB, JAG1, DLC1, and KL. Several of these genes are in the hypoxia-induced pathway: SHANK3, RGS5, EPAS1, KDR, JAG1, TGFBR2, FLT4, SDPR, DLC1, EDNRB.

Figure 4:
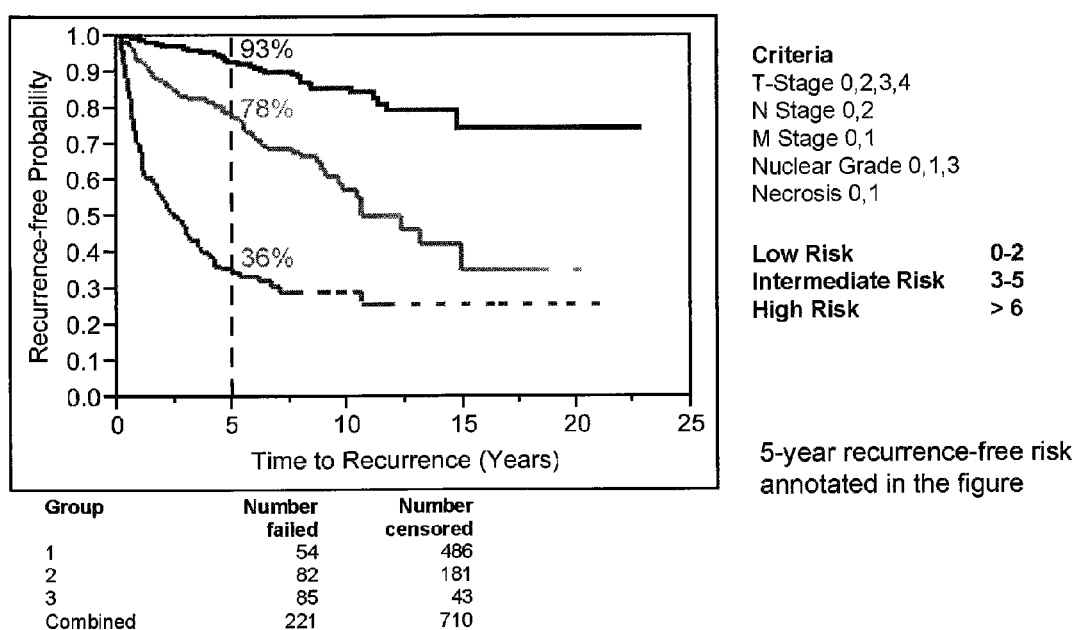
FIG. 4: Performance of Mayo prognostic tool applied to CCF data
Figure 5:
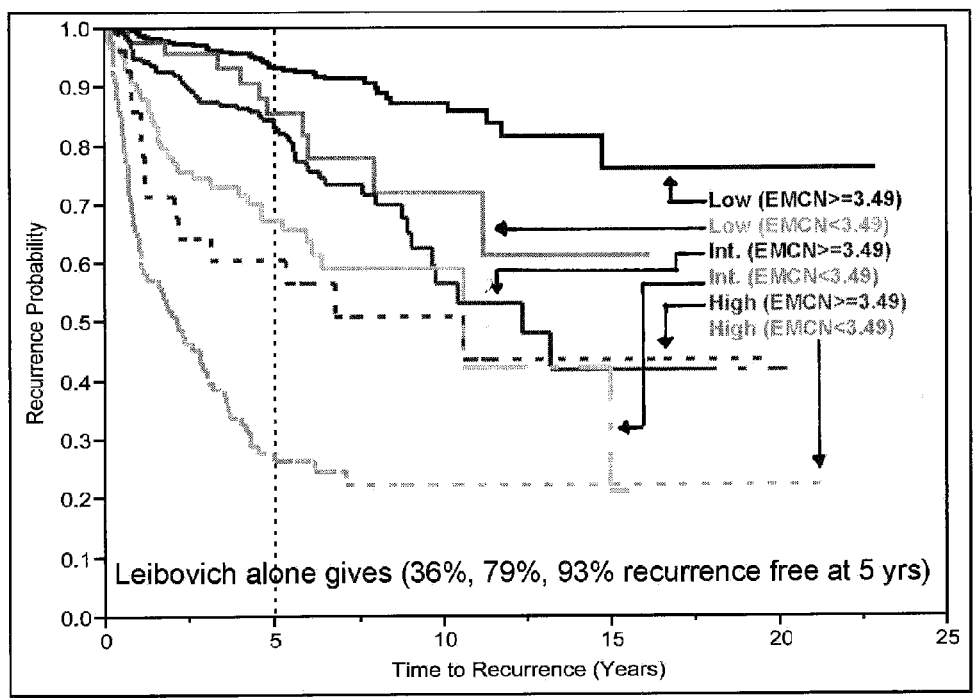
FIG. 5: Example of using one gene to improve estimate: EMCN in addition to Mayo Criteria
Figure 6:
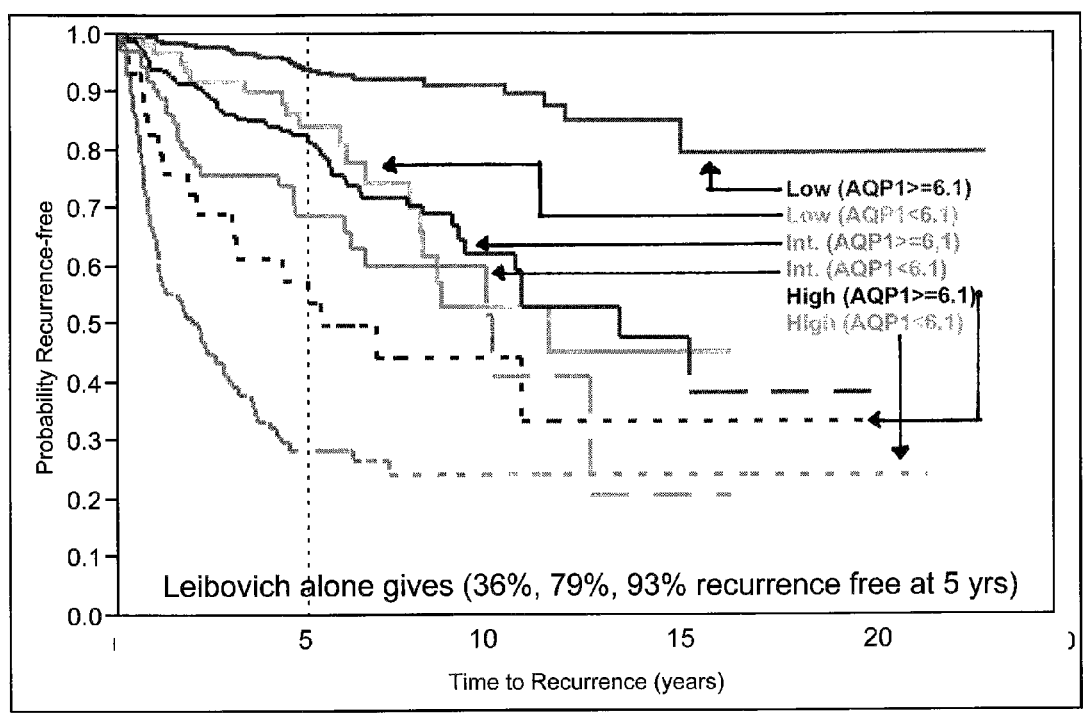
FIG. 6: Example of using one gene to improve estimate: AQP1 in addition to Mayo Criteria
Figure 7:
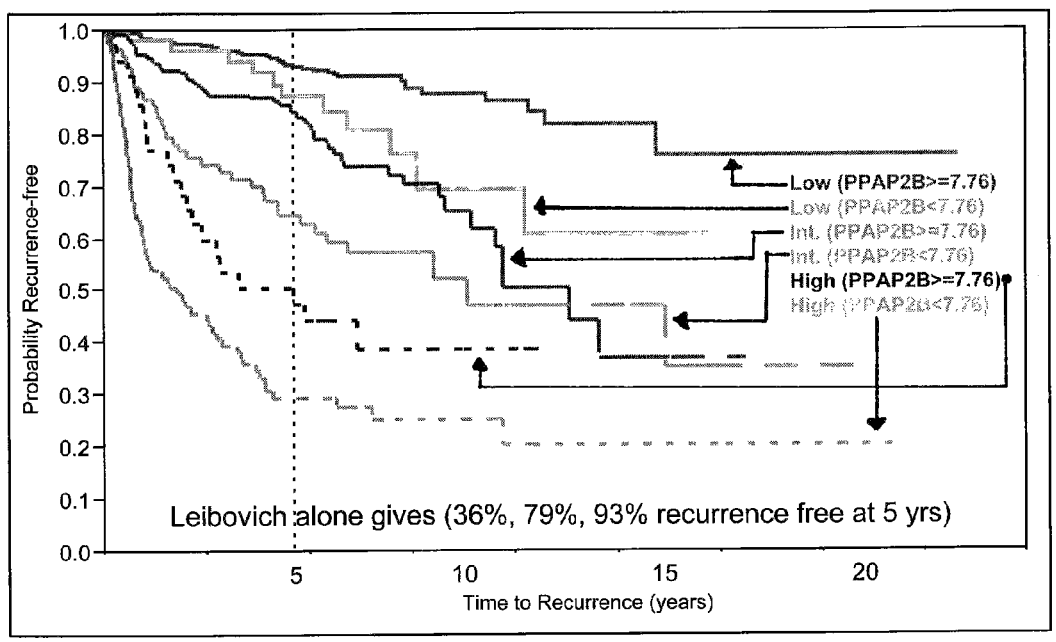
FIG. 7: Example of using one gene to improve estimate: PPAP2B in addition to Mayo Criteria

FIGS. 4-7 provide a comparison of patient stratification (Low, Intermediate, or High Risk) obtained by applying the Mayo prognostic tool (described in Leibovich et al. "prediction of progression after radical nephrectomy for patients with clear cell renal cell carcinoma" (2003) Cancer 97:1663-1671) CCF expression data. As shown in FIG. 4, the Mayo prognostic tool alone provides for stratification into three populations Low Risk (93% recurrence free at 5 years), Intermediate Risk (79% recurrence free at 5 years), and High Risk (36% recurrence free at 5 years). In contrast, use of expression data from even one gene (as exemplified by EMCN (FIG. 5.), AQP1 (FIG. 6), or PPAP2B (FIG. 7)) allowed for more detailed stratification of patients according to risk.

TABLE 3a

Genes for which increased expression is associated with lower risk of cancer recurrence (p-value ≤ .05)

| Gene | Official Symbol | Univariate Cox Analyses (No Covariate Adjustment) with RFI | |
|---|---|---|---|
| | | p-value for HR | HR |
| YB-1.2 | YBX1 | <0.0001 | 0.75 |
| XIAP.1 | XIAP | 0.0009 | 0.81 |
| WWOX.5 | WWOX | <0.0001 | 0.71 |
| VWF.1 | VWF | <0.0001 | 0.61 |
| VEGF.1 | VEGFA | <0.0001 | 0.75 |
| VCAM1.1 | VCAM1 | <0.0001 | 0.66 |
| USP34.1 | USP34 | 0.0003 | 0.79 |
| UMOD.1 | UMOD | <0.0001 | 0.68 |
| UGCG.1 | UGCG | <0.0001 | 0.71 |
| UBB.1 | UBB | <0.0001 | 0.62 |
| UBE1C.1 | UBA3 | 0.0003 | 0.79 |
| TS.1 | TYMS | 0.0056 | 0.83 |
| tusc4.2 | TUSC4 | <0.0001 | 0.76 |

TABLE 3a-continued

Genes for which increased expression is associated with lower risk of cancer recurrence (p-value ≤ .05)

| Gene | Official Symbol | Univariate Cox Analyses (No Covariate Adjustment) with RFI | |
|---|---|---|---|
| | | p-value for HR | HR |
| TSPAN7.2 | TSPAN7 | <0.0001 | 0.52 |
| TSC2.1 | TSC2 | 0.0043 | 0.82 |
| TSC1.1 | TSC1 | <0.0001 | 0.71 |
| P53.2 | TP53 | 0.0008 | 0.81 |
| TOP2B.2 | TOP2B | 0.0001 | 0.80 |
| TNFSF12.1 | TNFSF12 | <0.0001 | 0.68 |
| TRAIL.1 | TNFSF10 | 0.0065 | 0.83 |
| TNFRSF11B.1 | TNFRSF11B | 0.0002 | 0.78 |
| TNFRSF10D.1 | TNFRSF10D | <0.0001 | 0.76 |
| DR5.2 | TNFRSF10B | <0.0001 | 0.75 |
| TNFAIP6.1 | TNFAIP6 | 0.0005 | 0.79 |
| TMEM47.1 | TMEM47 | <0.0001 | 0.57 |
| TMEM27.1 | TMEM27 | <0.0001 | 0.58 |
| TLR3.1 | TLR3 | <0.0001 | 0.72 |
| TIMP3.3 | TIMP3 | <0.0001 | 0.50 |
| TIMP2.1 | TIMP2 | <0.0001 | 0.73 |
| THBS1.1 | THBS1 | 0.0002 | 0.79 |
| TGFBR2.3 | TGFBR2 | <0.0001 | 0.54 |
| TGFBR1.1 | TGFBR1 | <0.0001 | 0.71 |
| TGFB2.2 | TGFB2 | <0.0001 | 0.65 |
| TGFA.2 | TGFA | <0.0001 | 0.70 |
| TEK.1 | TEK | <0.0001 | 0.47 |
| TCF4.1 | TCF4 | <0.0001 | 0.62 |
| TAP1.1 | TAP1 | 0.0024 | 0.82 |
| TAGLN.1 | TAGLN | <0.0001 | 0.70 |
| TACSTD2.1 | TACSTD2 | <0.0001 | 0.72 |
| SUCLG1.1 | SUCLG1 | <0.0001 | 0.72 |
| STK11.1 | STK11 | <0.0001 | 0.76 |
| STAT5B.2 | STAT5B | <0.0001 | 0.71 |
| STAT5A.1 | STAT5A | <0.0001 | 0.72 |
| STAT3.1 | STAT3 | 0.0016 | 0.80 |
| SPRY1.1 | SPRY1 | <0.0001 | 0.68 |
| SPARCL1.1 | SPARCL1 | <0.0001 | 0.71 |
| SPARC.1 | SPARC | 0.0009 | 0.80 |
| SOD1.1 | SOD1 | 0.0114 | 0.84 |
| SNRK.1 | SNRK | <0.0001 | 0.54 |
| SNAI1.1 | SNAI1 | 0.0055 | 0.82 |
| MADH4.1 | SMAD4 | <0.0001 | 0.60 |
| MADH2.1 | SMAD2 | <0.0001 | 0.64 |
| SLC34A1.1 | SLC34A1 | 0.0004 | 0.76 |
| SLC22A6.1 | SLC22A6 | 0.0003 | 0.77 |
| SKIL.1 | SKIL | 0.0004 | 0.79 |
| SHANK3.1 | SHANK3 | <0.0001 | 0.53 |
| SGK.1 | SGK1 | <0.0001 | 0.67 |
| FRP1.3 | SFRP1 | 0.0355 | 0.86 |
| SEMA3F.3 | SEMA3F | <0.0001 | 0.67 |
| SELENBP1.1 | SELENBP1 | 0.0016 | 0.81 |
| SDPR.1 | SDPR | <0.0001 | 0.51 |
| SDHA.1 | SDHA | 0.0003 | 0.77 |
| SCNN1A.2 | SCNN1A | 0.0134 | 0.83 |
| SCN4B.1 | SCN4B | <0.0001 | 0.68 |
| KIAA1303 raptor.1 | RPTOR | <0.0001 | 0.77 |
| RPS6KB1.3 | RPS6KB1 | <0.0001 | 0.73 |
| RPS6KAI.1 | RPS6KA1 | 0.0291 | 0.86 |
| RPS23.1 | RPS23 | <0.0001 | 0.73 |
| ROCK2.1 | ROCK2 | <0.0001 | 0.66 |
| ROCK1.1 | ROCK1 | <0.0001 | 0.58 |
| RIPK1.1 | RIPK1 | <0.0001 | 0.64 |
| rhoC.1 | RHOC | 0.0213 | 0.86 |
| RhoB.1 | RHOB | <0.0001 | 0.63 |
| ARHA.1 | RHOA | <0.0001 | 0.64 |
| RGS5.1 | RGS5 | <0.0001 | 0.52 |
| FLJ22655.1 | RERGL | <0.0001 | 0.51 |
| NFKBp65.3 | RELA | 0.0027 | 0.82 |
| RB1.1 | RB1 | <0.0001 | 0.73 |
| RASSF1.1 | RASSF1 | 0.0040 | 0.83 |
| RARB.2 | RARB | <0.0001 | 0.57 |
| RALBP1.1 | RALBP1 | <0.0001 | 0.73 |
| RAF1.3 | RAF1 | 0.0008 | 0.81 |
| PTPRG.1 | PTPRG | <0.0001 | 0.57 |

TABLE 3a-continued

Genes for which increased expression is associated with lower risk of cancer recurrence (p-value ≤ .05)

Univariate Cox Analyses (No Covariate Adjustment) with RFI

| Gene | Official Symbol | p-value for HR | HR |
|---|---|---|---|
| PTPRB.1 | PTPRB | <0.0001 | 0.51 |
| PTN.1 | PTN | <0.0001 | 0.71 |
| PTK2.1 | PTK2 | <0.0001 | 0.61 |
| PTHR1.1 | PTH1R | <0.0001 | 0.55 |
| PTEN.2 | PTEN | <0.0001 | 0.74 |
| PSMB9.1 | PSMB9 | 0.0025 | 0.82 |
| PSMB8.1 | PSMB8 | 0.0239 | 0.85 |
| PRSS8.1 | PRSS8 | <0.0001 | 0.71 |
| PRPS2.1 | PRPS2 | 0.0156 | 0.85 |
| PRKCH.1 | PRKCH | <0.0001 | 0.63 |
| PPP2CA.1 | PPP2CA | <0.0001 | 0.77 |
| PPARG.3 | PPARG | <0.0001 | 0.59 |
| PPAP2B.1 | PPAP2B | <0.0001 | 0.50 |
| PLG.1 | PLG | <0.0001 | 0.70 |
| PLAT.1 | PLAT | <0.0001 | 0.64 |
| PLA2G4C.1 | PLA2G4C | <0.0001 | 0.67 |
| PIK3CA.1 | PIK3CA | <0.0001 | 0.75 |
| PI3K.2 | PIK3C2B | <0.0001 | 0.56 |
| PFKP.1 | PFKP | 0.0067 | 0.84 |
| CD31.3 | PECAM1 | <0.0001 | 0.60 |
| PDZK3.1 | PDZK3 | 0.0005 | 0.77 |
| PDZK1.1 | PDZK1 | <0.0001 | 0.69 |
| PDGFRb.3 | PDGFRB | <0.0001 | 0.74 |
| PDGFD.2 | PDGFD | <0.0001 | 0.58 |
| PDGFC.3 | PDGFC | <0.0001 | 0.66 |
| PDGFB.3 | PDGFB | <0.0001 | 0.63 |
| PDGFA.3 | PDGFA | <0.0001 | 0.75 |
| PCK1.1 | PCK1 | <0.0001 | 0.65 |
| PCCA.1 | PCCA | <0.0001 | 0.66 |
| PARD6A.1 | PARD6A | 0.0001 | 0.76 |
| Pak1.2 | PAK1 | 0.0011 | 0.81 |
| PAH.1 | PAH | 0.0296 | 0.86 |
| OGG1.1 | OGG1 | 0.0051 | 0.84 |
| BFGF.3 | NUDT6 | <0.0001 | 0.54 |
| NRG1.3 | NRG1 | 0.0049 | 0.81 |
| NPR1.1 | NPR1 | <0.0001 | 0.73 |
| NPM1.2 | NPM1 | <0.0001 | 0.73 |
| NOTCH3.1 | NOTCH3 | <0.0001 | 0.70 |
| NOTCH2.1 | NOTCH2 | 0.0040 | 0.84 |
| NOTCH1.1 | NOTCH1 | <0.0001 | 0.64 |
| NOS3.1 | NOS3 | <0.0001 | 0.55 |
| NOS2A.3 | NOS2 | <0.0001 | 0.66 |
| NOL3.1 | NOL3 | 0.0132 | 0.85 |
| NFX1.1 | NFX1 | <0.0001 | 0.67 |
| NFKBp50.3 | NFKB1 | 0.0001 | 0.77 |
| NFATC2.1 | NFATC2 | 0.0003 | 0.78 |
| NFAT5.1 | NFAT5 | 0.0010 | 0.82 |
| MYRIP.2 | MYRIP | 0.0002 | 0.75 |
| MYH11.1 | MYH11 | <0.0001 | 0.61 |
| cMYC.3 | MYC | 0.0002 | 0.79 |
| MVP.1 | MVP | 0.0052 | 0.83 |
| MUC1.2 | MUC1 | 0.0405 | 0.87 |
| FRAP1.1 | MTOR | <0.0001 | 0.75 |
| MSH3.2 | MSH3 | <0.0001 | 0.75 |
| MSH2.3 | MSH2 | <0.0001 | 0.71 |
| GBL.1 | MLST8 | 0.0246 | 0.87 |
| MIF.2 | MIF | 0.0012 | 0.80 |
| MICA.1 | MICA | <0.0001 | 0.71 |
| MGMT.1 | MGMT | <0.0001 | 0.68 |
| MCM3.3 | MCM3 | 0.0188 | 0.85 |
| MCAM.1 | MCAM | <0.0001 | 0.71 |
| MARCKS.1 | MARCKS | 0.0301 | 0.87 |
| ERK1.3 | MAPK3 | <0.0001 | 0.65 |
| ERK2.3 | MAPK1 | 0.0005 | 0.79 |
| MAP4.1 | MAP4 | <0.0001 | 0.65 |
| MAP2K3.1 | MAP2K3 | <0.0001 | 0.69 |
| MAP2K1.1 | MAP2K1 | 0.0046 | 0.83 |
| MAL2.1 | MAL2 | 0.0001 | 0.76 |
| MAL.1 | MAL | <0.0001 | 0.66 |
| LYZ.1 | LYZ | 0.0458 | 0.88 |
| LTF.1 | LTF | 0.0005 | 0.76 |
| LRP2.1 | LRP2 | <0.0001 | 0.67 |
| LMO2.1 | LMO2 | <0.0001 | 0.74 |
| LDB2.1 | LDB2 | <0.0001 | 0.52 |
| LDB1.2 | LDB1 | <0.0001 | 0.71 |
| LAMA4.1 | LAMA4 | 0.0279 | 0.86 |
| KRT7.1 | KRT7 | <0.0001 | 0.68 |
| K-ras.10 | KRAS | <0.0001 | 0.72 |
| KL.1 | KL | <0.0001 | 0.55 |
| Kitlng.4 | KITLG | <0.0001 | 0.67 |
| c-kit.2 | KIT | <0.0001 | 0.72 |
| KDR.6 | KDR | <0.0001 | 0.54 |
| KCNJ15.1 | KCNJ15 | <0.0001 | 0.63 |
| HTATIP.1 | KAT5 | <0.0001 | 0.64 |
| G-Catenin.1 | JUP | <0.0001 | 0.64 |
| AP-1 (JUN official).2 | JUN | 0.0001 | 0.76 |
| JAG1.1 | JAG1 | <0.0001 | 0.55 |
| ITGB1.1 | ITGB1 | 0.0085 | 0.83 |
| ITGA7.1 | ITGA7 | <0.0001 | 0.66 |
| ITGA6.2 | ITGA6 | <0.0001 | 0.63 |
| ITGA4.2 | ITGA4 | <0.0001 | 0.74 |
| ITGA3.2 | ITGA3 | 0.0002 | 0.79 |
| IQGAP2.1 | IQGAP2 | <0.0001 | 0.69 |
| INSR.1 | INSR | <0.0001 | 0.67 |
| IMP3.1 | IMP3 | <0.0001 | 0.69 |
| IL6ST.3 | IL6ST | <0.0001 | 0.66 |
| IL15.1 | IL15 | <0.0001 | 0.70 |
| IGFBP6.1 | IGFBP6 | 0.0004 | 0.79 |
| IGFBP3.1 | IGFBP3 | 0.0394 | 0.87 |
| IGFBP2.1 | IGFBP2 | 0.0134 | 0.84 |
| IGF1R.3 | IGF1R | <0.0001 | 0.58 |
| IFI27.1 | IFI27 | 0.0205 | 0.85 |
| ID3.1 | ID3 | <0.0001 | 0.69 |
| ID2.4 | ID2 | <0.0001 | 0.75 |
| ID1.1 | ID1 | <0.0001 | 0.55 |
| ICAM2.1 | ICAM2 | <0.0001 | 0.64 |
| HYAL2.1 | HYAL2 | <0.0001 | 0.60 |
| HYAL1.1 | HYAL1 | <0.0001 | 0.58 |
| HSPG2.1 | HSPG2 | <0.0001 | 0.60 |
| HSD11B2.1 | HSD11B2 | <0.0001 | 0.63 |
| Hepsin.1 | HPN | 0.0001 | 0.76 |
| HPCAL1.1 | HPCAL1 | 0.0031 | 0.82 |
| HMGB1.1 | HMGB1 | <0.0001 | 0.67 |
| HLA-DPB1.1 | HLA-DPB1 | <0.0001 | 0.70 |
| HIF1AN.1 | HIF1AN | <0.0001 | 0.77 |
| HDAC1.1 | HDAC1 | 0.0003 | 0.78 |
| HAVCR1.1 | HAVCR1 | 0.0003 | 0.79 |
| HADH.1 | HADH | <0.0001 | 0.68 |
| GZMA.1 | GZMA | 0.0125 | 0.84 |
| GSTp.3 | GSTP1 | <0.0001 | 0.76 |
| GSTM3.2 | GSTM3 | <0.0001 | 0.70 |
| GSTM1.1 | GSTM1 | <0.0001 | 0.72 |
| GRB7.2 | GRB7 | <0.0001 | 0.74 |
| GPX3.1 | GPX3 | <0.0001 | 0.75 |
| GJA1.1 | GJA1 | 0.0049 | 0.84 |
| GFRA1.1 | GFRA1 | 0.0003 | 0.77 |
| GCLC.3 | GCLC | <0.0001 | 0.68 |
| GBP2.2 | GBP2 | 0.0156 | 0.85 |
| GATM.1 | GATM | <0.0001 | 0.66 |
| GATA3.3 | GATA3 | 0.0001 | 0.75 |
| FOS.1 | FOS | <0.0001 | 0.74 |
| FOLR1.1 | FOLR1 | 0.0003 | 0.79 |
| FLT4.1 | FLT4 | <0.0001 | 0.54 |
| FLT3LG.1 | FLT3LG | 0.0001 | 0.73 |
| FLT1.1 | FLT1 | <0.0001 | 0.59 |
| FILIP1.1 | FILIP1 | <0.0001 | 0.72 |
| FIGF.1 | FIGF | 0.0014 | 0.76 |
| FHL1.1 | FHL1 | <0.0001 | 0.68 |
| FHIT.1 | FHIT | <0.0001 | 0.73 |
| FH.1 | FH | <0.0001 | 0.73 |
| FGFR2 isoform | FGFR2 | <0.0001 | 0.70 |

TABLE 3a-continued

Genes for which increased expression is associated with lower risk of cancer recurrence (p-value ≤ .05)

| Gene | Official Symbol | Univariate Cox Analyses (No Covariate Adjustment) with RFI | |
|---|---|---|---|
| | | p-value for HR | HR |
| 1.1 | | | |
| FGFR1.3 | FGFR1 | 0.0001 | 0.77 |
| FGF2.2 | FGF2 | <0.0001 | 0.73 |
| FGF1.1 | FGF1 | 0.0015 | 0.78 |
| FDPS.1 | FDPS | <0.0001 | 0.69 |
| FBXW7.1 | FBXW7 | 0.0001 | 0.75 |
| fas.1 | FAS | <0.0001 | 0.73 |
| FABP1.1 | FABP1 | 0.0455 | 0.86 |
| ESRRG.3 | ESRRG | 0.0008 | 0.79 |
| ERG.1 | ERG | <0.0001 | 0.60 |
| ERCC1.2 | ERCC1 | <0.0001 | 0.78 |
| ErbB3.1 | ERBB3 | 0.0001 | 0.77 |
| HER2.3 | ERBB2 | <0.0001 | 0.65 |
| EPHB4.1 | EPHB4 | <0.0001 | 0.64 |
| EPHA2.1 | EPHA2 | <0.0001 | 0.58 |
| EPAS1.1 | EPAS1 | <0.0001 | 0.55 |
| ENPP2.1 | ENPP2 | 0.0090 | 0.84 |
| ENPEP.1 | ENPEP | <0.0001 | 0.74 |
| CD105.1 | ENG | <0.0001 | 0.60 |
| EMP1.1 | EMP1 | <0.0001 | 0.71 |
| EMCN.1 | EMCN | <0.0001 | 0.43 |
| ELTD1.1 | ELTD1 | <0.0001 | 0.76 |
| EIF2C1.1 | EIF2C1 | <0.0001 | 0.67 |
| EGR1.1 | EGR1 | <0.0001 | 0.72 |
| EGLN3.1 | EGLN3 | 0.0002 | 0.80 |
| EGFR.2 | EGFR | 0.0005 | 0.80 |
| EFNB2.1 | EFNB2 | <0.0001 | 0.64 |
| EFNB1.2 | EFNB1 | <0.0001 | 0.68 |
| EEF1A1.1 | EEF1A1 | <0.0001 | 0.64 |
| EDNRB.1 | EDNRB | <0.0001 | 0.56 |
| EDN2.1 | EDN2 | 0.0005 | 0.77 |
| EDN1 endothelin.1 | EDN1 | <0.0001 | 0.62 |
| EBAG9.1 | EBAG9 | 0.0041 | 0.82 |
| DUSP1.1 | DUSP1 | 0.0029 | 0.82 |
| DPYS.1 | DPYS | 0.0112 | 0.84 |
| DPEP1.1 | DPEP1 | <0.0001 | 0.64 |
| DLL4.1 | DLL4 | <0.0001 | 0.76 |
| DLC1.1 | DLC1 | <0.0001 | 0.55 |
| DKFZP564O08 23.1 | DKFZP564O 0823 | <0.0001 | 0.62 |
| DICER1.2 | DICER1 | <0.0001 | 0.71 |
| DIAPH1.1 | DIAPH1 | 0.0009 | 0.80 |
| DIABLO.1 | DIABLO | 0.0134 | 0.84 |
| DHPS.3 | DHPS | <0.0001 | 0.70 |
| DET1.1 | DET1 | <0.0001 | 0.74 |
| DEFB1.1 | DEFB1 | 0.0025 | 0.81 |
| DDC.1 | DDC | <0.0001 | 0.68 |
| DCXR.1 | DCXR | 0.0081 | 0.83 |
| DAPK1.3 | DAPK1 | <0.0001 | 0.60 |
| CYR61.1 | CYR61 | <0.0001 | 0.70 |
| CYP3A4.2 | CYP3A4 | 0.0380 | 0.86 |
| CXCL9.1 | CXCL9 | 0.0362 | 0.87 |
| CXCL12.1 | CXCL12 | <0.0001 | 0.69 |
| CX3CR1.1 | CX3CR1 | <0.0001 | 0.72 |
| CX3CL1.1 | CX3CL1 | <0.0001 | 0.58 |
| CUL1.1 | CUL1 | 0.0003 | 0.80 |
| CUBN.1 | CUBN | <0.0001 | 0.61 |
| CTSS.1 | CTSS | 0.0016 | 0.82 |
| CTSH.2 | CTSH | <0.0001 | 0.78 |
| B-Catenin.3 | CTNNB1 | <0.0001 | 0.74 |
| A-Catenin.2 | CTNNA1 | <0.0001 | 0.77 |
| CTGF.1 | CTGF | 0.0004 | 0.79 |
| CSF1R.2 | CSF1R | 0.0015 | 0.82 |
| CSF1.1 | CSF1 | 0.0016 | 0.81 |
| CRADD | CRADD | 0.0021 | 0.81 |
| COL4A2.1 | COL4A2 | 0.0016 | 0.80 |
| COL18A1.1 | COL18A1 | 0.0007 | 0.79 |
| CLU.3 | CLU | 0.0151 | 0.85 |
| CLDN7.2 | CLDN7 | 0.0023 | 0.81 |
| CLDN10.1 | CLDN10 | <0.0001 | 0.69 |
| CLCNKB.1 | CLCNKB | 0.0002 | 0.74 |
| CFLAR.1 | CFLAR | <0.0001 | 0.65 |
| CEACAM1.1 | CEACAM1 | <0.0001 | 0.59 |
| p27.3 | CDKN1B | 0.0018 | 0.83 |
| p21.3 | CDKN1A | 0.0027 | 0.81 |
| CDH6.1 | CDH6 | <0.0001 | 0.75 |
| CDH5.1 | CDH5 | <0.0001 | 0.59 |
| CDH16.1 | CDH16 | <0.0001 | 0.75 |
| CDH13.1 | CDH13 | <0.0001 | 0.66 |
| CD4.1 | CD4 | 0.0009 | 0.81 |
| CD36.1 | CD36 | <0.0001 | 0.65 |
| CD34.1 | CD34 | <0.0001 | 0.62 |
| CCR7.1 | CCR7 | 0.0271 | 0.86 |
| CCR4.2 | CCR4 | 0.0106 | 0.83 |
| CCND1.3 | CCND1 | <0.0001 | 0.70 |
| CCL4.2 | CCL4 | 0.0012 | 0.80 |
| MCP1.1 | CCL2 | <0.0001 | 0.75 |
| CAT.1 | CAT | <0.0001 | 0.72 |
| CASP6.1 | CASP6 | 0.0369 | 0.87 |
| CASP10.1 | CASP10 | <0.0001 | 0.69 |
| CALD1.2 | CALD1 | <0.0001 | 0.61 |
| CA9.3 | CA9 | 0.0035 | 0.84 |
| CA2.1 | CA2 | 0.0006 | 0.79 |
| C7.1 | C7 | 0.0030 | 0.82 |
| ECRG4.1 | C2orf40 | <0.0001 | 0.57 |
| C13orf15.1 | C13orf15 | <0.0001 | 0.57 |
| BUB3.1 | BUB3 | 0.0002 | 0.77 |
| BTRC.1 | BTRC | 0.0006 | 0.81 |
| CIAP1.2 | BIRC2 | 0.0030 | 0.82 |
| BIN1.3 | BIN1 | 0.0005 | 0.80 |
| BGN.1 | BGN | <0.0001 | 0.76 |
| BCL2L12.1 | BCL2L12 | 0.0322 | 0.86 |
| Bclx.2 | BCL2L1 | <0.0001 | 0.74 |
| Bcl2.2 | BCL2 | <0.0001 | 0.57 |
| BBC3.2 | BBC3 | 0.0449 | 0.87 |
| BAG1.2 | BAG1 | <0.0001 | 0.64 |
| BAD.1 | BAD | 0.0076 | 0.85 |
| ATP6V1B1.1 | ATP6V1B1 | 0.0001 | 0.71 |
| ASS1.1 | ASS1 | <0.0001 | 0.75 |
| ARRB1.1 | ARRB1 | <0.0001 | 0.62 |
| ARHGDIB.1 | ARHGDIB | <0.0001 | 0.66 |
| AQP1.1 | AQP1 | <0.0001 | 0.50 |
| APOLD1.1 | APOLD1 | <0.0001 | 0.57 |
| APC.4 | APC | <0.0001 | 0.73 |
| ANXA4.1 | ANXA4 | 0.0018 | 0.81 |
| ANXA1.2 | ANXA1 | 0.0009 | 0.80 |
| ANTXR1.1 | ANTXR1 | 0.0043 | 0.82 |
| ANGPTL4.1 | ANGPTL4 | 0.0033 | 0.84 |
| ANGPTL3.3 | ANGPTL3 | 0.0003 | 0.75 |
| ANGPT1.1 | ANGPT1 | <0.0001 | 0.57 |
| ALDOB.1 | ALDOB | <0.0001 | 0.62 |
| ALDH6A1.1 | ALDH6A1 | <0.0001 | 0.63 |
| ALDH4.2 | ALDH4A1 | 0.0172 | 0.85 |
| AKT3.2 | AKT3 | <0.0001 | 0.57 |
| AKT2.3 | AKT2 | <0.0001 | 0.75 |
| AKT1.3 | AKT1 | <0.0001 | 0.71 |
| AIF1.1 | AIF1 | 0.0349 | 0.87 |
| AHR.1 | AHR | <0.0001 | 0.74 |
| AGTR1.1 | AGTR1 | <0.0001 | 0.57 |
| ADH1B.1 | ADH1B | 0.0002 | 0.77 |
| ADFP.1 | ADFP | 0.0332 | 0.88 |
| ADD1.1 | ADD1 | <0.0001 | 0.58 |
| ADAMTS5.1 | ADAMTS5 | 0.0010 | 0.78 |
| ADAMTS1.1 | ADAMTS1 | 0.0056 | 0.83 |
| ACE2.1 | ACE2 | <0.0001 | 0.62 |
| ACADSB.1 | ACADSB | <0.0001 | 0.71 |
| BCRP.1 | ABCG2 | <0.0001 | 0.58 |
| MRP4.2 | ABCC4 | <0.0001 | 0.74 |
| MRP3.1 | ABCC3 | 0.0107 | 0.85 |
| MRP1.1 | ABCC1 | <0.0001 | 0.75 |
| ABCB1.5 | ABCB1 | 0.0093 | 0.84 |

TABLE 3a-continued

Genes for which increased expression is associated with lower risk of cancer recurrence (p-value ≤ .05)

| Gene | Official Symbol | Univariate Cox Analyses (No Covariate Adjustment) with RFI | |
|---|---|---|---|
| | | p-value for HR | HR |
| NPD009 (ABAT official).3 | ABAT | 0.0001 | 0.76 |
| AAMP.1 | AAMP | 0.0008 | 0.80 |
| A2M.1 | A2M | <0.0001 | 0.56 |

TABLE 3b

Genes for which increased expression is associated with higher risk of cancer recurrence (p-value ≤ .05)

| Gene | Official Symbol | Univariate Cox Analyses (No Covariate Adjustment) with RFI | |
|---|---|---|---|
| | | p-value for HR | HR |
| WT1.1 | WT1 | 0.0002 | 1.25 |
| VTN.1 | VTN | 0.0097 | 1.17 |
| VDR.2 | VDR | 0.0031 | 1.22 |
| VCAN.1 | VCAN | 0.0036 | 1.22 |
| UBE2T.1 | UBE2T | <0.0001 | 1.38 |
| C20 orf1.1 | TPX2 | <0.0001 | 1.76 |
| TOP2A.4 | TOP2A | <0.0001 | 1.39 |
| TK1.2 | TK1 | 0.0018 | 1.22 |
| TIMP1.1 | TIMP1 | 0.0259 | 1.16 |
| TGFBI.1 | TGFBI | 0.0004 | 1.26 |
| SQSTM1.1 | SQSTM1 | 0.0089 | 1.20 |
| OPN, osteopontin.3 | SPP1 | <0.0001 | 1.43 |
| SPHK1.1 | SPHK1 | 0.0025 | 1.22 |
| SLC7A5.2 | SLC7A5 | <0.0001 | 1.38 |
| SLC2A1.1 | SLC2A1 | 0.0010 | 1.26 |
| SLC16A3.1 | SLC16A3 | <0.0001 | 1.38 |
| SLC13A3.1 | SLC13A3 | 0.0192 | 1.16 |
| SHC1.1 | SHC1 | 0.0086 | 1.19 |
| SFN.1 | SFN | 0.0001 | 1.26 |
| SERPINA5.1 | SERPINA5 | 0.0462 | 1.13 |
| SEMA3C.1 | SEMA3C | <0.0001 | 1.45 |
| SAA2.2 | SAA2 | <0.0001 | 1.59 |
| S100A1.1 | S100A1 | 0.0348 | 1.16 |
| RRM2.1 | RRM2 | 0.0002 | 1.27 |
| RPLP1.1 | RPLP1 | 0.0049 | 1.22 |
| PTTG1.2 | PTTG1 | <0.0001 | 1.45 |
| COX2.1 | PTGS2 | 0.0013 | 1.22 |
| PLAUR.3 | PLAUR | <0.0001 | 1.33 |
| PF4.1 | PF4 | 0.0034 | 1.20 |
| PCSK6.1 | PCSK6 | 0.0269 | 1.17 |
| MYBL2.1 | MYBL2 | <0.0001 | 1.33 |
| MT1X.1 | MT1X | 0.0070 | 1.20 |
| MMP9.1 | MMP9 | <0.0001 | 1.54 |
| MMP7.1 | MMP7 | 0.0312 | 1.15 |
| MMP14.1 | MMP14 | <0.0001 | 1.47 |
| Ki-67.2 | MKI67 | <0.0001 | 1.33 |
| mGST1.2 | MGST1 | <0.0001 | 1.38 |
| MDK.1 | MDK | 0.0001 | 1.31 |
| LOX.1 | LOX | <0.0001 | 1.42 |
| LMNB1.1 | LMNB1 | <0.0001 | 1.40 |
| LIMK1.1 | LIMK1 | <0.0001 | 1.43 |
| LGALS1.1 | LGALS1 | 0.0017 | 1.25 |
| LAMB3.1 | LAMB3 | <0.0001 | 1.34 |
| LAMB1.1 | LAMB1 | 0.0014 | 1.25 |
| L1CAM.1 | L1CAM | 0.0199 | 1.16 |
| IL-8.1 | IL8 | <0.0001 | 1.53 |
| IL6.3 | IL6 | <0.0001 | 1.41 |
| ICAM1.1 | ICAM1 | 0.0013 | 1.23 |
| HIST1H1D.1 | HIST1H1D | 0.0066 | 1.21 |
| FN1.1 | FN1 | 0.0105 | 1.19 |

TABLE 3b-continued

Genes for which increased expression is associated with higher risk of cancer recurrence (p-value ≤ .05)

| Gene | Official Symbol | Univariate Cox Analyses (No Covariate Adjustment) with RFI | |
|---|---|---|---|
| | | p-value for HR | HR |
| F3.1 | F3 | <0.0001 | 1.31 |
| F2.1 | F2 | <0.0001 | 1.30 |
| ESPL1.3 | ESPL1 | 0.0155 | 1.17 |
| EPHB2.1 | EPHB2 | 0.0456 | 1.14 |
| EPHB1.3 | EPHB1 | 0.0007 | 1.22 |
| ENO2.1 | ENO2 | <0.0001 | 1.38 |
| EIF4EBP1.1 | EIF4EBP1 | 0.0098 | 1.19 |
| CXCR4.3 | CXCR4 | 0.0066 | 1.21 |
| GRO1.2 | CXCL1 | <0.0001 | 1.30 |
| CTSB.1 | CTSB | 0.0233 | 1.17 |
| CRP.1 | CRP | 0.0314 | 1.13 |
| CP.1 | CP | 0.0002 | 1.32 |
| COL7A1.1 | COL7A1 | 0.0003 | 1.24 |
| COL1A1.1 | COL1A1 | 0.0029 | 1.23 |
| Chk1.2 | CHEK1 | 0.0002 | 1.26 |
| CENPF.1 | CENPF | <0.0001 | 1.36 |
| CD82.3 | CD82 | 0.0009 | 1.25 |
| CD44s.1 | CD44_s | 0.0065 | 1.21 |
| CCNE1.1 | CCNE1 | 0.0098 | 1.17 |
| CCNB1.2 | CCNB1 | <0.0001 | 1.42 |
| CCL20.1 | CCL20 | 0.0029 | 1.22 |
| CA12.1 | CA12 | <0.0001 | 1.48 |
| C3.1 | C3 | 0.0176 | 1.18 |
| BUB1.1 | BUB1 | <0.0001 | 1.59 |
| SURV.2 | BIRC5 | <0.0001 | 1.37 |
| cIAP2.2 | BIRC3 | 0.0484 | 1.15 |
| BCL2A1.1 | BCL2A1 | 0.0483 | 1.11 |
| STK15.2 | AURKA | 0.0002 | 1.28 |
| ANXA2.2 | ANXA2 | 0.0315 | 1.16 |
| ALOX5.1 | ALOX5 | 0.0473 | 1.14 |
| ADAM8.1 | ADAM8 | 0.0002 | 1.29 |
| MRP2.3 | ABCC2 | 0.0004 | 1.28 |

TABLE 4a

Proxy genes for which increased expression is associated with higher tumor stage (p-value ≤ .05)

| Gene | Official Symbol | Stage 3 vs. 1 | |
|---|---|---|---|
| | | p-value | OR |
| WT1.1 | WT1 | <0.0001 | 1.41 |
| VTN.1 | VTN | 0.0007 | 1.29 |
| VDR.2 | VDR | 0.0065 | 1.25 |
| UBE2T.1 | UBE2T | <0.0001 | 1.61 |
| TSPAN8.1 | TSPAN8 | 0.0072 | 1.23 |
| C20 orf1.1 | TPX2 | <0.0001 | 1.89 |
| TOP2A.4 | TOP2A | <0.0001 | 1.55 |
| TK1.2 | TK1 | 0.0001 | 1.34 |
| TIMP1.1 | TIMP1 | 0.0021 | 1.29 |
| TGFBI.1 | TGFBI | 0.0001 | 1.39 |
| OPN, osteopontin.3 | SPP1 | 0.0001 | 1.38 |
| SLC7A5.2 | SLC7A5 | <0.0001 | 1.51 |
| SLC2A1.1 | SLC2A1 | 0.0081 | 1.24 |
| SLC16A3.1 | SLC16A3 | <0.0001 | 1.46 |
| SFN.1 | SFN | 0.0001 | 1.36 |
| SEMA3C.1 | SEMA3C | <0.0001 | 1.42 |
| SELL.1 | SELL | 0.0313 | 1.19 |
| SAA2.2 | SAA2 | <0.0001 | 2.04 |
| RRM2.1 | RRM2 | <0.0001 | 1.47 |
| RPLP1.1 | RPLP1 | 0.0007 | 1.33 |
| RAD51.1 | RAD51 | 0.0010 | 1.31 |
| PTTG1.2 | PTTG1 | <0.0001 | 1.61 |
| COX2.1 | PTGS2 | 0.0011 | 1.29 |
| PTGIS.1 | PTGIS | 0.0034 | 1.27 |
| PLAUR.3 | PLAUR | <0.0001 | 1.51 |

TABLE 4a-continued

Proxy genes for which increased expression is associated with higher tumor stage (p-value ≤ .05)

| Gene | Official Symbol | Stage 3 vs. 1 p-value | OR |
|---|---|---|---|
| PF4.1 | PF4 | 0.0027 | 1.26 |
| PDGFRa.2 | PDGFRA | 0.0480 | 1.17 |
| PCSK6.1 | PCSK6 | 0.0041 | 1.27 |
| NNMT.1 | NNMT | 0.0003 | 1.34 |
| NME2.1 | NME2 | 0.0028 | 1.28 |
| MYBL2.1 | MYBL2 | <0.0001 | 1.50 |
| MT1X.1 | MT1X | 0.0192 | 1.21 |
| MMP9.1 | MMP9 | <0.0001 | 1.79 |
| MMP7.1 | MMP7 | 0.0252 | 1.20 |
| MMP14.1 | MMP14 | <0.0001 | 1.88 |
| Ki-67.2 | MKI67 | <0.0001 | 1.48 |
| mGST1.2 | MGST1 | 0.0004 | 1.37 |
| MDK.1 | MDK | <0.0001 | 1.42 |
| MDH2.1 | MDH2 | 0.0321 | 1.19 |
| LRRC2.1 | LRRC2 | 0.0259 | 1.19 |
| LOX.1 | LOX | <0.0001 | 1.78 |
| LMNB1.1 | LMNB1 | <0.0001 | 1.82 |
| LIMK1.1 | LIMK1 | <0.0001 | 1.46 |
| LAPTM5.1 | LAPTM5 | 0.0102 | 1.23 |
| LAMB3.1 | LAMB3 | <0.0001 | 1.53 |
| LAMB1.1 | LAMB1 | 0.0452 | 1.18 |
| LAMA3.1 | LAMA3 | 0.0121 | 1.22 |
| L1CAM.1 | L1CAM | 0.0091 | 1.22 |
| ISG20.1 | ISG20 | 0.0006 | 1.34 |
| IL-8.1 | IL8 | <0.0001 | 1.89 |
| IL6.3 | IL6 | <0.0001 | 1.68 |
| IGF1.2 | IGF1 | 0.0214 | 1.20 |
| ICAM1.1 | ICAM1 | <0.0001 | 1.42 |
| HIST1H1D.1 | HIST1H1D | 0.0005 | 1.33 |
| GPX2.2 | GPX2 | 0.0129 | 1.22 |
| FN1.1 | FN1 | 0.0002 | 1.36 |
| FAP.1 | FAP | 0.0455 | 1.18 |
| F3.1 | F3 | <0.0001 | 1.52 |
| F2.1 | F2 | <0.0001 | 1.79 |
| ESPL1.3 | ESPL1 | 0.0001 | 1.35 |
| EPB41L3.1 | EPB41L3 | 0.0067 | 1.24 |
| ENO2.1 | ENO2 | 0.0016 | 1.31 |
| EIF4EBP1.1 | EIF4EBP1 | 0.0036 | 1.27 |
| E2F1.3 | E2F1 | 0.0017 | 1.27 |
| DCN.1 | DCN | 0.0152 | 1.22 |
| CXCR6.1 | CXCR6 | 0.0013 | 1.30 |
| BLR1.1 | CXCR5 | 0.0232 | 1.19 |
| CXCR4.3 | CXCR4 | 0.0003 | 1.35 |
| GRO1.2 | CXCL1 | 0.0005 | 1.31 |
| CTSB.1 | CTSB | 0.0110 | 1.24 |
| CRP.1 | CRP | 0.0002 | 1.31 |
| CP.1 | CP | 0.0008 | 1.34 |
| COL7A1.1 | COL7A1 | 0.0010 | 1.28 |
| COL1A1.1 | COL1A1 | 0.0001 | 1.40 |
| Chk2.3 | CHEK2 | 0.0050 | 1.27 |
| Chk1.2 | CHEK1 | <0.0001 | 1.43 |
| CENPF.1 | CENPF | <0.0001 | 1.55 |
| CD82.3 | CD82 | 0.0001 | 1.38 |
| CD44s.1 | CD44_s | 0.0060 | 1.25 |
| CCNE2.2 | CCNE2_2 | 0.0229 | 1.19 |
| CCNB1.2 | CCNB1 | <0.0001 | 1.60 |
| CCL20.1 | CCL20 | 0.0010 | 1.30 |
| CA12.1 | CA12 | <0.0001 | 1.66 |
| C3.1 | C3 | 0.0009 | 1.32 |
| BUB1.1 | BUB1 | <0.0001 | 1.82 |
| SURV.2 | BIRC5 | <0.0001 | 1.46 |
| BCL2A1.1 | BCL2A1 | <0.0001 | 1.44 |
| STK15.2 | AURKA | 0.0002 | 1.36 |
| APOL1.1 | APOL1 | 0.0028 | 1.27 |
| ANXA2.2 | ANXA2 | 0.0174 | 1.21 |
| ADAM8.1 | ADAM8 | <0.0001 | 1.58 |
| MRP2.3 | ABCC2 | <0.0001 | 1.45 |

TABLE 4b

Proxy genes for which increased expression is associated with lower tumor stage (p-value ≤ .05)

| Gene | Official Symbol | Stage 3 vs. 1 p-value | OR |
|---|---|---|---|
| YB-1.2 | YBX1 | <0.0001 | 0.63 |
| XIAP.1 | XIAP | <0.0001 | 0.62 |
| WWOX.5 | WWOX | 0.0042 | 0.79 |
| WISP1.1 | WISP1 | 0.0096 | 0.81 |
| VWF.1 | VWF | <0.0001 | 0.46 |
| VEGF.1 | VEGFA | <0.0001 | 0.63 |
| VCAM1.1 | VCAM1 | <0.0001 | 0.55 |
| USP34.1 | USP34 | 0.0001 | 0.72 |
| UMOD.1 | UMOD | <0.0001 | 0.47 |
| UGCG.1 | UGCG | <0.0001 | 0.68 |
| UBB.1 | UBB | <0.0001 | 0.54 |
| UBE1C.1 | UBA3 | <0.0001 | 0.62 |
| TS.1 | TYMS | 0.0010 | 0.76 |
| tusc4.2 | TUSC4 | <0.0001 | 0.57 |
| TUSC2.1 | TUSC2 | 0.0295 | 0.83 |
| TSPAN7.2 | TSPAN7 | <0.0001 | 0.35 |
| TSC2.1 | TSC2 | <0.0001 | 0.66 |
| TSC1.1 | TSC1 | <0.0001 | 0.56 |
| P53.2 | TP53 | <0.0001 | 0.67 |
| TOP2B.2 | TOP2B | <0.0001 | 0.69 |
| TNIP2.1 | TNIP2 | 0.0359 | 0.85 |
| TNFSF12.1 | TNFSF12 | <0.0001 | 0.50 |
| TRAIL.1 | TNFSF10 | 0.0011 | 0.77 |
| TNFRSF11B.1 | TNFRSF11B | <0.0001 | 0.63 |
| TNFRSF10D.1 | TNFRSF10D | <0.0001 | 0.57 |
| DR5.2 | TNFRSF10B | <0.0001 | 0.64 |
| TNFAIP6.1 | TNFAIP6 | 0.0001 | 0.74 |
| TNF.1 | TNF | 0.0138 | 0.80 |
| TMEM47.1 | TMEM47 | <0.0001 | 0.41 |
| TMEM27.1 | TMEM27 | <0.0001 | 0.53 |
| TLR3.1 | TLR3 | <0.0001 | 0.68 |
| TIMP3.3 | TIMP3 | <0.0001 | 0.39 |
| TIMP2.1 | TIMP2 | <0.0001 | 0.68 |
| THBS1.1 | THBS1 | <0.0001 | 0.65 |
| TGFBR2.3 | TGFBR2 | <0.0001 | 0.41 |
| TGFBR1.1 | TGFBR1 | <0.0001 | 0.59 |
| TGFB2.2 | TGFB2 | <0.0001 | 0.50 |
| TGFb1.1 | TGFB1 | <0.0001 | 0.67 |
| TGFA.2 | TGFA | <0.0001 | 0.63 |
| TEK.1 | TEK | <0.0001 | 0.34 |
| TCF4.1 | TCF4 | <0.0001 | 0.47 |
| TAP1.1 | TAP1 | 0.0017 | 0.77 |
| TAGLN.1 | TAGLN | 0.0001 | 0.72 |
| TACSTD2.1 | TACSTD2 | <0.0001 | 0.58 |
| SUCLG1.1 | SUCLG1 | <0.0001 | 0.56 |
| STK11.1 | STK11 | <0.0001 | 0.58 |
| STAT5B.2 | STAT5B | <0.0001 | 0.50 |
| STAT5A.1 | STAT5A | <0.0001 | 0.60 |
| STAT3.1 | STAT3 | 0.0001 | 0.72 |
| STAT1.3 | STAT1 | 0.0344 | 0.84 |
| SPRY1.1 | SPRY1 | <0.0001 | 0.57 |
| SPAST.1 | SPAST | 0.0142 | 0.82 |
| SPARCL1.1 | SPARCL1 | <0.0001 | 0.59 |
| SPARC.1 | SPARC | <0.0001 | 0.69 |
| SOD1.1 | SOD1 | 0.0245 | 0.83 |
| SNRK.1 | SNRK | <0.0001 | 0.35 |
| SNAI1.1 | SNAI1 | <0.0001 | 0.70 |
| MADH4.1 | SMAD4 | <0.0001 | 0.47 |
| MADH2.1 | SMAD2 | <0.0001 | 0.50 |
| SLC9A1.1 | SLC9A1 | 0.0207 | 0.82 |
| SLC34A1.1 | SLC34A1 | <0.0001 | 0.63 |
| SLC22A6.1 | SLC22A6 | 0.0010 | 0.76 |
| SKIL.1 | SKIL | <0.0001 | 0.64 |
| PTPNS1.1 | SIRPA | 0.0075 | 0.81 |
| SHANK3.1 | SHANK3 | <0.0001 | 0.37 |
| SGK.1 | SGK1 | <0.0001 | 0.55 |
| FRP1.3 | SFRP1 | 0.0156 | 0.82 |
| SEMA3F.3 | SEMA3F | <0.0001 | 0.50 |
| SELPLG.1 | SELPLG | 0.0022 | 0.78 |
| SELENBP1.1 | SELENBP1 | 0.0003 | 0.75 |
| SDPR.1 | SDPR | <0.0001 | 0.42 |
| SDHA.1 | SDHA | <0.0001 | 0.65 |
| SCNN1A.2 | SCNN1A | 0.0024 | 0.77 |

TABLE 4b-continued

Proxy genes for which increased expression is associated with lower tumor stage (p-value ≤ .05)

| Gene | Official Symbol | Stage 3 vs. 1 p-value | OR |
|---|---|---|---|
| SCN4B.1 | SCN4B | <0.0001 | 0.50 |
| S100A2.1 | S100A2 | 0.0008 | 0.75 |
| KIAA1303 raptor.1 | RPTOR | <0.0001 | 0.60 |
| RPS6KB1.3 | RPS6KB1 | <0.0001 | 0.60 |
| RPS6KA1.1 | RPS6KA1 | 0.0002 | 0.71 |
| RPS23.1 | RPS23 | 0.0002 | 0.73 |
| ROCK2.1 | ROCK2 | <0.0001 | 0.52 |
| ROCK1.1 | ROCK1 | <0.0001 | 0.37 |
| RIPK1.1 | RIPK1 | <0.0001 | 0.55 |
| rhoC.1 | RHOC | <0.0001 | 0.66 |
| RhoB.1 | RHOB | <0.0001 | 0.57 |
| ARHA.1 | RHOA | <0.0001 | 0.50 |
| RHEB.2 | RHEB | <0.0001 | 0.61 |
| RGS5.1 | RGS5 | <0.0001 | 0.37 |
| FLJ22655.1 | RERGL | <0.0001 | 0.33 |
| RB1.1 | RB1 | <0.0001 | 0.61 |
| RASSF1.1 | RASSF1 | 0.0002 | 0.75 |
| RARB.2 | RARB | <0.0001 | 0.37 |
| RALBP1.1 | RALBP1 | <0.0001 | 0.43 |
| RAF1.3 | RAF1 | <0.0001 | 0.59 |
| RAC1.3 | RAC1 | 0.0356 | 0.84 |
| PTPRG.1 | PTPRG | <0.0001 | 0.35 |
| PTPRB.1 | PTPRB | <0.0001 | 0.31 |
| PTN.1 | PTN | <0.0001 | 0.56 |
| PTK2.1 | PTK2 | <0.0001 | 0.45 |
| PTHR1.1 | PTH1R | <0.0001 | 0.45 |
| PTEN.2 | PTEN | <0.0001 | 0.51 |
| PSMB9.1 | PSMB9 | 0.0139 | 0.82 |
| PSMB8.1 | PSMB8 | 0.0243 | 0.83 |
| PSMA7.1 | PSMA7 | 0.0101 | 0.81 |
| PRSS8.1 | PRSS8 | 0.0025 | 0.78 |
| PRPS2.1 | PRPS2 | 0.0190 | 0.82 |
| PRKCH.1 | PRKCH | <0.0001 | 0.48 |
| PRKCD.2 | PRKCD | 0.0001 | 0.72 |
| PPP2CA.1 | PPP2CA | <0.0001 | 0.58 |
| PPARG.3 | PPARG | <0.0001 | 0.40 |
| PPAP2B.1 | PPAP2B | <0.0001 | 0.31 |
| PLG.1 | PLG | <0.0001 | 0.53 |
| PLAT.1 | PLAT | <0.0001 | 0.54 |
| PLA2G4C.1 | PLA2G4C | <0.0001 | 0.65 |
| PIK3CA.1 | PIK3CA | <0.0001 | 0.53 |
| PI3K.2 | PIK3C2B | <0.0001 | 0.40 |
| PFKP.1 | PFKP | 0.0124 | 0.82 |
| CD31.3 | PECAM1 | <0.0001 | 0.42 |
| PDZK3.1 | PDZK3 | 0.0003 | 0.72 |
| PDZK1.1 | PDZK1 | <0.0001 | 0.58 |
| PDGFRb.3 | PDGFRB | <0.0001 | 0.62 |
| PDGFD.2 | PDGFD | <0.0001 | 0.43 |
| PDGFC.3 | PDGFC | <0.0001 | 0.51 |
| PDGFB.3 | PDGFB | <0.0001 | 0.40 |
| PDGFA.3 | PDGFA | <0.0001 | 0.57 |
| PCK1.1 | PCK1 | <0.0001 | 0.60 |
| PCCA.1 | PCCA | <0.0001 | 0.58 |
| PARD6A.1 | PARD6A | 0.0042 | 0.79 |
| Pak1.2 | PAK1 | <0.0001 | 0.69 |
| PAH.1 | PAH | 0.0309 | 0.84 |
| OGG1.1 | OGG1 | 0.0024 | 0.78 |
| BFGF.3 | NUDT6 | <0.0001 | 0.46 |
| NPR1.1 | NPR1 | <0.0001 | 0.58 |
| NPM1.2 | NPM1 | <0.0001 | 0.65 |
| NOTCH3.1 | NOTCH3 | <0.0001 | 0.58 |
| NOTCH2.1 | NOTCH2 | <0.0001 | 0.64 |
| NOTCH1.1 | NOTCH1 | <0.0001 | 0.44 |
| NOS3.1 | NOS3 | <0.0001 | 0.44 |
| NOS2A.3 | NOS2 | <0.0001 | 0.49 |
| NOL3.1 | NOL3 | 0.0003 | 0.76 |
| NFX1.1 | NFX1 | <0.0001 | 0.50 |
| NFKBp50.3 | NFKB1 | <0.0001 | 0.59 |
| NFATC2.1 | NFATC2 | <0.0001 | 0.64 |
| NFAT5.1 | NFAT5 | <0.0001 | 0.65 |
| MYRIP.2 | MYRIP | 0.0004 | 0.72 |
| MYH11.1 | MYH11 | <0.0001 | 0.50 |
| cMYC.3 | MYC | <0.0001 | 0.70 |
| MX1.1 | MX1 | 0.0103 | 0.81 |
| MVP.1 | MVP | 0.0002 | 0.74 |
| MUC1.2 | MUC1 | 0.0005 | 0.75 |
| FRAP1.1 | MTOR | <0.0001 | 0.61 |
| MSH3.2 | MSH3 | <0.0001 | 0.60 |
| MSH2.3 | MSH2 | <0.0001 | 0.53 |
| STMY3.3 | MMP11 | 0.0034 | 0.79 |
| GBL.1 | MLST8 | 0.0011 | 0.77 |
| MIF.2 | MIF | 0.0008 | 0.76 |
| MICA.1 | MICA | <0.0001 | 0.70 |
| MGMT.1 | MGMT | <0.0001 | 0.60 |
| MCM3.3 | MCM3 | <0.0001 | 0.68 |
| MCAM.1 | MCAM | <0.0001 | 0.52 |
| MARCKS.1 | MARCKS | 0.0001 | 0.73 |
| ERK1.3 | MAPK3 | <0.0001 | 0.48 |
| ERK2.3 | MAPK1 | 0.0221 | 0.83 |
| MAP4.1 | MAP4 | <0.0001 | 0.63 |
| MAP2K3.1 | MAP2K3 | <0.0001 | 0.59 |
| MAP2K1.1 | MAP2K1 | 0.0002 | 0.74 |
| MAL2.1 | MAL2 | <0.0001 | 0.64 |
| MAL.1 | MAL | <0.0001 | 0.49 |
| LYZ.1 | LYZ | 0.0318 | 0.84 |
| LTF.1 | LTF | 0.0131 | 0.80 |
| LRP2.1 | LRP2 | <0.0001 | 0.63 |
| LMO2.1 | LMO2 | <0.0001 | 0.56 |
| LDB2.1 | LDB2 | <0.0001 | 0.41 |
| LDB1.2 | LDB1 | <0.0001 | 0.54 |
| LAMA4.1 | LAMA4 | 0.0004 | 0.75 |
| KRT7.1 | KRT7 | <0.0001 | 0.60 |
| K-ras.10 | KRAS | <0.0001 | 0.68 |
| KL.1 | KL | <0.0001 | 0.49 |
| KitIng.4 | KITLG | <0.0001 | 0.43 |
| c-kit.2 | KIT | <0.0001 | 0.60 |
| KDR.1 | KDR | <0.0001 | 0.36 |
| KCNJ15.1 | KCNJ15 | <0.0001 | 0.54 |
| HTATIP.1 | KAT5 | <0.0001 | 0.40 |
| G-Catenin.1 | JUP | <0.0001 | 0.42 |
| AP-1 (JUN official).2 | JUN | 0.0001 | 0.73 |
| JAG1.1 | JAG1 | <0.0001 | 0.42 |
| ITGB5.1 | ITGB5 | 0.0115 | 0.81 |
| ITGB1.1 | ITGB1 | <0.0001 | 0.64 |
| ITGA7.1 | ITGA7 | <0.0001 | 0.54 |
| ITGA6.2 | ITGA6 | <0.0001 | 0.51 |
| ITGA5.1 | ITGA5 | 0.0325 | 0.84 |
| ITGA4.2 | ITGA4 | <0.0001 | 0.54 |
| ITGA3.2 | ITGA3 | <0.0001 | 0.61 |
| IQGAP2.1 | IQGAP2 | <0.0001 | 0.63 |
| INSR.1 | INSR | <0.0001 | 0.59 |
| IMP3.1 | IMP3 | <0.0001 | 0.54 |
| IL-7.1 | IL7 | 0.0444 | 0.85 |
| IL6ST.3 | IL6ST | <0.0001 | 0.50 |
| IL15.1 | IL15 | <0.0001 | 0.67 |
| IGFBP6.1 | IGFBP6 | 0.0001 | 0.73 |
| IGFBP3.1 | IGFBP3 | 0.0191 | 0.83 |
| IGF1R.3 | IGF1R | <0.0001 | 0.48 |
| ID3.1 | ID3 | <0.0001 | 0.54 |
| ID2.4 | ID2 | 0.0008 | 0.77 |
| ID1.1 | ID1 | <0.0001 | 0.34 |
| ICAM2.1 | ICAM2 | <0.0001 | 0.58 |
| HYAL2.1 | HYAL2 | <0.0001 | 0.41 |
| HYAL1.1 | HYAL1 | <0.0001 | 0.44 |
| HSPG2.1 | HSPG2 | <0.0001 | 0.44 |
| HSD11B2.1 | HSD11B2 | <0.0001 | 0.47 |
| Hepsin.1 | HPN | 0.0031 | 0.79 |
| HPCAL1.1 | HPCAL1 | 0.0004 | 0.75 |
| HNRNPAB.3 | HNRNPAB | 0.0039 | 0.78 |
| HMGB1.1 | HMGB1 | <0.0001 | 0.46 |
| HLA-DPB1.1 | HLA-DPB1 | <0.0001 | 0.55 |
| HIF1AN.1 | HIF1AN | <0.0001 | 0.57 |
| HIF1A.3 | HIF1A | 0.0076 | 0.80 |
| HGF.4 | HGF | 0.0067 | 0.80 |

TABLE 4b-continued

Proxy genes for which increased expression is associated with lower tumor stage (p-value ≤ .05)

| Gene | Official Symbol | Stage 3 vs. 1 p-value | OR |
|---|---|---|---|
| HDAC1.1 | HDAC1 | <0.0001 | 0.61 |
| HAVCR1.1 | HAVCR1 | 0.0001 | 0.73 |
| HADH.1 | HADH | <0.0001 | 0.62 |
| GSTT1.3 | GSTT1 | 0.0112 | 0.82 |
| GSTp.3 | GSTP1 | <0.0001 | 0.64 |
| GSTM3.2 | GSTM3 | <0.0001 | 0.57 |
| GSTM1.1 | GSTM1 | <0.0001 | 0.55 |
| GRB7.2 | GRB7 | <0.0001 | 0.66 |
| GRB14.1 | GRB14 | 0.0123 | 0.81 |
| GPX3.1 | GPX3 | 0.0120 | 0.82 |
| GNAS.1 | GNAS | 0.0003 | 0.74 |
| GJA1.1 | GJA1 | 0.0034 | 0.79 |
| GFRA1.1 | GFRA1 | 0.0164 | 0.82 |
| GCLM.2 | GCLM | 0.0056 | 0.80 |
| GCLC.3 | GCLC | <0.0001 | 0.49 |
| GBP2.2 | GBP2 | 0.0388 | 0.84 |
| GATM.1 | GATM | <0.0001 | 0.59 |
| GATA3.3 | GATA3 | 0.0002 | 0.72 |
| FOS.1 | FOS | <0.0001 | 0.65 |
| FOLR1.1 | FOLR1 | <0.0001 | 0.65 |
| FLT4.1 | FLT4 | <0.0001 | 0.37 |
| FLT3LG.1 | FLT3LG | <0.0001 | 0.61 |
| FLT1.1 | FLT1 | <0.0001 | 0.40 |
| FILIP1.1 | FILIP1 | <0.0001 | 0.47 |
| FIGF.1 | FIGF | <0.0001 | 0.53 |
| FHL1.1 | FHL1 | <0.0001 | 0.52 |
| FHIT.1 | FHIT | <0.0001 | 0.54 |
| FH.1 | FH | <0.0001 | 0.67 |
| FGFR2 isoform 1.1 | FGFR2 | <0.0001 | 0.62 |
| FGFR1.3 | FGFR1 | <0.0001 | 0.63 |
| FGF2.2 | FGF2 | <0.0001 | 0.58 |
| FGF1.1 | FGF1 | <0.0001 | 0.66 |
| FDPS.1 | FDPS | <0.0001 | 0.47 |
| FBXW7.1 | FBXW7 | <0.0001 | 0.66 |
| fas.1 | FAS | <0.0001 | 0.66 |
| ESRRG.3 | ESRRG | 0.0001 | 0.72 |
| ERG.1 | ERG | <0.0001 | 0.44 |
| ERCC1.2 | ERCC1 | <0.0001 | 0.60 |
| ERBB4.3 | ERBB4 | 0.0018 | 0.74 |
| ErbB3.1 | ERBB3 | 0.0031 | 0.79 |
| HER2.3 | ERBB2 | <0.0001 | 0.53 |
| EPHB4.1 | EPHB4 | <0.0001 | 0.51 |
| EPHA2.1 | EPHA2 | <0.0001 | 0.40 |
| EPAS1.1 | EPAS1 | <0.0001 | 0.38 |
| ENPP2.1 | ENPP2 | 0.0001 | 0.72 |
| ENPEP.1 | ENPEP | <0.0001 | 0.65 |
| CD105.1 | ENG | <0.0001 | 0.38 |
| EMP1.1 | EMP1 | <0.0001 | 0.64 |
| EMCN.1 | EMCN | <0.0001 | 0.27 |
| ELTD1.1 | ELTD1 | <0.0001 | 0.67 |
| EIF2C1.1 | EIF2C1 | <0.0001 | 0.51 |
| EGR1.1 | EGR1 | <0.0001 | 0.59 |
| EGLN3.1 | EGLN3 | 0.0002 | 0.75 |
| EGFR.2 | EGFR | 0.0072 | 0.81 |
| EGF.3 | EGF | 0.0051 | 0.77 |
| EFNB2.1 | EFNB2 | <0.0001 | 0.45 |
| EFNB1.2 | EFNB1 | <0.0001 | 0.55 |
| EEF1A1.1 | EEF1A1 | <0.0001 | 0.55 |
| EDNRB.1 | EDNRB | <0.0001 | 0.44 |
| EDN2.1 | EDN2 | 0.0012 | 0.74 |
| EDN1 endothelin.1 | EDN1 | <0.0001 | 0.53 |
| EBAG9.1 | EBAG9 | 0.0240 | 0.83 |
| DUSP1.1 | DUSP1 | 0.0130 | 0.82 |
| DPYS.1 | DPYS | 0.0355 | 0.85 |
| DPEP1.1 | DPEP1 | <0.0001 | 0.66 |
| DLL4.1 | DLL4 | <0.0001 | 0.66 |
| DLC1.1 | DLC1 | <0.0001 | 0.42 |
| DKFZP564O08 23.1 | DKFZP564O0823 | <0.0001 | 0.51 |
| DICER.2 | DICER1 | <0.0001 | 0.50 |
| DIAPH1.1 | DIAPH1 | 0.0219 | 0.83 |
| DIABLO.1 | DIABLO | 0.0022 | 0.78 |
| DHPS.3 | DHPS | <0.0001 | 0.55 |
| DET1.1 | DET1 | 0.0005 | 0.74 |
| DEFB1.1 | DEFB1 | 0.0002 | 0.73 |
| DDC.1 | DDC | <0.0001 | 0.72 |
| DAPK1.3 | DAPK1 | <0.0001 | 0.42 |
| CYR61.1 | CYR61 | <0.0001 | 0.59 |
| CXCL12.1 | CXCL12 | <0.0001 | 0.62 |
| CX3CR1.1 | CX3CR1 | <0.0001 | 0.46 |
| CX3CL1.1 | CX3CL1 | <0.0001 | 0.47 |
| CUL1.1 | CUL1 | <0.0001 | 0.64 |
| CUBN.1 | CUBN | <0.0001 | 0.55 |
| CTSS.1 | CTSS | 0.0007 | 0.76 |
| CTSH.2 | CTSH | <0.0001 | 0.64 |
| B-Catenin.3 | CTNNB1 | <0.0001 | 0.54 |
| A-Catenin.2 | CTNNA1 | <0.0001 | 0.65 |
| CTGF.1 | CTGF | <0.0001 | 0.71 |
| CSF2RA.2 | CSF2RA | 0.0037 | 0.78 |
| CSF1R.2 | CSF1R | <0.0001 | 0.67 |
| CSF1.1 | CSF1 | <0.0001 | 0.65 |
| CRADD.1 | CRADD | 0.0032 | 0.79 |
| COL4A2.1 | COL4A2 | <0.0001 | 0.65 |
| COL4A1.1 | COL4A1 | 0.0067 | 0.80 |
| COL18A1.1 | COL18A1 | 0.0001 | 0.72 |
| CLU.3 | CLU | 0.0004 | 0.75 |
| CLDN10.1 | CLDN10 | <0.0001 | 0.65 |
| CLCNKB.1 | CLCNKB | <0.0001 | 0.52 |
| CFLAR.1 | CFLAR | <0.0001 | 0.60 |
| CEACAM1.1 | CEACAM1 | <0.0001 | 0.55 |
| p21.3 | CDKN1A | 0.0002 | 0.73 |
| CDH6.1 | CDH6 | <0.0001 | 0.72 |
| CDH5.1 | CDH5 | <0.0001 | 0.44 |
| CDH2.1 | CDH2 | 0.0392 | 0.85 |
| CDH16.1 | CDH16 | <0.0001 | 0.70 |
| CDH13.1 | CDH13 | <0.0001 | 0.53 |
| CDC25B.1 | CDC25B | 0.0037 | 0.79 |
| CD4.1 | CD4 | <0.0001 | 0.72 |
| CD36.1 | CD36 | <0.0001 | 0.51 |
| CD34.1 | CD34 | <0.0001 | 0.48 |
| CD24.1 | CD24 | 0.0206 | 0.83 |
| CD14.1 | CD14 | 0.0152 | 0.82 |
| CCND1.3 | CCND1 | <0.0001 | 0.51 |
| CCL4.2 | CCL4 | 0.0017 | 0.77 |
| MCP1.1 | CCL2 | <0.0001 | 0.66 |
| CAT.1 | CAT | <0.0001 | 0.53 |
| CASP10.1 | CASP10 | 0.0001 | 0.72 |
| CALD1.2 | CALD1 | <0.0001 | 0.55 |
| CACNA2D1.1 | CACNA2D1 | 0.0352 | 0.84 |
| CA9.3 | CA9 | 0.0299 | 0.84 |
| CA2.1 | CA2 | <0.0001 | 0.58 |
| C3AR1.1 | C3AR1 | 0.0010 | 0.77 |
| ECRG4.1 | C2orf40 | <0.0001 | 0.47 |
| C1QA.1 | C1QA | 0.0119 | 0.82 |
| C13orf15.1 | C13orf15 | <0.0001 | 0.37 |
| BUB3.1 | BUB3 | <0.0001 | 0.67 |
| BTRC.1 | BTRC | <0.0001 | 0.65 |
| CIAP1.2 | BIRC2 | <0.0001 | 0.64 |
| BIN1.3 | BIN1 | 0.0001 | 0.73 |
| BGN.1 | BGN | <0.0001 | 0.63 |
| Bclx.1 | BCL2L1 | <0.0001 | 0.58 |
| Bcl2.2 | BCL2 | <0.0001 | 0.37 |
| Bax.1 | BAX | 0.0035 | 0.78 |
| Bak.2 | BAK1 | 0.0215 | 0.83 |
| BAG1.2 | BAG1 | <0.0001 | 0.40 |
| ATP6V1B1.1 | ATP6V1B1 | <0.0001 | 0.54 |
| ATP1A1.1 | ATP1A1 | 0.0037 | 0.78 |
| ASS1.1 | ASS1 | <0.0001 | 0.60 |
| ARRB1.1 | ARRB1 | <0.0001 | 0.45 |
| ARHGDIB.1 | ARHGDIB | <0.0001 | 0.50 |
| AQP1.1 | AQP1 | <0.0001 | 0.40 |
| APOLD1.1 | APOLD1 | <0.0001 | 0.54 |
| APC.4 | APC | <0.0001 | 0.57 |
| ANXA4.1 | ANXA4 | 0.0003 | 0.74 |

TABLE 4b-continued

Proxy genes for which increased expression is associated with lower tumor stage (p-value ≤ .05)

| Gene | Official Symbol | Stage 3 vs. 1 p-value | OR |
|---|---|---|---|
| ANXA1.2 | ANXA1 | 0.0001 | 0.73 |
| ANTXR1.1 | ANTXR1 | 0.0051 | 0.80 |
| ANGPTL4.1 | ANGPTL4 | 0.0041 | 0.80 |
| ANGPTL3.3 | ANGPTL3 | 0.0258 | 0.82 |
| ANGPTL2.1 | ANGPTL2 | 0.0015 | 0.77 |
| ANGPT2.1 | ANGPT2 | <0.0001 | 0.72 |
| ANGPT1.1 | ANGPT1 | <0.0001 | 0.45 |
| ALDOB.1 | ALDOB | <0.0001 | 0.60 |
| ALDH6A1.1 | ALDH6A1 | <0.0001 | 0.55 |
| ALDH4.2 | ALDH4A1 | 0.0124 | 0.82 |
| AKT3.2 | AKT3 | <0.0001 | 0.43 |
| AKT2.3 | AKT2 | <0.0001 | 0.64 |
| AKT1.3 | AKT1 | <0.0001 | 0.58 |
| AIF1.1 | AIF1 | 0.0002 | 0.74 |
| AHR.1 | AHR | <0.0001 | 0.59 |
| AGTR1.1 | AGTR1 | <0.0001 | 0.36 |
| ADH1B.1 | ADH1B | 0.0015 | 0.77 |
| ADD1.1 | ADD1 | <0.0001 | 0.40 |
| ADAMTS5.1 | ADAMTS5 | 0.0006 | 0.73 |
| ADAM17.1 | ADAM17 | <0.0001 | 0.72 |
| ACE2.1 | ACE2 | <0.0001 | 0.61 |
| ACADSB.1 | ACADSB | <0.0001 | 0.54 |
| BCRP.1 | ABCG2 | <0.0001 | 0.41 |
| MRP4.2 | ABCC4 | <0.0001 | 0.65 |
| MRP3.1 | ABCC3 | 0.0005 | 0.76 |
| MRP1.1 | ABCC1 | 0.0017 | 0.78 |
| ABCB1.5 | ABCB1 | 0.0003 | 0.75 |
| NPD009 (ABAT official).3 | ABAT | <0.0001 | 0.70 |
| AAMP.1 | AAMP | 0.0292 | 0.84 |
| A2M.1 | A2M | <0.0001 | 0.36 |

TABLE 5a

Proxy genes for which increased expression is associated with higher tumor grade (p-value ≤ .05)

| Gene | Official Symbol | CCF Grade p-value | OR |
|---|---|---|---|
| WT1.1 | WT1 | <0.0001 | 1.39 |
| VTN.1 | VTN | 0.0359 | 1.16 |
| VDR.2 | VDR | 0.0001 | 1.29 |
| UBE2T.1 | UBE2T | <0.0001 | 1.81 |
| TP.3 | TYMP | <0.0001 | 1.35 |
| C20orf1.1 | TPX2 | <0.0001 | 2.14 |
| TOP2A.4 | TOP2A | <0.0001 | 2.07 |
| TNFSF13B.1 | TNFSF13B | 0.0062 | 1.20 |
| TK1.2 | TK1 | <0.0001 | 1.66 |
| TGFBI.1 | TGFBI | 0.0452 | 1.14 |
| STAT1.3 | STAT1 | <0.0001 | 1.31 |
| SQSTM1.1 | SQSTM1 | 0.0003 | 1.27 |
| OPN, osteopontin.3 | SPP1 | 0.0002 | 1.29 |
| SLC7A5.2 | SLC7A5 | 0.0002 | 1.28 |
| SLC16A3.1 | SLC16A3 | 0.0052 | 1.21 |
| SLC13A3.1 | SLC13A3 | 0.0003 | 1.27 |
| SFN.1 | SFN | 0.0066 | 1.20 |
| SEMA3C.1 | SEMA3C | <0.0001 | 1.32 |
| SAA2.2 | SAA2 | <0.0001 | 2.13 |
| S100A1.1 | S100A1 | <0.0001 | 1.40 |
| RRM2.1 | RRM2 | <0.0001 | 1.71 |
| RPLP1.1 | RPLP1 | 0.0007 | 1.25 |
| RAD51.1 | RAD51 | <0.0001 | 1.53 |
| PTTG1.2 | PTTG1 | <0.0001 | 1.89 |
| PSMB9.1 | PSMB9 | 0.0010 | 1.25 |
| PSMB8.1 | PSMB8 | 0.0181 | 1.17 |
| PRKCB1.1 | PRKCB | 0.0218 | 1.16 |
| PDCD1.1 | PDCD1 | <0.0001 | 1.43 |
| PCSK6.1 | PCSK6 | 0.0009 | 1.25 |
| PCNA.2 | PCNA | 0.0041 | 1.21 |
| NME2.1 | NME2 | 0.0106 | 1.19 |
| MYBL2.1 | MYBL2 | <0.0001 | 1.70 |
| MMP9.1 | MMP9 | <0.0001 | 1.46 |
| MMP14.1 | MMP14 | 0.0003 | 1.28 |
| Ki-67.2 | MKI67 | <0.0001 | 1.70 |
| mGST1.2 | MGST1 | <0.0001 | 2.13 |
| cMet.2 | MET | <0.0001 | 1.57 |
| MDK.1 | MDK | <0.0001 | 1.55 |
| MDH2.1 | MDH2 | <0.0001 | 1.35 |
| MCM2.2 | MCM2 | <0.0001 | 1.33 |
| LOX.1 | LOX | <0.0001 | 1.35 |
| LMNB1.1 | LMNB1 | <0.0001 | 1.76 |
| LIMK1.1 | LIMK1 | <0.0001 | 1.43 |
| LAPTM5.1 | LAPTM5 | 0.0044 | 1.21 |
| LAMB3.1 | LAMB3 | <0.0001 | 1.49 |
| L1CAM.1 | L1CAM | 0.0338 | 1.15 |
| KLRK1.2 | KLRK1 | 0.0412 | 1.15 |
| CD18.2 | ITGB2 | 0.0069 | 1.21 |
| IL-8.1 | IL8 | 0.0088 | 1.19 |
| IL6.3 | IL6 | 0.0091 | 1.19 |
| ICAM1.1 | ICAM1 | 0.0014 | 1.24 |
| HSPA8.1 | HSPA8 | <0.0001 | 1.39 |
| HPD.1 | HPD | 0.0054 | 1.20 |
| HIST1H1D.1 | HIST1H1D | 0.0248 | 1.16 |
| HGD.1 | HGD | <0.0001 | 1.41 |
| GZMA.1 | GZMA | 0.0006 | 1.26 |
| GPX2.2 | GPX2 | 0.0182 | 1.18 |
| GPX1.2 | GPX1 | 0.0008 | 1.25 |
| FCGR3A.1 | FCGR3A | 0.0003 | 1.27 |
| fasl.2 | FASLG | 0.0045 | 1.21 |
| FABP1.1 | FABP1 | <0.0001 | 1.32 |
| F2.1 | F2 | <0.0001 | 1.77 |
| ESPL1.3 | ESPL1 | <0.0001 | 1.60 |
| E2F1.3 | E2F1 | <0.0001 | 1.36 |
| CXCR6.1 | CXCR6 | <0.0001 | 1.50 |
| BLR1.1 | CXCR5 | 0.0338 | 1.15 |
| CXCL9.1 | CXCL9 | 0.0001 | 1.29 |
| CXCL10.1 | CXCL10 | 0.0078 | 1.19 |
| GRO1.2 | CXCL1 | <0.0001 | 1.39 |
| CTSD.2 | CTSD | 0.0183 | 1.17 |
| CTSB.1 | CTSB | 0.0006 | 1.26 |
| CRP.1 | CRP | 0.0342 | 1.15 |
| CP.1 | CP | <0.0001 | 1.37 |
| Chk2.3 | CHEK2 | <0.0001 | 1.37 |
| Chk1.2 | CHEK1 | <0.0001 | 1.37 |
| CENPF.1 | CENPF | <0.0001 | 1.78 |
| CD8A.1 | CD8A | <0.0001 | 1.35 |
| CD82.3 | CD82 | <0.0001 | 1.50 |
| TNFSF7.1 | CD70 | <0.0001 | 1.43 |
| CCNE1.1 | CCNE1 | 0.0002 | 1.29 |
| CCNB1.2 | CCNB1 | <0.0001 | 1.75 |
| CCL5.2 | CCL5 | <0.0001 | 1.63 |
| CCL20.1 | CCL20 | 0.0082 | 1.19 |
| CAV2.1 | CAV2 | 0.0210 | 1.17 |
| CA12.1 | CA12 | <0.0001 | 1.41 |
| C3.1 | C3 | <0.0001 | 1.34 |
| C1QB.1 | C1QB | 0.0201 | 1.17 |
| BUB1.1 | BUB1 | <0.0001 | 2.16 |
| BRCA1.2 | BRCA1 | 0.0004 | 1.26 |
| SURV.2 | BIRC5 | <0.0001 | 1.93 |
| cIAP2.2 | BIRC3 | <0.0001 | 1.44 |
| STK15.2 | AURKA | <0.0001 | 1.38 |
| ATP5E.1 | ATP5E | <0.0001 | 1.45 |
| APOL1.1 | APOL1 | <0.0001 | 1.47 |
| APOE.1 | APOE | <0.0001 | 1.40 |
| APOC1.3 | APOC1 | <0.0001 | 1.42 |
| ANXA2.2 | ANXA2 | 0.0020 | 1.23 |
| ANGPTL3.3 | ANGPTL3 | <0.0001 | 1.32 |
| AMACR1.1 | AMACR | 0.0382 | 1.15 |
| ALOX5.1 | ALOX5 | 0.0001 | 1.29 |
| ALDH4.2 | ALDH4A1 | 0.0002 | 1.28 |

TABLE 5a-continued

Proxy genes for which increased expression is associated with higher tumor grade (p-value ≤ .05)

| Gene | Official Symbol | CCF Grade p-value | CCF Grade OR |
|---|---|---|---|
| ADAM8.1 | ADAM8 | 0.0006 | 1.26 |
| MRP2.3 | ABCC2 | <0.0001 | 1.97 |

TABLE 5b

Proxy genes for which increased expression is associated with lower tumor grade (p-value ≤ .05)

| Gene | Official Symbol | CCF Grade p-value | CCF Grade OR |
|---|---|---|---|
| ZHX2.1 | ZHX2 | 0.0061 | 0.83 |
| YB-1.2 | YBX1 | <0.0001 | 0.62 |
| XPNPEP2.2 | XPNPEP2 | 0.0040 | 0.82 |
| XIAP.1 | XIAP | <0.0001 | 0.64 |
| WISP1.1 | WISP1 | <0.0001 | 0.58 |
| VWF.1 | VWF | <0.0001 | 0.34 |
| VHL.1 | VHL | 0.0088 | 0.84 |
| VEGF.1 | VEGFA | <0.0001 | 0.48 |
| VCAN.1 | VCAN | 0.0023 | 0.82 |
| VCAM1.1 | VCAM1 | 0.0049 | 0.83 |
| USP34.1 | USP34 | <0.0001 | 0.62 |
| UMOD.1 | UMOD | <0.0001 | 0.69 |
| UGCG.1 | UGCG | <0.0001 | 0.58 |
| UBB.1 | UBB | <0.0001 | 0.62 |
| UBE1C.1 | UBA3 | <0.0001 | 0.67 |
| tusc4.2 | TUSC4 | <0.0001 | 0.61 |
| TUSC2.1 | TUSC2 | 0.0481 | 0.88 |
| TSPAN7.2 | TSPAN7 | <0.0001 | 0.29 |
| TSC2.1 | TSC2 | <0.0001 | 0.60 |
| TSC1.1 | TSC1 | <0.0001 | 0.52 |
| P53.2 | TP53 | <0.0001 | 0.66 |
| TOP2B.2 | TOP2B | <0.0001 | 0.68 |
| TNIP2.1 | TNIP2 | 0.0001 | 0.76 |
| TNFSF12.1 | TNFSF12 | <0.0001 | 0.54 |
| TNFRSF11B.1 | TNFRSF11B | <0.0001 | 0.73 |
| TNFRSF10D.1 | TNFRSF10D | <0.0001 | 0.51 |
| TNFRSF10C.3 | TNFRSF10C | 0.0003 | 0.78 |
| DR5.2 | TNFRSF10B | <0.0001 | 0.69 |
| TNFAIP6.1 | TNFAIP6 | 0.0338 | 0.87 |
| TNFAIP3.1 | TNFAIP3 | 0.0083 | 0.84 |
| TNF.1 | TNF | 0.0392 | 0.87 |
| TMEM47.1 | TMEM47 | <0.0001 | 0.33 |
| TMEM27.1 | TMEM27 | <0.0001 | 0.73 |
| TIMP3.3 | TIMP3 | <0.0001 | 0.29 |
| TIMP2.1 | TIMP2 | <0.0001 | 0.54 |
| THBS1.1 | THBS1 | <0.0001 | 0.58 |
| THBD.1 | THBD | <0.0001 | 0.66 |
| TGFBR2.3 | TGFBR2 | <0.0001 | 0.32 |
| TGFBR1.1 | TGFBR1 | <0.0001 | 0.59 |
| TGFB2.2 | TGFB2 | <0.0001 | 0.54 |
| TGFb1.1 | TGFB1 | <0.0001 | 0.66 |
| TGFA.2 | TGFA | <0.0001 | 0.68 |
| TEK.1 | TEK | <0.0001 | 0.34 |
| cripto (TDGF1 official).1 | TDGF1 | 0.0328 | 0.86 |
| TCF4.1 | TCF4 | <0.0001 | 0.33 |
| TAGLN.1 | TAGLN | <0.0001 | 0.58 |
| TACSTD2.1 | TACSTD2 | <0.0001 | 0.61 |
| SUCLG1.1 | SUCLG1 | <0.0001 | 0.76 |
| STK11.1 | STK11 | <0.0001 | 0.53 |
| STC2.1 | STC2 | 0.0085 | 0.84 |
| STAT5B.2 | STAT5B | <0.0001 | 0.40 |
| STAT5A.1 | STAT5A | <0.0001 | 0.60 |
| STAT3.1 | STAT3 | <0.0001 | 0.48 |
| SPRY1.1 | SPRY1 | <0.0001 | 0.40 |
| SPAST.1 | SPAST | 0.0002 | 0.78 |
| SPARCL1.1 | SPARCL1 | <0.0001 | 0.41 |
| SPARC.1 | SPARC | <0.0001 | 0.50 |
| SNRK.1 | SNRK | <0.0001 | 0.29 |
| SNAI1.1 | SNAI1 | <0.0001 | 0.54 |
| MADH4.1 | SMAD4 | <0.0001 | 0.39 |
| MADH2.1 | SMAD2 | <0.0001 | 0.40 |
| SLC9A1.1 | SLC9A1 | <0.0001 | 0.75 |
| SLC34A1.1 | SLC34A1 | 0.0001 | 0.76 |
| SKIL.1 | SKIL | <0.0001 | 0.52 |
| SHC1.1 | SHC1 | 0.0063 | 0.83 |
| SHANK3.1 | SHANK3 | <0.0001 | 0.27 |
| SGK.1 | SGK1 | <0.0001 | 0.60 |
| FRP1.3 | SFRP1 | 0.0003 | 0.78 |
| PAI1.3 | SERPINE1 | 0.0115 | 0.85 |
| SEMA3F.3 | SEMA3F | <0.0001 | 0.45 |
| SELENBP1.1 | SELENBP1 | <0.0001 | 0.63 |
| SELE.1 | SELE | <0.0001 | 0.74 |
| SDPR.1 | SDPR | <0.0001 | 0.35 |
| SDHA.1 | SDHA | <0.0001 | 0.69 |
| SCNN1A.2 | SCNN1A | 0.0011 | 0.80 |
| SCN4B.1 | SCN4B | <0.0001 | 0.47 |
| S100A2.1 | S100A2 | <0.0001 | 0.72 |
| RUNX1.1 | RUNX1 | 0.0001 | 0.77 |
| RRM1.2 | RRM1 | 0.0438 | 0.87 |
| KIAA1303 raptor.1 | RPTOR | <0.0001 | 0.53 |
| RPS6KB1.3 | RPS6KB1 | <0.0001 | 0.49 |
| RPS23.1 | RPS23 | <0.0001 | 0.59 |
| ROCK2.1 | ROCK2 | <0.0001 | 0.42 |
| ROCK1.1 | ROCK1 | <0.0001 | 0.31 |
| RIPK1.1 | RIPK1 | <0.0001 | 0.50 |
| rhoC.1 | RHOC | <0.0001 | 0.70 |
| RhoB.1 | RHOB | <0.0001 | 0.36 |
| ARHA.1 | RHOA | <0.0001 | 0.34 |
| RHEB.2 | RHEB | <0.0001 | 0.72 |
| RGS5.1 | RGS5 | <0.0001 | 0.30 |
| FLJ22655.1 | RERGL | <0.0001 | 0.42 |
| NFKBp65.3 | RELA | <0.0001 | 0.69 |
| RB1.1 | RB1 | <0.0001 | 0.74 |
| RASSF1.1 | RASSF1 | <0.0001 | 0.60 |
| RARB.2 | RARB | <0.0001 | 0.41 |
| RALBP1.1 | RALBP1 | <0.0001 | 0.47 |
| RAF1.3 | RAF1 | <0.0001 | 0.48 |
| RAC1.3 | RAC1 | <0.0001 | 0.75 |
| PXDN.1 | PXDN | <0.0001 | 0.74 |
| PTPRG.1 | PTPRG | <0.0001 | 0.29 |
| PTPRB.1 | PTPRB | <0.0001 | 0.27 |
| PTN.1 | PTN | <0.0001 | 0.58 |
| PTK2.1 | PTK2 | <0.0001 | 0.36 |
| PTHR1.1 | PTH1R | <0.0001 | 0.50 |
| PTEN.2 | PTEN | <0.0001 | 0.40 |
| PSMA7.1 | PSMA7 | 0.0002 | 0.78 |
| PRPS2.1 | PRPS2 | 0.0012 | 0.80 |
| PROM2.1 | PROM2 | 0.0326 | 0.87 |
| PRKCH.1 | PRKCH | <0.0001 | 0.45 |
| PRKCD.2 | PRKCD | <0.0001 | 0.76 |
| PPP2CA.1 | PPP2CA | <0.0001 | 0.68 |
| PPARG.3 | PPARG | <0.0001 | 0.42 |
| PPAP2B.1 | PPAP2B | <0.0001 | 0.32 |
| PMP22.1 | PMP22 | <0.0001 | 0.61 |
| PLG.1 | PLG | <0.0001 | 0.75 |
| PLAT.1 | PLAT | <0.0001 | 0.42 |
| PLA2G4C.1 | PLA2G4C | 0.0002 | 0.78 |
| PIK3CA.1 | PIK3CA | <0.0001 | 0.48 |
| PI3K.2 | PIK3C2B | <0.0001 | 0.53 |
| PGF.1 | PGF | <0.0001 | 0.74 |
| PFKP.1 | PFKP | 0.0008 | 0.80 |
| CD31.3 | PECAM1 | <0.0001 | 0.32 |
| PDZK3.1 | PDZK3 | <0.0001 | 0.72 |
| PDZK1.1 | PDZK1 | <0.0001 | 0.76 |
| PDGFRb.3 | PDGFRB | <0.0001 | 0.42 |
| PDGFRa.2 | PDGFRA | 0.0022 | 0.82 |
| PDGFD.2 | PDGFD | <0.0001 | 0.39 |
| PDGFC.3 | PDGFC | <0.0001 | 0.57 |
| PDGFB.3 | PDGFB | <0.0001 | 0.33 |

TABLE 5b-continued

Proxy genes for which increased expression is associated with lower tumor grade (p-value ≤ .05)

| Gene | Official Symbol | CCF Grade p-value | OR |
|---|---|---|---|
| PDGFA.3 | PDGFA | <0.0001 | 0.42 |
| PCK1.1 | PCK1 | <0.0001 | 0.71 |
| PCCA.1 | PCCA | <0.0001 | 0.75 |
| PARD6A.1 | PARD6A | 0.0088 | 0.84 |
| Pak1.2 | PAK1 | 0.0014 | 0.81 |
| PAH.1 | PAH | 0.0160 | 0.85 |
| OGG1.1 | OGG1 | 0.0139 | 0.85 |
| BFGF.3 | NUDT6 | <0.0001 | 0.63 |
| NPR1.1 | NPR1 | <0.0001 | 0.42 |
| NPM1.2 | NPM1 | <0.0001 | 0.61 |
| NOTCH3.1 | NOTCH3 | <0.0001 | 0.40 |
| NOTCH2.1 | NOTCH2 | <0.0001 | 0.58 |
| NOTCH1.1 | NOTCH1 | <0.0001 | 0.38 |
| NOS3.1 | NOS3 | <0.0001 | 0.42 |
| NOS2A.3 | NOS2 | <0.0001 | 0.56 |
| NOL3.1 | NOL3 | <0.0001 | 0.61 |
| NFX1.1 | NFX1 | <0.0001 | 0.53 |
| NFKBp50.3 | NFKB1 | <0.0001 | 0.59 |
| NFATC2.1 | NFATC2 | <0.0001 | 0.73 |
| NFAT5.1 | NFAT5 | <0.0001 | 0.58 |
| MYRIP.2 | MYRIP | <0.0001 | 0.63 |
| MYH11.1 | MYH11 | <0.0001 | 0.48 |
| cMYC.3 | MYC | <0.0001 | 0.68 |
| MX1.1 | MX1 | 0.0087 | 0.84 |
| MVP.1 | MVP | 0.0291 | 0.87 |
| MUC1.2 | MUC1 | 0.0043 | 0.83 |
| FRAP1.1 | MTOR | <0.0001 | 0.61 |
| MT1X.1 | MT1X | 0.0276 | 0.86 |
| MSH3.2 | MSH3 | 0.0001 | 0.76 |
| MSH2.3 | MSH2 | <0.0001 | 0.60 |
| MMP2.2 | MMP2 | <0.0001 | 0.74 |
| STMY3.3 | MMP11 | <0.0001 | 0.70 |
| MIF.2 | MIF | 0.0004 | 0.79 |
| MICA.1 | MICA | <0.0001 | 0.60 |
| MGMT.1 | MGMT | <0.0001 | 0.57 |
| MCM3.3 | MCM3 | <0.0001 | 0.73 |
| MCAM.1 | MCAM | <0.0001 | 0.42 |
| MARCKS.1 | MARCKS | <0.0001 | 0.63 |
| ERK1.3 | MAPK3 | <0.0001 | 0.35 |
| ERK2.3 | MAPK1 | <0.0001 | 0.71 |
| MAP4.1 | MAP4 | <0.0001 | 0.58 |
| MAP2K3.1 | MAP2K3 | <0.0001 | 0.60 |
| MAP2K1.1 | MAP2K1 | <0.0001 | 0.62 |
| MAL.1 | MAL | <0.0001 | 0.63 |
| LRP2.1 | LRP2 | 0.0275 | 0.86 |
| LMO2.1 | LMO2 | <0.0001 | 0.68 |
| LDB2.1 | LDB2 | <0.0001 | 0.28 |
| LDB1.2 | LDB1 | <0.0001 | 0.52 |
| LAMB1.1 | LAMB1 | <0.0001 | 0.73 |
| LAMA4.1 | LAMA4 | <0.0001 | 0.55 |
| KRT7.1 | KRT7 | <0.0001 | 0.61 |
| K-ras.10 | KRAS | <0.0001 | 0.54 |
| KL.1 | KL | <0.0001 | 0.62 |
| Kitlng.4 | KITLG | <0.0001 | 0.46 |
| c-kit.2 | KIT | <0.0001 | 0.48 |
| KDR.6 | KDR | <0.0001 | 0.33 |
| KCNJ15.1 | KCNJ15 | <0.0001 | 0.67 |
| HTATIP.1 | KAT5 | <0.0001 | 0.33 |
| G-Catenin.1 | JUP | <0.0001 | 0.39 |
| AP-1 (JUN official).2 | JUN | <0.0001 | 0.54 |
| JAG1.1 | JAG1 | <0.0001 | 0.28 |
| ITGB5.1 | ITGB5 | <0.0001 | 0.60 |
| ITGB3.1 | ITGB3 | <0.0001 | 0.68 |
| ITGB1.1 | ITGB1 | <0.0001 | 0.46 |
| ITGA7.1 | ITGA7 | <0.0001 | 0.40 |
| ITGA6.2 | ITGA6 | <0.0001 | 0.51 |
| ITGA5.1 | ITGA5 | <0.0001 | 0.62 |
| ITGA4.2 | ITGA4 | <0.0001 | 0.75 |
| ITGA3.2 | ITGA3 | 0.0128 | 0.85 |
| IQGAP2.1 | IQGAP2 | <0.0001 | 0.68 |
| INSR.1 | INSR | <0.0001 | 0.46 |
| INHBA.1 | INHBA | 0.0049 | 0.83 |
| IMP3.1 | IMP3 | <0.0001 | 0.67 |
| IL6ST.3 | IL6ST | <0.0001 | 0.43 |
| IL1B.1 | IL1B | 0.0102 | 0.84 |
| IL15.1 | IL15 | 0.0001 | 0.76 |
| IL10.3 | IL10 | 0.0239 | 0.86 |
| IGFBP6.1 | IGFBP6 | <0.0001 | 0.75 |
| IGFBP5.1 | IGFBP5 | <0.0001 | 0.74 |
| IGFBP2.1 | IGFBP2 | <0.0001 | 0.76 |
| IGF2.2 | IGF2 | <0.0001 | 0.69 |
| IGF1R.3 | IGF1R | <0.0001 | 0.43 |
| ID3.1 | ID3 | <0.0001 | 0.48 |
| ID2.4 | ID2 | <0.0001 | 0.64 |
| ID1.1 | ID1 | <0.0001 | 0.37 |
| ICAM2.1 | ICAM2 | <0.0001 | 0.42 |
| HYAL2.1 | HYAL2 | <0.0001 | 0.32 |
| HYAL1.1 | HYAL1 | <0.0001 | 0.52 |
| HSPG2.1 | HSPG2 | <0.0001 | 0.33 |
| HSPA1A.1 | HSPA1A | 0.0022 | 0.81 |
| HSP90AB1.1 | HSP90AB1 | <0.0001 | 0.68 |
| HSD11B2.1 | HSD11B2 | <0.0001 | 0.43 |
| HPCAL1.1 | HPCAL1 | <0.0001 | 0.69 |
| HNRPAB.3 | HNRNPAB | 0.0432 | 0.87 |
| HMGB1.1 | HMGB1 | <0.0001 | 0.47 |
| HIF1AN.1 | HIF1AN | <0.0001 | 0.64 |
| HIF1A.3 | HIF1A | <0.0001 | 0.55 |
| HGF.4 | HGF | 0.0022 | 0.81 |
| HDAC1.1 | HDAC1 | <0.0001 | 0.48 |
| HADH.1 | HADH | <0.0001 | 0.63 |
| GSTp.3 | GSTP1 | <0.0001 | 0.66 |
| GSTM3.2 | GSTM3 | <0.0001 | 0.53 |
| GSTM1.1 | GSTM1 | <0.0001 | 0.61 |
| GRB7.2 | GRB7 | <0.0001 | 0.73 |
| GRB14.1 | GRB14 | 0.0001 | 0.76 |
| GPC3.1 | GPC3 | 0.0012 | 0.80 |
| GNAS.1 | GNAS | <0.0001 | 0.70 |
| GMNN.1 | GMNN | 0.0006 | 0.80 |
| GJA1.1 | GJA1 | <0.0001 | 0.66 |
| GCLM.2 | GCLM | 0.0319 | 0.87 |
| GCLC.3 | GCLC | <0.0001 | 0.57 |
| GATM.1 | GATM | 0.0006 | 0.79 |
| GATA3.3 | GATA3 | 0.0029 | 0.82 |
| GAS2.1 | GAS2 | 0.0136 | 0.84 |
| GADD45B.1 | GADD45B | <0.0001 | 0.54 |
| FST.1 | FST | 0.0197 | 0.85 |
| FOS.1 | FOS | <0.0001 | 0.44 |
| FOLR1.1 | FOLR1 | <0.0001 | 0.75 |
| FLT4.1 | FLT4 | <0.0001 | 0.34 |
| FLT3LG.1 | FLT3LG | <0.0001 | 0.73 |
| FLT1.1 | FLT1 | <0.0001 | 0.29 |
| FILIP1.1 | FILIP1 | <0.0001 | 0.47 |
| FIGF.1 | FIGF | <0.0001 | 0.70 |
| FHL1.1 | FHL1 | <0.0001 | 0.54 |
| FHIT.1 | FHIT | <0.0001 | 0.72 |
| FH.1 | FH | 0.0203 | 0.86 |
| FGFR2 isoform 1.1 | FGFR2 | <0.0001 | 0.62 |
| FGFR1.3 | FGFR1 | <0.0001 | 0.48 |
| FGF2.2 | FGF2 | <0.0001 | 0.62 |
| FGF1.1 | FGF1 | <0.0001 | 0.61 |
| FDPS.1 | FDPS | <0.0001 | 0.52 |
| FBXW7.1 | FBXW7 | <0.0001 | 0.57 |
| FAP.1 | FAP | 0.0440 | 0.87 |
| ESRRG.3 | ESRRG | 0.0340 | 0.87 |
| ERG.1 | ERG | <0.0001 | 0.36 |
| ERCC4.1 | ERCC4 | 0.0337 | 0.87 |
| ERCC1.2 | ERCC1 | <0.0001 | 0.59 |
| ERBB4.3 | ERBB4 | <0.0001 | 0.66 |
| HER2.5 | ERBB2 | <0.0001 | 0.57 |
| EPHB4.1 | EPHB4 | <0.0001 | 0.43 |
| EPHA2.1 | EPHA2 | <0.0001 | 0.44 |
| EPAS1.1 | EPAS1 | <0.0001 | 0.26 |
| ENPP2.1 | ENPP2 | <0.0001 | 0.62 |
| ENPEP.1 | ENPEP | <0.0001 | 0.75 |

TABLE 5b-continued

Proxy genes for which increased expression is associated with lower tumor grade (p-value ≤ .05)

| Gene | Official Symbol | CCF Grade p-value | OR |
|---|---|---|---|
| ENO2.1 | ENO2 | 0.0449 | 0.88 |
| CD105.1 | ENG | <0.0001 | 0.30 |
| EMP1.1 | EMP1 | <0.0001 | 0.42 |
| EMCN.1 | EMCN | <0.0001 | 0.31 |
| ELTD1.1 | ELTD1 | <0.0001 | 0.59 |
| EIF2C1.1 | EIF2C1 | <0.0001 | 0.63 |
| EGR1.1 | EGR1 | <0.0001 | 0.50 |
| EGLN3.1 | EGLN3 | <0.0001 | 0.69 |
| EGF.3 | EGF | 0.0200 | 0.85 |
| EFNB2.1 | EFNB2 | <0.0001 | 0.36 |
| EFNB1.2 | EFNB1 | <0.0001 | 0.46 |
| EEF1A1.1 | EEF1A1 | <0.0001 | 0.39 |
| EDNRB.1 | EDNRB | <0.0001 | 0.33 |
| EDN2.1 | EDN2 | <0.0001 | 0.67 |
| EDN1 endothelin.1 | EDN1 | <0.0001 | 0.41 |
| EBAG9.1 | EBAG9 | 0.0057 | 0.83 |
| DUSP1.1 | DUSP1 | <0.0001 | 0.54 |
| DPEP1.1 | DPEP1 | 0.0001 | 0.76 |
| DLL4.1 | DLL4 | <0.0001 | 0.49 |
| DLC1.1 | DLC1 | <0.0001 | 0.33 |
| DKFZP564O0823.1 | DKFZP564O0823 | <0.0001 | 0.46 |
| DICER1.2 | DICER1 | <0.0001 | 0.41 |
| DIAPH1.1 | DIAPH1 | 0.0022 | 0.81 |
| DIABLO.1 | DIABLO | <0.0001 | 0.73 |
| DHPS.3 | DHPS | <0.0001 | 0.41 |
| DET1.1 | DET1 | <0.0001 | 0.63 |
| DEFB1.1 | DEFB1 | 0.0001 | 0.77 |
| DAPK1.3 | DAPK1 | <0.0001 | 0.48 |
| DAG1.1 | DAG1 | 0.0150 | 0.85 |
| CYR61.1 | CYR61 | <0.0001 | 0.49 |
| CXCL12.1 | CXCL12 | <0.0001 | 0.64 |
| CX3CR1.1 | CX3CR1 | 0.0008 | 0.80 |
| CX3CL1.1 | CX3CL1 | <0.0001 | 0.55 |
| CUL1.1 | CUL1 | <0.0001 | 0.62 |
| CUBN.1 | CUBN | 0.0081 | 0.84 |
| CTSL.2 | CTSL1 | 0.0328 | 0.87 |
| B-Catenin.3 | CTNNB1 | <0.0001 | 0.36 |
| A-Catenin.2 | CTNNA1 | <0.0001 | 0.73 |
| CTGF.1 | CTGF | <0.0001 | 0.61 |
| CSF1.1 | CSF1 | <0.0001 | 0.66 |
| CRADD.1 | CRADD | 0.0151 | 0.85 |
| COL5A2.2 | COL5A2 | 0.0155 | 0.85 |
| COL4A2.1 | COL4A2 | <0.0001 | 0.51 |
| COL4A1.1 | COL4A1 | <0.0001 | 0.59 |
| COL1A2.1 | COL1A2 | 0.0005 | 0.79 |
| COL18A1.1 | COL18A1 | <0.0001 | 0.53 |
| CLDN10.1 | CLDN10 | 0.0351 | 0.87 |
| CLCNKB.1 | CLCNKB | <0.0001 | 0.73 |
| CFLAR.1 | CFLAR | <0.0001 | 0.45 |
| CEACAM1.1 | CEACAM1 | <0.0001 | 0.64 |
| p27.3 | CDKN1B | <0.0001 | 0.65 |
| p21.3 | CDKN1A | <0.0001 | 0.52 |
| CDK4.1 | CDK4 | 0.0200 | 0.86 |
| CDH5.1 | CDH5 | <0.0001 | 0.31 |
| CDH16.1 | CDH16 | 0.0005 | 0.79 |
| CDH13.1 | CDH13 | <0.0001 | 0.40 |
| CD99.1 | CD99 | 0.0001 | 0.77 |
| CD44.1 | CD44_1 | 0.0216 | 0.86 |
| CD36.1 | CD36 | <0.0001 | 0.42 |
| CD34.1 | CD34 | <0.0001 | 0.39 |
| CD14.1 | CD14 | 0.0021 | 0.81 |
| CCND1.3 | CCND1 | <0.0001 | 0.63 |
| MCP1.1 | CCL2 | <0.0001 | 0.69 |
| CAT.1 | CAT | 0.0014 | 0.81 |
| CASP10.1 | CASP10 | <0.0001 | 0.65 |
| CALD1.2 | CALD1 | <0.0001 | 0.44 |
| CACNA2D1.1 | CACNA2D1 | 0.0003 | 0.78 |
| CA9.3 | CA9 | 0.0269 | 0.86 |
| CA2.1 | CA2 | 0.0001 | 0.77 |
| C7.1 | C7 | <0.0001 | 0.71 |
| C3AR1.1 | C3AR1 | 0.0032 | 0.82 |
| ECRG4.1 | C2orf40 | <0.0001 | 0.50 |
| C13orf15.1 | C13orf15 | <0.0001 | 0.37 |
| BUB3.1 | BUB3 | <0.0001 | 0.65 |
| BTRC.1 | BTRC | <0.0001 | 0.61 |
| BNIP3.1 | BNIP3 | 0.0018 | 0.81 |
| CIAP1.2 | BIRC2 | <0.0001 | 0.61 |
| BGN.1 | BGN | <0.0001 | 0.43 |
| Bclx.2 | BCL2L1 | <0.0001 | 0.76 |
| Bcl2.2 | BCL2 | <0.0001 | 0.45 |
| BAG1.2 | BAG1 | <0.0001 | 0.47 |
| AXL.1 | AXL | <0.0001 | 0.74 |
| ATP6V1B1.1 | ATP6V1B1 | <0.0001 | 0.65 |
| ASS1.1 | ASS1 | <0.0001 | 0.67 |
| ARRB1.1 | ARRB1 | <0.0001 | 0.49 |
| ARHGDIB.1 | ARHGDIB | <0.0001 | 0.50 |
| ARF1.1 | ARF1 | <0.0001 | 0.69 |
| AREG.2 | AREG | 0.0007 | 0.80 |
| AQP1.1 | AQP1 | <0.0001 | 0.49 |
| APOLD1.1 | APOLD1 | <0.0001 | 0.40 |
| APC.4 | APC | <0.0001 | 0.62 |
| APAF.2 | APAF1 | <0.0001 | 0.76 |
| ANXA1.2 | ANXA1 | <0.0001 | 0.65 |
| ANTXR1.1 | ANTXR1 | <0.0001 | 0.61 |
| ANGPTL4.1 | ANGPTL4 | <0.0001 | 0.75 |
| ANGPTL2.1 | ANGPTL2 | <0.0001 | 0.60 |
| ANGPT2.1 | ANGPT2 | <0.0001 | 0.61 |
| ANGPT1.1 | ANGPT1 | <0.0001 | 0.33 |
| ALDOB.1 | ALDOB | 0.0348 | 0.87 |
| ALDH6A1.1 | ALDH6A1 | <0.0001 | 0.61 |
| AKT3.2 | AKT3 | <0.0001 | 0.30 |
| AKT2.3 | AKT2 | <0.0001 | 0.65 |
| AKT1.3 | AKT1 | <0.0001 | 0.50 |
| AHR.1 | AHR | <0.0001 | 0.55 |
| AGTR1.1 | AGTR1 | <0.0001 | 0.44 |
| ADH1B.1 | ADH1B | <0.0001 | 0.70 |
| ADD1.1 | ADD1 | <0.0001 | 0.40 |
| ADAMTS9.1 | ADAMTS9 | <0.0001 | 0.64 |
| ADAMTS5.1 | ADAMTS5 | <0.0001 | 0.56 |
| ADAMTS4.1 | ADAMTS4 | <0.0001 | 0.66 |
| ADAMTS2.1 | ADAMTS2 | <0.0001 | 0.69 |
| ADAMTS1.1 | ADAMTS1 | <0.0001 | 0.51 |
| ADAM17.1 | ADAM17 | <0.0001 | 0.67 |
| ACADSB.1 | ACADSB | <0.0001 | 0.63 |
| BCRP.1 | ABCG2 | <0.0001 | 0.43 |
| MRP4.2 | ABCC4 | 0.0337 | 0.87 |
| AAMP.1 | AAMP | <0.0001 | 0.71 |
| A2M.1 | A2M | <0.0001 | 0.29 |

TABLE 6a

Proxy genes for which increased expression is associated with the presence of necrosis (p-value ≤ .05)

| Gene | Official Symbol | CCF Necrosis p-value | OR |
|---|---|---|---|
| WT1.1 | WT1 | <0.0001 | 1.57 |
| VTN.1 | VTN | <0.0001 | 1.38 |
| VDR.2 | VDR | 0.0013 | 1.34 |
| UBE2T.1 | UBE2T | <0.0001 | 2.08 |
| TP.3 | TYMP | 0.0008 | 1.37 |
| TSPAN8.1 | TSPAN8 | 0.0016 | 1.29 |
| C20orf1.1 | TPX2 | <0.0001 | 2.64 |
| TOP2A.4 | TOP2A | <0.0001 | 2.02 |
| TNFSF13B.1 | TNFSF13B | 0.0002 | 1.38 |
| TK1.2 | TK1 | <0.0001 | 1.71 |
| TIMP1.1 | TIMP1 | 0.0076 | 1.27 |
| TGFBI.1 | TGFBI | <0.0001 | 1.69 |
| OPN, osteopontin.3 | SPP1 | <0.0001 | 1.81 |

TABLE 6a-continued

Proxy genes for which increased expression is associated with the presence of necrosis (p-value ≤ .05)

| Gene | Official Symbol | CCF Necrosis p-value | OR |
|---|---|---|---|
| SPHK1.1 | SPHK1 | <0.0001 | 1.44 |
| SLC7A5.2 | SLC7A5 | <0.0001 | 2.12 |
| SLC2A1.1 | SLC2A1 | <0.0001 | 1.46 |
| SLC16A3.1 | SLC16A3 | 0.0001 | 1.48 |
| SLC13A3.1 | SLC13A3 | 0.0019 | 1.29 |
| SHC1.1 | SHC1 | 0.0156 | 1.24 |
| SFN.1 | SFN | <0.0001 | 1.57 |
| PAI.3 | SERPINE1 | 0.0164 | 1.25 |
| SERPINA5.1 | SERPINA5 | 0.0016 | 1.27 |
| SEMA3C.1 | SEMA3C | <0.0001 | 2.14 |
| SELL.1 | SELL | 0.0096 | 1.26 |
| SAA2.2 | SAA2 | <0.0001 | 2.50 |
| RRM2.1 | RRM2 | <0.0001 | 1.86 |
| RPLP1.1 | RPLP1 | 0.0025 | 1.32 |
| RND3.1 | RND3 | 0.0002 | 1.41 |
| RAD51.1 | RAD51 | <0.0001 | 1.51 |
| PTTG1.2 | PTTG1 | <0.0001 | 2.52 |
| COX2.1 | PTGS2 | 0.0002 | 1.36 |
| PRKCB1.1 | PRKCB | 0.0188 | 1.23 |
| PRKCA.1 | PRKCA | 0.0339 | 1.21 |
| PLAUR.3 | PLAUR | <0.0001 | 1.60 |
| upa.3 | PLAU | 0.0002 | 1.41 |
| PF4.1 | PF4 | 0.0003 | 1.34 |
| PDCD1.1 | PDCD1 | <0.0001 | 1.40 |
| PCSK6.1 | PCSK6 | 0.0297 | 1.22 |
| PCNA.2 | PCNA | 0.0025 | 1.33 |
| NNMT.1 | NNMT | 0.0206 | 1.22 |
| NME2.1 | NME2 | 0.0124 | 1.25 |
| MYBL2.1 | MYBL2 | <0.0001 | 1.90 |
| MT1X.1 | MT1X | 0.0003 | 1.39 |
| MMP9.1 | MMP9 | <0.0001 | 1.96 |
| MMP7.1 | MMP7 | <0.0001 | 1.50 |
| MMP14.1 | MMP14 | <0.0001 | 1.50 |
| Ki-67.2 | MKI67 | <0.0001 | 1.96 |
| mGST1.2 | MGST1 | <0.0001 | 1.63 |
| cMet.2 | MET | 0.0357 | 1.22 |
| MDK.1 | MDK | <0.0001 | 1.78 |
| MCM2.2 | MCM2 | 0.0003 | 1.40 |
| LRRC2.1 | LRRC2 | 0.0114 | 1.22 |
| LOX.1 | LOX | <0.0001 | 1.99 |
| LMNB1.1 | LMNB1 | <0.0001 | 2.04 |
| LIMK1.1 | LIMK1 | <0.0001 | 2.51 |
| LGALS9.1 | LGALS9 | 0.0136 | 1.25 |
| LGALS1.1 | LGALS1 | <0.0001 | 1.46 |
| LAPTM5.1 | LAPTM5 | <0.0001 | 1.47 |
| LAMB3.1 | LAMB5 | <0.0001 | 1.96 |
| L1CAM.1 | L1CAM | <0.0001 | 1.43 |
| KRT19.3 | KRT19 | 0.0001 | 1.43 |
| ITGB4.2 | ITGB4 | 0.0492 | 1.19 |
| ISG20.1 | ISG20 | 0.0006 | 1.38 |
| IL-8.1 | IL8 | <0.0001 | 2.40 |
| IL6.3 | IL6 | <0.0001 | 2.02 |
| ICAM1.1 | ICAM1 | <0.0001 | 1.75 |
| HSPA8.1 | HSPA8 | 0.0004 | 1.38 |
| HIST1H1D.1 | HIST1H1D | 0.0017 | 1.33 |
| GPX1.2 | GPX1 | <0.0001 | 1.46 |
| FZD2.2 | FZD2 | 0.0031 | 1.27 |
| FN1.1 | FN1 | <0.0001 | 1.45 |
| FCGR3A.1 | FCGR3A | 0.0001 | 1.43 |
| FCER1G.2 | FCER1G | <0.0001 | 1.50 |
| FAP.1 | FAP | 0.0395 | 1.20 |
| F3.1 | F3 | <0.0001 | 1.62 |
| F2.1 | F2 | <0.0001 | 1.76 |
| ESPL1.3 | ESPL1 | 0.0008 | 1.33 |
| EPHB2.1 | EPHB2 | 0.0037 | 1.28 |
| EPHB1.3 | EPHB1 | 0.0041 | 1.25 |
| EPB41L3.1 | EPB41L3 | 0.0410 | 1.19 |
| ENO2.1 | ENO2 | 0.0001 | 1.46 |
| EIF4EBP1.1 | EIF4EBP1 | <0.0001 | 1.60 |
| E2F1.3 | E2F1 | <0.0001 | 1.65 |
| CXCR6.1 | CXCR6 | <0.0001 | 1.48 |
| CXCR4.3 | CXCR4 | 0.0118 | 1.26 |
| GRO1.2 | CXCL1 | <0.0001 | 1.83 |
| CTSB.1 | CTSB | <0.0001 | 1.70 |
| CRP.1 | CRP | 0.0494 | 1.16 |
| CP.1 | CP | <0.0001 | 1.98 |
| COL7A1.1 | COL7A1 | <0.0001 | 1.47 |
| COL1A1.1 | COL1A1 | 0.0059 | 1.28 |
| Chk2.3 | CHEK2 | 0.0010 | 1.33 |
| Chk1.2 | CHEK1 | <0.0001 | 1.49 |
| CENPF.1 | CENPF | <0.0001 | 2.08 |
| CD82.3 | CD82 | <0.0001 | 2.09 |
| CD68.2 | CD68 | 0.0163 | 1.24 |
| CD44s.1 | CD44_s | <0.0001 | 1.66 |
| CCNE2.2 | CCNE2_2 | <0.0001 | 1.50 |
| CCNE1.1 | CCNE1 | <0.0001 | 1.44 |
| CCNB1.2 | CCNB1 | <0.0001 | 2.28 |
| CCL5.2 | CCL5 | <0.0001 | 1.45 |
| CCL20.1 | CCL20 | 0.0121 | 1.24 |
| CAV2.1 | CAV2 | 0.0003 | 1.35 |
| CA12.1 | CA12 | <0.0001 | 2.11 |
| C3.1 | C3 | <0.0001 | 1.58 |
| C1QB.1 | C1QB | 0.0032 | 1.31 |
| BUB1.1 | BUB1 | <0.0001 | 2.25 |
| BRCA1.2 | BRCA1 | 0.0006 | 1.35 |
| SURV.2 | BIRC5 | <0.0001 | 2.11 |
| cIAP2.2 | BIRC3 | <0.0001 | 1.47 |
| BCL2A1.1 | BCL2A1 | 0.0004 | 1.34 |
| STK15.2 | AURKA | <0.0001 | 1.61 |
| PRO2000.3 | ATAD2 | 0.0166 | 1.24 |
| APOL1.1 | APOL1 | <0.0001 | 1.54 |
| APOC1.3 | APOC1 | 0.0026 | 1.30 |
| ANXA2.2 | ANXA2 | <0.0001 | 1.71 |
| ALOX5.1 | ALOX5 | 0.0004 | 1.38 |
| ADAM8.1 | ADAM8 | <0.0001 | 1.89 |
| MRP2.3 | ABCC2 | 0.0002 | 1.39 |

TABLE 6b

Proxy genes for which increased expression is associated with the absence of necrosis (p-value ≤ .05)

| Gene | Official Symbol | CCF Necrosis p-value | OR |
|---|---|---|---|
| YB-1.2 | YBX1 | 0.0010 | 0.74 |
| XIAP.1 | XIAP | <0.0001 | 0.68 |
| WWOX.5 | WWOX | <0.0001 | 0.63 |
| WISP1.1 | WISP1 | 0.0002 | 0.71 |
| VWF.1 | VWF | <0.0001 | 0.35 |
| VHL.1 | VHL | 0.0086 | 0.78 |
| VEGF.1 | VEGFA | <0.0001 | 0.50 |
| VCAM1.1 | VCAM1 | <0.0001 | 0.55 |
| USP34.1 | USP34 | <0.0001 | 0.64 |
| UMOD.1 | UMOD | <0.0001 | 0.36 |
| UGCG.1 | UGCG | <0.0001 | 0.54 |
| UBB.1 | UBB | <0.0001 | 0.48 |
| UBE1C.1 | UBA3 | <0.0001 | 0.59 |
| TS.1 | TYMS | <0.0001 | 0.70 |
| tusc4.2 | TUSC4 | <0.0001 | 0.68 |
| TUSC2.1 | TUSC2 | 0.0462 | 0.83 |
| TSPAN7.2 | TSPAN7 | <0.0001 | 0.25 |
| TSC2.1 | TSC2 | <0.0001 | 0.45 |
| TSC1.1 | TSC1 | <0.0001 | 0.45 |
| P53.2 | TP53 | <0.0001 | 0.61 |
| TOP2B.2 | TOP2B | <0.0001 | 0.69 |
| TNFSF12.1 | TNFSF12 | <0.0001 | 0.51 |
| TRAIL.1 | TNFSF10 | <0.0001 | 0.68 |
| TNFRSF11B.1 | TNFRSF11B | <0.0001 | 0.59 |
| TNFRSF10D.1 | TNFRSF10D | <0.0001 | 0.58 |
| DR5.2 | TNFRSF10B | 0.0001 | 0.71 |
| TNFAIP6.1 | TNFAIP6 | <0.0001 | 0.67 |

TABLE 6b-continued

Proxy genes for which increased expression is associated with the absence of necrosis (p-value ≤ .05)

| Gene | Official Symbol | CCF Necrosis p-value | OR |
|---|---|---|---|
| TMEM47.1 | TMEM47 | <0.0001 | 0.29 |
| TMEM27.1 | TMEM27 | <0.0001 | 0.40 |
| TLR3.1 | TLR3 | <0.0001 | 0.64 |
| TIMP3.3 | TIMP3 | <0.0001 | 0.23 |
| TIMP2.1 | TIMP2 | <0.0001 | 0.52 |
| THBS1.1 | THBS1 | <0.0001 | 0.62 |
| TGFBR2.3 | TGFBR2 | <0.0001 | 0.34 |
| TGFBR1.1 | TGFBR1 | <0.0001 | 0.63 |
| TGFB2.2 | TGFB2 | <0.0001 | 0.55 |
| TGFb1.1 | TGFB1 | 0.0036 | 0.76 |
| TGFA.2 | TGFA | <0.0001 | 0.56 |
| TEK.1 | TEK | <0.0001 | 0.23 |
| TCF4.1 | TCF4 | <0.0001 | 0.36 |
| TAGLN.1 | TAGLN | <0.0001 | 0.50 |
| TACSTD2.1 | TACSTD2 | <0.0001 | 0.64 |
| SUCLG1.1 | SUCLG1 | <0.0001 | 0.50 |
| STK11.1 | STK11 | <0.0001 | 0.48 |
| STAT5B.2 | STAT5B | <0.0001 | 0.36 |
| STAT5A.1 | STAT5A | <0.0001 | 0.56 |
| STAT3.1 | STAT3 | <0.0001 | 0.63 |
| SPRY1.1 | SPRY1 | <0.0001 | 0.42 |
| SPAST.1 | SPAST | 0.0004 | 0.74 |
| SPARCL1.1 | SPARCL1 | <0.0001 | 0.48 |
| SPARC.1 | SPARC | <0.0001 | 0.54 |
| SOD1.1 | SOD1 | <0.0001 | 0.67 |
| SNRK.1 | SNRK | <0.0001 | 0.25 |
| SNAI1.1 | SNAI1 | 0.0004 | 0.71 |
| MADH4.1 | SMAD4 | <0.0001 | 0.33 |
| MADH2.1 | SMAD2 | <0.0001 | 0.40 |
| SLC34A1.1 | SLC34A1 | <0.0001 | 0.47 |
| SLC22A6.1 | SLC22A6 | <0.0001 | 0.52 |
| SKIL.1 | SKIL | <0.0001 | 0.59 |
| SHANK3.1 | SHANK3 | <0.0001 | 0.25 |
| SGK.1 | SGK1 | <0.0001 | 0.54 |
| FRP1.3 | SFRP1 | 0.0053 | 0.77 |
| SEMA3F.3 | SEMA3F | <0.0001 | 0.43 |
| SELENBP1.1 | SELENBP1 | <0.0001 | 0.62 |
| SDPR.1 | SDPR | <0.0001 | 0.28 |
| SDHA.1 | SDHA | <0.0001 | 0.47 |
| SCNN1A.2 | SCNN1A | 0.0013 | 0.73 |
| SCN4B.1 | SCN4B | <0.0001 | 0.35 |
| S100A2.1 | S100A2 | 0.0355 | 0.82 |
| KIAA1303 raptor.1 | RPTOR | <0.0001 | 0.49 |
| RPS6KB1.3 | RPS6KB1 | <0.0001 | 0.55 |
| RPS6KA1.1 | RPS6KA1 | 0.0002 | 0.68 |
| RPS23.1 | RPS23 | <0.0001 | 0.47 |
| ROCK2.1 | ROCK2 | <0.0001 | 0.39 |
| ROCK1.1 | ROCK1 | <0.0001 | 0.35 |
| RIPK1.1 | RIPK1 | <0.0001 | 0.45 |
| rhoC.1 | RHOC | 0.0001 | 0.70 |
| RhoB.1 | RHOB | <0.0001 | 0.41 |
| ARHA.1 | RHOA | <0.0001 | 0.45 |
| RHEB.2 | RHEB | 0.0002 | 0.69 |
| RGS5.1 | RGS5 | <0.0001 | 0.26 |
| FLJ22655.1 | RERGL | <0.0001 | 0.26 |
| NFKBp65.3 | RELA | <0.0001 | 0.71 |
| RB1.1 | RB1 | <0.0001 | 0.54 |
| RASSF1.1 | RASSF1 | <0.0001 | 0.63 |
| RARB.2 | RARB | <0.0001 | 0.28 |
| RALBP1.1 | RALBP1 | <0.0001 | 0.52 |
| RAF1.3 | RAF1 | <0.0001 | 0.58 |
| RAC1.3 | RAC1 | 0.0118 | 0.80 |
| PTPRG.1 | PTPRG | <0.0001 | 0.27 |
| PTPRB.1 | PTPRB | <0.0001 | 0.22 |
| PTN.1 | PTN | <0.0001 | 0.41 |
| PTK2.1 | PTK2 | <0.0001 | 0.33 |
| PTHR1.1 | PTH1R | <0.0001 | 0.32 |
| PTEN.2 | PTEN | <0.0001 | 0.44 |
| PSMA7.1 | PSMA7 | 0.0173 | 0.81 |
| PRSS8.1 | PRSS8 | <0.0001 | 0.62 |
| PRKCH.1 | PRKCH | <0.0001 | 0.43 |
| PRKCD.2 | PRKCD | <0.0001 | 0.68 |
| PPP2CA.1 | PPP2CA | <0.0001 | 0.53 |
| PPARG.3 | PPARG | <0.0001 | 0.37 |
| PPAP2B.1 | PPAP2B | <0.0001 | 0.27 |
| PMP22.1 | PMP22 | 0.0155 | 0.81 |
| PLG.1 | PLG | <0.0001 | 0.38 |
| PLAT.1 | PLAT | <0.0001 | 0.42 |
| PLA2G4C.1 | PLA2G4C | <0.0001 | 0.48 |
| PIK3CA.1 | PIK3CA | <0.0001 | 0.47 |
| PI3K.2 | PIK3C2B | <0.0001 | 0.42 |
| PGF.1 | PGF | 0.0153 | 0.80 |
| PFKP.1 | PFKP | <0.0001 | 0.70 |
| CD31.3 | PECAM1 | <0.0001 | 0.34 |
| PDZK3.1 | PDZK3 | <0.0001 | 0.49 |
| PDZK1.1 | PDZK1 | <0.0001 | 0.45 |
| PDGFRb.3 | PDGFRB | <0.0001 | 0.45 |
| PDGFD.2 | PDGFD | <0.0001 | 0.33 |
| PDGFC.3 | PDGFC | <0.0001 | 0.53 |
| PDGFB.3 | PDGFB | <0.0001 | 0.33 |
| PDGFA.3 | PDGFA | <0.0001 | 0.43 |
| PCK1.1 | PCK1 | <0.0001 | 0.44 |
| PCCA.1 | PCCA | <0.0001 | 0.47 |
| PARD6A.1 | PARD6A | 0.0045 | 0.77 |
| Pak1.2 | PAK1 | 0.0003 | 0.74 |
| PAH.1 | PAH | <0.0001 | 0.62 |
| OGG1.1 | OGG1 | <0.0001 | 0.62 |
| BFGF.3 | NUDT6 | <0.0001 | 0.45 |
| NRG1.3 | NRG1 | 0.0004 | 0.69 |
| NPR1.1 | NPR1 | <0.0001 | 0.36 |
| NPM1.2 | NPM1 | <0.0001 | 0.55 |
| NOTCH3.1 | NOTCH3 | <0.0001 | 0.40 |
| NOTCH2.1 | NOTCH2 | <0.0001 | 0.68 |
| NOTCH1.1 | NOTCH1 | <0.0001 | 0.38 |
| NOS3.1 | NOS3 | <0.0001 | 0.37 |
| NOS2A.3 | NOS2 | <0.0001 | 0.42 |
| NOL3.1 | NOL3 | <0.0001 | 0.67 |
| NFX1.1 | NFX1 | <0.0001 | 0.43 |
| NFKBp50.3 | NFKB1 | <0.0001 | 0.56 |
| NFATC2.1 | NFATC2 | <0.0001 | 0.67 |
| NFAT5.1 | NFAT5 | <0.0001 | 0.55 |
| MYRIP.2 | MYRIP | <0.0001 | 0.36 |
| MYH11.1 | MYH11 | <0.0001 | 0.35 |
| cMYC.3 | MYC | <0.0001 | 0.68 |
| MVP.1 | MVP | <0.0001 | 0.66 |
| FRAP1.1 | MTOR | <0.0001 | 0.56 |
| MSH3.2 | MSH3 | <0.0001 | 0.47 |
| MSH2.3 | MSH2 | <0.0001 | 0.51 |
| MMP2.1 | MMP2 | 0.0229 | 0.82 |
| STMY3.3 | MMP11 | <0.0001 | 0.66 |
| GBL.1 | MLST8 | 0.0193 | 0.82 |
| MIF.2 | MIF | <0.0001 | 0.69 |
| MICA.1 | MICA | <0.0001 | 0.52 |
| MGMT.1 | MGMT | <0.0001 | 0.50 |
| MCM3.3 | MCM3 | 0.0105 | 0.78 |
| MCAM.1 | MCAM | <0.0001 | 0.41 |
| MARCKS.1 | MARCKS | 0.0259 | 0.82 |
| ERK1.3 | MAPK3 | <0.0001 | 0.35 |
| ERK2.3 | MAPK1 | <0.0001 | 0.61 |
| MAP4.1 | MAP4 | <0.0001 | 0.54 |
| MAP2K3.1 | MAP2K3 | <0.0001 | 0.52 |
| MAP2K1.1 | MAP2K1 | 0.0172 | 0.81 |
| MAL2.1 | MAL2 | 0.0267 | 0.82 |
| MAL.1 | MAL | <0.0001 | 0.46 |
| LTF.1 | LTF | 0.0038 | 0.74 |
| LRP2.1 | LRP2 | <0.0001 | 0.52 |
| LMO2.1 | LMO2 | <0.0001 | 0.60 |
| LDB2.1 | LDB2 | <0.0001 | 0.26 |
| LDB1.2 | LDB1 | <0.0001 | 0.52 |
| LAMA4.1 | LAMA4 | <0.0001 | 0.67 |
| KRT7.1 | KRT7 | <0.0001 | 0.56 |
| K-ras.10 | KRAS | <0.0001 | 0.48 |
| KL.1 | KL | <0.0001 | 0.34 |
| Kitlng.4 | KITLG | <0.0001 | 0.46 |
| c-kit.2 | KIT | <0.0001 | 0.41 |

TABLE 6b-continued

Proxy genes for which increased expression is associated with the absence of necrosis (p-value ≤ .05)

| Gene | Official Symbol | CCF Necrosis p-value | OR |
|---|---|---|---|
| KDR.6 | KDR | <0.0001 | 0.28 |
| KCNJ15.1 | KCNJ15 | <0.0001 | 0.43 |
| HTATIP.1 | KAT5 | <0.0001 | 0.27 |
| G-Catenin.1 | JUP | <0.0001 | 0.32 |
| AP-1 (JUN official).2 | JUN | <0.0001 | 0.64 |
| JAG1.1 | JAG1 | <0.0001 | 0.23 |
| ITGB5.1 | ITGB5 | <0.0001 | 0.64 |
| ITGB3.1 | ITGB3 | 0.0468 | 0.84 |
| ITGB1.1 | ITGB1 | <0.0001 | 0.59 |
| ITGA7.1 | ITGA7 | <0.0001 | 0.38 |
| ITGA6.2 | ITGA6 | <0.0001 | 0.40 |
| ITGA5.1 | ITGA5 | 0.0298 | 0.83 |
| ITGA4.2 | ITGA4 | <0.0001 | 0.61 |
| ITGA3.2 | ITGA3 | 0.0018 | 0.76 |
| IQGAP2.1 | IQGAP2 | <0.0001 | 0.52 |
| INSR.1 | INSR | <0.0001 | 0.38 |
| IMP3.1 | IMP3 | <0.0001 | 0.53 |
| IL6ST.3 | IL6ST | <0.0001 | 0.36 |
| IL15.1 | IL15 | <0.0001 | 0.67 |
| IGFBP6.1 | IGFBP6 | <0.0001 | 0.66 |
| IGF2.2 | IGF2 | 0.0117 | 0.79 |
| IGF1R.3 | IGF1R | <0.0001 | 0.38 |
| ID3.1 | ID3 | <0.0001 | 0.44 |
| ID2.4 | ID2 | <0.0001 | 0.68 |
| ID1.1 | ID1 | <0.0001 | 0.32 |
| ICAM2.1 | ICAM2 | <0.0001 | 0.47 |
| HYAL2.1 | HYAL2 | <0.0001 | 0.28 |
| HYAL1.1 | HYAL1 | <0.0001 | 0.39 |
| HSPG2.1 | HSPG2 | <0.0001 | 0.33 |
| HSP90AB1.1 | HSP90AB1 | 0.0004 | 0.73 |
| HSD11B2.1 | HSD11B2 | <0.0001 | 0.32 |
| Hepsin.1 | HPN | <0.0001 | 0.59 |
| HPCAL1.1 | HPCAL1 | <0.0001 | 0.68 |
| HMGB1.1 | HMGB1 | <0.0001 | 0.42 |
| HLA-DPB1.1 | HLA-DPB1 | 0.0002 | 0.72 |
| HIF1AN.1 | HIF1AN | <0.0001 | 0.54 |
| HDAC1.1 | HDAC1 | <0.0001 | 0.55 |
| HAVCR1.1 | HAVCR1 | 0.0012 | 0.76 |
| HADH.1 | HADH | <0.0001 | 0.49 |
| GSTT1.3 | GSTT1 | 0.0067 | 0.80 |
| GSTp.3 | GSTP1 | <0.0001 | 0.55 |
| GSTM3.2 | GSTM3 | <0.0001 | 0.48 |
| GSTM1.1 | GSTM1 | <0.0001 | 0.54 |
| GRB7.2 | GRB7 | <0.0001 | 0.49 |
| GPX3.1 | GPX3 | <0.0001 | 0.59 |
| GPC3.1 | GPC3 | 0.0287 | 0.81 |
| GJA1.1 | GJA1 | 0.0004 | 0.74 |
| GFRA1.1 | GFRA1 | 0.0011 | 0.74 |
| GCLC.3 | GCLC | <0.0001 | 0.50 |
| GATM.1 | GATM | <0.0001 | 0.45 |
| GATA3.3 | GATA3 | 0.0159 | 0.79 |
| GADD45B.1 | GADD45B | <0.0001 | 0.67 |
| FOS.1 | FOS | <0.0001 | 0.56 |
| FOLR1.1 | FOLR1 | <0.0001 | 0.59 |
| FLT4.1 | FLT4 | <0.0001 | 0.27 |
| FLT3LG.1 | FLT3LG | <0.0001 | 0.62 |
| FLT1.1 | FLT1 | <0.0001 | 0.32 |
| FILIP1.1 | FILIP1 | <0.0001 | 0.42 |
| FIGF.1 | FIGF | 0.0001 | 0.62 |
| FHL1.1 | FHL1 | <0.0001 | 0.36 |
| FHIT.1 | FHIT | <0.0001 | 0.63 |
| FH.1 | FH | <0.0001 | 0.65 |
| FGFR2 isoform 1.1 | FGFR2 | <0.0001 | 0.51 |
| FGFR1.3 | FGFR1 | <0.0001 | 0.55 |
| FGF2.2 | FGF2 | <0.0001 | 0.61 |
| FGF1.1 | FGF1 | <0.0001 | 0.49 |
| FDPS.1 | FDPS | <0.0001 | 0.43 |
| FBXW7.1 | FBXW7 | <0.0001 | 0.60 |
| fas.1 | FAS | 0.0054 | 0.79 |
| ESRRG.3 | ESRRG | <0.0001 | 0.68 |
| ERG.1 | ERG | <0.0001 | 0.34 |
| ERCC4.1 | ERCC4 | 0.0197 | 0.81 |
| ERCC1.2 | ERCC1 | <0.0001 | 0.60 |
| ERBB4.3 | ERBB4 | 0.0037 | 0.72 |
| ErbB3.1 | ERBB3 | <0.0001 | 0.59 |
| HER2.3 | ERBB2 | <0.0001 | 0.40 |
| EPHB4.1 | EPHB4 | <0.0001 | 0.44 |
| EPHA2.1 | EPHA2 | <0.0001 | 0.36 |
| EPAS1.1 | EPAS1 | <0.0001 | 0.29 |
| ENPP2.1 | ENPP2 | <0.0001 | 0.50 |
| ENPEP.1 | ENPEP | <0.0001 | 0.56 |
| CD105.1 | ENG | <0.0001 | 0.31 |
| EMP1.1 | EMP1 | <0.0001 | 0.49 |
| EMCN.1 | EMCN | <0.0001 | 0.23 |
| ELTD1.1 | ELTD1 | <0.0001 | 0.59 |
| EIF2C1.1 | EIF2C1 | <0.0001 | 0.52 |
| EGR1.1 | EGR1 | <0.0001 | 0.54 |
| EGLN3.1 | EGLN3 | <0.0001 | 0.69 |
| EGFR.2 | EGFR | <0.0001 | 0.70 |
| EFNB2.1 | EFNB2 | <0.0001 | 0.34 |
| EFNB1.2 | EFNB1 | <0.0001 | 0.41 |
| EEF1A1.1 | EEF1A1 | <0.0001 | 0.32 |
| EDNRB.1 | EDNRB | <0.0001 | 0.31 |
| EDN2.1 | EDN2 | <0.0001 | 0.51 |
| EDN1 endothelin.1 | EDN1 | <0.0001 | 0.41 |
| EBAG9.1 | EBAG9 | 0.0007 | 0.74 |
| DUSP1.1 | DUSP1 | <0.0001 | 0.65 |
| DPYS.1 | DPYS | <0.0001 | 0.66 |
| DPEP1.1 | DPEP1 | <0.0001 | 0.34 |
| DLL4.1 | DLL4 | <0.0001 | 0.49 |
| DLC1.1 | DLC1 | <0.0001 | 0.36 |
| DKFZP564O0823.1 | DKFZP564O0823 | <0.0001 | 0.35 |
| DICER1.2 | DICER1 | <0.0001 | 0.46 |
| DIAPH1.1 | DIAPH1 | <0.0001 | 0.63 |
| DIABLO.1 | DIABLO | 0.0002 | 0.72 |
| DHPS.3 | DHPS | <0.0001 | 0.46 |
| DET1.1 | DET1 | <0.0001 | 0.61 |
| DEFB1.1 | DEFB1 | <0.0001 | 0.69 |
| DDC.1 | DDC | <0.0001 | 0.51 |
| DCXR.1 | DCXR | 0.0061 | 0.78 |
| DAPK1.3 | DAPK1 | <0.0001 | 0.47 |
| CYR61.1 | CYR61 | <0.0001 | 0.52 |
| CYP3A4.2 | CYP3A4 | 0.0398 | 0.82 |
| CYP2C8v2.1 | CYP2C8_21 | <0.0001 | 0.67 |
| CXCL12.1 | CXCL12 | <0.0001 | 0.53 |
| CX3CR1.1 | CX3CR1 | <0.0001 | 0.60 |
| CX3CL1.1 | CX3CL1 | <0.0001 | 0.34 |
| CUL1.1 | CUL1 | <0.0001 | 0.62 |
| CUBN.1 | CUBN | <0.0001 | 0.39 |
| CTSH.2 | CTSH | 0.0018 | 0.77 |
| B-Catenin.3 | CTNNB1 | <0.0001 | 0.38 |
| A-Catenin.2 | CTNNA1 | <0.0001 | 0.58 |
| CTGF.1 | CTGF | <0.0001 | 0.64 |
| CSF1R.2 | CSF1R | 0.0308 | 0.83 |
| CSF1.1 | CSF1 | 0.0002 | 0.73 |
| CRADD.1 | CRADD | <0.0001 | 0.60 |
| COL4A2.1 | COL4A2 | <0.0001 | 0.51 |
| COL4A1.1 | COL4A1 | <0.0001 | 0.66 |
| COL18A1.1 | COL18A1 | <0.0001 | 0.50 |
| CLU.3 | CLU | 0.0091 | 0.80 |
| CLDN7.2 | CLDN7 | 0.0029 | 0.76 |
| CLDN10.1 | CLDN10 | <0.0001 | 0.48 |
| CLCNKB.1 | CLCNKB | 0.0001 | 0.61 |
| CFLAR.1 | CFLAR | <0.0001 | 0.47 |
| CEACAM1.1 | CEACAM1 | <0.0001 | 0.43 |
| p27.3 | CDKN1B | 0.0002 | 0.73 |
| p21.3 | CDKN1A | <0.0001 | 0.65 |
| CDH6.1 | CDH6 | <0.0001 | 0.67 |
| CDH5.1 | CDH5 | <0.0001 | 0.33 |
| CDH2.1 | CDH2 | 0.0003 | 0.75 |
| CDH16.1 | CDH16 | <0.0001 | 0.51 |
| CDH13.1 | CDH13 | <0.0001 | 0.39 |
| CD36.1 | CD36 | <0.0001 | 0.41 |

TABLE 6b-continued

Proxy genes for which increased expression is associated with the absence of necrosis (p-value ≤ .05)

| Gene | Official Symbol | CCF Necrosis p-value | OR |
|---|---|---|---|
| CD34.1 | CD34 | <0.0001 | 0.34 |
| CD24.1 | CD24 | 0.0148 | 0.81 |
| CCND1.3 | CCND1 | <0.0001 | 0.51 |
| MCP1.1 | CCL2 | <0.0001 | 0.68 |
| CAT.1 | CAT | <0.0001 | 0.48 |
| CASP10.1 | CASP10 | <0.0001 | 0.62 |
| CALD1.2 | CALD1 | <0.0001 | 0.42 |
| CACNA2D1.1 | CACNA2D1 | 0.0006 | 0.74 |
| CA2.1 | CA2 | <0.0001 | 0.60 |
| C7.1 | C7 | <0.0001 | 0.65 |
| ECRG4.1 | C2orf40 | <0.0001 | 0.32 |
| C13orf15.1 | C13orf15 | <0.0001 | 0.31 |
| BUB3.1 | BUB3 | <0.0001 | 0.65 |
| BTRC.1 | BTRC | <0.0001 | 0.63 |
| BNIP3.1 | BNIP3 | 0.0021 | 0.77 |
| CIAP1.2 | BIRC2 | <0.0001 | 0.56 |
| BIN1.3 | BIN1 | <0.0001 | 0.67 |
| BGN.1 | BGN | <0.0001 | 0.47 |
| BCL2L12.1 | BCL2L12 | 0.0374 | 0.82 |
| Bclx.2 | BCL2L1 | <0.0001 | 0.60 |
| Bcl2.2 | BCL2 | <0.0001 | 0.31 |
| BAG1.2 | BAG1 | <0.0001 | 0.42 |
| BAD.1 | BAD | 0.0187 | 0.82 |
| AXL.1 | AXL | 0.0077 | 0.79 |
| ATP6V1B1.1 | ATP6V1B1 | <0.0001 | 0.52 |
| ASS1.1 | ASS1 | <0.0001 | 0.61 |
| ARRB1.1 | ARRB1 | <0.0001 | 0.48 |
| ARHGDIB.1 | ARHGDIB | <0.0001 | 0.48 |
| ARF1.1 | ARF1 | 0.0021 | 0.75 |
| AQP1.1 | AQP1 | <0.0001 | 0.28 |
| APOLD1.1 | APOLD1 | <0.0001 | 0.35 |
| APC.4 | APC | <0.0001 | 0.55 |
| APAF1.2 | APAF1 | 0.0264 | 0.82 |
| ANXA4.1 | ANXA4 | 0.0012 | 0.76 |
| ANXA1.2 | ANXA1 | 0.0201 | 0.81 |
| ANTXR1.1 | ANTXR1 | <0.0001 | 0.58 |
| ANGPTL4.1 | ANGPTL4 | <0.0001 | 0.71 |
| ANGPTL3.3 | ANGPTL3 | 0.0104 | 0.77 |
| ANGPTL2.1 | ANGPTL2 | <0.0001 | 0.63 |
| ANGPT2.1 | ANGPT2 | <0.0001 | 0.65 |
| ANGPT1.1 | ANGPT1 | <0.0001 | 0.30 |
| AMACR1.1 | AMACR | 0.0080 | 0.79 |
| ALDOB.1 | ALDOB | <0.0001 | 0.40 |
| ALDH6A1.1 | ALDH6A1 | <0.0001 | 0.38 |
| ALDH4.2 | ALDH4A1 | 0.0001 | 0.71 |
| AKT3.2 | AKT3 | <0.0001 | 0.30 |
| AKT2.3 | AKT2 | <0.0001 | 0.53 |
| AKT1.3 | AKT1 | <0.0001 | 0.47 |
| AHR.1 | AHR | <0.0001 | 0.60 |
| AGTR1.1 | AGTR1 | <0.0001 | 0.33 |
| AGT.1 | AGT | 0.0032 | 0.77 |
| ADH6.1 | ADH6 | 0.0011 | 0.71 |
| ADH1B.1 | ADH1B | <0.0001 | 0.69 |
| ADFP.1 | ADFP | 0.0001 | 0.73 |
| ADD1.1 | ADD1 | <0.0001 | 0.33 |
| ADAMTS9.1 | ADAMTS9 | <0.0001 | 0.69 |
| ADAMTS5.1 | ADAMTS5 | <0.0001 | 0.55 |
| ADAMTS1.1 | ADAMTS1 | <0.0001 | 0.56 |
| ADAM17.1 | ADAM17 | 0.0009 | 0.76 |
| ACE2.1 | ACE2 | <0.0001 | 0.45 |
| ACADSB.1 | ACADSB | <0.0001 | 0.46 |
| BCRP.1 | ABCG2 | <0.0001 | 0.27 |
| MRP4.2 | ABCC4 | <0.0001 | 0.61 |
| MRP3.1 | ABCC3 | 0.0011 | 0.76 |
| MRP1.1 | ABCC1 | 0.0008 | 0.75 |
| ABCB1.5 | ABCB1 | <0.0001 | 0.59 |
| NPD009 (ABAT official).3 | ABAT | 0.0001 | 0.70 |
| AAMP.1 | AAMP | <0.0001 | 0.62 |
| A2M.1 | A2M | <0.0001 | 0.28 |

TABLE 7a

Proxy genes for which increased expression is associated with the presence of nodal invasion (p-value ≤ .05)

| Gene | Official Symbol | Nodal Invasion p-value | OR |
|---|---|---|---|
| TUBB.1 | TUBB2A | 0.0242 | 2.56 |
| C20 orf1.1 | TPX2 | 0.0333 | 2.61 |
| TK1.2 | TK1 | 0.0361 | 1.75 |
| SPHK1.1 | SPHK1 | 0.0038 | 3.43 |
| SLC7A5.2 | SLC7A5 | 0.0053 | 4.85 |
| SILV.1 | SILV | 0.0470 | 1.54 |
| SELE.1 | SELE | 0.0311 | 1.93 |
| upa.3 | PLAU | 0.0450 | 2.78 |
| MMP9.1 | MMP9 | 0.0110 | 2.65 |
| MMP7.1 | MMP7 | 0.0491 | 2.34 |
| MMP14.1 | MMP14 | 0.0155 | 3.21 |
| LAMB1.1 | LAMB1 | 0.0247 | 3.04 |
| IL-8.1 | IL8 | 0.0019 | 3.18 |
| IL6.3 | IL6 | 0.0333 | 2.31 |
| HSPA1A.1 | HSPA1A | 0.0498 | 2.11 |
| GSTp.3 | GSTP1 | 0.0272 | 3.46 |
| GRB14.1 | GRB14 | 0.0287 | 2.32 |
| GMNN.1 | GMNN | 0.0282 | 3.00 |
| ENO2.1 | ENO2 | 0.0190 | 3.43 |
| CCNB1.2 | CCNB1 | 0.0387 | 1.87 |
| BUB1.1 | BUB1 | 0.0429 | 2.21 |
| BAG2.1 | BAG2 | 0.0346 | 2.54 |
| ADAMTS1.1 | ADAMTS1 | 0.0193 | 3.31 |

TABLE 7b

Proxy genes for which increased expression is associated with the absence of nodal invasion (p-value ≤ .05)

| Gene | Official Symbol | Nodal Invasion p-value | OR |
|---|---|---|---|
| VWF.1 | VWF | 0.0221 | 0.42 |
| VCAM1.1 | VCAM1 | 0.0212 | 0.42 |
| UBE1C.1 | UBA3 | 0.0082 | 0.32 |
| tusc4.2 | TUSC4 | 0.0050 | 0.28 |
| TSPAN7.2 | TSPAN7 | 0.0407 | 0.43 |
| TSC1.1 | TSC1 | 0.0372 | 0.38 |
| TMSB10.1 | TMSB10 | 0.0202 | 0.43 |
| TMEM47.1 | TMEM47 | 0.0077 | 0.32 |
| TMEM27.1 | TMEM27 | 0.0431 | 0.41 |
| TLR3.1 | TLR3 | 0.0041 | 0.32 |
| TIMP3.3 | TIMP3 | 0.0309 | 0.40 |
| TGFBR2.3 | TGFBR2 | 0.0296 | 0.35 |
| TGFB2.2 | TGFB2 | 0.0371 | 0.30 |
| TGFA.2 | TGFA | 0.0025 | 0.32 |
| TEK.1 | TEK | 0.0018 | 0.09 |
| TCF4.1 | TCF4 | 0.0088 | 0.38 |
| STAT5A.1 | STAT5A | 0.0129 | 0.49 |
| SPRY1.1 | SPRY1 | 0.0188 | 0.43 |
| SPARCL1.1 | SPARCL1 | 0.0417 | 0.50 |
| SOD1.1 | SOD1 | 0.0014 | 0.23 |
| SNRK.1 | SNRK | 0.0226 | 0.43 |
| MADH2.1 | SMAD2 | 0.0098 | 0.37 |
| SLC22A6.1 | SLC22A6 | 0.0051 | 0.00 |
| PTPNS1.1 | SIRPA | 0.0206 | 0.43 |
| SHANK3.1 | SHANK3 | 0.0024 | 0.30 |
| SGK.1 | SGK1 | 0.0087 | 0.35 |
| SELENBP1.1 | SELENBP1 | 0.0016 | 0.29 |
| SCN4B.1 | SCN4B | 0.0081 | 0.08 |
| ROCK1.1 | ROCK1 | 0.0058 | 0.41 |
| RhoB.1 | RHOB | 0.0333 | 0.43 |
| RGS5.1 | RGS5 | 0.0021 | 0.31 |
| FLJ22655.1 | RERGL | 0.0009 | 0.01 |
| RB1.1 | RB1 | 0.0281 | 0.48 |
| RASSF1.1 | RASSF1 | 0.0004 | 0.23 |
| PTPRB.1 | PTPRB | 0.0154 | 0.40 |
| PTK2.1 | PTK2 | 0.0158 | 0.38 |
| PTHR1.1 | PTH1R | <0.0001 | 0.01 |
| PRSS8.1 | PRSS8 | 0.0023 | 0.10 |
| PRKCH.1 | PRKCH | 0.0475 | 0.48 |

TABLE 7b-continued

Proxy genes for which increased expression is associated with the absence of nodal invasion (p-value ≤ .05)

| Gene | Official Symbol | Nodal Invasion p-value | OR |
|---|---|---|---|
| PPAP2B.1 | PPAP2B | 0.0110 | 0.40 |
| PLA2G4C.1 | PLA2G4C | 0.0002 | 0.03 |
| PI3K.2 | PIK3C2B | 0.0138 | 0.13 |
| PFKP.1 | PFKP | 0.0040 | 0.41 |
| CD31.3 | PECAM1 | 0.0077 | 0.38 |
| PDGFD.2 | PDGFD | 0.0169 | 0.35 |
| PDGFC.3 | PDGFC | 0.0053 | 0.36 |
| PDGFB.3 | PDGFB | 0.0359 | 0.47 |
| PCSK6.1 | PCSK6 | 0.0103 | 0.34 |
| PCK1.1 | PCK1 | 0.0003 | 0.02 |
| PCCA.1 | PCCA | 0.0074 | 0.12 |
| PARD6A.1 | PARD6A | 0.0243 | 0.21 |
| BFGF.3 | NUDT6 | 0.0082 | 0.15 |
| NRG1.3 | NRG1 | 0.0393 | 0.19 |
| NOS3.1 | NOS3 | 0.0232 | 0.34 |
| NOS2A.3 | NOS2 | 0.0086 | 0.11 |
| NFX1.1 | NFX1 | 0.0065 | 0.35 |
| MYH11.1 | MYH11 | 0.0149 | 0.36 |
| cMYC.3 | MYC | 0.0472 | 0.46 |
| MUC1.2 | MUC1 | 0.0202 | 0.26 |
| MIF.2 | MIF | 0.0145 | 0.39 |
| MICA.1 | MICA | 0.0015 | 0.15 |
| MGMT.1 | MGMT | 0.0414 | 0.50 |
| MAP2K1.1 | MAP2K1 | 0.0075 | 0.40 |
| LMO2.1 | LMO2 | 0.0127 | 0.07 |
| LDB2.1 | LDB2 | 0.0048 | 0.33 |
| Kitlng.4 | KITLG | 0.0146 | 0.18 |
| KDR.6 | KDR | 0.0106 | 0.34 |
| ITGB1.1 | ITGB1 | 0.0469 | 0.36 |
| ITGA7.1 | ITGA7 | 0.0290 | 0.38 |
| ITGA6.2 | ITGA6 | 0.0010 | 0.17 |
| ITGA4.2 | ITGA4 | 0.0089 | 0.44 |
| INSR.1 | INSR | 0.0057 | 0.32 |
| IMP3.1 | IMP3 | 0.0086 | 0.43 |
| IL6ST.3 | IL6ST | 0.0484 | 0.46 |
| IL15.1 | IL15 | 0.0009 | 0.08 |
| IFI27.1 | IFI27 | 0.0013 | 0.22 |
| HYAL2.1 | HYAL2 | 0.0099 | 0.36 |
| HYAL1.1 | HYAL1 | 0.0001 | 0.08 |
| Hepsin.1 | HPN | 0.0024 | 0.14 |
| HPCAL1.1 | HPCAL1 | 0.0024 | 0.38 |
| HMGB1.1 | HMGB1 | 0.0385 | 0.45 |
| HLA-DPB1.1 | HLA-DPB1 | 0.0398 | 0.43 |
| HADH.1 | HADH | 0.0093 | 0.33 |
| GSTM1.1 | GSTM1 | 0.0018 | 0.18 |
| GPX2.2 | GPX2 | 0.0211 | 0.07 |
| GJA1.1 | GJA1 | 0.0451 | 0.46 |
| GATM.1 | GATM | 0.0038 | 0.25 |
| GATA3.3 | GATA3 | 0.0188 | 0.06 |
| FOLR1.1 | FOLR1 | 0.0152 | 0.32 |
| FLT4.1 | FLT4 | 0.0125 | 0.22 |
| FLT1.1 | FLT1 | 0.0046 | 0.35 |
| FHL1.1 | FHL1 | 0.0435 | 0.47 |
| FHIT.1 | FHIT | 0.0061 | 0.29 |
| fas.1 | FAS | 0.0163 | 0.39 |
| ErbB3.1 | ERBB3 | 0.0145 | 0.33 |
| EPHA2.1 | EPHA2 | 0.0392 | 0.37 |
| EPAS1.1 | EPAS1 | 0.0020 | 0.28 |
| ENPEP.1 | ENPEP | 0.0002 | 0.34 |
| CD105.1 | ENG | 0.0112 | 0.38 |
| EMCN.1 | EMCN | 0.0022 | 0.19 |
| EIF2C1.1 | EIF2C1 | 0.0207 | 0.33 |
| EGLN3.1 | EGLN3 | 0.0167 | 0.52 |
| EFNB2.1 | EFNB2 | 0.0192 | 0.30 |
| EFNB1.2 | EFNB1 | 0.0110 | 0.37 |
| EDNRB.1 | EDNRB | 0.0106 | 0.36 |
| EDN1 endothelin.1 | EDN1 | 0.0440 | 0.42 |
| DPYS.1 | DPYS | 0.0454 | 0.43 |
| DKFZP564O0823.1 | DKFZP564O0823 | 0.0131 | 0.31 |
| DHPS.3 | DHPS | 0.0423 | 0.48 |
| DAPK1.3 | DAPK1 | 0.0048 | 0.39 |
| CYP2C8v2.1 | CYP2C8_21 | 0.0003 | 0.01 |
| CYP2C8.2 | CYP2C8_2 | 0.0269 | 0.07 |
| CX3CR1.1 | CX3CR1 | 0.0224 | 0.13 |
| CUBN.1 | CUBN | 0.0010 | 0.04 |
| CRADD.1 | CRADD | 0.0193 | 0.40 |
| CLDN10.1 | CLDN10 | 0.0005 | 0.21 |
| CFLAR.1 | CFLAR | 0.0426 | 0.49 |
| CEACAM1.1 | CEACAM1 | 0.0083 | 0.23 |
| CDKN2A.2 | CDKN2A | 0.0026 | 0.13 |
| p27.3 | CDKN1B | 0.0393 | 0.60 |
| CDH5.1 | CDH5 | 0.0038 | 0.33 |
| CDH13.1 | CDH13 | 0.0203 | 0.39 |
| CD99.1 | CD99 | 0.0173 | 0.38 |
| CD36.1 | CD36 | 0.0015 | 0.29 |
| CD34.1 | CD34 | 0.0250 | 0.38 |
| CD3z.1 | CD247 | 0.0419 | 0.33 |
| CCND1.3 | CCND1 | 0.0381 | 0.50 |
| CAT.1 | CAT | 0.0044 | 0.42 |
| CASP6.1 | CASP6 | 0.0136 | 0.36 |
| CALD1.2 | CALD1 | 0.0042 | 0.31 |
| CA9.3 | CA9 | 0.0077 | 0.48 |
| C13orf15.1 | C13orf15 | 0.0152 | 0.39 |
| BUB3.1 | BUB3 | 0.0157 | 0.26 |
| BIN1.3 | BIN1 | 0.0224 | 0.38 |
| Bclx.2 | BCL2L1 | 0.0225 | 0.52 |
| Bcl2.2 | BCL2 | 0.0442 | 0.45 |
| AXL.1 | AXL | 0.0451 | 0.44 |
| ATP6V1B1.1 | ATP6V1B1 | 0.0257 | 0.03 |
| ARRB1.1 | ARRB1 | 0.0337 | 0.43 |
| ARHGDIB.1 | ARHGDIB | 0.0051 | 0.32 |
| AQP1.1 | AQP1 | 0.0022 | 0.31 |
| APOLD1.1 | APOLD1 | 0.0222 | 0.42 |
| APC.4 | APC | 0.0165 | 0.47 |
| ANXA5.1 | ANXA5 | 0.0143 | 0.37 |
| ANXA4.1 | ANXA4 | 0.0019 | 0.30 |
| ANXA1.2 | ANXA1 | 0.0497 | 0.39 |
| ANGPTL7.1 | ANGPTL7 | 0.0444 | 0.16 |
| ANGPTL4.1 | ANGPTL4 | 0.0197 | 0.55 |
| ANGPT1.1 | ANGPT1 | 0.0055 | 0.15 |
| ALDOB | ALDOB | 0.0128 | 0.02 |
| ALDH4.2 | ALDH4A1 | 0.0304 | 0.33 |
| AGTR1.1 | AGTR1 | 0.0142 | 0.11 |
| ADH6.1 | ADH6 | 0.0042 | 0.03 |
| ADFP | ADFP | 0.0223 | 0.47 |
| ADD1.1 | ADD1 | 0.0135 | 0.42 |
| BCRP.1 | ABCG2 | 0.0098 | 0.19 |
| MRP3.1 | ABCC3 | 0.0247 | 0.44 |
| MRP1.1 | ABCC1 | 0.0022 | 0.32 |
| NPD009 (ABAT official).3 | ABAT | 0.0110 | 0.19 |
| A2M.1 | A2M | 0.0012 | 0.29 |

TABLE 8a

Genes for which increased expression is associated with lower risk of cancer recurrence after clinical/pathologic covariate adjustment (p < 0.05)

| Gene | Official Symbol | p-value | HR |
|---|---|---|---|
| ACE2.1 | ACE2 | 0.0261 | 0.85 |
| ADD1.1 | ADD1 | 0.0339 | 0.85 |
| ALDOB.1 | ALDOB | 0.0328 | 0.84 |
| ANGPTL3.3 | ANGPTL3 | 0.0035 | 0.79 |
| APOLD1.1 | APOLD1 | 0.0015 | 0.78 |
| AQP1.1 | AQP1 | 0.0014 | 0.79 |
| BFGF.3 | NUDT6 | 0.0010 | 0.77 |
| CASP10.1 | CASP10 | 0.0024 | 0.82 |
| CAV2.1 | CAV2 | 0.0191 | 0.86 |
| CCL4.2 | CCL4 | 0.0045 | 0.81 |
| CCL5.2 | CCL5 | 0.0003 | 0.78 |
| CCR2.1 | CCR2 | 0.0390 | 0.87 |

TABLE 8a-continued

Genes for which increased expression is associated with lower risk of cancer recurrence after clinical/pathologic covariate adjustment (p < 0.05)

| Gene | Official Symbol | p-value | HR |
|---|---|---|---|
| CCR4.2 | CCR4 | 0.0109 | 0.82 |
| CCR7.1 | CCR7 | 0.0020 | 0.80 |
| CD4.1 | CD4 | 0.0195 | 0.86 |
| CD8A.1 | CD8A | 0.0058 | 0.83 |
| CEACAM1.1 | CEACAM1 | 0.0022 | 0.81 |
| CFLAR.1 | CFLAR | 0.0308 | 0.87 |
| CTSS.1 | CTSS | 0.0462 | 0.87 |
| CX3CL1.1 | CX3CL1 | 0.0021 | 0.81 |
| CXCL10.1 | CXCL10 | 0.0323 | 0.86 |
| CXCL9.1 | CXCL9 | 0.0006 | 0.79 |
| CXCR6.1 | CXCR6 | 0.0469 | 0.88 |
| DAPK1.3 | DAPK1 | 0.0050 | 0.83 |
| DDC.1 | DDC | 0.0307 | 0.86 |
| DLC1.1 | DLC1 | 0.0249 | 0.83 |
| ECRG4.1 | C2orf40 | 0.0244 | 0.84 |
| EDNRB.1 | EDNRB | 0.0400 | 0.86 |
| EMCN.1 | EMCN | <0.0001 | 0.68 |
| EPAS1.1 | EPAS1 | 0.0411 | 0.84 |
| fas.1 | FAS | 0.0242 | 0.87 |
| FH.1 | FH | 0.0407 | 0.88 |
| GATA3.3 | GATA3 | 0.0172 | 0.83 |
| GZMA.1 | GZMA | 0.0108 | 0.84 |
| HLA-DPB1.1 | HLA-DPB1 | 0.0036 | 0.82 |
| HSPG2.1 | HSPG2 | 0.0236 | 0.84 |
| ICAM2.1 | ICAM2 | 0.0091 | 0.83 |
| ICAM3.1 | ICAM3 | 0.0338 | 0.87 |
| ID1.1 | ID1 | 0.0154 | 0.83 |
| IGF1R.3 | IGF1R | 0.0281 | 0.85 |
| IL15.1 | IL15 | 0.0059 | 0.83 |
| IQGAP2.1 | IQGAP2 | 0.0497 | 0.88 |
| KL.1 | KL | 0.0231 | 0.86 |
| KLRK1.2 | KLRK1 | 0.0378 | 0.87 |
| LDB2.1 | LDB2 | 0.0092 | 0.82 |
| LRP2.1 | LRP2 | 0.0193 | 0.86 |
| LTF.1 | LTF | 0.0077 | 0.82 |
| MAP4.1 | MAP4 | 0.0219 | 0.84 |
| MRP1.1 | ABCC1 | 0.0291 | 0.87 |
| NOS3.1 | NOS3 | 0.0008 | 0.78 |
| PI3K.2 | PIK3C2B | 0.0329 | 0.83 |
| PLA2G4C.1 | PLA2G4C | 0.0452 | 0.87 |
| PPAP2B.1 | PPAP2B | 0.0001 | 0.74 |
| PRCC.1 | PRCC | 0.0333 | 0.88 |
| PRKCB1.1 | PRKCB | 0.0353 | 0.87 |
| PRKCH.1 | PRKCH | 0.0022 | 0.82 |
| PRSS8.1 | PRSS8 | 0.0332 | 0.87 |
| PSMB9.1 | PSMB9 | 0.0262 | 0.87 |
| PTPRB.1 | PTPRB | 0.0030 | 0.80 |
| RGS5.1 | RGS5 | 0.0480 | 0.85 |
| SDPR.1 | SDPR | 0.0045 | 0.80 |
| SELE.1 | SELE | 0.0070 | 0.81 |
| SGK.1 | SGK1 | 0.0100 | 0.83 |
| SHANK3.1 | SHANK3 | 0.0311 | 0.84 |
| SNRK.1 | SNRK | 0.0026 | 0.81 |
| TEK.1 | TEK | 0.0059 | 0.78 |
| TGFBR2.3 | TGFBR2 | 0.0343 | 0.85 |
| TIMP3.3 | TIMP3 | 0.0165 | 0.83 |
| TMEM27.1 | TMEM27 | 0.0249 | 0.86 |
| TSPAN7.2 | TSPAN7 | 0.0099 | 0.83 |
| UBB.1 | UBB | 0.0144 | 0.85 |
| WWOX.5 | WWOX | 0.0082 | 0.83 |

TABLE 8b

Genes for which increased expression is associated with higher risk of cancer recurrence after clinical/pathologic covariate adjustment (p < 0.05)

| Gene | Official Symbol | p-value | HR |
|---|---|---|---|
| CIAP1.2 | BIRC2 | 0.0425 | 1.14 |
| BUB1.1 | BUB1 | 0.0335 | 1.15 |
| CCNB1.2 | CCNB1 | 0.0296 | 1.14 |
| ENO2.1 | ENO2 | 0.0284 | 1.17 |
| ITGB1.1 | ITGB1 | 0.0402 | 1.16 |
| ITGB5.1 | ITGB5 | 0.0016 | 1.25 |
| LAMB1.1 | LAMB1 | 0.0067 | 1.20 |
| MMP14.1 | MMP14 | 0.0269 | 1.16 |
| MMP9.1 | MMP9 | 0.0085 | 1.19 |
| PSMA7.1 | PSMA7 | 0.0167 | 1.16 |
| RUNX1.1 | RUNX1 | 0.0491 | 1.15 |
| SPHK1.1 | SPHK1 | 0.0278 | 1.16 |
| OPN, osteopontin.3 | SPP1 | 0.0134 | 1.17 |
| SQSTM1.1 | SQSTM1 | 0.0347 | 1.13 |
| C20 orf1.1 | TPX2 | 0.0069 | 1.20 |
| TUBB.1 | TUBB2A | 0.0046 | 1.21 |
| VCAN.1 | VCAN | 0.0152 | 1.18 |

TABLE 9

16 Significant Genes After Adjusting for Clinical/Pathologic Covariates and Allowing for an FDR of 10%

| Official Symbol | n | Gene Subset (Pathway) | HR | HR (95% CI) | LR ChiSq | LR p-value | q-value |
|---|---|---|---|---|---|---|---|
| EMCN | 928 | Angiogenesis | 0.68 | (0.57, 0.80) | 19.87 | <0.0001 | 0.0042 |
| PPAP2B | 928 | Angiogenesis | 0.74 | (0.65, 0.85) | 16.15 | 0.0001 | 0.0148 |
| CCL5 | 928 | Immune Response | 0.78 | (0.68, 0.89) | 12.98 | 0.0003 | 0.0529 |
| CXCL9 | 928 | Immune Response | 0.79 | (0.70, 0.91) | 11.74 | 0.0006 | 0.0772 |
| NOS3 | 928 | Angiogenesis | 0.78 | (0.68, 0.90) | 11.32 | 0.0008 | 0.0774 |
| NUDT6 | 926 | Angiogenesis | 0.77 | (0.66, 0.90) | 10.77 | 0.0010 | 0.0850 |
| AQP1 | 928 | Transport | 0.79 | (0.69, 0.91) | 10.15 | 0.0014 | 0.0850 |
| APOLD1 | 927 | Angiogenesis | 0.78 | (0.68, 0.91) | 10.07 | 0.0015 | 0.0850 |
| ITGB5 | 928 | Cell Adhesion/ Extracellular Matrix | 1.25 | (1.09, 1.43) | 9.92 | 0.0016 | 0.0850 |
| CCR7 | 928 | Immune Response | 0.80 | (0.69, 0.92) | 9.58 | 0.0020 | 0.0850 |
| CX3CL1 | 926 | Immune Response | 0.81 | (0.70, 0.92) | 9.44 | 0.0021 | 0.0850 |
| CEACAM1 | 928 | Angiogenesis | 0.81 | (0.70, 0.93) | 9.37 | 0.0022 | 0.0850 |
| PRKCH | 917 | Angiogenesis | 0.82 | (0.72, 0.93) | 9.36 | 0.0022 | 0.0850 |
| CASP10 | 927 | Apoptosis | 0.82 | (0.73, 0.93) | 9.25 | 0.0024 | 0.0850 |
| SNRK | 928 | Angiogenesis | 0.81 | (0.71, 0.92) | 9.09 | 0.0026 | 0.0863 |
| PTPRB | 927 | Angiogenesis | 0.80 | (0.69, 0.92) | 8.83 | 0.0030 | 0.0933 |

TABLE A

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| A-Catenin.2 | NM_001903 | NM_001903.1 | CTNNA1 | 765 | CGTTCCGATCTCT ATACTGCAT | 1 | AGGTCCCTGTTG GCCTTATAGG | 733 | ATGCCTACAGCACCC TGATGTCGCA | 1465 |
| A2M.1 | NM_000014 | NM_000014.4 | A2M | 6456 | CTCTCCCGCCTTCC TAGC | 2 | CCGTTTGCACAG ATGCAG | 734 | CGTTGTTCCTTCTC CACTGGGAC | 1466 |
| AAMP.1 | NM_001087 | NM_001087.3 | AAMP | 5474 | GTGTGGCAGGTGG ACACTAA | 3 | CTCCATCCACTC CAGTCTC | 735 | CGCTTCAAAGGACCA GACTCCTC | 1467 |
| ABCB1.5 | NM_000927 | NM_000927.2 | ABCB1 | 3099 | AAACACCACTGGAG CATTGA | 4 | CAAGCCTGGAAC CTATAGCC | 736 | CTCGCCAATGATGCT GCTCAAGTT | 1468 |
| ACADSB.1 | NM_001609 | NM_001609.3 | ACADSB | 6278 | TGGCGGAGAACTA GCCAT | 5 | AAGACAGCCCAG TCCTCAAAT | 737 | CCTCCTGAAGCCTG CCATCATTGT | 1469 |
| ACE.1 | NM_000789 | NM_000789.2 | ACE | 4257 | CCGCTGTACGAGG ATTTCA | 6 | CCGTGTCTGTGA AGCCGT | 738 | TGCCCTCAGCAATGA AGCCTACAA | 1470 |
| ACE2.1 | NM_021804 | NM_021804.1 | ACE2 | 6108 | TACAATGAGAGGCT CTGGGC | 7 | TAATGGCCTCAG CTGCTTG | 739 | CGACCTCAGATCTCC AGCTTTCCC | 1471 |
| ADAM17.1 | NM_003183 | NM_003183.3 | ADAM17 | 2617 | GAAGTGCCAGGAG GCGATTA | 8 | CGGGCACTCACT GCTATTACC | 740 | TGTACTTGCAAAGG CGTGTCCTACTGC | 1472 |
| ADAM8.1 | NM_001109 | NM_001109.2 | ADAM8 | 3978 | GTCACTGTGTCCAG CCCA | 9 | TGATGACCTGCT TTGGTGC | 741 | TTCCCAGTTCCTGTC TACACCGG | 1473 |
| ADAMTS1.1 | NM_006988 | NM_006988.2 | ADAMTS1 | 2639 | GGACAGTGCAAG CTCATCTG | 10 | ATCTACAACCTT GGGCTGCAA | 742 | CAAGCCAAAGGCATT GGCTACTTCTTCG | 1474 |
| ADAMTS2.1 | NM_014244 | NM_014244.1 | ADAMTS2 | 3979 | GAGAATGTCTGCC GCTGG | 11 | ATCGTGGTATTC ATCGTGGC | 743 | TACCTCCAGCAGAAG CCAGACACG | 1475 |
| ADAMTS4.1 | NM_005099 | NM_005099.3 | ADAMTS4 | 2642 | TTTGACAAGTGCAT GGTGTG | 12 | AATTTCCTGAAG GAGCCTGA | 744 | CTGCTTGTGCAACC AGAACCGT | 1476 |
| ADAMTS5.1 | NM_007038 | NM_007038.1 | ADAMTS5 | 2641 | CACTGTGGCTCAC GAAATCG | 13 | GGAACCAAAGGT CTCTTCACAGA | 745 | ATTTACTTGGCCTCT CCCATGACGATTCC | 1477 |
| ADAMTS8.1 | NM_007037 | NM_007037.2 | ADAMTS8 | 2640 | GCGAGTTCAAAGT GTTCGAG | 14 | CACAGATGGCCA GTGTTTCT | 746 | CACACAGGGTGCCA TCAATCACCT | 1478 |
| ADAMTS9.1 | NM_182920 | NM_182920.1 | ADAMTS9 | 6109 | GCACAGGTTACACA ACCCAA | 15 | CGACATTGGCAG TCATCG | 747 | CCCGGCTCCCGTTATA GGGACATTC | 1479 |
| ADD1.1 | NM_001119 | NM_001119.3 | ADD1 | 3980 | GTCTACCCAGCAG CTCCG | 16 | TCGTTCACAGGA GTCACCAT | 748 | CATGTTTAAGGCAGC CATCCCTCC | 1480 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| ADFP.1 | NM_001122 | NM_001122.2 | PLIN2 | 4503 | AAGACCATCACCTC CGTGG | 17 | CAATTTGCGGCT CTAGCTTC | 749 | ATGACCAGTGCTCTG CCCATCATC | 1481 |
| ADH1B.1 | NM_000668 | NM_000668.4 | ADH1B | 6325 | AAGCCAACAAACCT TCCTTC | 18 | AAAATGCAAGAA GTCACAGGAA | 750 | TTTCCTCAATGGCAA AGTGACACA | 1482 |
| ADH6.1 | NM_000672 | NM_000672.3 | ADH6 | 6111 | TGTTGGGAGTAAA CACTTGG | 19 | AACGATTCCAGC CCCTTC | 751 | TCTTGTATCCACCA TCTTGGGCC | 1483 |
| ADM.1 | NM_001124 | NM_001124.1 | ADM | 3248 | TAAGCCACAAGCAC ACGG | 20 | TGGGCGCCTAAA TCCTAA | 752 | CGAGTGGAAGTGCT CCCACTTTC | 1484 |
| AGR2.1 | NM_006408 | NM_006408.2 | AGR2 | 3245 | AGCCAACATGTGAC TAATTGGA | 21 | TCTGATCTCCAT CTGCCTCA | 753 | CAACACGTCACCACC CTTTGCTCT | 1485 |
| AGT.1 | NM_000029 | NM_000029.2 | AGT | 6112 | GATCCAGCCTCACT ATGCCT | 22 | CCAGTTGAGGGA GTTTTGCT | 754 | TGAGACCCTCCACCT TGTCCAGGT | 1486 |
| AGTR1.1 | NM_000685 | NM_000685.3 | AGTR1 | 4258 | AGCATTGATCGATA CCTGGC | 23 | CTACAAGCATTG TGCGTCG | 755 | ATTGTTCACCCAATG AAGTCCCGC | 1487 |
| AHR.1 | NM_001621 | NM_001621.2 | AHR | 3981 | GCGGCATAGAGAC CGACTT | 24 | ACATCTTGTGGG AAAGGCA | 756 | CAGGCTAGCCAAAC GGTCCAATC | 1488 |
| AIF1.1 | NM_032955 | NM_032955.1 | AIF1 | 6452 | GACGTTCAGCTACC CTGACTT | 25 | TCAGGATCATTT TTAGGATGGC | 757 | ATCTCTTGCCAGCA TCATCCTGA | 1489 |
| AKT1.3 | NM_005163 | NM_005163.1 | AKT1 | 18 | CGCTTCTATGGCG CTGAGAT | 26 | TCCCGGTACACC ACGTTCTT | 758 | CAGCCCTGACTAC CTGCACTCGG | 1490 |
| AKT2.3 | NM_001626 | NM_001626.2 | AKT2 | 358 | TCCTGCCACCCTTC AAACC | 27 | GGCGGTAAATTC ATCATCGAA | 759 | CAGTCACGTCCGA GGTCGACACA | 1491 |
| AKT3.2 | NM_005465 | NM_005465.1 | AKT3 | 21 | TTGTCTCTGCCTTG GACTATCTACA | 28 | CCAGCATTAGAT TCTCCACTTGA | 760 | TCACGGTACACAATC TTTCCGGA | 1492 |
| ALDH4A1.2 | NM_003748 | NM_003748.2 | ALDH4A1 | 2092 | GGACAGGGTAAGA CCGTGAT | 29 | AACCGGAAGAAG TCGATGAG | 761 | CTGCAGCGTCAATCT CCGCTTG | 1493 |
| ALDH6A1.1 | NM_005589 | NM_005589.2 | ALDH6A1 | 6114 | GGCTCTTTCAACAG CAGTCC | 30 | GCATGCTCCACC AGCTCT | 762 | CAGCCACTTCTTGGC TTCTCCAC | 1494 |
| ALDOA.1 | NM_000034 | NM_000034.2 | ALDOA | 3810 | GCCTGTACGTGCC AGCTC | 31 | TCATCGGAGCTT GATCTCG | 763 | TGCCAGAGCCTCAA CTGTCTCTGC | 1495 |
| ALDOB.1 | NM_000035 | NM_000035.2 | ALDOB | 6321 | CCCTCTACCAGAAG GACAGC | 32 | TAACTTGATTCC CACCACGA | 764 | TCCCCTTTTCCTTGA GGATGTTTCTG | 1496 |
| ALOX12.1 | NM_000697 | NM_000697.1 | ALOX12 | 3861 | AGTTCCTCAATGGT GCCAAC | 33 | AGCAGTAGCCTG GAGGGC | 765 | CATGCTGTTGAGAC GCTCGACCTC | 1497 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| ALOX5.1 | NM_000698 | NM_000698.2 | ALOX5 | 4259 | GAGCTGCAGGACT TCGTGA | 34 | GAAGCCTGAGGA CTTGCG | 766 | CCGCATGCCGTACA CGTAGACATC | 1498 |
| AMACR1.1 | NM_014324 | NM_014324.4 | AMACR | 3930 | GGACAGTCAGTTTT AGGGTTGC | 35 | GACAGCCCAGAG ACCCAC | 767 | CAGTAACTCGGGGC CTGTTTCCC | 1499 |
| ANGPT1.1 | NM_001146 | NM_001146.3 | ANGPT1 | 2654 | TCTACTTGGGGTGA CAGTGC | 36 | CCTTTTTAAAGC CCGACAGT | 768 | TCACGTGGCTCGAC TATAGAAACTCCA | 1500 |
| ANGPT2.1 | NM_001147 | NM_001147.1 | ANGPT2 | 2655 | CCGTGAAAGTGC TCTGTAA | 37 | TTGCAGTGGGAA GAACAGTG | 769 | AAGCTGACACAGCC CTCCCAAGTG | 1501 |
| ANGPTL2.1 | NM_012098 | NM_012098.2 | ANGPTL2 | 3982 | GCCATCTGCGTCAA CTCC | 38 | TAGCTCCTGCTT ATGCACTCG | 770 | TCTCCAGAAGCACCT CAGGCTCCT | 1502 |
| ANGPTL3.3 | NM_014495 | NM_014495.2 | ANGPTL3 | 6505 | GTTGCGATTACTGG CAATGT | 39 | TGCTTTGTGATC CCAAGTAGA | 771 | CCAATGCAATCCCG GAAAACAAAG | 1503 |
| ANGPTL4.1 | NM_016109 | NM_016109.2 | | 3237 | ATGACCTCAGATGG AGGCTG | 40 | CCGGTTGAAGTC CACTGAG | 772 | CATCGTGGCGCCTC TGAATTACTG | 1504 |
| ANGPTL7.1 | NM_021146 | NM_021146.2 | ANGPTL7 | 6115 | CTGCACAGACTCCA ACCTCA | 41 | GCCATCCAGGTG CTTATTGT | 773 | TCACCCAGGCGGTA GTACACTCCA | 1505 |
| ANTXR1.1 | NM_032208 | NM_032208.1 | ANTXR1 | 3363 | CTCCAGTGTGTACCT CCAACC | 42 | GAGAAGGCTGG GAGACTCTG | 774 | AGCCTTCTCCCACAG CTGCCTACA | 1506 |
| ANXA1.2 | NM_000700 | NM_000700.1 | ANXA1 | 1907 | GCCCCTATCCTACC TTCAATCC | 43 | CCTTTACCCATTA TGGCCTTATGC | 775 | TCCTCGGATGTCGCT GCCT | 1507 |
| ANXA2.2 | NM_004039 | NM_004039.1 | ANXA2 | 2269 | CAAGACACTAAGG GCGACTACCA | 44 | CGTGTCGGGCTT CAGTCAT | 776 | CCCACCACCAGGTAC AGCAGCCT | 1508 |
| ANXA4.1 | NM_001153 | NM_001153.2 | ANXA4 | 3984 | TGGGAGGGATGAA GGAAAT | 45 | CTCATACAGGTC CTGGGCA | 777 | TGTCTCACGAGAGCA TCGTCCAGA | 1509 |
| ANXA5.1 | NM_001154 | NM_001154.2 | ANXA5 | 3785 | GCTCAAGCCTGA AGATGAC | 46 | AGAACCACCAAC ATCCGCT | 778 | AGTACCCTGAAGTGT CCCCACCA | 1510 |
| AP-1 (JUN officia$$ | NM_002228 | NM_002228.2 | JUN | 2157 | GACTGCAAAGATG GAAACGA | 47 | TAGCCATAAGGT CCGCTCTC | 779 | CTATGACGATGCCCT CAACGCCTC | 1511 |
| AP1M2.1 | NM_005498 | NM_005498.3 | AP1M2 | 5104 | ACAACGACCGCAC CATCT | 48 | CTGAGGCGGTAT GACATGAG | 780 | CTTCATCCCGCCTGA TGGTGACTT | 1512 |
| APAF1.2 | NM_181861 | NM_181861.1 | APAF1 | 4086 | CACAAGGAAGAAG CTGGTGA | 49 | CATCCTGTTCA CCTTTCAA | 781 | TGCAATTCAGCAGAA GCTCCAAA | 1513 |
| APC.4 | NM_000038 | NM_000038.1 | APC | 41 | GGACAGCAGGAAT GTGTTTC | 50 | ACCCACTCGATT TGTTTCTG | 782 | CATTGGCTCCCCGT GACCTGTA | 1514 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| APOC1.3 | NM_001645 | NM_001645.3 | APOC1 | 6608 | CCAGCCTGAATAAAG GTCCTG | 51 | CACTCTGAATCC TTGCTGGA | 783 | AGGACAGGACCTCC CAACCAAGC | 1515 |
| APOE.1 | NM_000041 | NM_000041.2 | APOE | 4340 | GCCTCAAGAGCTG GTTCG | 52 | CCTGCACCTTCT CCACCA | 784 | ACTGGCGCTGCATG TCTTCCAC | 1516 |
| APOL1.1 | NM_003661 | NM_003661.2 | APOL1 | 6117 | CGGACCAAGAACT GTGACC | 53 | ATTTTGTCCTGG CCCCTG | 785 | AGGCATATCTCTCCT GGTGCTGC | 1517 |
| APOLD1.1 | NM_030817 | NM_030817.1 | APOLD1 | 6118 | GAGCAGCTGAGT CTCGG | 54 | AGAGATTTGAG GTCGTGGC | 786 | CAGTCTCGACCAA GTCCAGTCGT | 1518 |
| AQP1.1 | NM_198098 | NM_198098.1 | AQP1 | 5294 | GCTTGCTGTATGAC CCCTG | 55 | AAGGCTGACCTC TCCCCTC | 787 | ACAGCCTTCCCTG CAATTGACCT | 1519 |
| AREG.2 | NM_001657 | NM_001657.1 | AREG | 87 | TGTGAGTGAAATGC CTTCTAGTAGTGA | 56 | TTGTGGTTCGTT ATCATACTCTTCT | 788 | CCGTCCTCGGAGC CGACTATGA | 1520 |
| ARF1.1 | NM_001658 | NM_001658.2 | ARF1 | 2776 | CAGTAGAGATCCC CGCAACT | 57 | ACAAGCACATGG CTATGGAA | 789 | CTTGTCCTTGGGTCA CCCTGCA | 1521 |
| ARG99.1 | NM_031920 | NM_031920.2 | | 3873 | GCATGGGCTACTG CATCC | 58 | CCACATCGATTC AGCCAAG | 790 | AGTTGCTCAGTCC GTGCACAAAA | 1522 |
| ARGHEF18.1 | NM_015318 | NM_015318.2 | ARHGEF18 | 3008 | ACTCTGCTTCCCAA GGGC | 59 | GAAGCTAGAGGC CCGCTC | 791 | CTGTTCACACGCTCA GCCTGTCTG | 1523 |
| ARHA.1 | NM_001664 | NM_001664.1 | RHOA | 2981 | GGTCCTCCGTCGG TTCTC | 60 | GTCGCAAACTCG GAGACG | 792 | CCACGGTCTGGTCTT CAGTCACCC | 1524 |
| ARHGDIB.1 | NM_001175 | NM_001175.4 | ARHGDIB | 3987 | TGGTCCCTAGAACA AGAGGC | 61 | TGATGGAGGATC AGAGGGAG | 793 | TAAAACCGGGCTTTC ACCCAACCT | 1525 |
| ARRB1.1 | NM_004041 | NM_004041.2 | ARRB1 | 2656 | TGCAGGAACGCCT CATCAA | 62 | GGTTTGGAGGGA TCTCAAAGG | 794 | CTGGGCGAGCACGC TTACCCTTTC | 1526 |
| ASS1.1 | NM_054012 | NM_054012.3 | ASS1 | 6328 | CCCCAGATAAAG GTCATTG | 63 | TGCGTACTCCAT CAGTCAT | 795 | TCTACAACCGGTTCA AGGGCCG | 1527 |
| ATP1A1.1 | NM_000701 | NM_000701.6 | ATP1A1 | 6119 | AGAACGCCCTATTTG GAGCTG | 64 | GGCAGAAAGAGG TGGCAG | 796 | ACCTAGGACTCGTTC TCCGAGGC | 1528 |
| ATP5E.1 | NM_006886 | NM_006886.2 | ATP5E | 3535 | CCGCTTTTCGCTACA GCAT | 65 | TGGGAGTATCGG ATGTAGCTG | 797 | TCCAGCCTGTCTCCA GTAGCCAC | 1529 |
| ATP6V1B1.1 | NM_001692 | NM_001692.3 | ATP6V1B1 | 6293 | AACCATGGGGAAC GTCTG | 66 | GGTGATGATCCG CTCGAT | 798 | CTTCCTGAACTTGGC CAATGACCC | 1530 |
| AXL.1 | NM_001699 | NM_001699.3 | AXL | 3989 | TTGCAGCCCTGTCT TCCTAC | 67 | CTGCACAGAGAA GGGGAGG | 799 | TATCCCACCTCCATC CCAGACAGG | 1531 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| AZU1.1 | NM_001700 | NM_001700.3 | AZU1 | 6120 | CCGAGGCCCTGACTTCTT | 68 | GTCCCGGGTTGTTGAGAA | 800 | CCATCGATCCAGTCTCGGAAGAGC | 1532 |
| B-Catenin.3 | NM_001904 | NM_001904.1 | CTNNB1 | 769 | GGCTCTTGTGCGTACTGTCCTT | 69 | TCAGATGACGAAGAGCACAGATG | 801 | AGGCTCAGTGATGTCTTCCCTGTCACCAG | 1533 |
| B2M.4 | NM_004048 | NM_004048.1 | B2M | 467 | GGGATCGAGACATGTAAGCA | 70 | TGGAATTCATCCAATCCAAAT | 802 | CGGCATCTTCAAACCTCCATGATG | 1534 |
| BAD.1 | NM_032989 | NM_032989.2 | BAD | 7209 | GGGTCAGGGGCCTCGAGAT | 71 | CTGCTCACTCGGCTCAAACTC | 803 | TGGGCCCAGAGCATGTTCCAGATC | 1535 |
| BAG1.2 | NM_004323 | NM_004323.2 | BAG1 | 478 | CGTTGTCAGCACACTTGGAATACAA | 72 | GTTCAACCTCTTCCTGTGGACTGT | 804 | CCCAATTAACATGACCCGGCAACCAT | 1536 |
| BAG2.1 | NM_004282 | NM_004282.2 | BAG2 | 2808 | CTAGGGGCAAAAAGCATGA | 73 | CTAAATGCCAAGGTGACTG | 805 | TTCCATGCCAGACAGGAAAAAGCA | 1537 |
| Bak.2 | NM_001188 | NM_001188.1 | BAK1 | 82 | CCATTCCCACCATTCTACCT | 74 | GGGAACATAGACCCACCAAT | 806 | ACACCCCAGACGTCCTGGCCT | 1538 |
| Bax.1 | NM_004324 | NM_004324.1 | BAX | 10 | CCGCCGTGGACACAGACT | 75 | TTGCCGTCAGAAAACATGTCA | 807 | TGCCACTCGGAAAAAGACCTCTGG | 1539 |
| BBC3.2 | NM_014417 | NM_014417.1 | BBC3 | 574 | CCTGGAGGGTCCTGTACAAT | 76 | CTAATTGGGCTCCATCTCG | 808 | CATCATGGGACTCCTGCCCTTACC | 1540 |
| Bcl2.2 | NM_000633 | NM_000633.1 | BCL2 | 61 | CAGATGACCTTGAGTACCCACTGAGA | 77 | CCTATGATTAAGGGCATTTTTCC | 809 | TTCCACGCCGAAGGACAGCGAT | 1541 |
| BCL2A1.1 | NM_004049 | NM_004049.2 | BCL2A1 | 6322 | CCAGCCTCCATGTATCATCA | 78 | TGAAGCTGTTGAGGCAATGT | 810 | CAGTCAAGCTCAGTGAGCATTCTCAGC | 1542 |
| BCL2L12.1 | NM_138639 | NM_138639.1 | BCL2L12 | 3364 | AACCCACCCCTGTCTTGG | 79 | CTCAGCTGACGGGAAAGG | 811 | TCCGGTAGCTCTCAAACTCGAGG | 1543 |
| Bclx.2 | NM_001191 | NM_001191.1 | BCL2L1 | 83 | CTTTTGTGGAACTCTATGGGAACA | 80 | CAGCGGTTGAAGCGTTCCT | 812 | TTCGGCTCTCGGCTGCTGCA | 1544 |
| BCRP.1 | NM_004827 | NM_004827.1 | ABCG2 | 364 | TGTACTGGCAAGAATATTTGGTAAA | 81 | GCCACGTGATTCTTCCACAA | 813 | CAGGGCATCGATCTCTCACCCTGG | 1545 |
| BFGF.3 | NM_007083 | NM_007083.1 | NUDT6 | 345 | CCAGGAAGAATGCTTAAGATGTGA | 82 | TGGTGATGGGAGTTGTATTTTCAG | 814 | TTCCGCCAGTCATTGAGATCCATCCA | 1546 |
| BGN.1 | NM_001711 | NM_001711.3 | BGN | 3391 | GAGCTCCGCAAGGATGAC | 83 | CTTTGTTGTTCACCAGGACGA | 815 | CAAGGGTCTCCAGCACCTCTACG | 1547 |
| BHLHB3.1 | NM_030762 | NM_030762.1 | BHLHE41 | 6121 | AGGAAGATCCCTCGCAGC | 84 | TTGAACCTCCGTCCTTCG | 816 | AGGAAGCTCCCTGAATCCTTGCGT | 1548 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| BIK.1 | NM_001197 | NM_001197.3 | BIK | 2281 | ATTCCTATGGCTCTGCAATTGTC | 85 | GGCAGGAGTGAATGGCTCTC | 817 | CCGTTAACTGTGGCCTGTGCCC | 1549 |
| BIN1.3 | NM_004305 | NM_004305.1 | BIN1 | 941 | CCTGCAAAAGGAACAAGAG | 86 | CGTGGTTGACTCTGATCTCG | 818 | CTTCGCCTCCAGATGGCTCCC | 1550 |
| BLR1.1 | NM_001716 | NM_001716.3 | CXCR5 | 6280 | GACCAAGCAGGAAGCTCAGA | 87 | AGCGCTGTTTCGGTCACTCAA | 819 | CCAGGGGCAGCTACCTGAACTCAA | 1551 |
| BNIP3.1 | NM_004052 | NM_004052.2 | BNIP3 | 3937 | CTGGACGGAGTAGCTCCAAG | 88 | GGTATCTTGTGGTGTCTGCG | 820 | CTTCACTGTGACAGCCCACCTCG | 1552 |
| BRCA1.1 | NM_007294 | NM_007294.3 | BRCA1 | 7481 | TCAGGGGCTAGAAATCTGT | 89 | CCATTCCAGTTGATCTGTGG | 821 | CTATGGGCCCTTCACCAACATGC | 1553 |
| BTRC.1 | NM_033637 | NM_033637.2 | BTRC | 2555 | GTTGGGACACAGTTGGTCTG | 90 | TGAAGCAGTCAGTTGTGCTG | 822 | CAGTCGGCGCCAGGACGGTCTACT | 1554 |
| BUB1.1 | NM_004336 | NM_004336.1 | BUB1 | 1647 | CCGAGGTTAATCCAGCACGTA | 91 | AAGACATGGCGCTCTCAGTTC | 823 | TGCTGGGAGCCTACACTTGGCCC | 1555 |
| BUB3.1 | NM_004725 | NM_004725.1 | BUB3 | 3016 | CTGAAGCAGATGGTTCATCATT | 92 | GCTGATTCCCAAGAGTCTAACC | 824 | CCTCGCTTTGTTTAACAGCCCAGG | 1556 |
| c-kit.2 | NM_000222 | NM_000222.1 | KIT | 50 | GAGGCAACTGCTTATGGCTTAATTA | 93 | GGCACTCGGCTTGAGCAT | 825 | TTACAGCGACAGTCATGGCCGCAT | 1557 |
| C13orf15.1 | NM_014059 | NM_014059.2 | C13orf15 | 6122 | TAGAATCTGCTGCCAGAGGG | 94 | CAAGGGCTGATTTTAAGGTGA | 826 | TGCACTCAACCTTCTACCAGGCCA | 1558 |
| C1QA.1 | NM_015991 | NM_015991.2 | C1QA | 6123 | CGGTCATCACCAACCAGG | 95 | CGGGTACAGTGCAGACGA | 827 | AGAACCGTACCAGAACCACTCCGG | 1559 |
| C1QB.1 | NM_000491 | NM_000491.3 | C1QB | 6124 | CCAGTGGCCTCACAGGAC | 96 | CCCATGGGATCTTCATCATC | 828 | TCCCAGGAGGCGTCTGACACAGTA | 1560 |
| C20orf1.1 | NM_012112 | NM_012112.2 | TPX2 | 1239 | TCAGCTGTGAGCTGCGGATA | 97 | ACGGTCCTAGTTTGAGGTTAAGA | 829 | CAGTCCCATTGCCGGGCG | 1561 |
| C3.1 | NM_000064 | NM_000064.2 | C3 | 6125 | CGTGAAGGAGTGCAGAAAGA | 98 | ACTCGGTGTCCGGGACTT | 830 | ACATCCCACCTGCAGACCTCAGTG | 1562 |
| C3AR1.1 | NM_004054 | NM_004054.2 | C3AR1 | 6126 | AAGCCGCATCCCAGACTT | 99 | TGTTAAGTGCCCTTGCTGG | 831 | CAACCCCAGAGATTCCGATTCAG | 1563 |
| C7.1 | NM_000587 | NM_000587.2 | C7 | 6127 | ATGTCTGAGTGTGAGGCGG | 100 | AGGCCTTATGCTGGTGACAG | 832 | ATGTCTGCCCTCTGCATCTCAGA | 1564 |
| CA12.1 | NM_001218 | NM_001218.3 | CA12 | 6128 | CTCTCTGAAGTGTCCTGGC | 101 | ACAGGACTGAGGGTGCT | 833 | AGACCACCAGTGCTTCTCCAGGGCT | 1565 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| CA2.1 | NM_000067 | NM_000067.1 | CA2 | 5189 | CAACGTGGAGTTTGATGACTCT | 101 | CTGTAAGTGCCATCCAGGG | 834 | CCTCCCTTGAGCACTGCTTTGTCC | 1566 |
| CA9.3 | NM_001216 | NM_001216.1 | CA9 | 482 | ATCCTAGCCCTGGTTTTGG | 102 | CTGCCTTCATCTGCACAA | 835 | TTTGCTGTCACCAGCGTCGC | 1567 |
| CACNA2D1.1 | NM_000722 | NM_000722.2 | CACNA2D1 | 6129 | CAAACATTAGCTGGGCCTGT | 103 | CAGCCAGTGGGTGCCTTA | 836 | CCATGGCATAACACTAAGGCGCAG | 1568 |
| CALD1.2 | NM_004342 | NM_004342.4 | CALD1 | 1795 | CACTAAGGTTTGAGACAGTTCCAGAA | 104 | GCGAATTAGCCCTCTACAACTGA | 837 | AACCCAAGCTCAAGACGCAGGACGAG | 1569 |
| CASP1.1 | NM_033292 | NM_033292.2 | CASP1 | 6132 | AGAAAGCCCACATAGAGAGGA | 105 | TGTGGGATGTCTCCAAGAAA | 838 | CGCTTTCTGCTCTTCCACACCAGA | 1570 |
| CASP10.1 | NM_001230 | NM_001230.4 | CASP10 | 6133 | ACCTTTCTCTCTTGGCCGGAT | 106 | GTGGGGACTGTCCACTGC | 839 | TCTACTGCATCTGCCAGCCCTGAG | 1571 |
| CASP6.1 | NM_032992 | NM_032992.2 | CASP6 | 6134 | CCTCACACTGGTGAACAGGA | 107 | AATTGCACTTGGGTCTTTGC | 840 | AAAGTCCACTCGGCGCTGAGAAAC | 1572 |
| Caspase 3.1 | NM_032991 | NM_032991.2 | CASP3 | 5963 | TGAGCTGAGCAGAGACATGA | 108 | CCTTCCTGCGTGGTCCAT | 841 | TCAGCCTCTTCCATGAAGCAGAGC | 1573 |
| CAT.1 | NM_001752 | NM_001752.1 | CAT | 2745 | ATCCATTGCGATCTCACCAAGGT | 109 | TCCGGTTTAAGACCAGTTTACCA | 842 | TGGCCTCACAAGGACTACCCTCTCATCC | 1574 |
| CAV1.1 | NM_001753 | NM_001753.3 | CAV1 | 2557 | GTGGCTCAACATTGTGTTCC | 110 | CAATGGGCCTCCATTTTACAG | 843 | ATTTCAGCTGATCAGTGGGCTCC | 1575 |
| CAV2.1 | NM_198212 | NM_198212.1 | CAV2 | 6460 | CTTCCCTGGGACGACTTG | 111 | TTCCTGGTCACCCTTCTGG | 844 | CCCGTACTGTCATGCCTCAGAGCT | 1576 |
| CCL18.1 | NM_002988 | NM_002988.2 | CCL18 | 3994 | GCTCCTGTGCACAAGTTGG | 112 | TGGAATCTGCCAGGAGGTA | 845 | CAACAAAGAGCTCTGCTGCCTCGT | 1577 |
| CCL19.1 | NM_006274 | NM_006274.2 | CCL19 | 4107 | GAACGCATCATCCAGAGACTG | 113 | CCTCTGCACGGTCATAGGTT | 846 | CGCTTCATCTTGGCTGAGGCCTC | 1578 |
| CCL20.1 | NM_004591 | NM_004591.1 | CCL20 | 1998 | CCATGTGCTGTACCAAGAGTTTG | 114 | CGCCGCGAGGTGGAGTA | 847 | CAGCACTGACATCAAAGCACCAGGA | 1579 |
| CCL4.2 | NM_002984 | NM_002984.1 | CCL4 | 4148 | GGGTCCAGGAGTACGTGTATGAC | 115 | CCTTCCCTGAAGACTTCCTGTCT | 848 | ACTGAACTGAGCTGCTCA | 1580 |
| CCL5.2 | NM_002985 | NM_002985.2 | CCL5 | 4088 | AGGTTCTGAGCTCTGGCTTT | 116 | ATGCTGACTTCCTTCCTGGT | 849 | ACAGAGCCCTGGCAAAGCCAAG | 1581 |
| CCNB1.2 | NM_031966 | NM_031966.1 | CCNB1 | 619 | TTCAGGTTGTTGCAGGAGAC | 117 | CATCTTCTTGGGCACACAAT | 850 | TGTCTCCATTATTGATCGGTTCATGCA | 1582 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| CCND1.3 | NM_053056 | NM_001758.1 | CCND1 | 88 | GCATGTTCGTGGC CTCTAAGA | 119 | CGGTGTAGATGC ACAGCTTCTC | 851 | AAGAGACCATCCC CCTGACGGC | 1583 |
| CCNE1.1 | NM_001238 | NM_001238.1 | CCNE1 | 498 | AAAGAAGATGATGA CCGGGTTTAC | 120 | GAGCCTCTGGAT GGTGCAAT | 852 | CAAACTCAACGTGCA AGCCTCGA | 1584 |
| CCNE2 variant 1 | NM_057749 | NM_057749var1 | CCNE2 | 1650 | GGTCACCAAGAAAC ATCAGTATGAA | 121 | TTCAATGATAATG CAAGGACTGATC | 853 | CCCAGATAATACAGG TGGCCAACATTCCT | 1585 |
| CCNE2.2 | NM_057749 | NM_057749.1 | CCNE2 | 502 | ATGCTGTGGCTCCT TCCTAACT | 122 | ACCCAAATTGTG ATATACAAAAAG GTT | 854 | TACCAAGCAACCTAC ATGTCAAGAAGCCC | 1586 |
| CCR1.1 | NM_001295 | NM_001295.2 | CCR1 | 6135 | TCCAAGACCCAATG GGAA | 123 | TCGTAGGCTTTC GTGAGGA | 855 | ACTTCACCACCTGC AGCCTTCAC | 1587 |
| CCR2.1 | NM_000648 | NM_000648.1 | | 4109 | CTCGGGAATCCTG AAAACC | 124 | GACTCTCACTGC CCTATGCC | 856 | TCTTCTCGTTTCGAC ACCGAAGCA | 1588 |
| CCR4.2 | NM_005508 | NM_005508.4 | CCR4 | 6502 | AGACCCTGGTGGA GCTAGAA | 125 | AGAGTTCTGTG GCCTGGAT | 857 | TCCTTCAGGACTGCA CCTTTGAAAGA | 1589 |
| CCR5.1 | NM_000579 | NM_000579.1 | CCR5 | 4119 | CAGACTGAATGGG GGTGG | 126 | CTGGTTTGTCTG GAGAAGGC | 858 | TGGAATAAGTACCTA AGGCGCCCC | 1590 |
| CCR7.1 | NM_001838 | NM_001838.2 | CCR7 | 2661 | GGATGACATGCACT CAGCTC | 127 | CCTGACATTTCC CTTGTCCT | 859 | CTCCCATCCCAGTG GAGCCAA | 1591 |
| CD105.1 | NM_000118 | NM_000118.1 | ENG | 486 | GCAGGTGTCAGCA AGTATGATCAG | 128 | TTTTTCCCTGT GGTGATGA | 860 | CGACAGGATATTGAC CACCGCCTCATT | 1592 |
| CD14.1 | NM_000591 | NM_000591.1 | CD14 | 4341 | GTGTGCTAGCGTA CTCCCG | 129 | GCATGGTGCCG GTTATCT | 861 | CAAGGAACTGACGC TCGAGGACCT | 1593 |
| CD18.2 | NM_000211 | NM_000211.1 | ITGB2 | 49 | CGTCAGGACCCAC CATGTCT | 130 | GGTTAATTGGTG ACATCCTCAAGA | 862 | CGCGGCCGAGACAT GGCTTG | 1594 |
| CD1A.1 | NM_001763 | NM_001763.1 | CD1A | 4166 | GGAGTGGAAGGAA CTGGAAA | 131 | TCATGGGCGTAT CTACGAAT | 863 | CGCACCATTCGGTCA TTTGAGG | 1595 |
| CD24.1 | NM_013230 | NM_013230.1 | CD24 | 2364 | TCCAACTAATGCCA CCACCA | 132 | GAGAGAGTGAGA CCACGAAGAGACT | 864 | CTGTTGACTGCAGG GCACCACA | 1596 |
| CD274.2 | NM_014143 | NM_014143.2 | CD274 | 4076 | GCTCATGATCAG CTATGGT | 133 | TGTTGTATGGGG CATTGACT | 865 | CACAGTAATTCGCTT GTAGTCGGCACC | 1597 |
| CD31.3 | NM_000442 | NM_000442.1 | PECAM1 | 485 | TGTATTTCAAGACC TCTGTGCACTT | 134 | TTAGCCTGAGGA ATTGCTGTGTT | 866 | TTTATGAACCTGCCC TGCTCCCACA | 1598 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| CD34.1 | NM_001773 | NM_001773.1 | CD34 | 3814 | CCACTGCACACCTCAGA | 135 | CAGGAGTTTACCTGCCCT | 867 | CTGTTCTTGGGGCCCTACACCTTG | 1599 |
| CD36.1 | NM_000072 | NM_000072.2 | CD36 | 6138 | GTAACCCAGGACGCTGAGG | 136 | AAGGTTCGAAGATGGCACC | 868 | CACAGTCTCTTTCCTGCAGCCCAA | 1600 |
| CD3z.1 | NM_000734 | NM_000734.1 | CD247 | 64 | AGATGAAGTGGAAGGCGCTT | 137 | TGCCTCTGTAATCGGCAACTG | 869 | CACCGCGGCCATCCTGCA | 1601 |
| CD4.1 | NM_000616 | NM_000616.2 | CD4 | 4168 | GTGCTGGAGTCGGGACTAAC | 138 | TCCCTGCATTCAAGAGGC | 870 | CAGGTCCCTTGTCCCAAGTTCCAC | 1602 |
| CD44.1 | NM_000610 | NM_000610.3 | CD44 | 4267 | GGCACCACTGCTTATGAAGG | 139 | GATGCTCATGGTGAATGAGG | 871 | ACTCGAACCCAGAGCACCCTC | 1603 |
| CD44s.1 | M59040 | M59040.1 | | 1090 | GACGAGACAGTCCCTGGAT | 140 | ACTGGGGTGGAATGTGTCTT | 872 | CACCGACAGCACAGACAGAATCCC | 1604 |
| CD44v6.1 | AJ251595v6 | AJ251595v6 | | 1061 | CTCATACCAGCCATCCAATG | 141 | TTGGGTTGAAGAAATCAGTCC | 873 | CACCAAGCCCAGAGGACAGTTCCT | 1605 |
| CD53.1 | NM_000560 | NM_000560.3 | CD53 | 6139 | CGACAGCATCCACCGTTAC | 142 | TGCAGAAATGACTGGATGGA | 874 | CACGCTGCCTTGGTGCTATTGTCT | 1606 |
| CD68.2 | NM_001251 | NM_001251.1 | CD68 | 84 | TGGTTCCCAGCCCTGTGT | 143 | CTCCTCCACCCTGGGTTGT | 875 | CTCCAAGCCCAGATTCAGATTCGAGTCA | 1607 |
| CD82.2 | NM_002231 | NM_002231.2 | CD82 | 316 | GTGCAGGCTCAGGTGAAGTG | 144 | GACCTCCAGGGCGATTCATGA | 876 | TCAGCTTCTACAACTGGACAGACAACGCTG | 1608 |
| CD8A.1 | NM_171827 | NM_171827.1 | CD8A | 3804 | AGGGTGAGGTGCTTGAGTCT | 145 | GGGCACAGTATCCCAGGTA | 877 | CCAACGGCAAGGAACAAGTACTTCT | 1609 |
| CD99.1 | NM_002414 | NM_002414.3 | CD99 | 6323 | GTTCCTCCGGTAGCTTTTCA | 146 | ACCATCACTGCCTCCTTTTC | 878 | TCCACCTGAAACGCCATCCG | 1610 |
| cdc25A.4 | NM_001789 | NM_001789.1 | CDC25A | 90 | TCTTGCTGGCTACGCCTCTT | 147 | CTGCATTGTGGCACAGTTCTG | 879 | TGTCCCTGTTAGACGTCCTCCGTCCATA | 1611 |
| CDC25B.1 | NM_021873 | NM_021874.1 | CDC25B | 389 | AAACAGACAGTTTGCCATCAG | 148 | GTTGGTGATGTTCCGAAGCA | 880 | CCTTCACCGGCATAGACTGGAAGCG | 1612 |
| CDH1.3 | NM_004360 | NM_004360.2 | CDH1 | 11 | TGAGTGTCCCCGGTATCTTC | 149 | CAGCCGCTTTCAGATTTTCAT | 881 | TGCCAATCCCGATGAAATTGGAAATTT | 1613 |
| CDH13.1 | NM_001257 | NM_001257.3 | CDH13 | 6140 | GCTACTTCTCCACTGTCCCG | 150 | CCTCTCTGTGGACCTGCCT | 882 | AGTCTGAATGCTGCCACAACCAGC | 1614 |
| CDH16.1 | NM_004062 | NM_004062.2 | CDH16 | 4529 | GACTGTCTCGAATGGCCCAG | 151 | CCAGGGGACTCAGATGGA | 883 | CAGAGGCCAAGCTCCCAGCTAGAG | 1615 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| CDH2.1 | NM_001792 | NM_001792.2 | CDH2 | 3965 | TGACCGATAAGGATCAACCC | 152 | GATCTCCGCCACTGATTCTG | 884 | ATACACCAGCCTGAACGCAGTGT | 1616 |
| CDH5.1 | NM_001795 | NM_001795.2 | CDH5 | 6142 | ACAGGAGACGTGTTCGCC | 153 | CAGCAGTGAGGTGGTACTCTGA | 885 | TATTCTCCGGTCCAGCCTCTCAA | 1617 |
| CDH6.1 | NM_004932 | NM_004932.2 | CDH6 | 3998 | ACACAGGCGACATACAGGC | 154 | CTCGAAGGATGTAAACGGGT | 886 | TTTCTTCCCTGTCCAGCCTCTTGG | 1618 |
| CDK4.1 | NM_000075 | NM_000075.2 | CDK4 | 4176 | CCTTCCCATCAGCACAGTTC | 155 | TTGGGATGCTCAAAAGCC | 887 | CCAGTCGCCTCAGTAAAGCCACCT | 1619 |
| CDK6.1 | NM_001259 | NM_001259.5 | CDK6 | 6143 | AGTGCCCTGTCTCACCCA | 156 | GCAGGTGGGAATCCAGGT | 888 | TCTTTGCACCTTTCCAGGTCCTGG | 1620 |
| CDKN2A.2 | NM_000077 | NM_000077.3 | CDKN2A | 4278 | AGCACTTCACGCCCTAAGC | 157 | TCATGAGTCGACAGCTTCC | 889 | CGCAAGAAATGCCCACATGAATGT | 1621 |
| CEACAM1.1 | NM_001712 | NM_001712.2 | CEACAM1 | 2577 | ACTTGCCTGTTCAGAGCACTCA | 158 | TGGCAAATCCGAATTAGAGTGA | 890 | TCCTTCCACCCCCAGTCCTGTC | 1622 |
| CEBPA.1 | NM_004364 | NM_004364.2 | CEBPA | 2961 | TTGGTTTTGCTCGGATACTTG | 159 | GTCTCAGACCCTTCCCCC | 891 | AAAATGAGACTCTCCGTCGGCAGC | 1623 |
| CENPF.1 | NM_016343 | NM_016343.2 | CENPF | 3251 | CTCCCGTCAACAGCGTTC | 160 | GGGTGAGTCTGGCCTTCA | 892 | ACACTGGACCAGGAGTGCATCCAG | 1624 |
| CFLAR.1 | NM_003879 | NM_003879.3 | CFLAR | 6144 | GGACTTTTGTGTCCAGTGACAG | 161 | CGGCGCTTCTCTCCTACA | 893 | CTCCTCCCGTGGTCCTTGTGTCT | 1625 |
| CGA (CHGA offi$$ | NM_001275 | NM_001275.2 | CHGA | 1132 | CTGAAGGAGCTCCAAGACCT | 162 | CAAAACCGCTGTGTTTCTTC | 894 | TGTTGATGTGCCCTCTCCTTGG | 1626 |
| Chk1.2 | NM_001274 | NM_001274.1 | CHEK1 | 490 | GATAAATTGGTACAAGGGATCAGCTT | 163 | GGGTGCCAAGTAACTGACTATTCA | 895 | CCAGCCCACATGTCCTGATCATATGC | 1627 |
| Chk2.3 | NM_007194 | NM_007194.1 | CHEK2 | 494 | ATGTGAACCCCCACCTACTT | 164 | CAGTCCACAGCACGGTTATACC | 896 | AGTCCAACAGAGAAACAAGAACTTCAGGCG | 1628 |
| cIAP1.2 | NM_001166 | NM_001166.2 | BIRC2 | 326 | TGCCTGTGGTGGGAAGCT | 165 | GGAAAAATGCCTCCGGTGTT | 897 | TGACATAGCATCATCCTTTGGTTCCCAGTT | 1629 |
| cIAP2.2 | NM_001165 | NM_001165.2 | BIRC3 | 79 | GGATATTTCCGTGGCTCTTATTCA | 166 | CTTCCATCATCAAGGCAGAAAATCTT | 898 | TCTCCATCAAATCCTGTAAACTCCAGAGCA | 1630 |
| CLCNKB.1 | NM_000085 | NM_000085.1 | CLCNKB | 4308 | GTGACCCTGAAGCTGTCCC | 167 | GGTTCAACAGCTCAAAGAGGTT | 899 | AGAGACTTCCCTGCATGAGGCACA | 1631 |
| CLDN10.1 | NM_182848 | NM_182848.2 | CLDN10 | 6145 | GGTCTGTGGATGAACTGCG | 168 | GATAGTAAAATGCGTCGGC | 900 | TGGAAAGAACCCAACGCGTTACCT | 1632 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| CLDN7.2 | NM_001307 | NM_001307.3 | CLDN7 | 2287 | GGTCTGCCCTAGTCATCCTG | 169 | GTACCCAGCCTTGCTCTCAT | 901 | TGCACTGCTCTCCTGTTCCTGTCC | 1633 |
| CLU.3 | NM_001831 | NM_001831.1 | CLU | 2047 | CCCCAGATACCTACCACTACCT | 170 | TGCGGGACTTGGGAAAGA | 902 | CCCTTCAGCCTGCCCCACCG | 1634 |
| cMet.2 | NM_000245 | NM_000245.1 | MET | 52 | GACATTTCCAGTCCTGCAGTCA | 171 | CTCCGATCGCACACATTTGT | 903 | TGCCTCTCTGCCCCACCCTTTGT | 1635 |
| cMYC.3 | NM_002467 | NM_002467.1 | MYC | 45 | TCCCTCCACTCGGAAGGACTA | 172 | CGGTTGTTGCTGATCTGTCTCA | 904 | TCTGACACTGTCAACTTGACCCTCTT | 1636 |
| COL18A1.1 | NM_030582 | NM_030582.3 | COL18A1 | 6146 | AGCTGCCATCACGCCTAC | 173 | GTTGGCTACTTGGAGGCAGTC | 905 | CGTGCTCTGCATTGAGAACAGCTTC | 1637 |
| COL1A1.1 | NM_000088 | NM_000088.2 | COL1A1 | 1726 | GTGGCCATCCAGCTGACC | 174 | CAGTGGTAGGTGATGTTCTGGGA | 906 | TCCTGCGCTGATGTCCACCG | 1638 |
| COL1A2.1 | NM_000089 | NM_000089.2 | COL1A2 | 1727 | CAGCCAAGAACTGGTATAGGAGCT | 175 | AAACTGCTGCCAGCATTG | 907 | TCTCCTAGCCAGACGTGTTTCTTGTCCTTG | 1639 |
| COL4A1.1 | NM_001845 | NM_001845.4 | COL4A1 | 6147 | ACAAAGGCCTCCCAGGAT | 176 | GAGTCCCAGGAAGACCTGCT | 908 | CTCCTTTGACACCAGGGATGCCAT | 1640 |
| COL4A2.1 | NM_001846 | NM_001846.2 | COL4A2 | 6148 | CAACCCTGGTGATGTCTGC | 177 | CGCAGTGTGTAGAGAGCCAGT | 909 | ACTATGCCAGCCGGAACGACAAGT | 1641 |
| COL5A2.2 | NM_000393 | NM_000393.3 | COL5A2 | 6653 | GGTCGAGGAACCCAAGGT | 178 | GCCTGGGAGGTCCAACTCTG | 910 | CCAGGAAATCCTGTAGCACCAGGC | 1642 |
| COL7A1.1 | NM_000094 | NM_000094.2 | COL7A1 | 4984 | GGTGACAAAGGACCTCGG | 179 | ACCAGGCTCTCCCTTGCT | 911 | CTTGTCACCAGGGTCCCATTGTC | 1643 |
| COX2.1 | NM_000963 | NM_000963.1 | PTGS2 | 71 | TCTGCAGAGTTGGAAGCACTCTA | 180 | GCCGAGGCTTTTCTACCAGAA | 912 | CAGGATACAGCTCCACAGCATCGATGTC | 1644 |
| CP.1 | NM_000096 | NM_000096.1 | CP | 3244 | CGTGAGTACACAGATGCCT | 181 | CCAGGATGCCAAGATGCT | 913 | TCTTCAGGGCCTCTCTCCTTTCGA | 1645 |
| CPB2.1 | NM_001872 | NM_001872.3 | CPB2 | 6294 | GGCACATACGGATTCTTGCT | 182 | CAGCGGCAAAAGCTTCTCTA | 914 | CGGAGCGTTACATCAAACCCACCT | 1646 |
| CRADD.1 | NM_003805 | NM_003805.3 | CRADD | 6149 | GATGTGCCTCCAGCAAC | 183 | GAGTGAAAGTCAGGATTCAGCC | 915 | CATGACTCAGGGACACACTCCCCA | 1647 |
| cripto (TDGF1 of | NM_003212 | NM_003212.1 | TDGF1 | 1096 | GGGTCTGTGCCCCATGAC | 184 | TGACCGTGCCAGCATTTACA | 916 | CCTGGCTGCCAAGAAGTGTTCCCT | 1648 |
| CRP.1 | NM_000567 | NM_000567.2 | CRP | 4187 | GACGTGAACCACAGGGTGT | 185 | CTCCAGATAGGGAGTGTGGG | 917 | CTGTCAGGAGGAGCCCATCTCCCAT | 1649 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| CSF1.1 | NM_000757 | NM_000757.3 | CSF1 | 510 | TGCAGCGGCTGATTGACA | 186 | CAACTGTTCCTGGTCTACAAACTCA | 918 | TCAGATGAGACCTCGTGCCAAATTACA | 1650 |
| CSF1R.2 | NM_005211 | NM_005211.1 | CSF1R | 2289 | GAGCAACAACCAAACCTACGA | 187 | CCTGCAGAGATGGGTATGAA | 919 | AGCCACTCCCCACGCTGTTGT | 1651 |
| CSF2.1 | NM_000758 | NM_000758.2 | CSF2 | 2779 | GAACCTGAAGGACTTTCTGCTTGT | 188 | CTCATCTGGCCGGTCTCACT | 920 | ATCCCCTTTGACTGCTGGGAGCCAG | 1652 |
| CSF2RA.2 | NM_006140 | NM_006140.3 | CSF2RA | 4477 | TACCACACCCAGCATTCCTC | 189 | CTAGAGGCTGGTGCCACTGT | 921 | CGCAGATCCGATTTCTCTGGGATC | 1653 |
| CSF3.2 | NM_000759 | NM_000759.1 | CSF3 | 377 | CCCAGGCCTCTGTGTCCTT | 190 | GGAGGACAGGAGCTTTTTCTCA | 922 | TGCATTTCTGAGTTTCATTCTCCTGCCTG | 1654 |
| CTGF.1 | NM_001901 | NM_001901.1 | CTGF | 2153 | GAGTTCAAGTGCCCTGACG | 191 | AGTTGTAATGGCAGCACAG | 923 | AACATCATGTTCTTCTTCATGACCTCGC | 1655 |
| CTSB.1 | NM_001908 | NM_001908.1 | CTSB | 382 | GGCCGAGATCTACAAAAACG | 192 | GCAGGAAGTCCGAATACACA | 924 | CCCCGTGGAGGAGCTTTCTC | 1656 |
| CTSD.2 | NM_001909 | NM_001909.1 | CTSD | 385 | GTACATGATCCCCTGTGAGAAGGT | 193 | GGGACAGCTTGTAGCCTTTGC | 925 | ACCCTGCCCGCGATCACACTGA | 1657 |
| CTSH.2 | NM_004390 | NM_004390.1 | CTSH | 845 | GCAAGTTCCAACCTGGAAAG | 194 | CATCGCTTCCTCGTCATAGA | 926 | TGGTACATCCTTGACAAAGCCGA | 1658 |
| CTSL1.2 | NM_001912 | NM_001912.1 | CTSL1 | 446 | GGGAGGCTTATCTCACTGAGTGA | 195 | CCATTGCAGCCTTCATTGC | 927 | TTGAGGCCCAGAGCAGTTACCAGATTCT | 1659 |
| CTSL2.1 | NM_001333 | NM_001333.2 | CTSL2 | 1667 | TGTCTCACTGAGCGAGCAGAA | 196 | ACCATTGCAGCCCTGATTG | 928 | CTTGAGGACGCGAACAGTCCACCA | 1660 |
| CTSS.1 | NM_004079 | NM_004079.3 | CTSS | 1799 | TGACAACGGCTTTCCAGTACAT | 197 | TCCATGGCTTTGTAGGGATAGG | 929 | TGATAACAAGGGCATCGACTCAGACGCT | 1661 |
| CUBN.1 | NM_001081 | NM_001081.2 | CUBN | 4110 | GAGGCCGTTACTGTGGCA | 198 | GAATCTTCAGCGTCAGGGC | 930 | TGCCCCATCCTATCACATCCTTCA | 1662 |
| CUL1.1 | NM_003592 | NM_003592.2 | CUL1 | 1889 | ATGCCCTGGTAATGTCTGCAT | 199 | GCCACCACAAGCCTTATCAAG | 931 | CAGCCACAAAGCCAGCGTCATTGT | 1663 |
| CUL4A.1 | NM_003589 | NM_003589.1 | CUL4A | 2780 | AAGCATCTTCCTGTTCTTGGA | 200 | AATCCATATCCCAGATGGA | 932 | TATGTGCTGCAGAACTCCACGCTG | 1664 |
| CX3CL1.1 | NM_002996 | NM_002996.3 | CX3CL1 | 6150 | GACCCTTGCCGTCTACCTG | 201 | GGAGTGTTCCTAGCACCTGG | 933 | TAGAACCCAGCCCATAAGAGGCCC | 1665 |
| CX3CR1.1 | NM_001337 | NM_001337.3 | CX3CR1 | 4507 | TTCCCAGTTGTGACATGAGG | 202 | GCTAAATGCAACCGTCTCAGT | 934 | ACTGAGGGCCAGCCTCAGATCCT | 1666 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| CXCL10.1 | NM_001565 | NM_001565.1 | CXCL10 | 2733 | GGAGCAAAATCGAT GCAGT | 203 | TAGGGAAGTGAT GGGAGAGG | 935 | TCTGTGTGTCCATC CTTGGAAGC | 1667 |
| CXCL12.1 | NM_000609 | NM_000609.3 | CXCL12 | 2949 | GAGCTACAGATGC CCATGC | 204 | TTTGAGATGCTT GACGTTGG | 936 | TTCTTCGAAAGCCAT GTTGCCAGA | 1668 |
| CXCL14.1 | NM_004887 | NM_004887.3 | CXCL14 | 3247 | TGCGCCCTTTCCTC TGTA | 205 | CAATGCGCACATA TACTGGG | 937 | TACCCTTAAGAACGC CCCTCCAC | 1669 |
| CXCL9.1 | NM_002416 | NM_002416.1 | CXCL9 | 5191 | ACCAGACCATTGTC TCAGAGC | 206 | GTTACCAGAGGC TAGCCAACA | 938 | TGTGGCTCTTTCCT GGCTACTCC | 1670 |
| CXCR4.3 | NM_003467 | NM_003467.1 | CXCR4 | 2139 | TGACCGCTTCTACC CCAATG | 207 | AGGATAAGGCCA ACCATGATGT | 939 | CTGAAACTGGAACAC AACCACCACAAG | 1671 |
| CXCR6.1 | NM_006564 | NM_006564.1 | CXCR6 | 4002 | CAGAGCCTGACGG ATGTGT | 208 | GCAGAGTGCAGA CAAACACC | 940 | CTGGTGAACCTACCC CTGGCTGAC | 1672 |
| CYP2C8.2 | NM_000770 | NM_000770.2 | CYP2C8 | 505 | CCGTGTTCAAGAG GAAGCTC | 209 | AGTGGGATCACA GGGTGAAG | 941 | TTTTCTCAACTCCTC CACAAGGCA | 1673 |
| CYP2C8v2.1 | NM_030878 | NM_030878.1 | | 5423 | GCTGTAGTGCACG AGATCCA | 210 | CAGTGGTCACTG CATGGG | 942 | ATACAGTGACCTTGT CCCCACCGG | 1674 |
| CYP3A4.2 | NM_017460 | NM_017460.3 | CYP3A4 | 586 | AGAACAAGGACAAC ATAGATCCTTACAT AT | 211 | GCAAACCTCATG CCAATGC | 943 | CACACCCTTTGGAAG TGGACCCGAAA | 1675 |
| CYR61.1 | NM_001554 | NM_001554.3 | CYR61 | 2752 | TGCTCATTCTTGAG GAGCAT | 212 | GTGGCTGCATTA GTGTCCAT | 944 | CAGCACCCTTGGCA GTTTCGAAAT | 1676 |
| DAG1.1 | NM_004393 | NM_004393.2 | DAG1 | 5968 | GTGACTGGGCTCA TGCCT | 213 | ATCCCACTTGTG CTCCTGTC | 945 | CAAGTCAGAGTTTCC CTGGTGCC | 1677 |
| DAPK1.3 | NM_004938 | NM_004938.1 | DAPK1 | 636 | CGCTGACATCATGA ATGTTCCT | 214 | TCTCTTTCAGCA ACCATGTGTCTT | 946 | TCATATCCAAACTCG CCTCCAGCCG | 1678 |
| DCBLD2.1 | NM_080927 | NM_080927.3 | DCBLD2 | 3821 | TCACCAGGGCAGG AAGTTTA | 215 | GGTTGCATACTC AGGCCC | 947 | CATGCCTATGCTGAA CCACTCCA | 1679 |
| DCC.3 | NM_005215 | NM_005215.1 | DCC | 3763 | AAATGTCCTCCTCG ACTGCT | 216 | TGAATGCCATCT TTCTTCCA | 948 | ATCACTGGAACTCCT CGGTCGGAC | 1680 |
| DCN.1 | NM_001920 | NM_001920.3 | DCN | 6151 | GAAGGCCACTATCA TCCTCCT | 217 | GCCTCTCTGTTG AAACGGTC | 949 | CTGCTTGCACAAGTT TCCTGGGCT | 1681 |
| DCXR.1 | NM_016286 | NM_016286.2 | DCXR | 6311 | CCATAGCGTCTACT GCTCCA | 218 | AGTCTCAGGGCC ATCACCT | 950 | TCAGCATGTCCAAGG GCACCC | 1682 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| DDC.1 | NM_000790 | NM_000790.3 | DDC | 5411 | CAGAGCCCAGACACCATGA | 219 | CCACGTAATCCACCATCTCC | 951 | CCTCTCCTTCGGAATTCACTTGCG | 1683 |
| DEFB1.1 | NM_005218 | NM_005218.3 | DEFB1 | 4124 | GATGGCCTCAGTGGTAACT | 220 | TGCTGACGCAATTGTAATGAT | 952 | CTCACAGGCCTTGGCCCACAGATCT | 1684 |
| DET1.1 | NM_017996 | NM_017996.2 | DET1 | 2643 | CTTGTGGAGATCACCCAATCAG | 221 | CCCGCCTGGATCTCAAACT | 953 | CTATGCCCGGGACTCGGGCCT | 1685 |
| DHPS.3 | NM_013407 | NM_013407.1 | DHPS | 1722 | GGGAGAACGGGATCAATAGGAT | 222 | GCATCAGCCAGTCCTCAAACT | 954 | CTCATTGGGCACCAGCAGTTTCC | 1686 |
| DIABLO.1 | NM_019887 | NM_019887.1 | DIABLO | 348 | CACAATGGCGGCTCTGAAG | 223 | ACACAAACACTGTCTGTACCTGAAGA | 955 | AAGTTACGCTGCGCGACAGCCAA | 1687 |
| DIAPH1.1 | NM_005219 | NM_005219.2 | DIAPH1 | 2705 | CAAGCAGTCAAGGAGAACCA | 224 | AGTTTGCTCGCCTCATCTT | 956 | TTCTTCTGTCTCCCGCCGCTTC | 1688 |
| DICER1.2 | NM_177438 | NM_177438.1 | DICER1 | 1898 | TCCAATTCCAGCATCACTGT | 225 | GGCAGTGAAGGCGATAAAGT | 957 | AGAAAGCTGTTTGTCTCCCAGCA | 1689 |
| DKFZP564O0082$$ | NM_015393 | NM_015393.2 | PARM1 | 3874 | CAGCTACACTGTCGCAGTCC | 226 | ATGAGGGCTGGAGCTTGAGG | 958 | TGCTGAGCCTCCACACTCATCTC | 1690 |
| DLC1.1 | NM_006094 | NM_006094.3 | DLC1 | 3018 | GATTCAGACGAGGATGAGCC | 227 | CACCTCTTGCTGTCCCTTTG | 959 | AAAGTCCATTTGCCACTGATGGCA | 1691 |
| DLL4.1 | NM_019074 | NM_019074.2 | DLL4 | 5273 | CACGGAGGTATAAGGCAGGAG | 228 | AGAAGGAAGGTCCAGCCG | 960 | CTACCTGGACATCCCTGCTCAGCT | 1692 |
| DPEP1.1 | NM_004413 | NM_004413.2 | DPEP1 | 6295 | GGACTCCAGATGCCAGGA | 229 | TAAGCCCAGGCGTCCTCT | 961 | CACATGCAAGGACCAGCATCTCCT | 1693 |
| DPYS.1 | NM_001385 | NM_001385.1 | DPYS | 6152 | AAAGAATGGCACCATGCAG | 230 | AGTCGGGTGTTGAGGGGT | 962 | CACCATGTCATGGGTCCACCTTTG | 1694 |
| DR4.2 | NM_003844 | NM_003844.1 | TNFRSF10$$ | 896 | TGCACAGAGGGGTGTGGGTTAC | 231 | TCTTCATCTGATTTACAAGCTGTACATG | 963 | CAATGCTTCCAACAATTTGTTTGCTTGCC | 1695 |
| DR5.2 | NM_003842 | NM_003842.2 | TNFRSF10$$ | 902 | CTCTGAGACAGTGCTTCGATGACT | 232 | CCATGAGGCCCAACTTCCT | 964 | CAGACTTGGTGCCCTTTGACTCC | 1696 |
| DUSP1.1 | NM_004417 | NM_004417.2 | DUSP1 | 2662 | AGACATCAGCTCCTGGTTCA | 233 | GACAAACACCCTTCCTCCAG | 965 | CGAGGCCATTGACTTCATAGACTCCA | 1697 |
| DUSP9.1 | NM_001395 | NM_001395.1 | DUSP9 | 6324 | CGTCCTAATCAACGTGCCTA | 234 | CCCGCAAAGAAAAAGTAACAG | 966 | CGTCGGAGCCTGCCTCTTC | 1698 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| E2F1.3 | NM_005225 | NM_005225.1 | E2F1 | 1077 | ACTCCCTCTACCCT TGAGCA | 235 | CAGGCCTCAGTT CCTTCAGT | 967 | CAGAAGAACAGCTCA GGGACCCCT | 1699 |
| EBAG9.1 | NM_004215 | NM_004215.3 | EBAG9 | 4151 | CGCTCCTGTTTTC TCATCTGT | 236 | ACCGAAACTGGG TGATGG | 968 | CAGTGGGTTTTGATT CCCACCATG | 1700 |
| ECRG4.1 | NM_032411 | NM_032411.1 | C2orf40 | 3869 | GCTCCTGCTCCTGT GCTG | 237 | TTTTGAAGCATC AGCTTGAGTT | 969 | ATTTCCACTTATGCC ACCTGGGCC | 1701 |
| EDG2.1 | NM_001401 | NM_001401.3 | LPAR1 | 4673 | ACGAGTCCATTGCC TTCTTT | 238 | GCTTGCTGACTG TGTTCCAT | 970 | CGAAGTGGAAAGCA TCTTGCCACA | 1702 |
| EDN1 endothelin | NM_001955 | NM_001955.1 | EDN1 | 331 | TGCCACCTGGACAT CATTTG | 239 | TGGACCTAGGGC TTCCAAGTC | 971 | CACTCCCGAGCACG TTGTTCCGT | 1703 |
| EDN2.1 | NM_001956 | NM_001956.2 | EDN2 | 2646 | CGACAAGGAGTGC GTCTACTTCT | 240 | CAGGCCGTAAGG AGCTGTCT | 972 | CCACTTGGACATCAT CTGGGTGAACACTG | 1704 |
| EDNRA.2 | NM_001957 | NM_001957.1 | EDNRA | 3662 | TTTCCTCAAATTTG CCTCAAG | 241 | TTACACATCCAA CCAGTGCC | 973 | CCTTTGCCTCAGGG CATCCTTTT | 1705 |
| EDNRB.1 | NM_000115 | NM_000115.1 | EDNRB | 3185 | ACTGTGAACTGCCT GGTGC | 242 | ACCACAGCATGG GTGAGAG | 974 | TGTACCTGCCCCTT TGTCATGTG | 1706 |
| EEF1A1.1 | NM_001402 | NM_001402.5 | EEF1A1 | 5522 | CGAGTGGAGACTG GTGTTCTC | 243 | CCGTTGTAACGT TGACTGGA | 975 | CAAAGGTGACCACCA TACCGGGTT | 1707 |
| EFNB1.2 | NM_004429 | NM_004429.3 | EFNB1 | 3299 | GGAGCCCGTATCC TGGAG | 244 | GGATAGATCACC AAGCCCTTC | 976 | CCCTCAACCCCAAGT TCCTGAGTG | 1708 |
| EFNB2.1 | NM_004093 | NM_004093.2 | EFNB2 | 2597 | TGACATTATCATCC CGCTAAGGA | 245 | GTAGTCCCGCT GACCTTCTC | 977 | CGGACAGCGTCTTC TGCCCTCACT | 1709 |
| EGF.3 | NM_001963 | NM_001963.2 | EGF | 158 | CTTTGCCTTGCTCT GTCACAGT | 246 | AAATACCTGACA CCCTTATGACAA ATT | 978 | AGAGTTTAACAGCCC TGCTCTGGCTGACTT | 1710 |
| EGFR.2 | NM_005228 | NM_005228.1 | EGFR | 19 | TGTCGATGGACTTC CAGAAC | 247 | ATTGGGACAGCT TGGATCA | 979 | CACCTGGGCAGCTG CCAA | 1711 |
| EGLN3.1 | NM_022073 | NM_022073.2 | EGLN3 | 2970 | GCTGGTCCTCTACT GCGG | 248 | CCACCATTGCCT TAGACCTC | 980 | CCGCTGGGCAAAT ACTACGTCAA | 1712 |
| EGR1.1 | NM_001964 | NM_001964.2 | EGR1 | 2615 | GTCCCCGCTGCAG ATCTCT | 249 | CTCCAGCTTAGG GTAGTTGTCCAT | 981 | CGGATCCTTTCCTCA CTCGCCCA | 1713 |
| EIF2C1.1 | NM_012199 | NM_012199.2 | EIF2C1 | 6454 | CCCTCACGGACTCT CAGC | 250 | TGGGTGACTTCC ACCTTCA | 982 | CGTTCGCTTCACCAA GGAGATCAA | 1714 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| EIF4EBP1.1 | NM_004095 | NM_004095.2 | EIF4EBP1 | 4275 | GGCGTGAAGAGTCACAGT | 251 | TTGGTAGTGCTCCACACGAT | 983 | TGAGATGGACATTTAAAGCACCAGCC | 1715 |
| ELTD1.1 | NM_022159 | NM_022159.3 | ELTD1 | 6154 | AGGTCTTGTGCAAGAGGAGC | 252 | AACCCCAAAGATCCAGGTG | 984 | CTCGCTCTTCTGTTCCTTCTCGGC | 1716 |
| EMCN.1 | NM_016242 | NM_016242.2 | EMCN | 3875 | AGGCACTGAGGGTGGAAA | 253 | CACCGGCAAAATAATACTGA | 985 | AATGCAAGCACTTCAGCAACAGC | 1717 |
| EMP1.1 | NM_001423 | NM_001423.1 | EMP1 | 986 | GCTAGTACTTTGATGCTCCCTTGAT | 254 | GAACAGTTGGAGGCCAAGTC | 986 | CCAGAGAGCCTCCCTGCAGCCA | 1718 |
| ENO2.1 | NM_001975 | NM_001975.2 | ENO2 | 6155 | TCCTTGGCTTACCTGACCTC | 255 | AACCCCAATGAGTAGGGCA | 987 | CTGTCTCTGCTCGCCCTCCTTTCT | 1719 |
| ENPEP.1 | NM_001977 | NM_001977.3 | ENPEP | 6156 | CACCTACACGGAGAACGGAC | 256 | CCTGGCATCTGTTGTTCA | 988 | TCAAGAGCATAGTGGCCACCGATC | 1720 |
| ENPP2.1 | NM_006209 | NM_006209.3 | ENPP2 | 6174 | CTCTGCGCACTAATACCTTC | 257 | TCCCTGGATAATTGGGTCTG | 989 | TAACTTCCTCTGGCATGGTTGGCC | 1721 |
| EPAS1.1 | NM_001430 | NM_001430.3 | EPAS1 | 2754 | AAGCCTTGGAGGGTTTCATTG | 258 | TGCTGATGTTTTCTGACAGAAGA | 990 | TGTCGCCATCTTGGGTCACCACG | 1722 |
| EPB41L3.1 | NM_012307 | NM_012307.2 | EPB41L3 | 4554 | TCAGTGCCATACGCTCTCAC | 259 | CTTGGGCTCCAGGTAGCA | 991 | CTCTCCTTCCCTCTGGCTCTGTG | 1723 |
| EPHA2.1 | NM_004431 | NM_004431.2 | EPHA2 | 2297 | CGCCTGTTCACCAAGATTGAC | 260 | GTGGCGTGCCTCGAAGTC | 992 | TGGCCCCGATGAGATCACCG | 1724 |
| EPHB1.3 | NM_004441 | NM_004441.3 | EPHB1 | 6508 | CCTTGGGAGGGAAGATCC | 261 | GAAGTGAACTTGCGGTAGGC | 993 | ATGGCCTTGGAGCTGTCCATCTC | 1725 |
| EPHB2.1 | NM_004442 | NM_004442.4 | EPHB2 | 2967 | CAACCAGGCAGCTCCATC | 262 | GTAATGCTGTCCACGGTGC | 994 | CACCTGATGCATGATGGACACTGC | 1726 |
| EPHB4.1 | NM_004444 | NM_004444.3 | EPHB4 | 2620 | TGAACGGGGTATCCTCCTTA | 263 | AGGTACCTCTCGGTCAGTGG | 995 | CGTCCCATTTGAGCCTGTCAATGT | 1727 |
| EPO.1 | NM_000799 | NM_000799.2 | EPO | 5992 | CAGTGCCAGCAATGACATCT | 264 | CAAGTTGCCCCTGTGACAT | 996 | CTCTCTGGACAGTTCCTCTGGCCC | 1728 |
| ErbB3.1 | NM_001982 | NM_001982.1 | ERBB3 | 93 | CGGTTATGTCATGCCAGATACAC | 265 | GAACTGAGACCACTGAAGAAGG | 997 | CCTCAAAGTACTCCCTCCTCCCG | 1729 |
| ERBB4.3 | NM_005235 | NM_005235.1 | ERBB4 | 407 | TGGCTCTTAATCAGTTTCGTTACCT | 266 | CAAGGCATATCGATCCTCATAAAGT | 998 | TGTCCACAGAATAATGCGTAAATTCTCCAG | 1730 |
| ERCC1.2 | NM_001983 | NM_001983.1 | ERCC1 | 869 | GTCCAGGTGGATGTGAAAGA | 267 | CGGCCAGGATACACATCTTA | 999 | CAGGAGGCCCTCAAGGAGCTG | 1731 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| ERCC4.1 | NM_005236 | NM_005236.1 | ERCC4 | 5238 | CTGCTGGAGTACGAGCGAC | 268 | GGGCGCACACTACTAGCC | 1000 | CTGTGCTGGAACTGCTCGACACT | 1732 |
| EREG.1 | NM_001432 | NM_001432.1 | EREG | 309 | ATAACAAAGTGAGCTCTGACATGAATG | 269 | CACACCTGCAGTAGTTTTGACTCA | 1001 | TTGTTTGCATGGACAGTGCATCTATCTGT | 1733 |
| ERG.1 | NM_004449 | NM_004449.3 | ERG | 3884 | CCAACACTAGGCTCCCCA | 270 | CCTCCGCCAGGTCTTTAGT | 1002 | AGCCATATGCCTTCTCATCTGGGC | 1734 |
| ERK1.3 | NM_002746 | Z16696.1 | MAPK3 | 548 | ACGGATCACAGTGGAGGAAG | 271 | CTCATCCGTCGGGTCATAGT | 1003 | CGTTGGCTCACCCCTACCTG | 1735 |
| ERK2.3 | NM_002745 | NM_002745.1 | MAPK1 | 557 | AGTTCTTGACCCCTGGTCCT | 272 | AAACGGCTCAAAGGAGTCAA | 1004 | TCTCCAGCCCGTCTTGGCTT | 1736 |
| ESPL1.3 | NM_012291 | NM_012291.1 | ESPL1 | 2053 | ACCCCAGACCGGATCAG | 273 | TGTAGGGCAGACTTCCTCAAACA | 1005 | CTGGCCCTCCATGTCCCCTTCACG | 1737 |
| ESRRG.3 | NM_001438 | NM_001438.1 | ESRRG | 2225 | CCAGACCACCATTGTTGAAGAT | 274 | AGTCTCTTGGCATCGAGTT | 1006 | CCCCAGACCAAGTGTGAATACATGCT | 1738 |
| F2.1 | NM_000506 | NM_000506.2 | F2 | 2877 | GCTGCATGTCTGGAAGGTAACTG | 275 | CCTGACCGGGTGATGTTCAC | 1007 | CCTCGGTAGTTCGTACCCAGACCCTCAG | 1739 |
| F3.1 | NM_001993 | NM_001993.2 | F3 | 12871 | GTGAAGGATGTGAAGCAGACGTA | 276 | AACCGGTGCTCTCCACATTC | 1008 | TGGCACGGGTCTTCTCCTACC | 1740 |
| FABP1.1 | NM_001443 | NM_001443.1 | FABP1 | 16175 | GGGTCCAAAGTGATCCAAAA | 277 | CCCTGTCATTGTCTCCAGC | 1009 | ACATTCCTCCCCCACCGTGAATTC | 1741 |
| FABP7.1 | NM_001446 | NM_001446.3 | FABP7 | 4048 | GGAGACAAAGTGGTCATCAGG | 278 | CTCTTCTCCCAGCTGGAAACT | 1010 | TCTCAGCACATTCAAGAACACGAGA | 1742 |
| FAP.1 | NM_004460 | NM_004460.2 | FAP | 3403 | CTGACCAGAACCACGGCT | 279 | GGAAGTGGGTCATGTGGG | 1011 | CGGCCTGTCCACGAACCACTTATA | 1743 |
| fas.1 | NM_000043 | NM_000043.1 | FAS | 42 | GGATTGCTCAACAACCATGCT | 280 | GGCATTAACACTTTTGGACCATAA | 1012 | TCTGACCCTCCTACCTCTGGTTCTTACGT | 1744 |
| fasl.2 | NM_000639 | NM_000639.1 | FASLG | 94 | GCACTTTGGGATTCTTTCCATTAT | 281 | GCATGTAAGAAGACCCTCACTGAA | 1013 | ACAACATTCTCGGTGCCTGTAACAAGAA | 1745 |
| FBXW7.1 | NM_033632 | NM_033632.1 | FBXW7 | 2644 | CCCCAGTTTCAACGAGACTT | 282 | GTTCCAGGAATGAAAGCACA | 1014 | TCATTGCTCCCTAAAGAGTTGGCACTC | 1746 |
| FCER1G.2 | NM_004106 | NM_004106.1 | FCER1G | 4073 | TGCCATCCTGTTTCTGTATGGA | 283 | TGCCTTTCGCACTTGGATCT | 1015 | TTGTCCTCACCCTCCTCTACTGTCGACTG | 1747 |
| FCGR3A.1 | NM_000569 | NM_000569.4 | FCGR3A | 3080 | GTCTCCAGTGTGGAAGGGAAAA | 284 | AGGAATGCAGCTACTCACTGG | 1016 | CCCATGATCTTCAAGCAGGGAAGC | 1748 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| FDPS.1 | NM_002004 | NM_002004.1 | FDPS | 516 | GGATGATTACCTTGACCTCTTTGG | 285 | TGCATTGTTGTCCTGGATGTC | 1017 | CAGTGTGACCGGCAAAATGGCAC | 1749 |
| FEN1.1 | NM_004111 | NM_004111.4 | FEN1 | 3938 | GTGGAAGGGTACGCCAG | 286 | CTCATGGCAACCAGTCCC | 1018 | CGCTGAGAGACTCTGTTCTCCCTGG | 1750 |
| FGF1.1 | NM_000800 | NM_000800.2 | FGF1 | 4561 | GACACCGACGGGCTTTTA | 287 | CAGCCTTTCCAGGAACAAAC | 1019 | ACGGCTCACAGACACCAATGAGG | 1751 |
| FGF2.2 | NM_002006 | NM_002006.2 | FGF2 | 681 | AGATGCAGGAGAGAGGAAGC | 288 | GTTTTGCAGCCTTACCCAAT | 1020 | CCTGCAGACTGCTTTTTGCCCAAT | 1752 |
| FGF9.1 | NM_002010 | NM_002010.1 | FGF9 | 6177 | CACAGCTGCCATACTTCGAC | 289 | AAGTAAGACTGCACCCTCGC | 1021 | AGGCCACCAGCCAGAATCCTGATA | 1753 |
| FGFR1.3 | NM_023109 | NM_023109.1 |  | 353 | CACGGGACATTCACCACATC | 290 | GGGTGCCATCCACTTCACA | 1022 | ATAAAAAGACAACCAACGGCCGACTGC | 1754 |
| FGFR2 isoform | NM_000141 | NM_000141.2 | FGFR2 | 2632 | GAGGGACTGTTGGCATGCA | 291 | GAGTGAGAATTCGATCCAAGTCTTC | 1023 | TCCCAGAGACCAACGTTCAAGCAGTTG | 1755 |
| FH.1 | NM_000143 | NM_000143.2 | FH | 4938 | ATGGTTGCAGCCCAAGTC | 292 | CAAAATGTCCATTGCTGCC | 1024 | ACAGTGACAGCAACATGGTTCCCC | 1756 |
| FHIT.1 | NM_002012 | NM_002012.1 | FHIT | 871 | CCAGTGGAGCGCTTCCAT | 293 | CTCTCTGGGTCGTCTGAAACAA | 1025 | TCGGCCACTTCATCAGGACGCAG | 1757 |
| FHL1.1 | NM_001449 | NM_001449.3 | FHL1 | 4005 | ATCCAGCCTTTGCCGAATA | 294 | CCTTGTGTAGCTGGAGGGACC | 1026 | TCCTATCTGCCACACATCCAGCGT | 1758 |
| FIGF.1 | NM_004469 | NM_004469.2 | FIGF | 3160 | GGTTCCAGTCTTTCTGTAGCTGT | 295 | GCCGCAGTTCTAGTTGCT | 1027 | ATTGGTGGCCACACCACCTCCTTA | 1759 |
| FILIP1.1 | NM_015687 | NM_015687.2 | FILIP1 | 4510 | ACACCGGTCACAACGTCAT | 296 | CTGGGATGACCCGTCTTG | 1028 | CCTGACACTGACTGGGTTCCTCGA | 1760 |
| FKBP1A.1 | NM_000801 | NM_000801.2 | FKBP1A | 6330 | CTGCCCTGACTGAATGTGTT | 297 | TACGAGGAGAAAGGGGAAGA | 1029 | TCACTCAGCTTTGCTTCCGACACC | 1761 |
| FLJ22655.1 | NM_024730 | NM_024730.2 | RERGL | 3870 | CTCCTTCACACAGAACCTTTCA | 298 | AGGCAAACTGGGATCGCT | 1030 | CACACTCACCCTAACCTACTGGGG | 1762 |
| FLT1.1 | NM_002019 | NM_002019.3 | FLT1 | 6062 | GGCTCCTGAATCTATCTTTG | 299 | TCCCACAGCAATACTCCGTA | 1031 | CTACAGCACCAAGAGCGACGTG | 1763 |
| FLT3LG.1 | NM_001459 | NM_001459.2 | FLT3LG | 6178 | TGGGTCCAAGATGCAAGG | 300 | GAAAGGCACATTTGGTGACA | 1032 | AGTGTATCCGTGTTCACGCGCT | 1764 |
| FLT4.1 | NM_002020 | NM_002020.1 | FLT4 | 2782 | ACCAAGAAGCTGAGGACCTG | 301 | CCTGGAAGCTGTAGCAGACA | 1033 | AGCCCGTGACCATGGAAGATCT | 1765 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| FN1.1 | NM_002026 | NM_002026.2 | FN1 | 4528 | GGAAGTGACAGAC GTGAAGGT | 302 | ACACGGTAGCCG GTCACT | 1034 | ACTCTCAGGCGGTG TCCACATGAT | 1766 |
| FOLR1.1 | NM_016730 | NM_016730.1 | FOLR1 | 859 | GAACGCCAAGCAC CACAAG | 303 | CCAGGGTCGACA CTGCTCAT | 1035 | AAGCCAGGCCCCGA GGACAAGTT | 1767 |
| FOS.1 | NM_005252 | NM_005252.2 | FOS | 2418 | CGAGCCCTTTGATG ACTTCCT | 304 | GGAGCGGGCTG TCTCAGA | 1036 | TCCCAGCATCATCCA GGCCCAG | 1768 |
| FRAP1.1 | NM_004958 | NM_004958.2 | MTOR | 3095 | AGCGTAGAGACT GTGGACC | 305 | ATGATCCGGAG GCATAGT | 1037 | CCTGACGGAGTCC TGGATTTCAC | 1769 |
| FRP1.3 | NM_003012 | NM_003012.2 | SFRP1 | 648 | TTGGTACCTGTGG GTTAGCA | 306 | CACATCCAAATG CAAACTGG | 1038 | TCCCCAGGGTAGAAT TCAATCAGAGC | 1770 |
| FST.1 | NM_006350 | NM_006350.2 | FST | 2306 | GTAAGTCGGATGA GCCTGTCTGT | 307 | CAGCTTCCTTCA TGGCACACT | 1039 | CCAGTGACAATGCCA CTTATGCCAGC | 1771 |
| FZD2.2 | NM_001466 | NM_001466.2 | FZD2 | 3760 | TGGATCCTCACCTG GTCG | 308 | GCGCTGCATGTC TACCAA | 1040 | TGCGCTTCCACCTTC TTCACTGTC | 1772 |
| G-Catenin.1 | NM_002230 | NM_002230.1 | JUP | 770 | TCAGCAGCAAGGG CATCAT | 309 | GGTGGTTTTCTT GAGCGTGTACT | 1041 | CGCCCGCAGGCCTC ATCCT | 1773 |
| GADD45B.1 | NM_015675 | NM_015675.1 | GADD45B | 2481 | ACCCTGACACAGAC CACACT | 310 | TGGGAGTTCATG GGTACAGA | 1042 | AACTTCAGGCCCCAGC TCCCAAGTC | 1774 |
| GAS2.1 | NM_005256 | NM_005256.2 | GAS2 | 6451 | AACATGTCATGTC CGTGTG | 311 | GGGGTCGTGTTT CAACAAAT | 1043 | CCTGCAAAAGTTTCC CAGCCTCCT | 1775 |
| GATA3.3 | NM_002051 | NM_002051.1 | GATA3 | 1 | CAAAGGAGCTCACT GTGGTGCT | 312 | GAGTCAGAATGG CTTATTCACAGATG | 1044 | TGTTCCAACCACTGA ATCTGGACC | 1776 |
| GATM.1 | NM_001482 | NM_001482.2 | GATM | 6296 | GATCTCCGGCTTGG ACGAAC | 313 | GTAGCTGCCTGG GTGCTCT | 1045 | AAAGTTCGCTGCACC CATCCTGTC | 1777 |
| GBL.1 | NM_022372 | NM_022372.3 | MLST8 | 6302 | GCTGTCAATAGCAC CGGAA | 314 | GGTCACCTCGTC ACCAATG | 1046 | CCCCCGTCAGATTCC AGACATAGC | 1778 |
| GBP2.2 | NM_004120 | NM_004120.2 | GBP2 | 2060 | GCATGGGAACCAT CAACCA | 315 | TGAGGAGTTTGC CTTGATTCG | 1047 | CCATGGACCAACTTC ACTATGTGACAGAGC | 1779 |
| GCLC.3 | NM_001498 | NM_001498.1 | GCLC | 330 | CTGTTGCAGGAAG GCATTGA | 316 | GTCATGGGTCT CTTAATAAAGAGA TGAG | 1048 | CATCTCCTGGCCCA GCATGTT | 1780 |
| GCLM.2 | NM_002061 | NM_002061.1 | GCLM | 704 | TGTAGAATCAAACT CTTCATCATCAACT AG | 317 | CACAGAATCCAG CTGTGCAACT | 1049 | TGCAGTTGACATGG CCTGTTCAGTCC | 1781 |

TABLE A-continued

| Gene | Accession Num | Sequence_ID | Official Symbol | Gene ID Version | F Primer Seq | SEQ ID NO. | R Primer Seq | SEQ ID NO. | Probe Seq | SEQ ID NO. |
|---|---|---|---|---|---|---|---|---|---|---|
| GFRA1.1 | NM_005264 | NM_005264.3 | GFRA1 | 6179 | TCCGGGTTAAGAAC AAGCC | 318 | GTGGCAAAACAT GAGTGGG | 1050 | TTTCATTCTCAGACC CTGCTGGCC | 1782 |
| GJA1.1 | NM_000165 | NM_000165.2 | GJA1 | 2600 | GTTCACTGGGCGT GTATGG | 319 | AAATACCAACAT GCACCCTCTT | 1051 | ATCCCCTCCCTCCC ACCCATCTA | 1783 |
| GLYAT1 | NM_201648 | NM_201648.2 | GLYAT | 6180 | TACCATTGCAAGGT GCCC | 320 | GGATGCTGGGA GGCTCTT | 1052 | AGGATTTCTCCAGCA TCTGCAGCA | 1784 |
| GMNN.1 | NM_015895 | NM_015895.3 | GMNN | 3880 | GTTCGCTACGAGG ATTGAGC | 321 | TGCGTACCACT TCCTGC | 1053 | CCTCTTGCCCACTTA CTGGGTGGA | 1785 |
| GNAS.1 | NM_000516 | NM_000516.3 | GNAS | 2665 | GAACGTGCCTGAC TTTGACTT | 322 | ACTCCTTCATCC TCCCACAG | 1054 | CCTCCCGAATTCTAT GAGCATGCC | 1786 |
| GPC3.1 | NM_004484 | NM_004484.2 | GPC3 | 659 | TGATGCGCCTGAA AACAGT | 323 | CGAGGTTGTGAA AGTGCTTATC | 1055 | AGCAGGCAACTCCG AAGGACAACG | 1787 |
| GPX1.2 | NM_000581 | NM_000581.2 | GPX1 | 2955 | GCTTATGACCGACC CCAA | 324 | AAAGTTCCAGGC AACATCGT | 1056 | CTCATCACCTGGTCT CCGGTGTGT | 1788 |
| GPX2.2 | NM_002083 | NM_002083.1 | GPX2 | 890 | CACACAGATCTCCT ACTCCATCA | 325 | GGTCCAGCAGTG TCTCCTGAA | 1057 | CAATGCTGATCCTAA GGCTCCTCAGG | 1789 |
| GPX3.1 | NM_002084 | NM_002084.3 | GPX3 | 6271 | GCTCTAGGTCCAAT TGTTCTGC | 326 | TGGAGGCAGTG GGAGATG | 1058 | ACTGATACCTCAACC TTGGGGCCA | 1790 |
| GRB14.1 | NM_004490 | NM_004490.1 | GRB14 | 2784 | TCCCACTGAAGCC CTTTCAG | 327 | AGTGCCCAGGC GTAAACATC | 1059 | CCTCCAAGCGAGTC CTTCTTCAACCG | 1791 |
| GRB7.2 | NM_005310 | NM_005310.1 | GRB7 | 20 | CCATCTGCATCCAT CTTGTT | 328 | GGCCACCAGGG TATTATCTG | 1060 | CTCCCCACCCTTGAG AAGTGCCT | 1792 |
| GRO1.2 | NM_001511 | NM_001511.1 | CXCL1 | 86 | CGAAAAGATGCTGA ACAGTGACA | 329 | TCAGGAACAGCC ACCAGTGA | 1061 | CTTCCTCCTCCCTTC TGGTCAGTTGGAT | 1793 |
| GSTM1.1 | NM_000561 | NM_000561.1 | GSTM1 | 727 | AAGCTATGAGGAAA AGAAGTACACGAT | 330 | GGCCCAGCTTGA ATTTTTCA | 1062 | TCAGCCACTGGCTTC TGTCATAATCAGGAG | 1794 |
| GSTM3.2 | NM_000849 | NM_000849.3 | GSTM3 | 731 | CAATGCCATCTTGC GCTACAT | 331 | GTCCACTCGAAT CTTTTCTTTCA | 1063 | CTCCAAGCACAACA TGTGTGGTGAGA | 1795 |
| GSTp.3 | NM_000852 | NM_000852.2 | GSTP1 | 66 | GAGACCCTGCTGT CCCAGAA | 332 | GGTTGTAGTCAG CGAAGGAGATC | 1064 | TCCCACAATGAAGGT CTTGCCTCCCT | 1796 |
| GSTT1.3 | NM_000853 | NM_000853.1 | GSTT1 | 813 | CACCATCCCCACCC TGTCT | 333 | GGCCTCAGTGTG CATCATTCT | 1065 | CACAGCCGCCTGAA AGCCACAAT | 1797 |
| GZMA.1 | NM_006144 | NM_006144.2 | GZMA | 4111 | GAAAGAGTTTCCCT ATCCATGC | 334 | TGCTTTTTCCGT CAGCTGTAA | 1066 | AGCCACACGCGAAG GTGACCTTAA | 1798 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| HADH.1 | NM_005327 | NM_005327.2 | HADH | 6181 | CCACCAGACAAGACCGATTC | 335 | CCACAAGTTCATGACAGGC | 1067 | CTGCCTCCATTCTTCAACCCAG | 1799 |
| HAVCR1.1 | NM_012206 | NM_012206.2 | HAVCR1 | 6284 | CCACCCAAGGTCACGACTAC | 336 | GAACAGTGGTGCTCGTTCG | 1068 | TCACAACTGTTCCAACCGTCACGA | 1800 |
| HDAC1.1 | NM_004964 | NM_004964.2 | HDAC1 | 2602 | CAAGTACCACAGCGATGACTACATTAA | 337 | GCTTGCTGTACTCCGACATGTT | 1069 | TTCTTGCGCTCCATCCGTCCAGA | 1801 |
| Hepsin.1 | NM_002151 | NM_002151.1 | HPN | 814 | AGGCTGCTGGAGGTCATCTC | 338 | CTTCCTCCGGCCACAGTCT | 1070 | CCAGAGGCCGTTTCTTGGCCG | 1802 |
| HER2.3 | NM_004448 | NM_004448.1 | ERBB2 | 13 | CGGTGTGAGAAGTGCAGCAA | 339 | CCTCTCCGCAAGTGCTCCAT | 1071 | CCAGACCATAGCACACTCGGGCAC | 1803 |
| HGD.1 | NM_000187 | NM_000187.2 | HGD | 6303 | CTCAGGTCTGCCCCTACAAT | 340 | TTATTGGTGCTCCGTGGAC | 1072 | CTGAGCAGCTCTCAGGATCGGGTT | 1804 |
| HGF.4 | M29145 | M29145.1 |  | 457 | CCGAAATCCAGATGATGATG | 341 | CCCAAGGAATGAGTGGATTT | 1073 | CTCATGGACCCTGTGCTACACG | 1805 |
| HGFAC.1 | NM_001528 | NM_001528.2 | HGFAC | 2704 | CAGGACACAAGTGCCAGATT | 342 | GCAGGGAGCTGGAGTAGC | 1074 | CGCTTCACGTTCTCATCCAAGTGG | 1806 |
| HIF1A.3 | NM_001530 | NM_001530.1 | HIF1A | 399 | TGAACATAAAGTCTGCAACATGAA | 343 | TGAGGTTGGTTACTGTTGGTATCATATA | 1075 | TTGCACTGCACAGGCCCATTCAC | 1807 |
| HIF1AN.1 | NM_017902 | NM_017902.2 | HIF1AN | 7211 | TGTTGGCCAGGTCTCACTG | 344 | GCATCATAGGGCCTGGAG | 1076 | CTCTAGCACCAGTTAGCCTCGGGCAG | 1808 |
| HIST1H1D.1 | NM_005320 | NM_005320.2 | HIST1H1D | 4013 | AAAAAGGCGAAGAAGGCAG | 345 | GCTCAGATACTGGGGGTCC | 1077 | AACTGCTGGGAAACGCAAAGCATC | 1809 |
| HLA-B.1 | NM_005514 | NM_005514.6 | HLA-B | 6334 | CTTGTGAGGGACTGAGATGC | 346 | TGCAGAAGAGATGCCAGAG | 1078 | TCTTCACGCCTCCCCTTTGTGA | 1810 |
| HLA-DPA1.1 | NM_033554 | NM_033554.2 | HLA-DPA1 | 6314 | CGCCCTGAAGACAGAATGT | 347 | TCCGAGACTCAGCAGGAAA | 1079 | TGATCTTGAGAGCCCTCTCCTTGGC | 1811 |
| HLA-DPB1.1 | NM_002121 | NM_002121.4 | HLA-DPB1 | 1740 | TCCATGATGGTTCTGCAGGTT | 348 | TGAGCAGCACCATCAGTAACG | 1080 | CCCCGGACAGTGGCTCTGACG | 1812 |
| HLA-DQB1.1 | NM_002123 | NM_002123.3 | HLA-DQB1 | 6304 | GGTCTGCTCGGTGACAGATT | 349 | CTTCCTGATCATTCCGAAACC | 1081 | TATCCAGGCCAGATCAAAGTCCGG | 1813 |
| HLADQA1.2 | NM_002122 | NM_002122.3 | HLA-DQA1 | 4071 | CATCTTTCCTCTGTGGTCA | 350 | GCTGGTCTCAGAAACACCTTC | 1082 | TGTGACTGACTGCCCATTGCTCAG | 1814 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| HMGB1.1 | NM_002128 | NM_002128.3 | HMGB1 | 2162 | TGGCCTGTCCATTGGTGAT | 351 | GCTTGTCATCTGCAGCAGTGTT | 1083 | TTCCACATCTCTCCCAGTTCTTCGCAA | 1815 |
| HNRPAB.1 | NM_004499 | NM_004499.3 | HNRNPAB | 6051 | AGCAGGAGCGACCAACTGA | 352 | GTTTGCCAAGTTAAATTGGTACATAAT | 1084 | CTCCATATCCAAACAAAGCATGTGCG | 1816 |
| HPCAL1.1 | NM_002149 | NM_002149.2 | HPCAL1 | 6182 | CAGGCAGATGGACACCAA | 353 | GTCGCTCTTGGCACCTCT | 1085 | TCTTCCAAGGACAGTTTGCCGTCA | 1817 |
| HPD.1 | NM_002150 | NM_002150.2 | HPD | 6183 | AGCTGAAGACCGCCAAGAT | 354 | CGTCGTAGTCCACCAGGATT | 1086 | AGCTCCTCCAGGGCATCAATGTTC | 1818 |
| HSD11B2.1 | NM_000196 | NM_000196.3 | HSD11B2 | 6185 | CCAACCTGCCTCAAGAGC | 355 | GGAACTGCCCATGCAAGT | 1087 | CTGCAGGCCTACGGCAAGGACTAC | 1819 |
| HSP90AB1.1 | NM_007355 | NM_007355.2 | HSP90AB1 | 5456 | GCATTGTGACCAGCACCTAC | 356 | GAAGTGCCTGGGCTTTCAT | 1088 | ATCCGCTCCATATTGGCTGTCCAG | 1820 |
| HSPA1A.1 | NM_005345 | NM_005345.4 | HSPA1A | 2412 | CTGCTCGACAGTCCACTA | 357 | CAGGTTCGCTCTGGGAAG | 1089 | AGAGTGACTCCCGTTGTCCCAAGG | 1821 |
| HSPA8.1 | NM_006597 | NM_006597.3 | HSPA8 | 2563 | CCTCCCTCTGGTGGTGCTT | 358 | GCTACATCTACACTTGGTTGGCTTAA | 1090 | CTCAGGGCCCACCATTGAAGAGTTG | 1822 |
| HSPB1.1 | NM_001540 | NM_001540.2 | HSPB1 | 2416 | CCGACTGGAGGAGCATAAA | 359 | ATGCTGGCTGACTCTGCTC | 1091 | CGCACTTTTCTGAGCAGACGTCCA | 1823 |
| HSPG2.1 | NM_005529 | NM_005529.2 | HSPG2 | 1783 | GAGTACGTGTGCCGAGTGTT | 360 | CTCAATGGTGACCAGGACA | 1092 | CAGCTCCGTGCCTCTAGAGGCCT | 1824 |
| HTATIP.1 | NM_006388 | NM_006388.2 | KAT5 | 3893 | TCGAATTGTTTGGGCACTG | 361 | GCCTGGTGCTGACGGTAT | 1093 | TGAGGACTCCCAGGACAGCTCTGA | 1825 |
| HYAL1.1 | NM_153281 | NM_153281.1 | HYAL1 | 4524 | TGGCTGTGGAGTTCAAATGT | 362 | CCAATCACCACATGCTCTTC | 1094 | CGATGTCTACCCTGGCTGGCAG | 1826 |
| HYAL2.1 | NM_033158 | NM_033158.2 | HYAL2 | 5192 | CAACCATGCACTCCCAGTC | 363 | ACTAAGCCCCGTGAGCCT | 1095 | TCTTCACGACACCACCTACAGCC | 1827 |
| HYAL3.1 | NM_003549 | NM_003549.2 | HYAL3 | 6298 | TATGTCCGCCTTCACACACC | 364 | CAATGGACTGCACAAGGTCA | 1096 | TGGGACAGGAACCTCCCAGATCTC | 1828 |
| ICAM1.1 | NM_000201 | NM_000201.1 | ICAM1 | 1761 | GCAGCAGTGACCATCTACAGCTT | 365 | CTTCTGAGACCTCTGGCTTCGT | 1097 | CCGCGCCCAACGTGATTCT | 1829 |
| ICAM2.1 | NM_000873 | NM_000873.2 | ICAM2 | 2472 | GGTCATCCTGACACTGCAAC | 366 | TGCACTCAATGGTGAAGGAC | 1098 | TTGCCAAGCCACCAAAGTG | 1830 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| ICAM3.1 | NM_002162 | NM_002162.3 | ICAM3 | 7219 | GCCTTCAATCTCAGCAACG | 367 | GAGAGCCATTGCAGTACAC | 1099 | CAGAGGATCCGACTGTTGCCAGTC | 1831 |
| ID1.1 | NM_002165 | NM_002165.1 | ID1 | 354 | AGAACCGCAAGTGAGCAA | 368 | TCCAACTGAAGGTCCCTGATG | 1100 | TGGAGATTCTCCAGCACGTCATCGAC | 1832 |
| ID2.4 | NM_002166 | NM_002166.1 | ID2 | 37 | AACGACTGCTACTCCAAGCTCAA | 369 | GGATTTCCATCTTGCTCACCTT | 1101 | TGCCCAGCATCCCCAGAACAA | 1833 |
| ID3.1 | NM_002167 | NM_002167.3 | ID3 | 6052 | CTTCACCAAATCCCTTCCTG | 370 | CTCTGGTCTTCAGGCCACA | 1102 | TCACAGTCTCTTCGCTCCTGAGCAC | 1834 |
| IFI27.1 | NM_005532 | NM_005532.2 | IFI27 | 2770 | CTCTCCGGATTGACCAAGTT | 371 | TAGAACCTCGCAATGACAGC | 1103 | CAGACCCAATGGAGCCCAGGAT | 1835 |
| IGF1.2 | NM_000618 | NM_000618.1 | IGF1 | 60 | TCCGGAGCTGTGATCTAAGGA | 372 | CGGACAGAGCGAGCTGACTT | 1104 | TGTATTGCGCACCCCTCAAGCCTG | 1836 |
| IGF1R.3 | NM_000875 | NM_000875.2 | IGF1R | 413 | GCATGGTAGCCGAAGATTTCA | 373 | TTTCCGGTAATAGTCTGTCTCATAGATATC | 1105 | CGGTCATACCAAAATCTCCGATTTTGA | 1837 |
| IGF2.2 | NM_000612 | NM_000612.2 | IGF2 | 166 | CCGTGCTTCCGGACAACTT | 374 | TGGACTGCTTCCAGGTGTCA | 1106 | TACCCCGTGGGCAAGTTCTTCCAA | 1838 |
| IGFBP2.1 | NM_000597 | NM_000597.1 | IGFBP2 | 373 | GTGGACAGCACCATGAACA | 375 | CCTTCATACCCGACTTGAGG | 1107 | CTTCCGGCCAGCACTGCCTC | 1839 |
| IGFBP3.1 | NM_000598 | NM_000598.4 | IGFBP3 | 6657 | ACATCCCAACGCATGCTC | 376 | CCACGCCCTTGTTTCAGA | 1108 | ACACCACAGAAGGCTGTGAGCTCC | 1840 |
| IGFBP5.1 | NM_000599 | NM_000599.1 | IGFBP5 | 594 | TGGACAAGTACGGGATGAAGCT | 377 | CGAAGGTGTGGCACTGACCTGG | 1109 | CCCGTCAACGTACTCCATGCCTGG | 1841 |
| IGFBP6.1 | NM_002178 | NM_002178.1 | IGFBP6 | 836 | TGAACCGCAGAGACCAACAG | 378 | GTCTTGACACCCGCAGCAAT | 1110 | ATCAGGCACCTCTACCAGCCCCTC | 1842 |
| IL-7.1 | NM_000880 | NM_000880.2 | IL7 | 2084 | GCGGTGATTCGAAATTCG | 379 | CTCTCCTGGCACCTGCTT | 1111 | CTCTGGTCCTCATCCAGGTGCGC | 1843 |
| IL-8.1 | NM_000584 | NM_000584.2 | IL8 | 2087 | AAGGACCATCTCACTGTGTGTAAAC | 380 | ATCAGGAAGGCTGCCAAGAG | 1112 | TGACTTCCAAGCTGGCCGTGGC | 1844 |
| IL10.3 | NM_000572 | NM_000572.1 | IL10 | 909 | GGCGCTGTGTCATCGATTTCTT | 381 | TGGAGCTTATTAAAGGCATTCTTCA | 1113 | CTGTCCACGGCCTTGCTCTTG | 1845 |
| IL11.2 | NM_000641 | NM_000641.2 | IL11 | 2166 | TGGAAGGTTCCACAAGTCAC | 382 | TCTTGACCTTGTAGTTTGT | 1114 | CCTGTGATCAACAGTACCCGTATGGG | 1846 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| IL15.1 | NM_000585 | NM_000585.2 | IL15 | 6187 | GGCTGGGTACCAATGCTG | 383 | TGAGAGCCAGTAGTCAGTGTT | 1115 | CAGCTATGCTGGTAGGCTCCTGCC | 1847 |
| IL1B.1 | NM_000576 | NM_000576.2 | IL1B | 2755 | AGCTGAGGAAGATGCTGGTT | 384 | GGAAAGAAGGTGCTCAGGTC | 1116 | TGCCCACAGACCTTCCAGGAGAAT | 1848 |
| IL6.3 | NM_000600 | NM_000600.1 | IL6 | 324 | CCTGAACCTTCCAAAGATGG | 385 | ACCAGGCAAGTCTCCTCATT | 1117 | CCAGATTGGAAGCATCCATCTTTTTCA | 1849 |
| IL6ST.3 | NM_002184 | NM_002184.2 | IL6ST | 2317 | GGCCTAATGTTCCAGATCCT | 386 | AAAATTGTGCCTTGGAGAG | 1118 | CATATTGCCCAGTGGTCACCTCACA | 1850 |
| ILT-2.2 | NM_006669 | NM_006669.1 | LILRB1 | 583 | AGCCATCACTCTCAGTGCAG | 387 | ACTGCAGAGTCAGGGTCTCC | 1119 | CAGGTCCTATCGTGGCCCCTGA | 1851 |
| IMP3.1 | NM_018285 | NM_018285.2 | IMP3 | 4751 | GTGGACTCGTCCAAGATCAA | 388 | GGCTTCCAGATCGAAGTCAT | 1120 | CTCATTGTACTCTAGCACGTGCCGC | 1852 |
| INDO.1 | NM_002164 | NM_002164.3 | IDO1 | 5124 | CGCCTTGCACGTCTAGTTC | 389 | ATCTCCATGATGACCTTTGCCC | 1121 | ACATATGCCATGGTGATGCATCCC | 1853 |
| INHBA.1 | NM_002192 | NM_002192.1 | INHBA | 2635 | GTGCCCGAGCCATATAGCA | 390 | CGGTAGTGGTTGATGACTGTTGA | 1122 | ACGTCCGGTCCTCACTGTCCTTCC | 1854 |
| INHBB.1 | NM_002193 | NM_002193.1 | INHBB | 2636 | AGCCTCCAGGATACCAGCAA | 391 | TCTCCGACTGACAGGCATTTG | 1123 | AGCTAAGCTGCCATTTGTCACCG | 1855 |
| INSR.1 | NM_001079817 | NM_001079817 | INSR | 6455 | CAGTCTCCGAGAGCGGATT | 392 | GTGATGGCAGGTGAAGCC | 1124 | AGTTCCTCAATGAGGCCTCGGTCA | 1856 |
| IQGAP2.1 | NM_006633 | NM_006633.2 | IQGAP2 | 6453 | AGAGACACCAGCAACTGCG | 393 | ATCATTGCACGGCTCACC | 1125 | CCGTGGCATGGTCTACCTCCTGTT | 1857 |
| ISG20.1 | NM_002201 | NM_002201.4 | ISG20 | 6189 | GTGTCAGACTGAAGCCCCAT | 394 | GTTGCTGTCCCAAAAAGCC | 1126 | AAAGCCTCAGTCCCTGCGGAACG | 1858 |
| ITGA3.2 | NM_002204 | NM_002204.1 | ITGA3 | 840 | CCATGATCCTCACTCTGCTG | 395 | GAAGCTTTGTAGCCCGGTGAT | 1127 | CACTCCAGACCTCGCTTAGCATGG | 1859 |
| ITGA4.2 | NM_000885 | NM_000885.2 | ITGA4 | 2867 | CAACGCTTCAGTGATCAATCC | 396 | GTCTGGCCGGGATTCTTT | 1128 | CGATCCTGCCATCTGTAAATCGCCC | 1860 |
| ITGA5.1 | NM_002205 | NM_002205.1 | ITGA5 | 2668 | AGGCCAGCCTACATTATCA | 397 | GTCTTCTCCACAGTCCAGCA | 1129 | TCTGAGCCTTGTCCTCTATCCGGC | 1861 |
| ITGA6.2 | NM_000210 | NM_000210.1 | ITGA6 | 2791 | CAGTGACAAACAGCCCTTCC | 398 | GTTTAGCCTCATGGGCGTC | 1130 | TCGCCATCTTTTGTGGGATTCCTT | 1862 |
| ITGA7.1 | NM_002206 | NM_002206.1 | ITGA7 | 259 | GATATGATTGGTCGCTGCTTTG | 399 | AGAACTTCCATTCCCCACCAT | 1131 | CAGCCAGGAGGACCTGGCCATCG | 1863 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| ITGAV.1 | NM_002210 | NM_002210.2 | ITGAV | 2671 | ACTCGGACTGCACAAGCTATT | 400 | TGCCATCACCATTGAAATCT | 1132 | CCGACAGCCACAGAATAACCAAA | 1864 |
| ITGB1.1 | NM_002211 | NM_002211.2 | ITGB1 | 2669 | TCAGAATTGGATTTGGCTCA | 401 | CCTGAGCTTAGCTGGTGTTG | 1133 | TGCTAATGTAAGGCATCACAGTCTTTCCA | 1865 |
| ITGB3.1 | NM_000212 | NM_000212.2 | ITGB3 | 6056 | ACCGGGGAGCCCTACATGA | 402 | CCTTAAGCTCTTTCACTGACTCAATCT | 1134 | AAATACCTGCAACCGTTACTGCCGTGAC | 1866 |
| ITGB4.2 | NM_000213 | NM_000213.2 | ITGB4 | 2793 | CAAGGTGCCCTCAGTGGA | 403 | GCGCACACCTTCATCTCAT | 1135 | CACCAACCTGTACCCGTATTGCGA | 1867 |
| ITGB5.1 | NM_002213 | NM_002213.3 | ITGB5 | 2670 | TCGTGAAAGATGACCAGGAG | 404 | GGTGAACATCATGACGCAGT | 1136 | TGTATGTTTCTACAAAACCGCCAAGG | 1868 |
| JAG1.1 | NM_000214 | NM_000214.1 | JAG1 | 4190 | TGGCTTACACTGGCAATGG | 405 | GCATAGCTGTGAGATGCGG | 1137 | ACTCGATTTCCCAGCCAACCACAG | 1869 |
| K-ras.10 | NM_033360 | NM_033360.2 | KRAS | 3090 | GTCAAAATGGGAGGGACTA | 406 | CAGGACCACCACAGAGTGAG | 1138 | TGTATCTTGTTGAGCTATCCAAACTGCCC | 1870 |
| KCNJ15.1 | NM_002243 | NM_002243.3 | KCNJ15 | 6299 | GGACGTTCTACCTGCCTTGA | 407 | AGGCTCTGGAAACACTGGTC | 1139 | TCACTCCGCAGGTCAGGTGTCTTC | 1871 |
| KDR.6 | NM_002253 | NM_002253.1 | KDR | 463 | GAGGACGAAGGCTCTACAC | 408 | AAAAATGCCTCCACTTTTGC | 1140 | CAGGCATGCAGTGTTCTTGGCTGT | 1872 |
| Ki-67.2 | NM_002417 | NM_002417.1 | MKI67 | 145 | CGGACTTTGGGTGCGACTT | 409 | TTACAACTCTTCCACTGGGACGAT | 1141 | CCACTTGTCGAACCACCGCTCGT | 1873 |
| KIAA1303 raptor. | NM_020761 | NM_020761.2 | RPTOR | 6300 | ACTACAGCGGGAGCAGGAG | 410 | GGCATCTGAGCAAGAGGGT | 1142 | TGGAGGTAGCTGCAATCAACCAA | 1874 |
| KIF1A.1 | NM_004321 | NM_004321.4 | KIF1A | 4015 | CTCCTACTGGTCGCACACC | 411 | TCCCGGTACACCTGCTTC | 1143 | CCTGAGGACATCAACTACCGCTCG | 1875 |
| Kitlng.4 | NM_000899 | NM_000899.1 | KITLG | 68 | GTCCCCGGGATGGATGTT | 412 | GATCAGTTCAAGCTGTCTGACAATTG | 1144 | CATCTCGCTTATCCAACAATGACTTGGCA | 1876 |
| KL.1 | NM_004795 | NM_004795.2 | KL | 6191 | GAGGTCCTGTCTAAACCCTGTG | 413 | CTATGTGCAAGGCCCTCAA | 1145 | CCTGAGGGATCGTCTCACTGGCA | 1877 |
| KLK3.1 | NM_001648 | NM_001648.2 | KLK3 | 4172 | CCAAGCTTACCACCTGCAC | 414 | AGGGTGAGGAAGACAACCG | 1146 | ACCCACATGTGACACAGCTCTCC | 1878 |
| KLRK1.2 | NM_007360 | NM_007360.1 | KLRK1 | 3805 | TGAGAGCCAGGCTTCTTGTA | 415 | ATCCTGTCCTCTTTGCTGT | 1147 | TGTCTCAAAATGCCAGCCTTCTGAA | 1879 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| KRT19.3 | NM_002276 | NM_002276.1 | KRT19 | 521 | TGAGCGGCAGAAT CAGGAGTA | 416 | TGCGGTAGGTGG CAATCTC | 1148 | CTCATGGACATCAAG TCGCGGCTG | 1880 |
| KRT5.3 | NM_000424 | NM_000424.2 | KRT5 | 58 | TCAGTGAGAAGG AGTTGGA | 417 | TGCCATATCCAG AGGAAACA | 1149 | CCAGTCAACATCTCT GTTGTCACAAGCA | 1881 |
| KRT7.1 | NM_005556 | NM_005556.3 | KRT7 | 4016 | TTCAGAGATGAACC GGGC | 418 | ACTTGGCACGCT GGTTCT | 1150 | ATGTTGTCGATTCA GCCTGCAGC | 1882 |
| L1CAM.1 | NM_000425 | NM_000425.2 | L1CAM | 4096 | CTTGCTGGCCAATG CCTA | 419 | TGATTGTCCGCA GTCAGG | 1151 | ATTACGTTGTCCAG CTGCCAGCC | 1883 |
| LAMA3.1 | NM_000227 | NM_000227.2 | LAMA3 | 2529 | CAGATGAGGCACA TGGAGAC | 420 | TTGAAATGGCAG AACGGTAG | 1152 | CTGATTCCTCAGGTC CTTGGCCTG | 1884 |
| LAMA4.1 | NM_002290 | NM_002290.3 | LAMA4 | 5990 | GATGCACTGCGT TAGCAG | 421 | CAGAGGATACGC TCAGCACC | 1153 | CTCTCCATCGAGGAA GGCAAATCC | 1885 |
| LAMB1.1 | NM_002291 | NM_002291.1 | LAMB1 | 3894 | CAAGGAGACTGGG AGGTGTC | 422 | CGGCAGAACTGA CAGTGTTC | 1154 | CAAGTGCCTGTACCA CACGAAGG | 1886 |
| LAMB3.1 | NM_000228 | NM_000228.1 | LAMB3 | 2530 | ACTGACCAAGCCT GAGACCT | 423 | GTCACACTTGCA GCATTTCA | 1155 | CCACTCGCCATACTG GGTGCAGT | 1887 |
| LAMC2.2 | NM_005562 | NM_005562.1 | LAMC2 | 997 | ACTCAAGCGGAAAT TGAAGCA | 424 | ACTCCCTGAAGC CGAGACACT | 1156 | AGGTCTTATCAGCAC AGTTCCGCCTCC | 1888 |
| LAPTM5.1 | NM_006762 | NM_006762.1 | LAPTM5 | 4017 | TGCTGGACTTCTGC CTGAG | 425 | TGAGATAGGTGG GCACTTCC | 1157 | TCCTGACCCTCTGCA GCTCCTACA | 1889 |
| LDB1.2 | NM_003893 | NM_003893.4 | LDB1 | 6720 | AACACCCAGTTTGA CGCAG | 426 | CCAGTGCAGGG GAGTGT | 1158 | AAAGCTGTCCTCGTC GTCAATGCC | 1890 |
| LDB2.1 | NM_001290 | NM_001290.2 | LDB2 | 3871 | ATCACCGTGGACT GCGAC | 427 | TACCTTGGTAAA CATGGGCTTC | 1159 | AGTGTACCATGGTCA CCCAGCACG | 1891 |
| LDHA.2 | NM_005566 | NM_005566.1 | LDHA | 3935 | AGGCTACACATCCT GGGCTA | 428 | CCCGCCTAAGAT TCTTCATT | 1160 | TCTGCCAAATCTGCT ACAGAGAGTCCA | 1892 |
| LGALS1.1 | NM_002305 | NM_002305.3 | LGALS1 | 6305 | GGGTGGAGTCTTC TGACAGC | 429 | AGACCACAAGCC ATGATTGA | 1161 | CCCGGGAACATCCT CCTGGAC | 1893 |
| LGALS3.1 | NM_002306 | NM_002306.1 | LGALS3 | 2371 | AGCGGAAAATGC AGACAAT | 430 | CTTGAGGGTTTG GGTTTCCA | 1162 | ACCCAGATAACGCAT CATGAGCGA | 1894 |
| LGALS9.1 | NM_009587 | NM_009587.2 | LGALS9 | 5458 | AGTACTTCCACCGC GTGC | 431 | GACAGCTGCACA GAGCCAT | 1163 | CTTCCACCGTGTGG ACACCATCTC | 1895 |
| LIMK1.1 | NM_016735 | NM_016735.1 | LIMK1 | 3888 | GCTTCAGGTGTTGT GACTGC | 432 | AAGAGCTGCCCA TCCTTCTC | 1164 | TGCTCCCTGTCGC ACCAGTACTA | 1896 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| LMNB1.1 | NM_005573 | NM_005573.1 | LMNB1 | 1708 | TGCAAACGCTGGTGTCACA | 433 | CCCCACGAGTTCTGTTCTTC | 1165 | CAGCCCCCCAACTGACCTCATC | 1897 |
| LMO2.1 | NM_005574 | NM_005574.2 | LMO2 | 5346 | GGCTGCCAGCAGAACATC | 434 | CTCAGGCAGTCCTCGTGC | 1166 | CGCTACTTCCTGAAGGCCATCGAC | 1898 |
| LOX.1 | NM_002317 | NM_002317.3 | LOX | 3394 | CCAATGGGAGAACAACGG | 435 | CGCTGAGGCTGGTACTGTG | 1167 | CAGGCTCAGCAAGCTGAACACCTG | 1899 |
| LRP2.1 | NM_004525 | NM_004525.1 | LRP2 | 4112 | GGCTGTAGACTGGGTTTCCA | 436 | GAGACAAGAGGCCATCCAG | 1168 | CGGGCATCCAACCAGTAGAGCTTT | 1900 |
| LRRC2.1 | NM_024512 | NM_024512.2 | LRRC2 | 6315 | CCAGTGTCCCAATCTGTGTC | 437 | GGTCAGGTTATTGCTGCTGA | 1169 | CCACTGCAAATTCGACATCCGC | 1901 |
| LTF.1 | NM_002343 | NM_002343.2 | LTF | 6269 | AACGGAAGCCTGTGACTGA | 438 | AGACACCACGGCATGATTC | 1170 | CTAGAAGCTGCCATCTTGCCATGG | 1902 |
| LYZ.1 | NM_000239 | NM_000239.1 | LYZ | 6268 | TTGCTGCAAGATAACATCGC | 439 | ACCCATGTCTAATGCCTTG | 1171 | CACGGACAACCCTCTTTGCACAAG | 1903 |
| MADH2.1 | NM_005901 | NM_005901.2 | SMAD2 | 2672 | GCTGCCTTTGGTAAGAACATGTC | 440 | ATCCCAGCAGTCTCTTCACAACT | 1172 | TCCATCTTGCCATTCACGCCGC | 1904 |
| MADH4.1 | NM_005359 | NM_005359.3 | SMAD4 | 2565 | GGACATTACTGCCTGTTCACA | 441 | ACCAATACTCAGGAGCAGGATGA | 1173 | TGCATTCCAGCCTCCCATTTCCA | 1905 |
| MAL.1 | NM_002371 | NM_002371.2 | MAL | 6194 | GTTGGGAGCTTGCTGTGTC | 442 | CACAAACAGGAGGTGACCCT | 1174 | ACCTCCAACTGCTGTGCTGTGC | 1906 |
| MAL2.1 | NM_052886 | NM_052886.1 | MAL2 | 5113 | CCTTCGTCTGCCTGGAGAT | 443 | GGAACATTGGAGGAGGCAA | 1175 | CAAAATCCAGACAAGACCCCGAA | 1907 |
| MAP2K1.1 | NM_002755 | NM_002755.2 | MAP2K1 | 2674 | GCCTTTCTTACCCAGAAGCAGAA | 444 | CAGCCCCCAGCTCACTGAT | 1176 | TCTCAAAGTCGTCATCCTTCAGTTCTCCCA | 1908 |
| MAP2K3.1 | NM_002756 | NM_002756.2 | MAP2K3 | 4372 | GCCCTCCAATGTCCTTATCA | 445 | GTAGCCACTGATGCCAAAGTC | 1177 | CACATCTTCACATGGCCCTCCTG | 1909 |
| MAP4.1 | NM_002375 | NM_002375.2 | MAP4 | 2066 | GCCGGTCAGGCACACAAG | 446 | GCAGCATACACACAACAAAATGG | 1178 | ACCAACCAGTCCACGCTCCAAGGG | 1910 |
| MARCKS.1 | NM_002356 | NM_002356.4 | MARCKS | 4021 | CCCCTCTTGGATCTGTTGAG | 447 | CGGTCTTGGAGAACTGGG | 1179 | CCCATGCTGGCTTCTTCAACAAAG | 1911 |
| Maspin.2 | NM_002639 | NM_002639.1 | SERPINB5 | 362 | CAGATGGCCACTTTGAGAACATT | 448 | GGCAGCATTAACCACAAGGATT | 1180 | AGCTGACAACAGTGTGAACGACCAGACC | 1912 |
| MCAM.1 | NM_006500 | NM_006500.2 | MCAM | 3972 | CGAGTTCCAGTGGCTGAGA | 449 | TGCAACTGAAGCACAGGC | 1181 | CTTTCCAGCACCTGGCCTGTCTCT | 1913 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| MCM2.2 | NM_004526 | NM_004526.1 | MCM2 | 580 | GACTTTTGCCCGCTACCTTTC | 450 | GCCACTAACTGCTTCAGTATGAAGAG | 1182 | ACAGCTCATTGTTGTCACGCCGGA | 1914 |
| MCM3.3 | NM_002388 | NM_002388.2 | MCM3 | 524 | GGAGAACAATCCCCTTGAGA | 451 | ATCTCCTGGATGGTGATGGT | 1183 | TGGCCTTTCTGTCTACAAGGATCACCA | 1915 |
| MCM6.3 | NM_005915 | NM_005915.2 | MCM6 | 614 | TGATGGTCCTATGTGTCACATTCA | 452 | TGGGACAGGAAACACACCAA | 1184 | CAGGTTTCATACCAACACAGGCTTCAGCAC | 1916 |
| MCP1.1 | NM_002982 | NM_002982.1 | CCL2 | 700 | CGCTCAGCCAGATGCAATC | 453 | GCACTGAGATCTTCCTATTGGTGAA | 1185 | TGCCCCAGTCACCTGCTGTTA | 1917 |
| MDH2.1 | NM_005918 | NM_005918.2 | MDH2 | 2849 | CCAACACCTTTGTTGCAGAG | 454 | CAATGACAGGGACGTTGACT | 1186 | CGAGCTGGATCCAAACCCTTCAG | 1918 |
| MDK.1 | NM_002391 | NM_002391.2 | MDK | 3231 | GGAGCCGACTGCAAGTACA | 455 | GACTTTGGTGCCTGTGCC | 1187 | ATCACACGCACCCCAGTTCTCAAA | 1919 |
| MDM2.1 | NM_002392 | NM_002392.1 | MDM2 | 359 | CTACAGGGACGCCATCGAA | 456 | ATCCAACCAATCACCTGAATGTT | 1188 | CTTACACCAGCATCAAGATCCGG | 1920 |
| MGMT.1 | NM_002412 | NM_002412.1 | MGMT | 689 | GTGAAATGAAACGCACCACA | 457 | GACCCTGCTCACAACCAGAC | 1189 | CAGCCCTTTGGGAAGCTGG | 1921 |
| mGST1.2 | NM_020300 | NM_020300.2 | MGST1 | 806 | ACGGATCTACCACACCATTGC | 458 | TCCATATCCAACAAAAAACTCAAAG | 1190 | TTTGACACCCCTTCCCCAGCCA | 1922 |
| MICA.1 | NM_000247 | NM_000247.1 | MICA | 5449 | ATGGTGAATGTCACCCGC | 459 | AAGCCAGAAGCCCTGCAT | 1191 | CGAGCCTCAGAGGGCAACATTAC | 1923 |
| MIF.2 | NM_002415 | NM_002415.1 | MIF | 3907 | CCGGACCAGGGTCTACATCA | 460 | GGTGGAGTTGTTCCAGCC | 1192 | CTATTACGACATGAACGCGCCAA | 1924 |
| MMP1.1 | NM_002421 | NM_002421.2 | MMP1 | 2167 | GGGAGATCATCGGGACAACTC | 461 | GGGCCTGTTGAAAAGCAT | 1193 | AGCAAGATTTCCTCCAGGTCCATCAAAAGG | 1925 |
| MMP10.1 | NM_002425 | NM_002425.1 | MMP10 | 4920 | TGTACCCACTCTACAACTCATTCACA | 462 | TGAATGCCATTCACATCATCTTG | 1194 | AGCTCGCCCAGTTCCGCCTTTC | 1926 |
| MMP14.1 | NM_004995 | NM_004995.2 | MMP14 | 4022 | GCTGTGGAGCTCTCAGGAA | 463 | AGCAAGGACAGGGACCAA | 1195 | CCTGAGGAGGCACACTTGCTCCT | 1927 |
| MMP2.2 | NM_004530 | NM_004530.1 | MMP2 | 672 | CCATGATGGAGAGGCAGACA | 464 | GGAGTCCGTCCTTACCGTCAA | 1196 | CTGGGAGCATGGCGATGATACCC | 1928 |
| MMP7.1 | NM_002423 | NM_002423.2 | MMP7 | 2647 | GGATGTAGCAGTCTAGGGATTAACT | 465 | GGAATGTCCCATACCCAAAGAA | 1197 | CCTGTATGCTGCAACTCATGAACTTGGC | 1929 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| MMP9.1 | NM_004994 | NM_004994.1 | MMP9 | 304 | GAGAACCAATCTCACCGACA | 466 | CACCCGAGTGTAACCATAGC | 1198 | ACAGGTATTCCTCTGCCAGCTGCC | 1930 |
| MRP1.1 | NM_004996 | NM_004996.2 | ABCC1 | 15 | TCATGGTGCCCGTCAATG | 467 | CGATTGTCTTTGCTCTTCATGTG | 1199 | ACCTGATACGTCTTGGTCTTCATCGCCAT | 1931 |
| MRP2.3 | NM_000392 | NM_000392.1 | ABCC2 | 55 | AGGGGATGACTTGGACACAT | 468 | AAAACTGCATGGCTTTGTCA | 1200 | CTGCCATTCGACATGACTCAATTT | 1932 |
| MRP3.1 | NM_003786 | NM_003786.2 | ABCC3 | 8 | TCATCCTGGCGATCTACTTCCT | 469 | CCGTTGAGTGGAATCAGCAA | 1201 | TCTGTCCTGGCTGGAGTCGCTTTCAT | 1933 |
| MRP4.2 | NM_005845 | NM_005845.3 | ABCC4 | 6057 | AGCGCCTGGAATCTACAACT | 470 | AGAGCCCCTGAGAGAAGAT | 1202 | CGGAGTCCAGTGTTTTCCCACTTA | 1934 |
| MSH2.3 | NM_000251 | NM_000251.1 | MSH2 | 2127 | GATGCAGAATTGAGGCAGAC | 471 | TCTTGGCAAGTCGGTTAAGA | 1203 | CAAGAAGATTTACTTCGTCGATTCCCAGA | 1935 |
| MSH3.2 | NM_002439 | NM_002439.1 | MSH3 | 2132 | TGATTACCATCATGGCTCAGA | 472 | CTTGTGAAAATGCCATCCAC | 1204 | TCCCAATTGTCGCTTCTTCTGCAG | 1936 |
| MSH6.3 | NM_000179 | NM_000179.1 | MSH6 | 2136 | TCTATTGGGGATTGGTAGG | 473 | CAAATTGCGAGTGGTGAAAT | 1205 | CCGTTACCAGCTGGAAATTCCTGAGA | 1937 |
| MT1B.1 | NM_005947 | NM_005947.1 | MT1B | 5355 | GTGGGCTGTGCCAAGTGT | 474 | ACAGCAGGGCACTTCTC | 1206 | ATGAGCCTTTGCAGACACAGCCCT | 1938 |
| MT1G.1 | NM_005950 | NM_005950.1 | MT1G | 6333 | GTGCACCCACTGCCTCTT | 475 | AGCAGTTGGGGTCCATTG | 1207 | CCCGAGGCGAGACTAGAGTTCCC | 1939 |
| MT1H.1 | NM_005951 | NM_005951.2 | MT1H | 6332 | CGTGTTCCACTGCCTCTTC | 476 | AGCAGTTGGGGTCCATTG | 1208 | CCGAGGTGAGACTGGAGTTCCCA | 1940 |
| MT1X.1 | NM_005952 | NM_005952.2 | MT1X | 3897 | CTCCTGCAAATGCAAAGAGTG | 477 | ACTTGGCACAGCCCACAG | 1209 | CACCTCCTGCAAGAAGAGCTGCTG | 1941 |
| MUC1.2 | NM_002456 | NM_002456.1 | MUC1 | 335 | GGCCAGGATCTGTGGTGGTA | 478 | CTCCACGTCGTGGACATTGA | 1210 | CTCTGGCCTTCCGAGAAGGTACC | 1942 |
| MVP.1 | NM_017458 | NM_017458.1 | MVP | 30 | ACGAGAACGAGGGCATCTATGT | 479 | GCATGTAGGTGCTTCCAATCAC | 1211 | CGCACCTTTCCGGTCTTGACATCCT | 1943 |
| MX1.1 | NM_002462 | NM_002462.2 | MX1 | 2706 | GAAGGAATGGGAATCAGTCATGA | 480 | GTCTATTAGAGTCAGATCCGGGACAT | 1212 | TCACCCTGGAGATCAGCTCCCGA | 1944 |
| MYBL2.1 | NM_002466 | NM_002466.1 | MYBL2 | 1137 | GCCGAGATCGCCAAGATG | 481 | CTTTTGATGGTAGAGTTCCAGTGATTC | 1213 | CAGCATTGTCTGTCCTCCCTGGCA | 1945 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| MYH11.1 | NM_002474 | NM_002474.1 | MYH11 | 1734 | CGGTACTTCTCAGG GCTAATATATACG | 482 | CCGAGTAGATGG GCAGGTGTT | 1214 | CTTTTCTGCGTGTG GTCAACCCTA | 1946 |
| MYRIP.2 | NM_015460 | NM_015460.1 | MYRIP | 1704 | CCTTCACCTTCCTC GTCAAC | 483 | AGCAGCTCTTGC AGACATTG | 1215 | ATTTGCAATCTCCAC ACTGGCGCT | 1947 |
| NBN.1 | NM_002485 | NM_002485.4 | NBN | 4121 | GCATCTACTTGCCA GAACCAA | 484 | TCCCCTTGCAGCT GGAGTT | 1216 | CTTCCAAGTTCTGGC TGCTTGCAG | 1948 |
| NCF1.1 | NM_000265 | NM_000265.2 | NCF1 | 4676 | GACACCTTCATCCG TCACAT | 485 | ATAGTGTGGCT GGGTACG | 1217 | AAGCGCTTCTCAAAG CCCAGCAG | 1949 |
| NFAT5.1 | NM_006599 | NM_006599.2 | NFAT5 | 3071 | CTGAACCCCTCTCC TGGTC | 486 | AGGAAACCATGG CGAGGT | 1218 | CGAGAATCAGTCCC CGTGGAGTTC | 1950 |
| NFATC2.1 | NM_173091 | NM_173091.2 | NFATC2 | 5123 | CAGTCAAGGTCAG AGGCTGAG | 487 | CTTTGGCTCGTG GCATTC | 1219 | CGGGTTCCTACCCC ACAGTCATTC | 1951 |
| NFKBp50.3 | NM_003998 | NM_003998.1 | NFKB1 | 3439 | CAGACCAAGGAGA TGGACCT | 488 | AGCTGCCAGTGC TATCCG | 1220 | AAGCTGTAAACATGA GCCCACCA | 1952 |
| NFKBp65.3 | NM_021975 | NM_021975.1 | RELA | 39 | CTGCCGGGATGGC TTCTAT | 489 | CCAGGTTCTGGA AACTGTGGAT | 1221 | CTGAGCTCTGCCCG GACCGCT | 1953 |
| NFX1.1 | NM_002504 | NM_002504.3 | NFX1 | 4025 | CCCTGCCATACCA GCTCA | 490 | CGTCCACATTCA CACTGTAGC | 1222 | CCTGCCCTGTGACT GCTTGTAAAGC | 1954 |
| NME2.1 | NM_002512 | NM_002512.2 | NME2 | 3899 | ATGCTTGGGGAGA CCAATC | 491 | CTGAATGCAGAA GTCCCCAC | 1223 | AGCAGATTCAAAGCC AGGCACCAT | 1955 |
| NNMT.1 | NM_006169 | NM_006169.2 | NNMT | 5101 | CCTAGGGCAGGGA TGGAG | 492 | CTAGTCCAGCCA AACATCCC | 1224 | CCCTCTCCTCATGCC CAGACTCTC | 1956 |
| NOL3.1 | NM_003946 | NM_003946.3 | NOL3 | 6307 | CAGCCTTGGGAAG TGAGACT | 493 | ATGATGTGTGTG GCCTTTGT | 1225 | CTCAAGGTCCCTTTC TGCTCCCT | 1957 |
| NOS2A.3 | NM_000625 | NM_000625.3 | NOS2 | 6509 | GGGTCCATTATGAC TCCCAA | 494 | GCTCATCTGGAG GGGTAGG | 1226 | TGTCCCTGGGTCCT CTGGTCAAAC | 1958 |
| NOS3.1 | NM_000603 | NM_000603.2 | NOS3 | 2624 | ATCTCCGCCTCGCT CATG | 495 | TCGGAGCCATAC AGGATTGTC | 1227 | TTCACTCGCTTCGCC ATCACCG | 1959 |
| NOTCH1.1 | NM_017617 | NM_017617.2 | NOTCH1 | 2403 | CGGGTCCACAGT TTGAATG | 496 | GTTGTATTGGTT CGGCACCAT | 1228 | CCGCTCTGCAGCCG GGACA | 1960 |
| NOTCH2.1 | NM_024408 | NM_024408.2 | NOTCH2 | 2406 | CACTTCCCTGCTGG GATTAT | 497 | AGTTGTCAAACA GGCACTCG | 1229 | CCGTGTTGCACAGC TCATCACACT | 1961 |
| NOTCH3.1 | NM_000435 | NM_000435.2 | NOTCH3 | 6464 | TGTGGACGAGTGT GCTGG | 498 | ACTCCCCTGCCAG GTTGGT | 1230 | ACCCTGTGCCCCTC ATGGTATCTG | 1962 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| NPD009 (ABAT $$ | NM_020686 | NM_020686.2 | ABAT | 1707 | GGCTGTGGCTGAGGCTGTAG | 499 | GGAGCATTCGAGGTCAAATCA | 1231 | TTCCCAGAGTGTCTCACTTCCAGCAGAG | 1963 |
| NPM1.2 | NM_002520 | NM_002520.2 | NPM1 | 2328 | AATGTTGTCCAGGTTCTATTGC | 500 | CAAGCAAAGGGTGGAGTTC | 1232 | AACAGGCATTTTGAACAACACATTCTTG | 1964 |
| NPPB.1 | NM_002521 | NM_002521.2 | NPPB | 6196 | GACACCTGCTTCTGATTCCAC | 501 | TGAGTCACTTCAAAGGCGG | 1233 | AGGGGCTTTTTCCTCAACCCTGTG | 1965 |
| NPR1.1 | NM_000906 | NM_000906.2 | NPR1 | 6197 | ACATTCTGCAGTCCCCTG | 502 | CACACAAGCAGCTTCCA | 1234 | CCTTCAGAACCCTCATGCTCCTGG | 1966 |
| NPY1R.1 | NM_000909 | NM_000909.4 | NPY1R | 4513 | GGATCTTCCCCACTCTGCT | 503 | TTGTCTTTTTCGCTCCTGC | 1235 | CCTTCCATTCCCACCCTTCCTTCT | 1967 |
| NRG1.3 | NM_013957 | NM_013957.1 | NRG1 | 410 | CGAGACTCTCCTCATAGTGAAAGGTAT | 504 | CTTGGCGTGTGGAAATCTACAG | 1236 | ATGACCACCCCGGCTCGTATGTCA | 1968 |
| NUDT1.1 | NM_002452 | NM_002452.3 | NUDT1 | 4564 | ACTGGTTTCCACTCCTGCTT | 505 | GTCCAGGATGGTGTCCTGA | 1237 | CCACGGGTACTTCAAGTTCCAGGG | 1969 |
| OGG1.1 | NM_002542 | NM_002542.4 | OGG1 | 6198 | ACCAAGGTGGCTGACTGC | 506 | ATATGGACATCCACGGGC | 1238 | TCTGCCTGATGGCCCTAGACAAGC | 1970 |
| OPN, osteoponti$$ | NM_000582 | NM_000582.1 | SPP1 | 764 | CAACCGAAGTTTTCACTCCAGTT | 507 | CCTCAGTCCATAAACCACTATCA | 1239 | TCCCCACAGTAGACACATATGATGGCCG | 1971 |
| p21.3 | NM_000389 | NM_000389.1 | CDKN1A | 33 | TGGAGACTCTCAGGGTCGAAA | 508 | GGCGTTTGGAGTGGTAGAAATC | 1240 | CGGGGCGAGACCAGCATGAC | 1972 |
| p27.3 | NM_004064 | NM_004064.1 | CDKN1B | 38 | CGGTGACCACGAAGAGTTAA | 509 | GGCTCGCTCTTCCATGTC | 1241 | CCGGGACTTGGAGAAGCACTGCA | 1973 |
| P53.2 | NM_000546 | NM_000546.2 | TP53 | 59 | CTTTGAACCCTTGCTTGCAA | 510 | CCCGGGACAAAGCAAATG | 1242 | AAGTCCTGGGTGCTTCTGACGCACA | 1974 |
| PAH.1 | NM_000277 | NM_000277.1 | PAH | 6199 | TGGCTGATTCCATTAACAGTGA | 511 | CACATTCTGTCCATGGCTTTAC | 1243 | ATCCTTTGCAGTGCCCTCCAGAAA | 1975 |
| PAI1.3 | NM_000602 | NM_000602.1 | SERPINE1 | 36 | CCGCAACGTGGTTTCTCA | 512 | TGCTGGGTTTCTCCTCCTGTT | 1244 | CTCGTGTTGGCCATGCTCCAG | 1976 |
| Pak1.2 | NM_002576 | NM_002576.3 | PAK1 | 3421 | GAGCTGTGGGTTGTTATGGA | 513 | CCATGCAAGTTTCTGTCACC | 1245 | ACATCTGTCAAGGAGCCTCCAGCC | 1977 |
| PARD6A.1 | NM_016948 | NM_016948.2 | PARD6A | 4514 | GATCCTCGAGGTCAATGGC | 514 | ACCATCATGTCCGTCACTTG | 1246 | TCCAAGGTCTTCCCGGCTACTTCA | 1978 |
| PBOV1.1 | NM_021635 | NM_021635.1 | PBOV1 | 3936 | GCAAAGCCTTTCCAGAAAAA | 515 | GGCTGGGCTTAAACAGTCAT | 1247 | TGGTAGCAGAATTGCCTTTTCAACCA | 1979 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| PCCA.1 | NM_000282 | NM_000282.2 | PCCA | 6250 | GGTGAAATCTGCACTGTCA | 516 | ATTCCAGCTCCACCAGCA | 1248 | TCCCTTCTCCAACTGTGTCTCCA | 1980 |
| PCK1.1 | NM_002591 | NM_002591.2 | PCK1 | 6251 | CTTAGCATGGCCCAGCAC | 517 | CTTCCGGAACCAGTTGACA | 1249 | CAGCCAAACTGCCCAAGATCTTCC | 1981 |
| PCNA.2 | NM_002592 | NM_002592.1 | PCNA | 148 | GAAGGTGTTGGAGGCACTCAAG | 518 | GGTTTACACCGCTGGAGCTAA | 1250 | ATCCAGCAGGCCTCGTTGATGAG | 1982 |
| PCSK6.1 | NM_002570 | NM_002570.3 | PCSK6 | 6282 | ACCTTGAGTAGCAGAGGCCC | 519 | GTTGCTGAGCCATTTCAC | 1251 | CACACCTTCCTCCAGAATGACCCC | 1983 |
| PDCD1.1 | NM_005018 | NM_005018.2 | PDCD1 | 6286 | GACAACGCCACCTTCACC | 520 | GGCTCATCGCGTACCAGT | 1252 | TCTCCAACACATCGGAGAGCTTCG | 1984 |
| PDE4DIP.1 | NM_014644 | NM_014644.4 | PDE4DIP | 6417 | GCTTCGTCTTGCTGTGAGAG | 521 | AGCTTCATTGGAGGGAGAGAG | 1253 | TCGCGCAGTCTCTCTAAGTCATGATCTC | 1985 |
| PDGFA.3 | NM_002607 | NM_002607.2 | PDGFA | 56 | TTGTTGGTGTGCCCTGGTG | 522 | TGGGTTCTGTCCAAACACTGG | 1254 | TGGTGGCGGTCACTCCCCTGC | 1986 |
| PDGFB.3 | NM_002608 | NM_002608.1 | PDGFB | 67 | ACTGAAGGAGACCCTTGGAG | 523 | TAAATAACCCTGCCCACACA | 1255 | TCTCCTGCCGATGCCCCTAGG | 1987 |
| PDGFC.3 | NM_016205 | NM_016205.1 | PDGFC | 29 | AGTTACTAAAAATACCACGAGGTCCTT | 524 | GTCGGTGAGTGATTTGTGCAA | 1256 | CCCTGACACGGTCTTTGGTCTCAACT | 1988 |
| PDGFD.2 | NM_025208 | NM_025208.2 | PDGFD | 31 | TATCGAGGCAGGTCATACCA | 525 | TAACGCTTGGCATCATCATT | 1257 | TCCAGGTCAACTTTTGACTTCCGGT | 1989 |
| PDGFRa.2 | NM_006206 | NM_006206.2 | PDGFRA | 24 | GGGAGTTTCAAGAGATGGA | 526 | CTTCAACCACCTTCCCAAAC | 1258 | CCCAAGACCCGACCAAGCACTAG | 1990 |
| PDGFRb.3 | NM_002609 | NM_002609.2 | PDGFRB | 464 | CCAGCTCTCCTTCCAGCTAC | 527 | GGGTGGCTCTCACTTAGCTC | 1259 | ATCAATGTCCCTGTCCGAGTGCTG | 1991 |
| PDZK1.1 | NM_002614 | NM_002614.3 | PDZK1 | 6319 | AATGACCTCCACCTTCAACC | 528 | CGCAGGAAGAAGCCATAGTT | 1260 | TGCCCTTCTTGCTTGGACAGTTTACA | 1992 |
| PDZK3.1 | NM_015022 | NM_015022.2 | | 3885 | GAGCTGAGAGCCTTGAGCAT | 529 | CTCGGCCCTGCTGAGTAA | 1261 | CTCGCTGCAGAGCTTGTCAAGGTC | 1993 |
| PF4.1 | NM_002619 | NM_002619.1 | PF4 | 6326 | GCAGTGCCTGTGTGTGAAG | 530 | GGCCTTGATCACCTCCAG | 1262 | TCCGTCCCAGGCACATCACC | 1994 |
| PFKP.1 | NM_002627 | NM_002627.3 | PFKP | 6252 | AGCTGATGCCGCATACATT | 531 | GGTGCTCCACGTTGGACT | 1263 | CAGATCCCTGATGTCGAAGGGCTC | 1995 |
| PFN2.1 | NM_053024 | NM_053024.1 | PFN2 | 3426 | TCTATACGTCGATGGTGACTGC | 532 | GCCGACAGCCACATTGTAT | 1264 | CTCCCCACCTTGACTCTTTGTCCG | 1996 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| PGF.1 | NM_002632 | NM_002632.4 | PGF | 4026 | GTGGTTTTCCCTCGGAGC | 533 | AGCAAGGGAACAGCTCAT | 1265 | ATCTTCTCAGACGTCCCGAGCCAG | 1997 |
| PI3K.2 | NM_002646 | NM_002646.2 | PIK3C2B | 368 | TGCTACCTGGACAGCCCG | 534 | AGCCGTCCTTCAGTAACCA | 1266 | TCCTCCTGAAACGAGCTGTGTCTGACTT | 1998 |
| PI3KC2A.1 | NM_002645 | NM_002645.2 | PIK3C2A | 6064 | ATACCAATCACCGCACAAAC | 535 | CACACTAGCATTTTCTCCGCATA | 1267 | TGTCGTGTGACTGGACTTAACAAATAGCCT | 1999 |
| PIK3CA.1 | NM_006218 | NM_006218.1 | PIK3CA | 2962 | GTGATTGAAGAGCATGCCAA | 536 | GTCCTGCGTGGGAATAGC | 1268 | TCCTGCTTCTCCGGATACAGACCA | 2000 |
| PLA2G4C.1 | NM_003706 | NM_003706.1 | PLA2G4C | 6249 | CCCTTTCCCCAAGTAGAAGAG | 537 | AGGATGTAGCAGCTGGCG | 1269 | CCTTGGACCACAAATCCAGCTCAG | 2001 |
| PLAT.1 | NM_033011 | NM_033011.2 | PLAT | 6459 | GATTTGCTGGGAAGTGCTGT | 538 | TAGCTGATGCCCTGGTCC | 1270 | TAGATACCAGGGCCACGTGCTACG | 2002 |
| PLAUR.3 | NM_002659 | NM_002659.1 | PLAUR | 708 | CCCATGCGATGCTCCTCTGAA | 539 | CCGGTGGCTACCAGACATTG | 1271 | CATTGACTGCCGAGGCCCATG | 2003 |
| PLG.1 | NM_000301 | NM_000301.1 | PLG | 6310 | GGCAAAATTTCCAAGACCAT | 540 | ATGTATCCATGAGCGTGTGG | 1272 | TGCCAGGCCTGGGACTCTCA | 2004 |
| PLN.1 | NM_002667 | NM_002667.2 | PLN | 3886 | TGATGCTTCTCTGAAGTTCTGC | 541 | CCTGTCTGCATGGGATGAC | 1273 | AGATCTGCAGCTTGCCACATCAGC | 2005 |
| PLOD2.1 | NM_000935 | NM_000935.2 | PLOD2 | 3820 | CAGGGAGGTGTTGCAAAT | 542 | TCTCCCAGGATGCATGAAG | 1274 | TCCAGCCTTTTCGTGGTGACTCAA | 2006 |
| PLP1.1 | NM_000533 | NM_000533.3 | PLP1 | 4027 | AGAACAGACTGCCTGAGGA | 543 | CAGAGGGCCATCTCAGGTT | 1275 | CACCATTAGCCACCAGCAGCTGCT | 2007 |
| PMP22.1 | NM_000304 | NM_000304.2 | PMP22 | 6254 | CCATCTACACGGTGAGGCA | 544 | TGTAGGCGAAACCGTAGGA | 1276 | AATCCGAGTTGAGATGCCACTCCG | 2008 |
| PPAP2B.1 | NM_003713 | NM_003713.3 | PPAP2B | 6457 | ACAAGCACCATCCCAGTGA | 545 | CACGAAGAAAACTATGCAGCAG | 1277 | ACCAGGGCTCCTTGAGCAAATCCT | 2009 |
| PPARG.3 | NM_005037 | NM_005037.3 | PPARG | 1086 | TGACTTTATGGAGCCCAAGTT | 546 | GCCAAGTGCTGTCATCTAA | 1278 | TTCCAGTGCATTGAACTTCACAGCA | 2010 |
| PPP1R3C.1 | NM_005398 | NM_005398.4 | PPP1R3C | 6320 | TTCCTTCCCTCTCAATCCAC | 547 | CACAGTTTCATCACCATC | 1279 | CCTTCCTCAACTTTTCCTTGCCCA | 2011 |
| PPP2CA.1 | NM_002715 | NM_002715.2 | PPP2CA | 3879 | GCAATCATGGAACTTGACGA | 548 | ATGTGGCTGCCTCTACG | 1280 | TTTCTTGCAGTTTGACCCAGCACC | 2012 |
| PRCC.1 | NM_005973 | NM_005973.4 | PRCC | 6002 | GAGGAAGAGGAGGCGGTG | 549 | CAGGGAGAGAAGCGAACAA | 1281 | CTACATCTGGGCCCGCTTTAGGG | 2013 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| PRKCA.1 | NM_002737 | NM_002737.1 | PRKCA | 2626 | CAAGCAATGCGTCATCAATGT | 550 | GTAAATCCGCCCCCTCTTCT | 1282 | CAGCCTCTGCGAATGGATCACACT | 2014 |
| PRKCB1.1 | NM_002738 | NM_002738.5 | PRKCB | 3739 | GACCCAGCTCCACTCCTG | 551 | CCCATTCACGTACTCCATCA | 1283 | CCAGACCATGGACCGCTGTACTT | 2015 |
| PRKCD.2 | NM_006254 | NM_006254.1 | PRKCD | 626 | CTGACACTTGCCGCAGAGAA | 552 | AGGTGGTCCTTGGTCTGGAA | 1284 | CCCTTTCTCACCCACCTCATCTGCAC | 2016 |
| PRKCH.1 | NM_006255 | NM_006255.3 | PRKCH | 4370 | CTCCACCTATGAGCGTCTGTC | 553 | CACACTTTCCCTCCTTTTGG | 1285 | TCCTGTTAACATCCCAAGCCCACA | 2017 |
| PRO2000.3 | NM_014109 | NM_014109.2 | ATAD2 | 1666 | ATTGGAAAAACCTCGTCACC | 554 | TCCGTATCTTGGTCTTGCAG | 1286 | CCCAACATATTTTATAGTGGCCCAGC | 2018 |
| PROM1.1 | NM_006017 | NM_006017.1 | PROM1 | 4516 | CTATGACAGGCATGCCACC | 555 | CTCCAACCATGAGGAAGACG | 1287 | ACCCGAGGCTGTGTCTCCAACAC | 2019 |
| PROM2.1 | NM_144707 | NM_144707.1 | PROM2 | 5108 | CTTCAGCGCATCCACTACC | 556 | CCATGCTGGTCTTCACCAC | 1288 | CTTCCTCGTTCAGATCCAGAGCC | 2020 |
| PRPS2.1 | NM_001039091 | NM_001039091$ | PRPS2 | 4694 | CACTGCCACCAAGATTCAGGT | 557 | ATTGTGTGTCCTTCGGATTG | 1289 | TTGACATTTCCATGATCTTGGCCG | 2021 |
| PRSS8.1 | NM_002773 | NM_002773.2 | PRSS8 | 4742 | GTACACTCTGGCCTCCAGCTA | 558 | CCACACGAGGCTGGAGTT | 1290 | TCCTGGATCCAAAGCAAGTGACA | 2022 |
| PSMA7.1 | NM_002792 | NM_002792.2 | PSMA7 | 6255 | GCCAAACTGCAGGATGAAAG | 559 | AGGCCATGCAGACGTTGT | 1291 | CCAAAGCACAGATCTTCCGCACTG | 2023 |
| PSMB8.1 | NM_148919 | NM_148919.3 | PSMB8 | 6461 | CAGTGCCTATCGGCCTAATC | 560 | TAAGCAATAGCCCTGCGG | 1292 | CAAGGTCATAGGCCTCTTCAGGGC | 2024 |
| PSMB9.1 | NM_148954 | NM_148954.2 | PSMB9 | 6462 | GGGGTGTCATCTACCTGGTC | 561 | CATTGCCCAAGATGACTCG | 1293 | TGGTCCACACCGGCAGCTGTAATA | 2025 |
| PTEN.2 | NM_000314 | NM_000314.1 | PTEN | 54 | TGGCTAAGTGAAGATGACAATCATG | 562 | TGCACATATCATTACACCAGTTCGT | 1294 | CCTTTCCAGCTTTACAGTGAATTGCTGCA | 2026 |
| PTGIS.1 | NM_000961 | NM_000961.3 | PTGIS | 5429 | CCACACTGGCATCTCCCT | 563 | GCCCATGGGATGAGAAACT | 1295 | CCTTCTCCAGGGACAGAAGCAGGA | 2027 |
| PTHR1.1 | NM_000316 | NM_000316.1 | PTH1R | 2375 | CGAGGTACAAGCTGAGATCAAGAA | 564 | GCGTGCTTTCGCTTGAA | 1296 | CCAGTGCCAGTGTCCAGCGGCT | 2028 |
| PTK2.1 | NM_005607 | NM_005607.3 | PTK2 | 2678 | GACCGGTCGAATGATAAGGT | 565 | CTGGACATCTCGATGACAGC | 1297 | ACCAGGCCCGTCACATTCTGTAC | 2029 |
| PTK2B.1 | NM_004103 | NM_004103.3 | PTK2B | 2883 | CAAGCCCAGCCGACCTAAG | 566 | GAACCTGAACTGCAGCTTTG | 1298 | CTCCGCAAACCAACCTCCTGGCT | 2030 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| PTN.1 | NM_002825 | NM_002825.5 | PTN | 3964 | CCTTCCAGTCCAAAAATCCC | 567 | CCCCTCTCTCCACTTTGGAT | 1299 | TTCCTCTGCTCTGGGGCTCTCTG | 2031 |
| PTPNS1.1 | NM_080792 | NM_080792.1 | SIRPA | 2896 | CTCCAGCTAGCACTAAGCAACATC | 568 | TTTCAAGATTGCACGTTTCACAT | 1300 | TCTCAGTAATTACAGGGTCCACAG | 2032 |
| PTPRB.1 | NM_002837 | NM_002837.2 | PTPRB | 3881 | GATATGCGGTGAGGAACAGC | 569 | CTGGCCACACCGTATAGTGA | 1301 | ATGCACACAAGACTCATCCGCCACT | 2033 |
| PTPRC.1 | NM_080921 | NM_080921.2 | PTPRC | 6450 | TGGCCCGTCAATGGAAGAG | 570 | GGACATCTTTTGTGCTGGTTG | 1302 | CAACATCTCCAAAAGCCCGAGTGC | 2034 |
| PTPRG.1 | NM_002841 | NM_002841.2 | PTPRG | 2682 | GGACAGCGACAAAGACTTGA | 571 | GGACTCGGAACAGGTAAAGG | 1303 | CACCATTAGCCATGTCTCACCCGA | 2035 |
| PTTG1.2 | NM_004219 | NM_004219.2 | PTTG1 | 1724 | GGCTACTCTGATCTATGTTGATAAGGAA | 572 | GCTTCAGCCCATCCTTAGCA | 1304 | CACACGGGTGCCTGGTTCTCCA | 2036 |
| PVALB.1 | NM_002854 | NM_002854.2 | PVALB | 4316 | AAACCAAGATGCTGATGGCT | 573 | CAGCCACCAGAGTGGAGAA | 1305 | TTTTGCCGTCCCCATCTTTGTCTC | 2037 |
| PXDN.1 | NM_012293 | NM_012293.1 | PXDN | 6257 | GCTGCTCAAGCTGAACCC | 574 | ACCCACGATCTTCCTGGTC | 1306 | ACTGGGACGGCGACACCATCTACT | 2038 |
| RAC1.3 | NM_006908 | NM_006908.3 | RAC1 | 2698 | TGTTGTAAATGTCTCAGCCCC | 575 | TTGAGCAAAGCGTACAAAGG | 1307 | CGTTCTTGGTCCTGTCCCTTGGA | 2039 |
| RAD51.1 | NM_002875 | NM_002875.2 | RAD51 | 3976 | AGACTACTCGGGTCGAGGTG | 576 | AGCATCCGCAGAAACCTG | 1308 | CTTTCAGCAGGCAGATGCACTTG | 2040 |
| RAF1.3 | NM_002880 | NM_002880.1 | RAF1 | 2130 | CGTCGTATGCGAGAGTCTGT | 577 | TGAAGGCGTGAGGTGTAGAA | 1309 | TCCAGGATGCCTGTTAGTTCTCAGCA | 2041 |
| RALBP1.1 | NM_006788 | NM_006788.2 | RALBP1 | 2105 | GGTGTCAGATATAAATGTGCAAATGC | 578 | TTCGATATTGCCAGCAGCTATAAA | 1310 | TGCTGTCCTGTCGGTCTCAGTACGTTCA | 2042 |
| RARB.2 | NM_016152 | NM_016152.2 | RARB | 687 | TGCCTGGACATCCTGATTCT | 579 | AAGGCCGTCTGAGAAAGTCA | 1311 | TGCACCAGTATACCCCAGAACAAGA | 2043 |
| RASSF1.1 | NM_007182 | NM_007182.4 | RASSF1 | 6658 | AGGGCACGTGAAGTCATTG | 580 | AAAGAGTGCAAACTTGCGG | 1312 | CACCACCAAGAACTTTCCGCACAG | 2044 |
| RB1.1 | NM_000321 | NM_000321.1 | RB1 | 956 | AGGAGCCCTTACAAGTTTCC | 581 | GGACTCTTTCAGGGGTGAAAT | 1313 | CCCTTACGGATTCCTGGAGGGAAC | 2045 |
| RBM35A.1 | NM_017697 | NM_017697.2 | ESRP1 | 5109 | TGGTTTTGAATCACCAGGG | 582 | CTCTGTCCGCAGACTTCATCT | 1314 | CGCCCATCAGGAGATGCCTTTATC | 2046 |
| REG4.1 | NM_032044 | NM_032044.2 | REG4 | 3226 | TGCTAACTCCTCCTGCACAGCC | 583 | TGCTAGGTTCCCCCTCTGAA | 1315 | TCCTCTTCCTTTCTGCTAGCCTGGC | 2047 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| RET.1 | NM_020630 | NM_020630.3 | RET | 5001 | GCCTGTGCAGTTCT TGTGC | 584 | GGAAGGGCAGA CCCTCAC | 1316 | AACATCAGCGTGGC CTACAGGCTC | 2048 |
| RGS1.1 | NM_002922 | NM_002922.3 | RGS1 | 6258 | TGCCCTGTAAAGCA GAAGAGAT | 585 | CTCGAGTGCGGA AGTCAATA | 1317 | AGCAGCATCTGAATG CACAAATGCT | 2049 |
| RGS5.1 | NM_003617 | NM_003617.1 | RGS5 | 2004 | TTCAAACGGAGGCT CCTAAAGAG | 586 | GAAGGTTCCACC AGTTCTTCA | 1318 | AATATTGACCACTTC ACTAGGACATCACA | 2050 |
| RHEB.2 | NM_005614 | NM_005614.3 | RHEB | 6609 | GATGATTGAGAACA GCCTTGC | 587 | GCTCCCAAGACT CTGACACA | 1319 | TGTCACTGTCCTAGA ACACCCTGGAGTT | 2051 |
| RhoB.1 | NM_004040 | NM_004040.2 | RHOB | 2951 | AAGCATGAACAGGA CTTGACC | 588 | CCTCCCCAAGTC AGTTGC | 1320 | CTTTCCAACCCCTGG GGAAGACAT | 2052 |
| rhoC.1 | NM_175744 | NM_175744.1 | RHOC | 773 | CCCGTTCGGTCTG AGGAA | 589 | GAGCACTCAAGG TAGCCAAAGG | 1321 | TCCGGTTCGCCATGT CCCG | 2053 |
| RIPK1.1 | NM_003804 | NM_003804.3 | RIPK1 | 6259 | AGTACCTTCAAGCC GGTCAC | 590 | AAGTCCCTGGGA ACTGTGC | 1322 | CAGCCACAGAACAG CCTGGTTCAC | 2054 |
| RND3.1 | NM_005168 | NM_005168.3 | RND3 | 5381 | TCGGAATTGGACTT GGGAG | 591 | CTGGTTACTCCC CTCAACA | 1323 | TTTTAAGCTGACTC CTACCGCG | 2055 |
| ROCK1.1 | NM_005406 | NM_005406.1 | ROCK1 | 2959 | TGTGCACATAGGAA TGAGCTC | 592 | GTTTAGCACGCA ATTGCTCA | 1324 | TCACTCTCTTTGCTG GCCAACTGC | 2056 |
| ROCK2.1 | NM_004850 | NM_004850.3 | ROCK2 | 2992 | GATCCGAGACCCT CGCTC | 593 | AGGACCAAGGAA TTTAAGCCA | 1325 | CCCATCAACGTGGA GAGCTTGCT | 2057 |
| RPLP1.1 | NM_213725 | NM_213725.1 | RPLP1 | 5478 | CAAGGTGCTCGGT CCTTC | 594 | GTCGCCGGATGA AGTGAG | 1326 | CCTCACCCCAACGCA GCCTTAGCT | 2058 |
| RPS23.1 | NM_001025 | NM_001025.1 | RPS23 | 3320 | GTTCTGGTTGCTG GATTTGG | 595 | CCTTAAAGCGGA CTCCAGG | 1327 | ATCACCAACAGCATG ACCTTTGCG | 2059 |
| RPS27A.1 | NM_002954 | NM_002954.3 | RPS27A | 6329 | CTTACGGGGAAGA CCATCAC | 596 | TCCTGGATCTTG GCCTTTAC | 1328 | TCGTATCCGAGGGTT CAACCTCG | 2060 |
| RPS6KA1.1 | NM_002953 | NM_002953.3 | RPS6KA1 | 3865 | GCTCATGGAGCTA GTGCCTC | 597 | CGGCTGAAGTCC AGTTCT | 1329 | ACCCGGAGAATGGA CAGACCTCAG | 2061 |
| RPS6KB1.3 | NM_003161 | NM_003161.1 | RPS6KB1 | 928 | GCTCATTATGAAAA ACATCCCAAAC | 598 | AAGAAACAGAAG TTGTCTGCTTT CT | 1330 | CACACCAACCAATAA TTTCGCATT | 2062 |
| RRM1.2 | NM_001033 | NM_001033.1 | RRM1 | 1000 | GGGCTACTGGCAG CTACATT | 599 | CTCTCAGCATCG GTACAAGG | 1331 | CATTGGAATTGCCAT TAGTCCCAGC | 2063 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| RRM2.1 | NM_001034 | NM_001034.1 | RRM2 | 2546 | CAGCGGGATTAAACAGTCCT | 600 | ATCTGCCTTGAAGCAGTGAG | 1332 | CCAGCACAGCCAGTTAAAGATGCA | 2064 |
| RUNX1.1 | NM_001754 | NM_001754.3 | RUNX1 | 6067 | AACAGAGACATTGCCAACCA | 601 | GTGATTTGCCCAGGAAAGTTT | 1333 | TTGGATCTGCTTGCTGTCCAAACC | 2065 |
| S100A1.1 | NM_006271 | NM_006271.1 | S100A1 | 2851 | TGGACAAGGTGATGAAGGAG | 602 | AGCACCACATACTCCTGGAA | 1334 | CCTCCCCGTCTCCATTCTCGTCTA | 2066 |
| S100A10.1 | NM_002966 | NM_002966.1 | S100A10 | 3579 | ACACCAAAAATGCCATCTCAA | 603 | TTTATCCCCAGCGAATTTGT | 1335 | CAGCCATGGAAACCATGATGTTT | 2067 |
| S100A2.1 | NM_005978 | NM_005978.2 | S100A2 | 2369 | TGGCTGTGCTGGTCACTACCT | 604 | TCCCCCTTACTCAGCTTGAACT | 1336 | CACAAGTACTCCTGCCAAGAGGGCGAC | 2068 |
| SAA2.2 | NM_030754 | NM_030754.2 | SAA2 | 6655 | CTACAGCACAGATCAGCACCA | 605 | TGCTGACACTCAGGACCAAG | 1337 | AGCTTCTCACGGGCCTGGTTTCT | 2069 |
| SCN4B.1 | NM_174934 | NM_174934.3 | SCN4B | 7223 | GCCTTCCTGGAGTACCCG | 606 | GTGGCCCTCAATTCCCCAAGT | 1338 | TGCTCCCTATGCCTTTCCAAGCAT | 2070 |
| SCNN1A.2 | NM_001038 | NM_001038.4 | SCNN1A | 3263 | ATCAACACATCCTGTCGAGGCT | 607 | GAAGTTGCCCAGCGTGTC | 1339 | AGAGACTCTGCCATCCCTGGAGGA | 2071 |
| SDHA.1 | NM_004168 | NM_004168.1 | SDHA | 5443 | GCAGAACTGAAGATGGGAAGAT | 608 | CCCTTTCCAAAACTTGAGGC | 1340 | CTGTCCACCAAATGCACGCTGATA | 2072 |
| SDPR.1 | NM_004657 | NM_004657.4 | SDPR | 3877 | ACCAGCACACAAGATGGAGCA | 609 | GGTCATTCTGGATGCCCTT | 1341 | CGGAGCCCTCCAAACTGATCTGTC | 2073 |
| SELE.1 | NM_000450 | NM_000450.1 | SELE | 5383 | ACACTGGTCTGCCCTGCTAC | 610 | AAAGTCCAGCTACCAAGGGAA | 1342 | CCTGTGAAGCTCCCACTGAGTCCA | 2074 |
| SELENBP1.1 | NM_003944 | NM_003944.2 | SELENBP1 | 6200 | GGTACCAGCCTCGACACAA | 611 | CCATCTCGTAAGACATTGGGA | 1343 | TGCCCACTCAGTGCTGATCATGAC | 2075 |
| SELL.1 | NM_000655 | NM_000655.3 | SELL | 5483 | TGCAACTGTGATGTGGGG | 612 | CCTCCAAAGGCTCACACTG | 1344 | CACAAACTGACACTGGGGCCCATA | 2076 |
| SELPLG.1 | NM_003006 | NM_003006.3 | SELPLG | 6316 | TGGCCACTATCTTCTTCGTG | 613 | GTAATTACGCACGGGGTACA | 1345 | CACTGTGGTGCTGGCGGTCC | 2077 |
| SEMA3B.1 | NM_004636 | NM_004636.1 | SEMA3B | 1013 | GCTCCAGGATGTGTTTCTGTTG | 614 | ACGTGAGAAGACGGCATAGA | 1346 | TCGCGGGACCACCGGACC | 2078 |
| SEMA3C.1 | NM_006379 | NM_006379.2 | SEMA3C | 5409 | ATGGCCATTCCTGTTCCAG | 615 | GTCTCACATCTTGTCTTCGGC | 1347 | CCTCCGTTTCCCAGTTGGGTAGAA | 2079 |
| SEMA3F.3 | NM_004186 | NM_004186.1 | SEMA3F | 1008 | CGCGAGCCCCTCATTATACA | 616 | CACTCGCGCGTTGACATCCT | 1348 | CTCCCCACAGCGCATCGAGGAA | 2080 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| SEMA5B.1 | NM_001031702 | NM_001031702. | SEMA5B | 5003 | CTCGAGGACAGCTCCAACAT | 617 | TCACATTCCGCACAGGAC | 1349 | AGCCTCTGACCCAGAACATCACC | 2081 |
| SERPINA5.1 | NM_000624 | NM_000624.3 | SERPINA5 | 6201 | CAGCATGGTAGTGGCAAAGA | 618 | CTTTGTGCACTGAGCTGG | 1350 | AGGTCCAGAGTCCTGGCCCTTGAT | 2082 |
| SFN.1 | NM_006142 | NM_006142.3 | SFN | 3580 | GAGAGAGCCAGTCTGATCCA | 619 | AGGCTGCCATGTCCTCATA | 1351 | CTGCTCTGCCAGCTTGGCCTTC | 2083 |
| SGK.1 | NM_005627 | NM_005627.2 | SGK1 | 2960 | TCCGCAAGACACCTCCTG | 620 | TGAAGTCATCCTTGGCCC | 1352 | TGTCCTGTCCTTCTGCAGGAGGC | 2084 |
| SHANK3.1 | XM_037493 | XM_037493.5 | | 3887 | CTGTGCCCTCTACAACCAGG | 621 | GGACATCCCTGTTAGCTCCA | 1353 | AGCTGTGCTCGTGTCCTGCTCTTC | 2085 |
| SHC1.1 | NM_003029 | NM_003029.3 | SHC1 | 2342 | CCAACACCTTCTTGGCTTCT | 622 | CTGTTATCCCAACCCAAACC | 1354 | CCTGTGTTCTTGCTGAGCACCCTC | 2086 |
| SILV.1 | NM_006928 | NM_006928.3 | SILV | 4113 | CCGCATCTTCTGCTCTTGT | 623 | ACTCAGACCTGCTGCCCA | 1355 | TTGGTGAGAATAGCCCCCTCCTCA | 2087 |
| SKIL.1 | NM_005414 | NM_005414.2 | SKIL | 5272 | AGAGGCTGAATATGCAGGACA | 624 | CTATCGGCCTCAGCATGG | 1356 | CCAATCTCTGCCTCAGTTCTGCCA | 2088 |
| SLC13A3.1 | NM_022829 | NM_022829.4 | SLC13A3 | 6202 | CTTGCCCTCCAACAAGGTC | 625 | AGCCACTGAGGAAGAGGA | 1357 | CCCCCAGTACTTCCTCGACACCAA | 2089 |
| SLC16A3.1 | NM_004207 | NM_004207.1 | SLC16A3 | 4569 | ATGCGACCCAGCTCTACAT | 626 | AATCAGGAGGAGGTGAGC | 1358 | CCCCGCCAGGATGAACACGTAC | 2090 |
| SLC22A3.1 | NM_021977 | NM_021977.2 | SLC22A3 | 6506 | ATCGTCAGGACGAGTTTGACCT | 627 | CAGGATGGCTTGGGTGAG | 1359 | CAGCATCCACGCATTGACACAGAC | 2091 |
| SLC22A6.1 | NM_153277 | NM_153277.1 | SLC22A6 | 6463 | TCCGCCACTCTTCCTCT | 628 | GACCAGCCATAGTATGCAAAG | 1360 | CTCTCCATGCTGTGGTTTGCCACT | 2092 |
| SLC2A1.1 | NM_006516 | NM_006516.1 | SLC2A1 | 2966 | GCCTGAGTCTCCTGTGCC | 629 | AGTCTCCACCCTCAGGCAT | 1361 | ACATCCCAGGCTTCACCCTGAATG | 2093 |
| SLC34A1.1 | NM_003052 | NM_003052.3 | SLC34A1 | 6203 | GCTGAGACCCACTGACCTG | 630 | AGCCTCTCTCCGTAGGACAA | 1362 | TCCTGGGCACCCACTATGAGGTCT | 2094 |
| SLC7A5.2 | NM_003486 | NM_003486.4 | SLC7A5 | 3268 | GCGCAGAGGCAGTTAAA | 631 | AGCTGAGCTGTGGGTTGC | 1363 | AGATCACCTCCTCGAACCCACTCC | 2095 |
| SLC9A1.1 | NM_003047 | NM_003047.2 | SLC9A1 | 5385 | CTTCGAGATCTCCCTCTGGA | 632 | AGTGGGGATCACATGGAAAC | 1364 | CCTTCTGGCCTGCCTCATGAAGAT | 2096 |
| SLIT2.2 | NM_004787 | NM_004787.1 | SLIT2 | 3708 | TTTACCGATGCACCTGTCC | 633 | ATGCAGGCATGAATTGGG | 1365 | CACAGTCCTGCCCCTTGAACCAT | 2097 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| SNAI1.1 | NM_005985 | NM_005985.2 | SNAI1 | 2205 | CCCAATCGGAAGC CTAACTA | 634 | GTAGGGCTGCTG GAAGGTAA | 1366 | TCTGGATTAGAGTCC TGCAGCTCGC | 2098 |
| SNRK.1 | NM_017719 | NM_017719.4 | SNRK | 6710 | GAGGAAAAGTCAG GGCCG | 635 | GCCGGCTTTCAG AATCATC | 1367 | CCAGCTGCAGTAGTT CGGAGACCA | 2099 |
| SOD1.1 | NM_000454 | NM_000454.3 | SOD1 | 2742 | TGAAGAGAGGCAT GTTGGAG | 636 | AATAGACACATC GGCCACA | 1368 | TTTGTCAGCAGTCAC ATTGCCCAA | 2100 |
| SP3.1 | NM_001017371 | NM_001017371. | SP3 | 5430 | TCAAGAGTCTCAGC AGCCAA | 637 | CCATGGATTGTC TGTGGTGT | 1369 | CAGTCAAGCCCAAAT TGTGCAAGG | 2101 |
| SPARC.1 | NM_003118 | NM_003118.1 | SPARC | 2378 | TCTTCCCTGTACAC TGGCAGTTC | 638 | AGCTCGGTGTGG GAGAGGTA | 1370 | TGGACCAGCACCCC ATTGACGG | 2102 |
| SPARCL1.1 | NM_004684 | NM_004684.2 | SPARCL1 | 3904 | GGCACAGTGCAAG TGATGA | 639 | GATTGAGCTCTC TCCGCCT | 1371 | ACTTCATCCCAAGCC AGGCCTTTC | 2103 |
| SPAST.1 | NM_014946 | NM_014946.3 | SPAST | 4033 | CCTGAGTTGTTCAC AGGGC | 640 | ATTCCCAGGTGG ACCAAAG | 1372 | TAACAGCCCCTCTGGC AGGAGCTCT | 2104 |
| SPHK1.1 | NM_021972 | NM_021972.2 | SPHK1 | 4178 | GGCAGCTTCCTTGA ACCAT | 641 | GCAGTTGGTCAG GAGGTCTT | 1373 | TGTGACCTGCTCAT AGCCAGCAT | 2105 |
| SPRY1.1 | AK026960 | AK026960.1 | | 1051 | CAGACCAGTCCCT GGTCATAGG | 642 | CCTTCAAGTCAT CCACAATCAGTT | 1374 | CTGGGTCCGGATTG CCCTTTCAG | 2106 |
| SQSTM1.1 | NM_003900 | NM_003900.3 | SQSTM1 | 4662 | GGAACCCGTCTACA GGTGAAC | 643 | GCTTGGC GGCTCCAGAGA | 1375 | CAGTCCCTACAGATG CCAGAATCCG | 2107 |
| STAT1.3 | NM_007315 | NM_007315.1 | STAT1 | 530 | GGGCTCAGCTTTCA GAAGTG | 644 | ACATGTTCAGCT GGTCCACA | 1376 | TGGCAGTTTTCTTCT GTCACCAAAA | 2108 |
| STAT3.1 | NM_003150 | NM_003150.1 | STAT3 | 537 | TCCACATGCCACTTT GGTGTT | 645 | CTTGCAGGAAGC GGCTATAC | 1377 | TCCTGGGAGAGATT GACCAGCA | 2109 |
| STAT5A.1 | NM_003152 | NM_003152.1 | STAT5A | 403 | GAGGGCCTCAACA TGAAATTC | 646 | GCCAGGACACG AGGTTCTC | 1378 | CGGTTGCTCTGCACT TCGGCCT | 2110 |
| STAT5B.2 | NM_012448 | NM_012448.1 | STAT5B | 857 | CCAGTGGTGGTGA TCGTTCA | 647 | GCAAAAGCATTG TCCCAGAGA | 1379 | CAGCCAGGACAACA ATGCGACGG | 2111 |
| STC2.1 | NM_003714 | NM_003714.2 | STC2 | 6507 | AAGGAGGCCATCA CCCAC | 648 | AGATGAGCACA GGCTTCC | 1380 | TTCTGCTCACACTGA ACCTGCACG | 2112 |
| STK11.1 | NM_000455 | NM_000455.3 | STK11 | 3383 | GGACTCGGAGACG CTGTG | 649 | GGGATCCTTCGC AACTTCTT | 1381 | TTCTTGAGGATCTTG ACGGCCCTC | 2113 |
| STK15.2 | NM_003600 | NM_003600.1 | AURKA | 341 | CATCTTCCAGGAG GACCACT | 650 | TCCGACCTTCAA TCATTTCA | 1382 | CTCTGTGGCACCCT GGACTACCTG | 2114 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| STK4.1 | NM_006282 | NM_006282.2 | STK4 | 5424 | GAGCCATCTTCCTG CAACTT | 651 | CTGAGGTGCAAC CCAGTCA | 1383 | ACCTCCTTCCCTCAG ATGGGAGC | 2115 |
| STMY3.3 | NM_005940 | NM_005940.2 | MMP11 | 741 | CCTGGAGGCTGCA ACATACC | 652 | TACAATGGCTTT GGAGGATAGCA | 1384 | ATCCTCCTGAAGCCC TTTTCGCAGC | 2116 |
| SUCLG1.1 | NM_003849 | NM_003849.2 | SUCLG1 | 6205 | CAAGCCTGTAGT GTCCTTCA | 653 | CGGCCATGACCCA TTCTTC | 1385 | CCCAGGAGAGCAG TTAACCAGC | 2117 |
| SULT1C2.1 | NM_001056 | NM_001056.3 | SULT1C2 | 6206 | GGGACCCAAAGCA TGAAAT | 654 | AGCACTGTTTCA TCCACCTTC | 1386 | TTCCCATGAACTGCA TCACCTTCC | 2118 |
| SURV.2 | NM_001168 | NM_001168.1 | BIRC5 | 81 | TGTTTTGATTCCCG GGCTTA | 655 | CAAAGCTGTCAG CTCTAGCAAAAG | 1387 | TGCCTTCTTCCTCCC TCACTTCTCACCT | 2119 |
| TACSTD2.1 | NM_002353 | NM_002353.2 | TACSTD2 | 6335 | ATCACCAACCGGA GAAAGTC | 656 | AAGCTCGGTTCC TTTCTCAA | 1388 | CCCCCAGTTCCTTGA TCTCCACC | 2120 |
| TAGLN.1 | NM_003186 | NM_003186.3 | TAGLN | 6073 | GATGGAGCAGGTG GCTCAGT | 657 | AGTCTGGAACAT GTCAGTCTTGATG | 1389 | CCCATAGTCCTCAGC CGCCTTCAG | 2121 |
| TAP1.1 | NM_000593 | NM_000593.5 | TAP1 | 3966 | GTATGCTGCTGAAA GTGGGAA | 658 | TCCCACTGCTTA CAGCCC | 1390 | CACCAGCTGCCCAC CAATGTAGAG | 2122 |
| TCF4.1 | NM_003199 | NM_003199.1 | TCF4 | 4097 | CACACCCTGGAAT GGGAG | 659 | ATGTGGCAACTT GGACCCT | 1391 | CGCATCGAATCACAT GGGACAGAT | 2123 |
| TCOF1.2 | NM_001008656 | NM_001008656. | TCOF1 | 6719 | AGCGAGGATGAGG ACGTG | 660 | CACCACATTGGT TCTGATGC | 1392 | TCCCCGCTACACAGT GCTTGACTC | 2124 |
| TEK.1 | NM_000459 | NM_000459.1 | TEK | 2345 | ACTTCGGTGTCTACT TAACAACTTACATC | 661 | CCTGGGCTTGG TGTTGAC | 1393 | AGTTCGGACCACGT ACTGCTCCCTG | 2125 |
| TERT.1 | NM_003219 | NM_003219.1 | | 992 | GACATGGAGAACAA GCTGTTTGC | 662 | GAGGTGTCACCA ACAAGAAATCAT | 1394 | ACCAAACGCAGGAG CAGCCCG | 2126 |
| TFAP2B.1 | NM_003221 | NM_003221.3 | TFAP2B | 6207 | CGTGTGACGTGCG AGAGA | 663 | CCACACGCTTC AGGACC | 1395 | ATGACGCGCCTTG CTCTTACTGT | 2127 |
| TFAP2C.1 | NM_003222 | NM_003222.3 | TFAP2C | 4663 | CATGCCTCACCAGA TGGA | 664 | CTGTCTGATCGT GCAGCAAC | 1396 | CTGGTCGTCGACATT CTGCACCTC | 2128 |
| TFPI.1 | NM_006287 | NM_006287.4 | TFPI | 6270 | CCGAATGGTTTCCA GGTG | 665 | TTGCGGAGTCAG GGAGTTA | 1397 | ATGGAACCCAGTCA ATGCTGTGA | 2129 |
| TGFA.2 | NM_003236 | NM_003236.1 | TGFA | 161 | GGTGTGCCACAGA CCTTCCT | 666 | ACGGAGTTCTTG ACAGAGTTTTGA | 1398 | TTGGCCTGTAATCAC CTGTGCAGCCTT | 2130 |
| TGFb1.1 | NM_000660 | NM_000660.3 | TGFB1 | 4041 | CTGTATTTAAGGAC ACCCGTGC | 667 | TGACACAGAGAT CCGCAGTC | 1399 | TCTCCATCTTTAA TGGGCCCC | 2131 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| TGFB2.2 | NM_003238 | NM_003238.1 | TGFB2 | 2017 | ACCAGTCCCCAG AAGACTA | 668 | CCTGGTGCTGTT GTAGATGG | 1400 | TCCTGAGCCCGAGG AAGTCCC | 2132 |
| TGFBI.1 | NM_000358 | NM_000358.1 | TGFBI | 3768 | GCTACGAGTGCTG TCCTGG | 669 | AGTGGTAGGGCT GCTGGAC | 1401 | CCTTCTCCCCAGGG ACCTTTCAT | 2133 |
| TGFBR1.1 | NM_004612 | NM_004612.1 | TGFBR1 | 3385 | GTCATCACCTGGC CTTGG | 670 | GCAGACGAAGCA CACTGGT | 1402 | AGCAATGACAGCTG CCAGTTCCAC | 2134 |
| TGFBR2.3 | NM_003242 | NM_003242.2 | TGFBR2 | 864 | AACACCAATGGGTT CCATCT | 671 | CCTCTTCATCAG GCCAAACT | 1403 | TTTGGGCTCCTGAT TGCTCAAGC | 2135 |
| THBD.1 | NM_000361 | NM_000361.2 | THBD | 4050 | AGATCTGCGACCG ACTGC | 672 | GGAAATGACATC GGCAGC | 1404 | CACCTAATGACAGTG CGTCCTCG | 2136 |
| THBS1.1 | NM_003246 | NM_003246.1 | THBS1 | 2348 | CATCCGCAAAGTGA CTGAAGAG | 673 | GTACTGAACTCC GTTGTGATAGCA TAG | 1405 | CCAATGAGCTGAGG CGGCCTCC | 2137 |
| TIMP1.1 | NM_003254 | NM_003254.2 | TIMP1 | 6075 | TCCCTGCGGTCCC AGATAG | 674 | GTGGGAACAGG GTGGACACT | 1406 | ATCCTGCCCGGAGT GGAAGCTGAAGC | 2138 |
| TIMP2.1 | NM_003255 | NM_003255.2 | TIMP2 | 606 | TCACCCTCTGTGAC TTCATCGT | 675 | TGTGGTTCAGGC TCTTCTCTG | 1407 | CCCTGGGACACCCT GAGCACCA | 2139 |
| TIMP3.3 | NM_000362 | NM_000362.2 | TIMP3 | 593 | CTACCTGCCTTGCT TTGTGA | 676 | ACCGAAATTGGA GAGCATGT | 1408 | CCAAGAACGAGTGT CTCTGGACCG | 2140 |
| TK1.2 | NM_003258 | NM_003258.1 | TK1 | 264 | GCCGGGAAGACCG TAATTGT | 677 | CAGCGGCACCAG GTTCAG | 1409 | CAAATGGCTTCCTCT GGAAGGTCCCA | 2141 |
| TLR3.1 | NM_003265 | NM_003265.2 | TLR3 | 6289 | GGTTGGGCCACCT AGAAGT | 678 | CCATTCCTGGCC TGTGAG | 1410 | CTTGCCCAATTTCAT TAAGCCCA | 2142 |
| TMEM27.1 | NM_020665 | NM_020665.2 | TMEM27 | 3878 | CCCTGAAAGADATGT TGTGGC | 679 | TCTGCACCTGGT TGACAGAG | 1411 | TCTGGTGACTGCCAT TCATGCTGA | 2143 |
| TMEM47.1 | NM_031442 | NM_031442.3 | TMEM47 | 6713 | GGATTCCACTGTTA GAGCCCTT | 680 | GCAAATAACCAA CAGCCAATG | 1412 | CCGCCTGCTTATCCT ACCCAATGA | 2144 |
| TMSB10.1 | NM_021103 | NM_021103.3 | TMSB10 | 6076 | GAAATCGCCAGCTT CGATAA | 681 | GTCGGCAGGGT GTTCTTCT | 1413 | CGTCTCCGTTTTCTT CAGCTTGGC | 2145 |
| TNF.1 | NM_000594 | NM_000594.1 | TNF | 2852 | GGAGAGGGTGAC CGACTCA | 682 | TGCCCAGACTCG GCAAAG | 1414 | CGTGAGATCAATCG GCCCGACTA | 2146 |
| TNFAIP3.1 | NM_006290 | NM_006290.2 | TNFAIP3 | 6290 | ATCGTCTTGGCTGA GAAAGG | 683 | GTGGAATGGCTC TGCTTC | 1415 | CAACCCACGCGACTT GTGTGTCTT | 2147 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| TNFAIP6.1 | NM_007115 | NM_007115.2 | TNFAIP6 | 6291 | AGGAGTGAAGATGGGATGC | 684 | CTGTAAAGACGCCACCACAC | 1416 | ATTGCTACAACCCACACGCAAAGG | 2148 |
| TNFRSF10C.3 | NM_003841 | NM_003841.2 | TNFRSF10$$ | 6652 | GGAGTTGACCAGAGATGCAA | 685 | CTCTGTCCCCAGAGTTCCC | 1417 | AACGTAGGAAGCGCTCCTTCACC | 2149 |
| TNFRSF10D.1 | NM_003840 | NM_003840.3 | TNFRSF10$$ | 4406 | CCTCTCGCTTCTGGTGGTC | 686 | GCTCAGGAATCTCTGCCCTA | 1418 | AGGCATCCAGGGACTCAGTTCAC | 2150 |
| TNFRSF11B.1 | NM_002546 | NM_002546.2 | TNFRSF11$$ | 4675 | TGGCGACCAAGACACCTT | 687 | GGGAAAGTGGTACGTCTTTGAG | 1419 | AGGGCCTAATGCACGCACTAAAGC | 2151 |
| TNFRSF1A.1 | NM_001065 | NM_001065.2 | TNFRSF1A | 4943 | ACTGCCCTGAGCCCAAAT | 688 | GTCAGGCACGGTGGAGAG | 1420 | TGCCAGACAGCTATGGCCTCTCAC | 2152 |
| TNFSF12.1 | NM_003809 | NM_003809.2 | TNFSF12 | 2987 | TAGGCCAGGAGGTTCCCAA | 689 | CACAGGGAATTCTCAAGGGA | 1421 | TTGTCTTGTTTCTCGCCCCTCACA | 2153 |
| TNFSF13B.1 | NM_006573 | NM_006573.3 | TNFSF13B | 4944 | CCTACGCCATGGGACATC | 690 | TCGAAACAAAGTCACCAGACTC | 1422 | TCCCCAAAGACATGGACCTTCTTCC | 2154 |
| TNFSF7.1 | NM_001252 | NM_001252.2 | CD70 | 4101 | CCAACTCACTGGGACACTT | 691 | ACCCACTGCACTCCAAAGAA | 1423 | TGCCTTCCCGAAACACTGATGAGA | 2155 |
| TNIP2.1 | NM_024309 | NM_024309.2 | TNIP2 | 3872 | CATGTCAGAAAGGGCCGA | 692 | GCGACCTTTTCCTCCAGTT | 1424 | AATCCTACTTTGAGCCCGTTCCCG | 2156 |
| TOP2A.4 | NM_001067 | NM_001067.1 | TOP2A | 74 | AATCCAAGGGGGAGAGTGAT | 693 | GTACAGATTTTGCCCGAGGA | 1425 | CATATGGACTTTGACTCAGTGTGGC | 2157 |
| TOP2B.2 | NM_001068 | NM_001068.1 | TOP2B | 75 | TGTGGACATCTTTCCCTCAGA | 694 | CTAGCCCGACCGGTTCGT | 1426 | TTCCCTACTGAGCCACCTTCTCTG | 2158 |
| TP.3 | NM_001953 | NM_001953.2 | TYMP | 91 | CTATATGCAGCCAGAGATGTGACA | 695 | CCACGAGTTTCTTACTGAGAATGG | 1427 | ACAGCCTGCCACTCATCACAGCC | 2159 |
| TRAIL.1 | NM_003810 | NM_003810.1 | TNFSF10 | 898 | CTTCCACAGTGCTGTCCTGCAGTCT | 696 | CATCTGCTTCAGCTCGTTGGT | 1428 | AAGTACACGTAAGTTACAGCCACACA | 2160 |
| TS.1 | NM_001071 | NM_001071.1 | TYMS | 76 | GCCTCGGTGTGCCTTTCA | 697 | CGTGATGTGCGCAATCATG | 1429 | CATGCCAGCTACGCCCTGCTC | 2161 |
| TSC1.1 | NM_000368 | NM_000368.3 | TSC1 | 6292 | TCACCAAATCCAGCCCG | 698 | GTGTCAGCATAAGGGCTGGT | 1430 | TTTCCTCATCGTTCAGCCGATGTC | 2162 |
| TSC2.1 | NM_000548 | NM_000548 | TSC2 | 5132 | CACAGTGGCCTCTTTCTCCT | 699 | CAGGAAACGCTCCTGTGC | 1431 | TACCAGTCCAGCTGCCAAGGACAG | 2163 |
| TSPAN7.2 | NM_004615 | NM_004615.3 | TSPAN7 | 6721 | ATCACTGGGGTGATCCTGC | 700 | GGGAGATATAGGTGCCAGAG | 1432 | AAGTTGCCCCAGACTCCAACAGC | 2164 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| TSPAN8.1 | NM_004616 | NM_004616.2 | TSPAN8 | 6317 | CAGAAATCTCTGCAGGCAAGT | 701 | AATCCAGATGCCGTGAATTT | 1433 | TGTCCAGAGCATATTGCAGGACA | 2165 |
| TUBB.1 | NM_001069 | NM_001069.1 | TUBB2A | 2094 | CGAGGACGAGGCTTAAAAAC | 702 | ACCATGCTTGAGGACAACAG | 1434 | TCTCAGATCAATCGTGCATCCTTAGTGAA | 2166 |
| TUSC2.1 | NM_007275 | NM_007275.1 | TUSC2 | 6208 | CACCAAGAACGGGCAGAA | 703 | CGATGCCCTGAGGAATCA | 1435 | TCTTATGCACTCGCCTCAGCTTGG | 2167 |
| tusc4.2 | NM_006545 | NM_006545.4 | TUSC4 | 3764 | GGAGGAGCTAAATGCCTCAG | 704 | CCTTCAAGTGGATGGTGTTG | 1436 | ACTCATCAATGGGCAGAGTGCACC | 2168 |
| TXLNA.1 | NM_175852 | NM_175852.3 | TXLNA | 6209 | GCCAGAACGGCTCAGTCT | 705 | ATGTCTTCCAGTTGGCGG | 1437 | TCCTCAGAGACATCACGAAGGGCC | 2169 |
| UBB.1 | NM_018955 | NM_018955.1 | UBB | 3303 | GAGTGCACCCTGACCTG | 706 | GCGAATGCCATGACTGAA | 1438 | AATTAACAGCCACCCCTCAGGCG | 2170 |
| UBA3 | NM_003968 | NM_003968.3 | UBA3 | 2575 | GAATGCACGCTGGAACTTTA | 707 | CTGGTAGCCTGGGCATAGA | 1439 | AATTTTCCCATGTGCACCATTGCA | 2171 |
| UBE1C.1 | NM_007019 | NM_007019.2 | UBE2C | 2550 | TGTCTGGCGATAAAGGGATT | 708 | ATGGTCCTACCCATTTGAA | 1440 | TCTGCCTTCCCTGAATCAGACAACC | 2172 |
| UBE2C.1 | NM_014176 | NM_014176.1 | UBE2T | 3882 | TGTTCTCAAATTGCCACCAA | 709 | AGAGGTCAACACAGTTGCGA | 1441 | AGGTGCTTGGAGACCATCCCTCAA | 2173 |
| UBE2T.1 | NM_003358 | NM_003358.1 | UGCG | 6210 | GGCAACTGACAAACAGCCTT | 710 | AGGATCTACCCCTTTCAGTGG | 1442 | CAAGCTCCCAGGTGTCTCTCTTCTGA | 2174 |
| UGCG.1 | NM_003361 | NM_003361.2 | UMOD | 6211 | GCGTGGACCTGATGAGT | 711 | TTACGCAGCTGCTGTTGG | 1443 | CCATTCCTGGAGCTCACAACTGCT | 2175 |
| UMOD.1 | NM_002658 | NM_002658.1 | PLAU | 89 | GTGGATGTGCCCTGAAGGA | 712 | CTGCGGATCCAGGGTAAGAA | 1444 | AAGCCAGGCGTCTACACGAGAGTCTCAC | 2176 |
| upa.3 | NM_014709 | NM_014709.2 | USP34 | 4040 | AAGCTGTGATGGCCAAGC | 713 | GGAATGGCCACAACTGAGA | 1445 | TCCCAGGACCCTGAGGTTGCTTTA | 2177 |
| USP34.1 | NM_001078 | NM_001078.2 | VCAM1 | 1220 | TGGCTTCAGGAGCTGAATACC | 714 | TGCTGTCGTGATGAGAAATAGTG | 1446 | CAGGCACACACAGGTGGGACACAAAT | 2178 |
| VCAM1.1 | NM_004385 | NM_004385.2 | VCAN | 5979 | CCTGCTACACAGCCAACAAG | 715 | AGAAAGCGCCTGAGTCC | 1447 | CCCACTGTGGAAGACAAAGAGGCC | 2179 |
| VCAN.1 | NM_000376 | NM_000376.1 | VDR | 971 | GCCCTGGATTTCAGAAAGAG | 716 | AGTTACAAGCCAGGGAAGGA | 1448 | CAAGTCTGGATCTGGGACCCTTTCC | 2180 |
| VDR.2 | NM_003376 | NM_003376.3 | VEGFA | 7 | CTGCTGTCTTTGGGTGCATTG | 717 | GCAGCCTGGGACCACTTG | 1449 | TTGCTTGCTGCTCTACCTCCACCA | 2181 |

TABLE A-continued

| Gene | Accession Num | Sequence_ID | Official Symbol | Gene Version ID | F Primer Seq | SEQ ID NO. | R Primer Seq | SEQ ID NO. | Probe Seq | SEQ ID NO. |
|---|---|---|---|---|---|---|---|---|---|---|
| VEGFB.1 | NM_003377 | NM_003377.2 | VEGFB | 964 | TGACGATGGCCTGGAGTGT | 718 | GGTACCGGATCATGAGGATCTG | 1450 | CTGGGCAGCACCAAGTCCGGA | 2182 |
| VHL.1 | NM_000551 | NM_000551.2 | VHL | 4102 | CGGTTGTGACTTGTCTGC | 719 | AAGACTTGTCCCTGCCTCAC | 1451 | ATGCCTCAGTCTTCCCAAAGCAGG | 2183 |
| VIM.3 | NM_003380 | NM_003380.1 | VIM | 339 | TGCCCTTAAAGGAACCAATGA | 720 | GCTTCAACGGCAAAGTTCTT | 1452 | ATTTCACGCATCTGGCGTTCCA | 2184 |
| VTCN1.1 | NM_024626 | NM_024626.2 | VTCN1 | 4754 | ACAGTGGTCTGGGCATCC | 721 | GCTCAAAGCTGGTATTGGAGAC | 1453 | CGAGAAGTTGGCTCCCTGGTCAAC | 2185 |
| VTN.1 | NM_000638 | NM_000638.2 | VTN | 4502 | AGTCAATCTTCCCACACGG | 722 | GTACTGAGCGATGGAGCGT | 1454 | TGGACACTGTGGACCCTCCCTACC | 2186 |
| VWF.1 | NM_000552 | NM_000552.3 | VWF | 6212 | TGAAGCACAGTGCCCTCTC | 723 | CCAGTCTCCCATTCACCGT | 1455 | CTCCATGTCACTGTGCAGCTCGAC | 2187 |
| WIF.1 | NM_007191 | NM_007191.3 | WIF1 | 6077 | AACAAGCTGAGTGCCCAGG | 724 | CACTCGCAGATGCGTCTTT | 1456 | TACAAAAGCCTCCATTTCCGCACC | 2188 |
| WISP1.1 | NM_003882 | NM_003882.2 | WISP1 | 603 | AGAGGCATCCATGAACTTCACA | 725 | CAAAACTCCACAGTACTTGGGTTGA | 1457 | CGGGCTGCATCAGCACACGC | 2189 |
| WT1.1 | NM_000378 | NM_000378.3 | WT1 | 6458 | TGTACGGTCGGCATCTGAG | 726 | TTATTGCAGCCTGGGTAAGC | 1458 | CAGTGAGAAACGCCCCTTCATGTG | 2190 |
| WWOX.5 | NM_016373 | NM_016373.1 | WWOX | 974 | ATCGCAGCTGTGGGTGTAC | 727 | AGTCCCCTGTTGCATGGACTT | 1459 | CTGCTGTTTACCTTGGCGAGGCCTTTC | 2191 |
| XDH.1 | NM_000379 | NM_000379.3 | XDH | 5089 | TGGTGGCAGACATCCCTT | 728 | GCCACACTGTCCCAGTCTT | 1460 | TGAAGCCAACCTTGTATCTGGCCA | 2192 |
| XIAP.1 | NM_001167 | NM_001167.1 | XIAP | 80 | GCAGTTGGAAGACACAGAAAGT | 729 | TGCGTGGCACTATTTTCAAGA | 1461 | TCCCCAAATTGCAGATTTATCAACGGC | 2193 |
| XPNPEP2.2 | NM_003399 | NM_003399.5 | XPNPEP2 | 6503 | CACCCTGCACTGAACATACC | 730 | AAGGAGGATGAATGCAAAGG | 1462 | CCTGCTGGCCCATTGCCTAGAA | 2194 |
| YB-1.2 | NM_004559 | NM_004559.1 | YBX1 | 395 | AGACTGTGGAGTTTGATGTTGTTGA | 731 | GGAACACCACCAGGACCTGTAA | 1463 | TTGCTGCCTCCGCACCCCTTTCT | 2195 |
| ZHX2.1 | NM_014943 | NM_014943.3 | ZHX2 | 6215 | GAGTACGACCAGTTAGCGGC | 732 | TCTCCTTGAACCAACGCAC | 1464 | ATCTCAGTTCGGACCAGGCCAGTC | 2196 |

TABLE B

| Gene | Target Sequence Length | Amplicon Sequence | SEQ ID NO. |
|---|---|---|---|
| A-Catenin.2 | 78 | CGTTCCGATCCTCTATACTGCATCCCAGGCATGCCTACAGCACCCTGATGTCGCAGCCTAT AAGGCCAACAGGGACCT | 2197 |
| A2M.1 | 66 | CTCTCCCGCCTTCCTAGCTGTCCCAGTGGAGAAGGAACAAGCGCCTCACTGCATCTGTGCA AACGG | 2198 |
| AAMP.1 | 66 | GTGTGGCAGGTGGACACTAAGGAGGAGGTCTGGTCCTTTGAAGCGGGAGACCTGGAGTGGA TGGAG | 2199 |
| ABCB1.5 | 77 | AAACACCACTGGAGCATTGACTACCAGGCTCGCCAATGATGCTGCTCAAGTTAAAGGGGCT ATAGGTTCCAGGCTTG | 2200 |
| ACADSB.1 | 68 | TGGCGGAGAACTAGCCATCAGCCTCCTGAAGCCTGCCATCATTGTTAATTTGAGGACTGGG CTGTCTT | 2201 |
| ACE.1 | 67 | CCGCTGTACGAGGATTTCACTGCCCTCAGCAATGAAGCCTACAAGCAGGACGGCTTCACAG ACACGG | 2202 |
| ACE2.1 | 66 | TACAATGAGAGGCTCTGGGCTTGGGAAAGCTGGAGATCTGAGGTCGGCAAGCAGCTGAGGC CATTA | 2203 |
| ADAM17.1 | 73 | GAAGTGCCAGGAGGCGATTAATGCTACTTGCAAAGGCGTGTCCTACTGCACAGGTAATAGC AGTGAGTGCCCG | 2204 |
| ADAM8.1 | 67 | GTCACTGTGTCCAGCCCACCCTTCCCAGTTCCTGTCTACACCCGGCAGGCACCAAAGCAGG TCATCA | 2205 |
| ADAMTS1.1 | 73 | GGACAGGTGCAAGCTCATCTGCCAAGCCAAAGGCATTGGCTACTTCTTCGTTTTGCAGCCC AAGGTTGTAGAT | 2206 |
| ADAMTS2.1 | 66 | GAGAATGTCTGCCGCTGGGCCTACCTCCAGCAGAAGCCAGACACGGGCCACGATGAATACC ACGAT | 2207 |
| ADAMTS4.1 | 71 | TTTGACAAGTGCATGGTGTGCGGAGGGGACGGTTCTGGTTGCAGCAAGCAGTCAGGCTCCT TCAGGAAATT | 2208 |
| ADAMTS5.1 | 79 | CACTGTGGCTCACGAAATCGGACATTTACTTGGCCTCTCCCATGACGATTCCAAATTCTGT GAAGAGACCTTTGGTTCC | 2209 |
| ADAMTS8.1 | 72 | GCGAGTTCAAAGTGTTCGAGGCCAAGGTGATTGATGGCACCCTGTGTGGGCCAGAAACACT GGCCATCTGTG | 2210 |
| ADAMTS9.1 | 66 | GCACAGGTTACACAACCCAACAGAATGTCCCTATAACGGGAGCCGGCGCGATGACTGCCAA TGTCG | 2211 |
| ADD1.1 | 74 | GTCTACCCAGCAGCTCCGCAAGGAGGGATGGCTGCCTTAAACATGAGTCTTGGTATGGTGA CTCCTGTGAACGA | 2212 |
| ADFP.1 | 67 | AAGACCATCACCTCCGTGGCCATGACCAGTGCTCTGCCCATCATCCAGAAGCTAGAGCCGC AAATTG | 2213 |
| ADH1B.1 | 84 | AAGCCAACAAACCTTCCTTCTTAACCATTCTACTGTGTCACCTTTGCCATTGAGGAAAAT ATTCCTGTGACTTCTTGCATTTT | 2214 |
| ADH6.1 | 68 | TGTTGGGGAGTAAACACTTGGACCTCTTGTATCCCACCATCTTGGGCCATGAAGGGGCTGG AATCGTT | 2215 |
| ADM.1 | 75 | TAAGCCACAAGCACACGGGGCTCCAGCCCCCCCGAGTGGAAGTGCTCCCCACTTTCTTTAG GATTTAGGCGCCCA | 2216 |
| AGR2.1 | 70 | AGCCAACATGTGACTAATTGGAAGAAGAGCAAAGGGTGGTGACGTGTTGATGAGGCAGATG GAGATCAGA | 2217 |
| AGT.1 | 73 | GATCCAGCCTCACTATGCCTCTGACCTGGACAAGGTGGAGGGTCTCACTTTCCAGCAAAAC TCCCTCAACTGG | 2218 |
| AGTR1.1 | 67 | AGCATTGATCGATACCTGGCTATTGTTCACCCAATGAAGTCCCGCCTTCGACGCACAATGC TTGTAG | 2219 |
| AHR.1 | 69 | GCGGCATAGAGACCGACTTAATACAGAGTTGGACCGTTTGGCTAGCCTGCTGCCTTTCCCA CAAGATGT | 2220 |
| AIF1.1 | 71 | GACGTTCAGCTACCCTGACTTTCTCAGGATGATGCTGGGCAAGAGATCTGCCATCCTAAAA ATGATCCTGA | 2221 |

TABLE B-continued

| Gene | Target Sequence Length | Amplicon Sequence | SEQ ID NO. |
|---|---|---|---|
| AKT1.3 | 71 | CGCTTCTATGGCGCTGAGATTGTGTCAGCCCTGGACTACCTGCACTCGGAGAAGAACGTGG TGTACCGGGA | 2222 |
| AKT2.3 | 71 | TCCTGCCACCCTTCAAACCTCAGGTCACGTCCGAGGTCGACACAAGGTACTTCGATGATGA ATTTACCGCC | 2223 |
| AKT3.2 | 75 | TTGTCTCTGCCTTGGACTATCTACATTCCGGAAAGATTGTGTACCGTGATCTCAAGTTGGA GAATCTAATGCTGG | 2224 |
| ALDH4.2 | 68 | GGACAGGGTAAGACCGTGATCCAAGCGGAGATTGACGCTGCAGCGGAACTCATCGACTTCT TCCGGTT | 2225 |
| ALDH6A1.1 | 66 | GGCTCTTTCAACAGCAGTCCTTGTGGGAGAAGCCAAGAAGTGGCTGCCAGAGCTGGTGGAG CATGC | 2226 |
| ALDOA.1 | 69 | GCCTGTACGTGCCAGCTCCCCGACTGCCAGAGCCTCAACTGTCTCTGCTTCGAGATCAAGC TCCGATGA | 2227 |
| ALDOB.1 | 80 | CCCTCTACCAGAAGGACAGCCAGGGAAAGCTGTTCAGAAACATCCTCAAGGAAAAGGGATC GTGGTGGGAATCAAGTTA | 2228 |
| ALOX12.1 | 67 | AGTTCCTCAATGGTGCCAACCCCATGCTGTTGAGACGCTCGACCTCTCTGCCCTCCAGGCT AGTGCT | 2229 |
| ALOX5.1 | 66 | GAGCTGCAGGACTTCGTGAACGATGTCTACGTGTACGGCATGCGGGGCCGCAAGTCCTCAG GCTTC | 2230 |
| AMACR1.1 | 71 | GGACAGTCAGTTTTAGGGTTGCCTGTATCCAGTAACTCGGGGCCTGTTTCCCCGTGGGTCT CTGGGCTGTC | 2231 |
| ANGPT1.1 | 71 | TCTACTTGGGGTGACAGTGCTCACGTGGCTCGACTATAGAAAACTCCACTGACTGTCGGGC TTTAAAAAGG | 2232 |
| ANGPT2.1 | 69 | CCGTGAAAGCTGCTCTGTAAAAGCTGACACAGCCCTCCCAAGTGAGCAGGACTGTTCTTCC CACTGCAA | 2233 |
| ANGPTL2.1 | 66 | GCCATCTGCGTCAACTCCAAGGAGCCTGAGGTGCTTCTGGAGAACCGAGTGCATAAGCAGG AGCTA | 2234 |
| ANGPTL3.3 | 78 | GTTGCGATTACTGGCAATGTCCCCAATGCAATCCCGGAAAACAAAGATTTGGTGTTTTCTA CTTGGGATCACAAAGCA | 2235 |
| ANGPTL4.1 | 66 | ATGACCTCAGATGGAGGCTGGACAGTAATTCAGAGGCGCCACGATGGCTCAGTGGACTTCA ACCGG | 2236 |
| ANGPTL7.1 | 67 | CTGCACAGACTCCAACCTCAATGGAGTGTACTACCGCCTGGGTGAGCACAATAAGCACCTG GATGGC | 2237 |
| ANTXR1.1 | 67 | CTCCAGGTGTACCTCCAACCCTAGCCTTCTCCCACAGCTGCCTACAACAGAGTCTCCCAGC CTTCTC | 2238 |
| ANXA1.2 | 67 | GCCCCTATCCTACCTTCAATCCATCCTCGGATGTCGCTGCCTTGCATAAGGCCATAATGGT TAAAGG | 2239 |
| ANXA2.2 | 71 | CAAGACACTAAGGGCGACTACCAGAAAGCGCTGCTGTACCTGTGTGGTGGAGATGACTGAA GCCCGACACG | 2240 |
| ANXA4.1 | 67 | TGGGAGGGATGAAGGAAATTATCTGGACGATGCTCTCGTGAGACAGGATGCCCAGGACCTG TATGAG | 2241 |
| ANXA5.1 | 67 | GCTCAAGCCTGGAAGATGACGTGGTGGGGACACTTCAGGGTACTACCAGCGGATGTTGGT GGTTCT | 2242 |
| AP-1 (JUN official).2 | 81 | GACTGCAAAGATGGAAACGACCTTCTATGACGATGCCCTCAACGCCTCGTTCCTCCCGTCC GAGAGCGGACCTTATGGCTA | 2243 |
| AP1M2.1 | 67 | ACAACGACCGCACCATCTCCTTCATCCCGCCTGATGGTGACTTTGAGCTCATGTCATACCG CCTCAG | 2244 |
| APAF1.2 | 66 | CACAAGGAAGAAGCTGGTGAATGCAATTCAGCAGAAGCTCTCCAAATTGAAAGGTGAACCA GGATG | 2245 |
| APC.4 | 69 | GGACAGCAGGAATGTGTTTCTCCATACAGGTCACGGGGAGCCAATGGTTCAGAAACAAATC GAGTGGGT | 2246 |

TABLE B-continued

| Gene | Target Sequence Length | Amplicon Sequence | SEQ ID NO. |
|---|---|---|---|
| APOC1.3 | 70 | CCAGCCTGATAAAGGTCCTGCGGGCAGGACAGGACCTCCCAACCAAGCCCTCCAGCAAGGATTCAGAGTG | 2247 |
| APOE.1 | 75 | GCCTCAAGAGCTGGTTCGAGCCCCTGGTGGAAGACATGCAGCGCCAGTGGGCCGGGCTGGTGGAGAAGGTGCAGG | 2248 |
| APOL1.1 | 73 | CGGACCAAGAACTGTGACCACAGGGCAGGGCAGCCACCAGGAGAGATATGCCTGGCAGGGGCCAGGACAAAAT | 2249 |
| APOLD1.1 | 66 | GAGCAGCTGGAGTCTCGGGTTCAGCTCTGCACCAAGTCCAGTCGTGGCCACGACCTCAAGATCTCT | 2250 |
| AQP1.1 | 66 | GCTTGCTGTATGACCCCTGGCCACAGCCTTCCCTCTGCATTGACCTGGAGGGGAGAGGTCAGCCTT | 2251 |
| AREG.2 | 82 | TGTGAGTGAAATGCCTTCTAGTAGTGAACCGTCCTCGGGAGCCGACTATGACTACTCAGAAGAGTATGATAACGAACCACAA | 2252 |
| ARF1.1 | 64 | CAGTAGAGATCCCCGCAACTCGCTTGTCCTTGGGTCACCCTGCATTCCATAGCCATGTGCTTGT | 2253 |
| ARG99.1 | 67 | GCATGGGCTACTGCATCCTTTTTGTGCACGGACTGAGCAAGCTCTGCACTTGGCTGAATCGATGTGG | 2254 |
| ARGHEF18.1 | 71 | ACTCTGCTTCCCAAGGGCAACCGTTGCTGTTCACACGCTCAGCCTGTCTGGGGGAGCGGGCCTCTAGCTTC | 2255 |
| ARHA.1 | 73 | GGTCCTCCGTCGGTTCTCTCATTAGTCCACGGTCTGGTCTTCAGCTACCCGCCTTCGTCTCCGAGTTTGCGAC | 2256 |
| ARHGDIB.1 | 66 | TGGTCCCTAGAACAAGAGGCTTAAAACCGGGCTTTCACCCAACCTGCTCCCTCTGATCCTCCATCA | 2257 |
| ARRB1.1 | 69 | TGCAGGAACGCCTCATCAAGAAGCTGGGCGAGCACGCTTACCCTTTCACCTTTGAGATCCCTCCAAACC | 2258 |
| ASS1.1 | 85 | CCCCCAGATAAAGGTCATTGCTCCCTGGAGGATGCCTGAATTCTACAACCGGTTCAAGGGCCGCAATGACCTGATGGAGTACGCA | 2259 |
| ATP1A1.1 | 67 | AGAACGCCTATTTGGAGCTGGGGGGCCTCGGAGAACGAGTCCTAGGTTTCTGCCACCTCTTTCTGCC | 2260 |
| ATP5E.1 | 66 | CCGCTTTCGCTACAGCATGGTGGCCTACTGGAGACAGGCTGGACTCAGCTACATCCGATACTCCCA | 2261 |
| ATP6V1B1.1 | 67 | AACCATGGGGAACGTCTGCCTCTTCCTGAACTTGGCCAATGACCCCACGATCGAGCGGATCATCACC | 2262 |
| AXL.1 | 66 | TTGCAGCCCTGTCTTCCTACCTATCCCACCTCCATCCCAGACAGGTCCCTCCCCTTCTCTGTGCAG | 2263 |
| AZU1.1 | 74 | CCGAGGCCCTGACTTCTTCACCCGAGTGGCGCTCTTCCGAGACTGGATCGATGGTGTTCTCAACAACCCGGGAC | 2264 |
| B-Catenin.3 | 80 | GGCTCTTGTGCGTACTGTCCTTCGGGCTGGTGACAGGGAAGACATCACTGAGCCTGCCATCTGTGCTCTTCGTCATCTGA | 2265 |
| B2M.4 | 67 | GGGATCGAGACATGTAAGCAGCATCATGGAGGTTTGAAGATGCCGCATTTGGATTGGATGAATTCCA | 2266 |
| BAD.1 | 73 | GGGTCAGGGGCCTCGAGATCGGGCTTGGGCCCAGAGCATGTTCCAGATCCCAGAGTTTGAGCCGAGTGAGCAG | 2267 |
| BAG1.2 | 81 | CGTTGTCAGCACTTGGAATACAAGATGGTTGCCGGGTCATGTTAATTGGGAAAAAGAACAGTCCACAGGAAGAGGTTGAAC | 2268 |
| BAG2.1 | 69 | CTAGGGGCAAAAGCATGACTGCTTTTTCCTGTCTGGCATGGAATCACGCAGTCACCTTGGGCATTTAG | 2269 |
| Bak.2 | 66 | CCATTCCCACCATTCTACCTGAGGCCAGGACGTCTGGGGTGTGGGATTGGTGGGTCTATGTTCCC | 2270 |
| Bax.1 | 70 | CCGCCGTGGACACAGACTCCCCCCGAGAGGTCTTTTTCCGAGTGGCAGCTGACATGTTTTCTGACGGCAA | 2271 |

TABLE B-continued

| Gene | Target Sequence Length | Amplicon Sequence | SEQ ID NO. |
|---|---|---|---|
| BBC3.2 | 83 | CCTGGAGGGTCCTGTACAATCTCATCATGGGACTCCTGCCCTTACCCAGGGGCCACAGAGCCCCCGAGATGGAGCCCAATTAG | 2272 |
| Bcl2.2 | 73 | CAGATGGACCTAGTACCCACTGAGATTTCCACGCCGAAGGACAGCGATGGGAAAAATGCCCTTAAATCATAGG | 2273 |
| BCL2A1.1 | 79 | CCAGCCTCCATGTATCATCATGTGTCATAACTCAGTCAAGCTCAGTGAGCATTCTCAGCACATTGCCTCAACAGCTTCA | 2274 |
| BCL2L12.1 | 73 | AACCCACCCCTGTCTTGGAGCTCCGGGTAGCTCTCAAACTCGAGGCTGCGCACCCCCTTTCCCGTCAGCTGAG | 2275 |
| Bclx.2 | 70 | CTTTTGTGGAACTCTATGGGAACAATGCAGCAGCCGAGAGCCGAAAGGGCCAGGAACGCTTCAACCGCTG | 2276 |
| BCRP.1 | 74 | TGTACTGGCGAAGAATATTTGGTAAAGCAGGGCATCGATCTCTCACCCTGGGGCTTGTGGAAGAATCACGTGGC | 2277 |
| BFGF.3 | 71 | CCAGGAAGAATGCTTAAGATGTGAGTGGATGGATCTCAATGACCTGGCGAAGACTGAAAATACAACTCCCATCACCA | 2278 |
| BGN.1 | 66 | GAGCTCCGCAAGGATGACTTCAAGGGTCTCCAGCACCTCTACGCCCTCGTCCTGGTGAACAACAAG | 2279 |
| BHLHB3.1 | 68 | AGGAAGATCCCTCGCAGCCAGGAAAGGAAGCTCCCTGAATCCTTGCGTCCCGAAGGACGGAGGTTCAA | 2280 |
| BIK.1 | 70 | ATTCCTATGGCTCTGCAATTGTCACCGGTTAACTGTGGCCTGTGCCCAGGAAGAGCCATTCACTCCTGCC | 2281 |
| BIN1.3 | 76 | CCTGCAAAAGGGAACAAGAGCCCTTCGCCTCCAGATGGCTCCCCTGCCGCCACCCCGAGATCAGAGTCAACCACG | 2282 |
| BLR1.1 | 67 | GACCAAGCAGGAAGCTCAGACTGGTTGAGTTCAGGTAGCTGCCCCTGGCTCTGACCGAAACAGCGCT | 2283 |
| BNIP3.1 | 68 | CTGGACGGAGTAGCTCCAAGAGCTCTCACTGTGACAGCCCACCTCGCTCGCAGACACCACAGATACC | 2284 |
| BRCA1.1 | 65 | TCAGGGGGCTAGAAATCTGTTGCTATGGGCCCTTCACCAACATGCCCACAGATCAACTGGAATGG | 2285 |
| BTRC.1 | 63 | GTTGGGACACAGTTGGTCTGCAGTCGGCCCAGGACGGTCTACTCAGCACAACTGACTGCTTCA | 2286 |
| BUB1.1 | 68 | CCGAGGTTAATCCAGCACGTATGGGGCCAAGTGTAGGCTCCCAGCAGGAACTGAGAGCGCCATGTCTT | 2287 |
| BUB3.1 | 73 | CTGAAGCAGATGGTTCATCATTTCCTGGGCTGTTAAACAAAGCGAGGTTAAGGTTAGACTCTTGGGAATCAGC | 2288 |
| c-kit.2 | 75 | GAGGCAACTGCTTATGGCTTAATTAAGTCAGATGCGGCCATGACTGTCGCTGTAAAGATGCTCAAGCCGAGTGCC | 2289 |
| C13orf15.1 | 84 | TAGAATCTGCTGCCAGAGGGGACAAAGACGTGCACTCAACCTTCTACCAGGCCACTCTCAGGCTCACCTTAAAATCAGCCCTTG | 2290 |
| C1QA.1 | 66 | CGGTCATCACCAACCAGGAAGAACCGTACCAGAACCACTCCGGCCGATTCGTCTGCACTGTACCCG | 2291 |
| C1QB.1 | 70 | CCAGTGGCCTCACAGGACACCAGCTTCCCAGGAGGCGTCTGACACAGTATGATGATGAAGATCCCATGGG | 2292 |
| C20orf1.1 | 65 | TCAGCTGTGAGCTGCGGATACCGCCCGGCAATGGGACCTGCTCTTAACCTCAAACCTAGGACCGT | 2293 |
| C3.1 | 67 | CGTGAAGGAGTGCAGAAAGAGGACATCCCACCTGCAGACCTCAGTGACCAAGTCCCGGACACCGAGT | 2294 |
| C3AR1.1 | 66 | AAGCCGCATCCCAGACTTGCTGAATCGGAATCTCTGGGGGTTGGGACCCAGCAAGGGCACTTAACA | 2295 |
| C7.1 | 69 | ATGTCTGAGTGTGAGGCGGGCGCTCTGAGATGCAGAGGGCAGAGCATCTCTGTCACCAGCA | 2296 |
| CA12.1 | 66 | CTCTCTGAAGGTGTCCTGGCCAGCCCTGGAGAAGCACTGGTGTCTGCAGCACCCCTCAGTTCCTGT | 2297 |

TABLE B-continued

| Gene | Target Sequence Length | Amplicon Sequence | SEQ ID NO. |
|---|---|---|---|
| CA2.1 | 69 | CAACGTGGAGTTTGATGACTCTCAGGACAAAGCAGTGCTCAAGGGAGGACCCCTGGATGGCACTTACAG | 2298 |
| CA9.3 | 72 | ATCCTAGCCCTGGTTTTTGGCCTCCTTTTTGCTGTCACCAGCGTCGCGTTCCTTGTGCAGATGAGAAGGCAG | 2299 |
| CACNA2D1.1 | 68 | CAAACATTAGCTGGGCCTGTTCCATGGCATAACACTAAGGCGCAGACTCCTAAGGCACCCACTGGCTG | 2300 |
| CALD1.2 | 78 | CACTAAGGTTTGAGACAGTTCCAGAAAGAACCCAAGCTCAAGACGCAGGACGAGCTCAGTTGTAGAGGGCTAATTCGC | 2301 |
| CASP1.1 | 77 | AGAAAGCCCACATAGAGAAGGATTTTATCGCTTTCTGCTCTTCCACACCAGATAATGTTTCTTGGAGACATCCCACA | 2302 |
| CASP10.1 | 66 | ACCTTTCTCTTGGCCGGATGTCCTCAGGGCTGGCAGATGCAGTAGACTGCAGTGGACAGTCCCCAC | 2303 |
| CASP6.1 | 67 | CCTCACACTGGTGAACAGGAAAGTTTCTCAGCGCCGAGTGGACTTTTGCAAAGACCCAAGTGCAATT | 2304 |
| Caspase 3.1 | 66 | TGAGCCTGAGCAGAGACATGACTCAGCCTGTTCCATGAAGGCAGAGCCATGGACCACGCAGGAAGG | 2305 |
| CAT.1 | 78 | ATCCATTCGATCTCACCAAGGTTTGGCCTCACAAGGACTACCCTCTCATCCCAGTTGGTAAACTGGTCTTAAACCGGA | 2306 |
| CAV1.1 | 74 | GTGGCTCAACATTGTGTTCCCATTTCAGCTGATCAGTGGGCCTCCAAGGAGGGGCTGTAAAATGGAGGCCATTG | 2307 |
| CAV2.1 | 66 | CTTCCCTGGGACGACTTGCCAGCTCTGAGGCATGACAGTACGGGCCCCCAGAAGGGTGACCAGGAG | 2308 |
| CCL18.1 | 68 | GCTCCTGTGCACAAGTTGGTACCAACAAAGAGCTCTGCTGCCTCGTCTATACCTCCTGGCAGATTCCA | 2309 |
| CCL19.1 | 78 | GAACGCATCATCCAGAGACTGCAGAGGACCTCAGCCAAGATGAAGCGCCGCAGCAGTTAACCTATGACCGTGCAGAGG | 2310 |
| CCL20.1 | 69 | CCATGTGCTGTACCAAGAGTTTGCTCCTGGCTGCTTTGATGTCAGTGCTGCTACTCCACCTCTGCGGCG | 2311 |
| CCL4.2 | 70 | GGGTCCAGGAGTACGTGTATGACCTGGAACTGAACTGAGCTGCTCAGAGACAGGAAGTCTTCAGGGAAGG | 2312 |
| CCL5.2 | 65 | AGGTTCTGAGCTCTGGCTTTGCCTTGGCTTTGCCAGGGCTCTGTGACCAGGAAGGAAGTCAGCAT | 2313 |
| CCNB1.2 | 84 | TTCAGGTTGTTGCAGGAGACCATGTACATGACTGTCTCCATTATTGATCGGTTCATGCAGAATAATTGTGTGCCCAAGAAGATG | 2314 |
| CCND1.3 | 69 | GCATGTTCGTGGCCTCTAAGATGAAGGAGACCATCCCCCTGACGGCCGAGAAGCTGTGCATCTACACCG | 2315 |
| CCNE1.1 | 71 | AAAGAAGATGATGACCGGGTTTACCCAAACTCAACGTGCAAGCCTCGGATTATTGCACCATCCAGAGGCTC | 2316 |
| CCNE2 variant 1.1 | 85 | GGTCACCAAGAAACATCAGTATGAAATTAGGAATTGTTGGCCACCTGTATTATCTGGGGGGATCAGTCCTTGCATTATCATTGAA | 2317 |
| CCNE2.2 | 82 | ATGCTGTGGCTCCTTCCTAACTGGGGCTTTCTTGACATGTAGGTTGCTTGGTAATAACCTTTTTGTATATCACAATTTGGGT | 2318 |
| CCR1.1 | 66 | TCCAAGACCCAATGGGAATTCACTCACCACACCTGCAGCCTTCACTTTCCTCACGAAAGCCTACGA | 2319 |
| CCR2.1 | 67 | CTCGGGAATCCTGAAAACCCTGCTTCGGTGTCGAAACGAGAAGAAGAGGCATAGGGCAGTGAGAGTC | 2320 |
| CCR4.2 | 82 | AGACCCTGGTGGAGCTAGAAGTCCTTCAGGACTGCACCTTTGAAAGATACTTGGACTATGCCATCCAGGCCACAGAAACTCT | 2321 |
| CCR5.1 | 67 | CAGACTGAATGGGGTGGGGGGGCGCCTTAGGTACTTATTCCAGATGCCTTCTCCAGACAAACCAG | 2322 |

TABLE B-continued

| Gene | Target Sequence Length | Amplicon Sequence | SEQ ID NO. |
|---|---|---|---|
| CCR7.1 | 64 | GGATGACATGCACTCAGCTCTTGGCTCCACTGGGATGGGAGGAGAGGACAAGGGAAATGTCAGG | 2323 |
| CD105.1 | 75 | GCAGGTGTCAGCAAGTATGATCAGCAATGAGGCGGTGGTCAATATCCTGTCGAGCTCATCACCACAGCGGAAAAA | 2324 |
| CD14.1 | 66 | GTGTGCTAGCGTACTCCCGCCTCAAGGAACTGACGCTCGAGGACCTAAAGATAACCGGCACCATGC | 2325 |
| CD18.2 | 81 | CGTCAGGACCCACCATGTCTGCCCCATCACGCGGCCGAGACATGGCTTGGCCACAGCTCTTGAGGATGTCACCAATTAACC | 2326 |
| CD1A.1 | 78 | GGAGTGGAAGGAACTGGAAACATTATTCCGTATACGCACCATTCGGTCATTTGAGGGAATTCGTAGATACGCCCATGA | 2327 |
| CD24.1 | 77 | TCCAACTAATGCCACCACCAAGGCGGCTGGTGGTGCCCTGCAGTCAACAGCCAGTCTCTTCGTGGTCTCACTCTCTC | 2328 |
| CD274.2 | 69 | GCTGCATGATCAGCTATGGTGGTGCCGACTACAAGCGAATTACTGTGAAAGTCAATGCCCCATACAACA | 2329 |
| CD31.3 | 75 | TGTATTTCAAGACCTCTGTGCACTTATTTATGAACCTGCCCTGCTCCCACAGAACACAGCAATTCCTCAGGCTAA | 2330 |
| CD34.1 | 67 | CCACTGCACACACCTCAGAGGCTGTTCTTGGGGCCCTACACCTTGAGGAGGGGCAGGTAAACTCCTG | 2331 |
| CD36.1 | 67 | GTAACCCAGGACGCTGAGGACAACACAGTCTCTTTCCTGCAGCCCAATGGTGCCATCTTCGAACCTT | 2332 |
| CD3z.1 | 65 | AGATGAAGTGGAAGGCGCTTTTCACCGCGGCCATCCTGCAGGCACAGTTGCCGATTACAGAGGCA | 2333 |
| CD4.1 | 67 | GTGCTGGAGTCGGGACTAACCCAGGTCCCTTGTCCCAAGTTCCACTGCTGCCTCTTGAATGCAGGGA | 2334 |
| CD44.1 | 67 | GGCACCACTGCTTATGAAGGAAACTGGAACCCAGAAGCACACCCTCCCCTCATTCACCATGAGCATC | 2335 |
| CD44s.1 | 78 | GACGAAGACAGTCCCTGGATCACCGACAGCACAGACAGAATCCCTGCTACCAGAGACCAAGACACATTCCACCCCAGT | 2336 |
| CD44v6.1 | 78 | CTCATACCAGCCATCCAATGCAAGGAAGGACAACACCAAGCCCAGAGGACAGTTCCTGGACTGATTTCTTCAACCCAA | 2337 |
| CD53.1 | 72 | CGACAGCATCCACCGTTACCACTCAGACAATAGCACCAAGGCAGCGTGGGACTCCATCCAGTCATTTCTGCA | 2338 |
| CD68.2 | 74 | TGGTTCCCAGCCCTGTGTCCACCTCCAAGCCCAGATTCAGATTCGAGTCATGTACACAACCCAGGGTGGAGGAG | 2339 |
| CD82.3 | 84 | GTGCAGGCTCAGGTGAAGTGCTGCGGCTGGGTCAGCTTCTACAACTGGACAGACAACGCTGAGCTCATGAATCGCCCTGAGGTC | 2340 |
| CD8A.1 | 68 | AGGGTGAGGTGCTTGAGTCTCCAACGGCAAGGGAACAAGTACTTCTTGATACCTGGGATACTGTGCCC | 2341 |
| CD99.1 | 77 | GTTCCTCCGGTAGCTTTTCAGATGCTGACCTTGCGGATGGCGTTTCAGGTGGAGAAGGAAAGGAGGCAGTGATGGT | 2342 |
| cdc25A.4 | 71 | TCTTGCTGGCTACGCCTCTTCTGTCCCTGTTAGACGTCCTCCGTCCATATCAGAACTGTGCCACAATGCAG | 2343 |
| CDC25B.1 | 85 | AAACGAGCAGTTTGCCATCAGACGCTTCCAGTCTATGCCGGTGAGGCTGCTGGGCCACAGCCCCGTGCTTCGGAACATCACCAAC | 2344 |
| CDH1.3 | 81 | TGAGTGTCCCCCGGTATCTTCCCCGCCCTGCCAATCCCGATGAAATTGGAAATTTTATTGATGAAATCTGAAAGCGGCTG | 2345 |
| CDH13.1 | 67 | GCTACTTCTCCACTGTCCCGTTCAGTCTGAATGCTGCCACAACCAGCCAGGCAGGTCCACAGAGAGG | 2346 |
| CDH16.1 | 67 | GACTGTCTGAATGGCCCAGGCAGCTCTAGCTGGGAGCTTGGCCTCTGGCTCCATCTGAGTCCCTGG | 2347 |

TABLE B-continued

| Gene | Target Sequence Length | Amplicon Sequence | SEQ ID NO. |
|---|---|---|---|
| CDH2.1 | 66 | TGACCGATAAGGATCAACCCCATACACCAGCCTGGAACGCAGTGTACAGAATCAGTGGCGGAGATC | 2348 |
| CDH5.1 | 67 | ACAGGAGACGTGTTCGCCATTGAGAGGCTGGACCGGGAGAATATCTCAGAGTACCACCTCACTGCTG | 2349 |
| CDH6.1 | 66 | ACACAGGCGACATACAGGCCACCAAGAGGCTGGACAGGGAAGAAAAACCCGTTTACATCCTTCGAG | 2350 |
| CDK4.1 | 66 | CCTTCCCATCAGCACAGTTCGTGAGGTGGCTTTACTGAGGCGACTGGAGGCTTTTGAGCATCCCAA | 2351 |
| CDK6.1 | 67 | AGTGCCCTGTCTCACCCATACTTCCAGGACCTGGAAAGGTGCAAAGAAAACCTGGATTCCCACCTGC | 2352 |
| CDKN2A.2 | 79 | AGCACTCACGCCCTAAGCGCACATTCATGTGGGCATTTCTTGCGAGCCTCGCAGCCTCCGGAAGCTGTCGACTTCATGA | 2353 |
| CEACAM1.1 | 71 | ACTTGCCTGTTCAGAGCACTCATTCCTTCCCACCCCCAGTCCTGTCCTATCACTCTAATTCGGATTTGCCA | 2354 |
| CEBPA.1 | 66 | TTGGTTTTGCTCGGATACTTGCCAAAATGAGACTCTCCGTCGGCAGCTGGGGAAGGGTCTGAGAC | 2355 |
| CENPF.1 | 68 | CTCCCGTCAACAGCGTTCTTTCCAAACACTGGACCAGGAGTGCATCCAGATGAAGGCCAGACTCACCC | 2356 |
| CFLAR.1 | 66 | GGACTTTTGTCCAGTGACAGCTGAGACAACAAGGACCACGGGAGGAGGTGTAGGAGAGAAGCGCCG | 2357 |
| CGA (CHGA official).1 | 76 | CTGAAGGAGCTCCAAGACCTCGCTCTCCAAGGCGCCAAGGAGAGGGCACATCAGCAGAAGAAACACAGCGGTTTTG | 2358 |
| Chk1.2 | 82 | GATAAATTGGTACAAGGGATCAGCTTTTCCCAGCCCACATGTCCTGATCATATGCTTTTGAATAGTCAGTTACTTGGCACCC | 2359 |
| Chk2.3 | 78 | ATGTGGAACCCCCACCTACTTGGCGCCTGAAGTTCTTGTTTCTGTTGGGACTGCTGGGTATAACCGTGCTGTGGACTG | 2360 |
| CIAP1.2 | 72 | TGCCTGTGGTGGGAAGCTCAGTAACTGGGAACCAAAGGATGATGCTATGTCAGAACACCGGAGGCATTTTCC | 2361 |
| cIAP2.2 | 86 | GGATATTTCCGTGGCTCTTATTCAAACTCTCCATCAAATCCTGTAAACTCCAGAGCAAATCAAGATTTTCTGCCTTGATGAGAAG | 2362 |
| CLCNKB.1 | 67 | GTGACCCTGAAGCTGTCCCCAGAGACTTCCCTGCATGAGGCACACAACCTCTTTGAGCTGTTGAACC | 2363 |
| CLDN10.1 | 66 | GGTCTGTGGATGAACTGCGCAGGTAACGCGTTGGGTTCTTTCCATTGCCGACCGCATTTTACTATC | 2364 |
| CLDN7.2 | 74 | GGTCTGCCCTAGTCATCCTGGGAGGTGCACTGCTCTCCTGTTCCTGTCCTGGGAATGAGAGCAAGGCTGGGTAC | 2365 |
| CLU.3 | 76 | CCCCAGGATACCTACCACTACCTGCCCCTTCAGCCTGCCCCACCGGAGGCCTCACTTCTTCTTTCCCAAGTCCCGCA | 2366 |
| cMet.2 | 86 | GACATTTCCAGTCCTGCAGTCAATGCCTCTCTGCCCCACCCTTTGTTCAGTGTGGCTGGTGCCACGACAAATGTGTGCGATCGGAG | 2367 |
| cMYC.3 | 84 | TCCCTCCACTCGGAAGGACTATCCTGCTGCCAAGAGGGTCAAGTTGGACAGTGTCAGAGTCCTGAGACAGATCAGCAACAACCG | 2368 |
| COL18A1.1 | 67 | AGCTGCCATCACGCCTACATCGTGCTCTGCATTGAGAACAGCTTCATGACTGCCTCCAAGTAGCCAC | 2369 |
| COL1A1.1 | 68 | GTGGCCATCCAGCTGACCTTCCTGCGCCTGATGTCCACCGAGGCCTCCCAGAACATCACCTACCACTG | 2370 |
| COL1A2.1 | 80 | CAGCCAAGAACTGGTATAGGAGCTCCAAGGACAAGAAACACGTCTGGCTAGGAGAAACTATCAATGCTGGCAGCCAGTTT | 2371 |
| COL4A1.1 | 66 | ACAAAGGCCTCCCAGGATTGGATGGCATCCCTGGTGTCAAAGGAGAAGCAGGTCTTCCTGGGACTC | 2372 |

TABLE B-continued

| Gene | Target Sequence Length | Amplicon Sequence | SEQ ID NO. |
|---|---|---|---|
| COL4A2.1 | 67 | CAACCCTGGTGATGTCTGCTACTATGCCAGCCGGAACGACAAGTCCTACTGGCTCTCTACCACTGCG | 2373 |
| COL5A2.2 | 72 | GGTCGAGGAACCCAAGGTCCGCCTGGTGCTACAGGATTTCCTGGTTCTGCGGGCAGAGTTGGACCTCCAGGC | 2374 |
| COL7A1.1 | 66 | GGTGACAAAGGACCTCGGGGAGACAATGGGGACCCTGGTGACAAGGGCAGCAAGGGAGAGCCTGGT | 2375 |
| COX2.1 | 79 | TCTGCAGAGTTGGAAGCACTCTATGGTGACATCGATGCTGTGGAGCTGTATCCTGCCCTTCTGGTAGAAAAGCCTCGGC | 2376 |
| CP.1 | 73 | CGTGAGTACACAGATGCCTCCTTCACAAATCGAAAGGAGAGAGGCCCTGAAGAAGAGCATCTTGGCATCCTGG | 2377 |
| CPB2.1 | 67 | GGCACATACGGATTCTTGCTGCCGGAGCGTTACATCAAACCCACCTGTAGAGAAGCTTTTGCCGCTG | 2378 |
| CRADD.1 | 69 | GATGGTGCCTCCAGCAACCGCTGGGGAGTGTGTCCCTGAGTCATGTGGGCTGAATCCTGACTTTCACTC | 2379 |
| cripto (TDGF1 official | 65 | GGGTCTGTGCCCCATGACACCTGGCTGCCCAAGAAGTGTTCCCTGTGTAAATGCTGGCACGGTCA | 2380 |
| CRP.1 | 66 | GACGTGAACCACAGGGTGTCCTGTCAGAGGAGCCCATCTCCCATCTCCCCAGCTCCCTATCTGGAG | 2381 |
| CSF1.1 | 74 | TGCAGCGGCTGATTGACAGTCAGATGGAGACCTCGTGCCAAATTACATTTGAGTTTGTAGACCAGGAACAGTTG | 2382 |
| CSF1R.2 | 80 | GAGCACAACCAAACCTACGAGTGCAGGGCCCACAACAGCGTGGGGAGTGGCTCCTGGGCCTTCATACCCATCTCTGCAGG | 2383 |
| CSF2.1 | 76 | GAACCTGAAGGACTTTCTGCTTGTCATCCCCTTTGACTGCTGGGAGCCAGTCCAGGAGTGAGACCGGCCAGATGAG | 2384 |
| CSF2RA.2 | 67 | TACCACACCCAGCATTCCTCCTGATCCCAGAGAAATCGGATCTGCGAACAGTGGCACCAGCCTCTAG | 2385 |
| CSF3.2 | 79 | CCCAGGCCTCTGTGTCCTTCCCTGCATTTCTGAGTTTCATTCTCCTGCCTGTAGCAGTGAGAAAAAGCTCCTGTCCTCC | 2386 |
| CTGF.1 | 76 | GAGTTCAAGTGCCCTGACGGCGAGGTCATGAAGAAGAACATGATGTTCATCAAGACCTGTGCCTGCCATTACAACT | 2387 |
| CTSB.1 | 62 | GGCCGAGATCTACAAAAACGGCCCCGTGGAGGGAGCTTTCTCTGTGTATTCGGACTTCCTGC | 2388 |
| CTSD.2 | 80 | GTACATGATCCCCTGTGAGAAGGTGTCCACCCTGCCCGCGATCACACTGAAGCTGGGAGGCAAAGGCTACAAGCTGTCCC | 2389 |
| CTSH.2 | 77 | GCAAGTTCCAACCTGGAAAGGCCATCGGCTTTGTCAAGGATGTAGCCAACATCACAATCTATGACGAGGAAGCGATG | 2390 |
| CTSL.2 | 74 | GGGAGGCTTATCTCACTGAGTGAGCAGAATCTGGTAGACTGCTCTGGGCCTCAAGGCAATGAAGGCTGCAATGG | 2391 |
| CTSL2.1 | 67 | TGTCTCACTGAGCGAGCAGAATCTGGTGGACTGTTCGCGTCCTCAAGGCAATCAGGGCTGCAATGGT | 2392 |
| CTSS.1 | 76 | TGACAACGGCTTTCCAGTACATCATTGATAACAAGGGCATCGACTCAGACGCTTCCTATCCCTACAAAGCCATGGA | 2393 |
| CUBN.1 | 71 | GAGGCCGTTACTGTGGCACCGACATGCCCCATCCTATCACATCCTTCAGCAGCGCCCTGACGCTGAGATTC | 2394 |
| CUL1.1 | 71 | ATGCCCTGGTAATGTCTGCATTCAACAATGACGCTGGCTTTGTGGCTGCTCTTGATAAGGCTTGTGGTCGC | 2395 |
| CUL4A.1 | 75 | AAGCATCTTCCTGTTCTTGGACCGCACCTATGTGCTGCAGAACTCCACGCTGCCCTCCATCTGGGATATGGGATT | 2396 |
| CX3CL1.1 | 66 | GACCCTTGCCGTCTACCTGAGGGGCCTCTTATGGGCTGGGTTCTACCCAGGTGCTAGGAACACTCC | 2397 |

TABLE B-continued

| Gene | Target Sequence Length | Amplicon Sequence | SEQ ID NO. |
|---|---|---|---|
| CX3CR1.1 | 68 | TTCCCAGTTGTGACATGAGGAAGGATCTGAGGCTGGCCCTCAGTGTGACTGAGACGGTTGCATTTAGC | 2398 |
| CXCL10.1 | 68 | GGAGCAAAATCGATGCAGTGCTTCCAAGGATGGACCACACAGAGGCTGCCTCTCCCATCACTTCCCTA | 2399 |
| CXCL12.1 | 67 | GAGCTACAGATGCCCATGCCGATTCTTCGAAAGCCATGTTGCCAGAGCCAACGTCAAGCATCTCAAA | 2400 |
| CXCL14.1 | 74 | TGCGCCCTTTCCTCTGTACATATACCCTTAAGAACGCCCCCTCCACACACTGCCCCCCAGTATATGCCGCATTG | 2401 |
| CXCL9.1 | 70 | ACCAGACCATTGTCTCAGAGCAGGTGCTGGCTCTTTCCTGGCTACTCCATGTTGGCTAGCCTCTGGTAAC | 2402 |
| CXCR4.3 | 72 | TGACCGCTTCTACCCCAATGACTTGTGGGTGGTTGTGTTCCAGTTTCAGCACATCATGGTTGGCCTTATCCT | 2403 |
| CXCR6.1 | 67 | CAGAGCCTGACGGATGTGTTCCTGGTGAACCTACCCCTGGCTGACCTGGTGTTTGTCTGCACTCTGC | 2404 |
| CYP2C8.2 | 73 | CCGTGTTCAAGAGGAAGCTCACTGCCTTGTGGAGGAGTTGAGAAAAACCAAGGCTTCACCCTGTGATCCCACT | 2405 |
| CYP2C8v2.1 | 70 | GCTGTAGTGCACCAGATCCAGAGATACAGTGACCTTGTCCCCACCGGTGTGCCCCATGCAGTGACCACTG | 2406 |
| CYP3A4.2 | 79 | AGAACAAGGACAACATAGATCCTTACATATACACACCCTTTGGAAGTGGACCCAGAAACTGCATTGGCATGAGGTTTGC | 2407 |
| CYR61.1 | 76 | TGCTCATTCTTGAGGAGCATTAAGGTATTTCGAAACTGCCAAGGGTGCTGGTGCGGATGGACACTAATGCAGCCAC | 2408 |
| DAG1.1 | 67 | GTGACTGGGCTCATGCCTCCAAGTCAGAGTTTCCCTGGTGCCCCAGAGACAGGAGCACAAGTGGGAT | 2409 |
| DAPK1.3 | 77 | CGCTGACATCATGAATGTTCCTCGACCGGCTGGAGGCGAGTTTGGATATGACAAAGACACATCGTTGCTGAAAGAGA | 2410 |
| DCBLD2.1 | 69 | TCACCAGGGCAGGAAGTTTATCATGCCTATGCTGAACCACTCCCAATTACGGGGCCTGAGTATGCAACC | 2411 |
| DCC.3 | 75 | AAATGTCCTCCTCGACTGCTCCGCGGAGTCCGACCGAGGAGTTCCAGTGATCAAGTGGAAGAAAGATGGCATTCA | 2412 |
| DCN.1 | 67 | GAAGGCCACTATCATCCTCCTTCTGCTTGCACAAGTTTCCTGGGCTGGACCGTTTCAACAGAGAGGC | 2413 |
| DCXR.1 | 66 | CCATAGCGTCTACTGCTCCACCAAGGGTGCCCTGGACATGCTGACCAAGGTGATGGCCCTAGAGCT | 2414 |
| DDC.1 | 67 | CAGAGCCCAGACACCATGAACGCAAGTGAATTCCGAAGGAGAGGGAAGGAGATGGTGGATTACGTGG | 2415 |
| DEFB1.1 | 68 | GATGGCCTCAGGTGGTAACTTTCTCACAGGCCTTGGCCACAGATCTGATCATTACAATTGCGTCAGCA | 2416 |
| DET1.1 | 70 | CTTGTGGAGATCACCCAATCAGGTTCTATGCCCGGGACTCGGGCCTGCTCAAGTTTGAGATCCAGGCGGG | 2417 |
| DHPS.3 | 78 | GGGAGAACGGGATCAATAGGATCGGAAACCTGCTGGTGCCCAATGAGAATTACTGCAAGTTTGAGGACTGGCTGATGC | 2418 |
| DIABLO.1 | 73 | CACAATGGCGGCTCTGAAGAGTTGGCTGTCGCGCAGCGTAACTTCATTCTTCAGGTACAGACAGTGTTTGTGT | 2419 |
| DIAPH1.1 | 62 | CAAGCAGTCAAGGAGAACCAGAAGCGGCGGGAGACAGAAGAAAGATGAGGCGAGCAAAACT | 2420 |
| DICER1.2 | 68 | TCCAATTCCAGCATCACTGTGGAGAAAAGCTGTTTGTCTCCCCAGCATACTTTATCGCCTTCACTGCC | 2421 |
| DKFZP56400823.1 | 66 | CAGCTACACTGTCGCAGTCCGCTGCTGAGCCTCCCACACTCATCTCCCCTCAAGCTCCAGCCTCAT | 2422 |

TABLE B-continued

| Gene | Target Sequence Length | Amplicon Sequence | SEQ ID NO. |
|---|---|---|---|
| DLC1.1 | 68 | GATTCAGACGAGGATGAGCCTTGTGCCATCAGTGGCAAATGGACTTTCCAAAGGGACAGCAAGAGGTG | 2423 |
| DLL4.1 | 67 | CACGGAGGTATAAGGCAGGAGCCTACCTGGACATCCCTGCTCAGCCCCGCGGCTGGACCTTCCTTCT | 2424 |
| DPEP1.1 | 72 | GGACTCCAGATGCCAGGAGCCCTGCTGCCCACATGCAAGGACCAGCATCTCCTGAGAGGACGCCTGGGCTTA | 2425 |
| DPYS.1 | 70 | AAAGAATGGCACCATGCAGCCCACCATGTCATGGGTCCACCTTTGCGACCAGACCCCTCAACACCCGACT | 2426 |
| DR4.2 | 83 | TGCACAGAGGGTGTGGGTTACACCAATGCTTCCAACAATTTGTTTGCTTGCCTCCCATGTACAGCTTGTAAATCAGATGAAGA | 2427 |
| DR5.2 | 84 | CTCTGAGACAGTGCTTCGATGACTTTGCAGACTTGGTGCCCTTTGACTCCTGGGAGCCGCTCATGAGGAAGTTGGGCCTCATGG | 2428 |
| DUSP1.1 | 76 | AGACATCAGCTCCTGGTTCAACGAGGCCATTGACTTCATAGACTCCATCAAGAATGCTGGAGGAAGGGTGTTTGTC | 2429 |
| DUSP9.1 | 77 | CGTCCTAATCAACGTGCCTATGGCGGGACCACGCTCGGAGCCTGCCTCTTCTGCGACTGTTACTTTTTCTTTGCGGG | 2430 |
| E2F1.3 | 75 | ACTCCCTCTACCCTTGAGCAAGGGCAGGGGTCCCTGAGCTGTTCTTCTGCCCCATACTGAAGGAACTGAGGCCTG | 2431 |
| EBAG9.1 | 66 | CGCTCCTGTTTTTCTCATCTGTGCAGTGGGTTTTGATTCCCACCATGGCCATCACCCAGTTTCGGT | 2432 |
| ECRG4.1 | 66 | GCTCCTGCTCCTGTGCTGGGGCCCAGGTGGCATAAGTGGAAATAAACTCAAGCTGATGCTTCAAAA | 2433 |
| EDG2.1 | 72 | ACGAGTCCATTGCCTTCTTTTATAACCGAAGTGGAAAGCATCTTGCCACAGAATGGAACACAGTCAGCAAGC | 2434 |
| EDN1 endothelin.1 | 73 | TGCCACCTGGACATCATTTGGGTCAACACTCCCGAGCACGTTGTTCCGTATGGACTTGGAAGCCCTAGGTCCA | 2435 |
| EDN2.1 | 79 | CGACAAGGAGTGCGTCTACTTCTGCCACTTGGACATCATCTGGGTGAACACTCCTGAACAGACAGCTCCTTACGGCCTG | 2436 |
| EDNRA.2 | 76 | TTTCCTCAAATTTGCCTCAAGATGGAAACCCTTTGCCTCAGGGCATCCTTTTGGCTGGCACTGGTTGGATGTGTAA | 2437 |
| EDNRB.1 | 72 | ACTGTGAACTGCCTGGTGCAGTGTCCACATGACAAAGGGGCAGGTAGCACCCTCTCTCACCCATGCTGTGGT | 2438 |
| EEF1A1.1 | 67 | CGAGTGGAGACTGGTGTTCTCAAACCCGGTATGGTGGTCACCTTTGCTCCAGTCAACGTTACAACGG | 2439 |
| EFNB1.2 | 66 | GGAGCCCGTATCCTGGAGCTCCCTCAACCCCAAGTTCCTGAGTGGGAAGGGCTTGGTGATCTATCC | 2440 |
| EFNB2.1 | 73 | TGACATTATCATCCCGCTAAGGACTGCGGACAGCGTCTTCTGCCCTCACTACGAGAAGGTCAGCGGGGACTAC | 2441 |
| EGF.3 | 84 | CTTTGCCTTGCTCTGTCACAGTGAAGTCAGCCAGAGCAGGGCTGTTAAACTCTGTGAAATTTGTCATAAGGGTGTCAGGTATTT | 2442 |
| EGFR.2 | 62 | TGTCGATGGACTTCCAGAACCACCTGGGCAGCTGCCAAAAGTGTGATCCAAGCTGTCCCAAT | 2443 |
| EGLN3.1 | 68 | GCTGGTCCTCTACTGCGGGAGCCGGCTGGGCAAATACTACGTCAAGGAGAGGTCTAAGGCAATGGTGG | 2444 |
| EGR1.1 | 76 | GTCCCCGCTGCAGATCTCTGACCCGTTCGGATCCTTTCCTCACTCGCCCACCATGGACAACTACCCTAAGCTGGAG | 2445 |
| EIF2C1.1 | 67 | CCCTCACGGACTCTCAGCGCGTTCGCTTCACCAAGGAGATCAAGGGCCTGAAGGTGGAAGTCACCCA | 2446 |
| EIF4EBP1.1 | 66 | GGCGGTGAAGAGTCACAGTTTGAGATGGACATTTAAAGCACCAGCCATCGTGTGGAGCACTACCAA | 2447 |

TABLE B-continued

| Gene | Target Sequence Length | Amplicon Sequence | SEQ ID NO. |
|---|---|---|---|
| ELTD1.1 | 66 | AGGTCTTGTGCAAGAGGAGCCCTCGCTCTTCTGTTCCTTCTCGGCACCACCTGGATCTTTGGGGTT | 2448 |
| EMCN.1 | 73 | AGGCACTGAGGGTGGAAAAAATGCAAGCACTTCAGCAACCAGCCGGTCTTATTCCAGTATTATTTTGCCGGTG | 2449 |
| EMP1.1 | 75 | GCTAGTACTTTGATGCTCCCTTGATGGGGTCCAGAGAGCCTCCCTGCAGCCACCAGACTTGGCCTCCAGCTGTTC | 2450 |
| ENO2.1 | 67 | TCCTTGGCTTACCTGACCTCTTGCTGTCTCTGCTCGCCCTCCTTTCTGTGCCCTACTCATTGGGGTT | 2451 |
| ENPEP.1 | 67 | CACCTACACGGAGAACGGACAAGTCAAGAGCATAGTGGCCACCGATCATGAACCAACAGATGCCAGG | 2452 |
| ENPP2.1 | 67 | CTCCTGCGCACTAATACCTTCAGGCCAACCATGCCAGAGGAAGTTACCAGACCCAATTATCCAGGGA | 2453 |
| EPAS1.1 | 72 | AAGCCTTGGAGGGTTTCATTGCCGTGGTGACCCAAGATGGCGACATGATCTTTCTGTCAGAAAACATCAGCA | 2454 |
| EPB41L3.1 | 66 | TCAGTGCCATACGCTCTCACTCTCTCCTTCCCTCTGGCTCTGTGCCTCTGCTACCTGGAGCCCAAG | 2455 |
| EPHA2.1 | 72 | CGCCTGTTCACCAAGATTGACACCATTGCGCCCGATGAGATCACCGTCAGCAGCGACTTCGAGGCACGCCAC | 2456 |
| EPHB1.3 | 67 | CCTTGGGAGGGAAGATCCCTGTGAGATGGACAGCTCCAGAGGCCATCGCCTACCGCAAGTTCACTTC | 2457 |
| EPHB2.1 | 66 | CAACCAGGCAGCTCCATCGGCAGTGTCCATCATGCATCAGGTGAGCCGCACCGTGGACAGCATTAC | 2458 |
| EPHB4.1 | 77 | TGAACGGGGTATCCTCCTTAGCCACGGGGCCCGTCCCATTTGAGCCTGTCAATGTCACCACTGACCGAGAGGTACCT | 2459 |
| EPO.1 | 84 | CAGTGCCAGCAATGACATCTCAGGGGCCAGAGGAACTGTCCAGAGAGCAACTCTGAGATCTAAGGATGTCACAGGGCCAACTTG | 2460 |
| ErbB3.1 | 81 | CGGTTATGTCATGCCAGATACACACCTCAAAGGTACTCCCTCCTCCCGGGAAGGCACCCTTTCTTCAGTGGGTCTCAGTTC | 2461 |
| ERBBR.3 | 86 | TGGCTCTTAATCAGTTTCGTTACCTGCCTCTGGAGAATTTACGCATTATTCGTGGGACAAAACTTTATGAGGATCGATATGCCTTG | 2462 |
| ERCC1.2 | 67 | GTCCAGGTGGATGTGAAAGATCCCCAGCAGGCCCTCAAGGAGCTGGCTAAGATGTGTATCCTGGCCG | 2463 |
| ERCC4.1 | 67 | CTGCTGGAGTACGAGCGACAGCTGGTGCTGGAACTGCTCGACACTGACGGGCTAGTAGTGTGCGCCCC | 2464 |
| EREG.1 | 91 | ATAACAAAGTGTAGCTCTGACATGAATGGCTATTGTTTGCATGGACAGTGCATCTATCTGGTGGACATGAGTCAAAACTACTGCAGGTGTG | 2465 |
| ERG.1 | 70 | CCAACACTAGGCTCCCCACCAGCCATATGCCTTCTCATCTGGGCACTTACTACTAAAGACCTGGCGGAGG | 2466 |
| ERK1.3 | 67 | ACGGATCACAGTGGAGGAAGCGCTGGCTCACCCCTACCTGGAGCAGTACTATGACCCGACGGATGAG | 2467 |
| ERK2.3 | 68 | AGTTCTTGACCCCTGGTCCTGTCTCCAGCCCGTCTTGGCTTATCCACTTTGACTCCTTTGAGCCGTTT | 2468 |
| ESPL1.3 | 70 | ACCCCCAGACCGGATCAGGCAAGCTGGCCCTCATGTCCCCTTCACGGTGTTTGAGGAAGTCTGCCCTACA | 2469 |
| ESRRG.3 | 67 | CCAGCACCATTGTTGAAGATCCCCAGACCAAGTGTGAATACATGCTCAACTCGATGCCCAAGAGACT | 2470 |
| F2.1 | 77 | GCTGCATGTCTGGAAGGTAACTGTGCTGAGGGTCTGGGTACGAACTACCGAGGGCATGAAACATCACCCGGTCAGG | 2471 |
| F3.1 | 73 | GTGAAGGATGTGAAGCAGACGTACTTGGCACGGGTCTTCTCCTACCCGGCAGGGAATGTGGAGAGCACCGGTT | 2472 |

TABLE B-continued

| Gene | Target Sequence Length | Amplicon Sequence | SEQ ID NO. |
|---|---|---|---|
| FABP1.1 | 66 | GGGTCCAAAGTGATCCAAAACGAATTCACGGTGGGGGAGGAATGTGAGCTGGAGACAATGACAGGG | 2473 |
| FABP7.1 | 72 | GGAGACAAAGTGGTCATCAGGACTCTCAGCACATTCAAGAACACGGAGATTAGTTTCCAGCTGGGAGAAGAG | 2474 |
| FAP.1 | 66 | CTGACCAGAACCACGGCTTATCCGGCCTGTCCACGAACCACTTATACACCCACATGACCCACTTCC | 2475 |
| fas.1 | 91 | GGATTGCTCAACAACCATGCTGGGCATCTGGACCCTCCTACCTCTGGTTCTTACGTCTGTTGCTAGATTATCGTCCAAAAGTGTTAATGCC | 2476 |
| fasl.2 | 80 | GCACTTTGGGATTCTTTCCATTATGATTCTTTGTTACAGGCACCGAGAATGTTGTATTCAGTGAGGGTCTTCTTACATGC | 2477 |
| FBXW7.1 | 73 | CCCCAGTTTCAACGAGACTTCATTTCATTGCTCCCTAAAGAGTTGGCACTCTATGTGCTTTCATTCCTGGAAC | 2478 |
| FCER1G.2 | 73 | TGCCATCCTGTTTCTGTATGGAATTGTCCTCACCCTCCTCTACTGTCGACTGAAGATCCAAGTGCGAAAGGCA | 2479 |
| FCGR3A.1 | 67 | GTCTCCAGTGGAAGGGAAAAGCCCATGATCTTCAAGCAGGGAAGCCCCAGTGAGTAGCTGCATTCCT | 2480 |
| FDPS.1 | 77 | GGATGATTACCTTGACCTCTTTGGGGACCCCAGTGTGACCGGCAAAATTGGCACTGACATCCAGGACAACAAATGCA | 2481 |
| FEN1.1 | 66 | GTGGAGAAGGGTACGCCAGGGTCGCTGAGAGACTCTGTTCTCCCTGGAGGGACTGGTTGCCATGAG | 2482 |
| FGF1.1 | 66 | GACACCGACGGGCTTTTATACGGCTCACAGACACCAAATGAGGAATGTTTGTTCCTGGAAAGGCTG | 2483 |
| FGF2.2 | 76 | AGATGCAGGAGAGAGGAAGCCTTGCAAACCTGCAGACTGCTTTTTGCCCAATATAGATTGGGTAAGGCTGCAAAAC | 2484 |
| FGF9.1 | 67 | CACAGCTGCCATACTTCGACTTATCAGGATTCTGGCTGGTGGCCTGCGCGAGGGTGCAGTCTTACTT | 2485 |
| FGFR1.3 | 74 | CACGGGACATTCACCACATCGACTACTATAAAAAGACAACCAACGGCCGACTGCCTGTGAAGTGGATGGCACCC | 2486 |
| FGFR2 isoform 1.1 | 80 | GAGGGACTGTTGGCATGCAGTGCCCTCCCAGAGACCAACGTTCAAGCAGTTGGTAGAAGACTTGGATCGAATTCTCACTC | 2487 |
| FH.1 | 67 | ATGGTTGCAGCCCAAGTCATGGGGAACCATGTTGCTGTCACTGTCGGAGGCAGCAATGGACATTTTG | 2488 |
| FHIT.1 | 67 | CCAGTGGAGCGCTTCCATGACCTGCGTCCTGATGAAGTGGCCGATTTGTTTCAGACGACCCAGAGAG | 2489 |
| FHL1.1 | 66 | ATCCAGCCTTTGCCGAATACATCCTATCTGCCACACATCCAGCGTGAGGTCCCTCCAGCTACAAGG | 2490 |
| FIGF.1 | 72 | GGTTCCAGCTTTCTGTAGCTGTAAGCATTGGTGGCCACACCACCTCCTTACAAAGCAACTAGAACCTGCGGC | 2491 |
| FILIP1.1 | 66 | ACACCGGTCACAACGTCATCTGCTCGAGGAACCCAGTCAGTGTCAGGACAAGACGGGTCATCCCAG | 2492 |
| FKBP1A.1 | 76 | CTGCCCTGACTGAATGTGTTCTGTCACTCAGCTTTGCTTCCGACACCTCTGTTTCCTCTTCCCCTTTCTCCTCGTA | 2493 |
| FLJ22655.1 | 82 | CTCCTTCACACAGAACCTTTCATTTATTGTACAACATCACACTCACCCTAACCTACTGGCGGACAGCGATCCCAGTTTGCCT | 2494 |
| FLT1.1 | 75 | GGCTCCTGAATCTATCTTTGACAAAATCTACAGCACCAAGAGCGACGTGTGGTCTTACGGAGTATTGCTGTGGGA | 2495 |
| FLT3LG.1 | 71 | TGGGTCCAAGATGCAAGGCTTGCTGGAGCGCGTGAACACGGAGATACACTTTGTCACCAAATGTGCCTTTC | 2496 |
| FLT4.1 | 69 | ACCAAGAAGCTGAGGACCTGTGGCTGAGCCCGCTGACCATGGAAGATCTTGTCTGCTACAGCTTCCAGG | 2497 |

TABLE B-continued

| Gene | Target Sequence Length | Amplicon Sequence | SEQ ID NO. |
|---|---|---|---|
| FN1.1 | 69 | GGAAGTGACAGACGTGAAGGTCACCATCATGTGGACACCGCCTGAGAGTGCAGTGACCGGCTACCGTGT | 2498 |
| FOLR1.1 | 67 | GAACGCCAAGCACCACAAGGAAAAGCCAGGCCCCGAGGACAAGTTGCATGAGCAGTGTCGACCCTGG | 2499 |
| FOS.1 | 67 | CGAGCCCTTTGATGACTTCCTGTTCCCAGCATCATCCAGGCCCAGTGGCTCTGAGACAGCCCGCTCC | 2500 |
| FRAP1.1 | 66 | AGCGCTAGAGACTGTGGACCGCCTGACGGAGTCCCTGGATTTCACTGACTATGCCTCCCGGATCAT | 2501 |
| FRP1.3 | 75 | TTGGTACCTGTGGGTTAGCATCAAGTTCTCCCCAGGGTAGAATTCAATCAGAGCTCCAGTTTGCATTTGGATGTG | 2502 |
| FST.1 | 72 | GTAAGTCGGATGAGCCTGTCTGTGCCAGTGACAATGCCACTTATGCCAGCGAGTGTGCCATGAAGGAAGCTG | 2503 |
| FZD2.2 | 78 | TGGATCCTCACCTGGTCGGTGCTGTGCTGCGCTTCCACCTTCTTCACTGTCACCACGTACTTGGTAGACATGCAGCGC | 2504 |
| G-Catenin.1 | 68 | TCAGCAGCAAGGGCATCATGGAGGAGGATGAGGCCTGCGGGCGCCAGTACACGCTCAAGAAAACCACC | 2505 |
| GADD45B.1 | 70 | ACCCTCGACAAGACCACACTTTGGGACTTGGGAGCTGGGGCTGAAGTTGCTCTGTACCCATGAACTCCCA | 2506 |
| GAS2.1 | 68 | AACATGTCATGGTCCGTGTGGGAGGAGGCTGGGAAACTTTTGCAGGGTATTTGTTGAAACACGACCCC | 2507 |
| GATA3.3 | 75 | CAAAGGAGCTCACTGTGGTGTCTGTGTTCCAACCACTGAATCTGGACCCCATCTGTGAATAAGCCATTCTGACTC | 2508 |
| GATM.1 | 67 | GATCTCGGCTTGGACGAACCTTGACAGGATGGGTGCAGCGAACTTTCCAGAGCACCCAGGCAGCTAC | 2509 |
| GBL.1 | 66 | GCTGTCAATAGCACCGGAAACTGCTATGTCTGGAATCTGACGGGGGCATTGGTGACGAGGTGACC | 2510 |
| GBP2.2 | 83 | GCATGGGAACCATCAACCAGCAGGCCATGGACCAACTTCACTATGTGACAGAGCTGACAGATCGAATCAAGGCAAACTCCTCA | 2511 |
| GCLC.3 | 71 | CTGTTGCAGGAAGGCATTGATCATCTCCTGGCCCAGCATGTTGCTCATCTCTTTATTAGAGACCCACTGAC | 2512 |
| GCLM.2 | 85 | TGTAGAATCAAACTCTTCATCATCAACTAGAAGTGCAGTTGACATGGCCTGTTCAGTCCTTGGAGTTGCACAGCTGGATTCTGTG | 2513 |
| GFRA1.1 | 69 | TCCGGGTTAAGAACAAGCCCCTGGGGCCAGCAGGGTCTGAGAATGAAATTCCCACTCATGTTTTGCCAC | 2514 |
| GJA1.1 | 68 | GTTCACTGGGGGTGTATGGGGTAGATGGGTGGAGAGGGAGGGGATAAGAGAGGTGCATGTTGGTATTT | 2515 |
| GLYAT.1 | 68 | TACCATTGCAAGGTGCCCAGATGCTGCAGATGCTGGAGAAATCCTTGAGGAAGAGCCTCCCAGCATCC | 2516 |
| GMNN.1 | 67 | GTTCGCTACGAGGATTGAGCGTCTCCACCCAGTAAGTGGGCAAGAGGCGGCAGGAAGTGGGTACGCA | 2517 |
| GNAS.1 | 72 | GAACGTGCCTGACTTTGACTTCCCTCCCGAATTCTATGAGCATGCCAAGGCTCTGTGGGAGGATGAAGGAGT | 2518 |
| GPC3.1 | 68 | TGATGCGCCTGGAAACAGTCAGCAGGCAACTCCGAAGGACAACGAGATAAGCACCTTTCACAACCTCG | 2519 |
| GPX1.2 | 67 | GCTTATGACCGACCCCAAGCTCATCACCTGGTCTCCGGTGTGTCGCAACGATGTTGCCTGGAACTTT | 2520 |
| GPX2.2 | 75 | CACACAGATCTCCTACTCCATCCAGTCCTGAGGAGCCTTAGGATGCAGCATGCCTTCAGGAGACACTGCTGGACC | 2521 |
| GPX3.1 | 69 | GCTCTAGGTCCAATTGTTCTGCTCTAACTGATACCTCAACCTTGGGGCCAGCATCTCCCACTGCCTCCA | 2522 |

TABLE B-continued

| Gene | Target Sequence Length | Amplicon Sequence | SEQ ID NO. |
|---|---|---|---|
| GRB14.1 | 76 | TCCCACTGAAGCCCTTTCAGTTGCGGTTGAAGAAGACTCGCTTGGAGGAAAAAAGGATGTT TACGCCTGGGCACT | 2523 |
| GRB7.2 | 67 | CCATCTGCATCCATCTTGTTTGGGCTCCCCACCCTTGAGAAGTGCCTCAGATAATACCCTG GTGGCC | 2524 |
| GRO1.2 | 73 | CGAAAAGATGCTGAACAGTGACAAATCCAACTGACCAGAAGGGAGGAGGAAGCTCACTGGT GGCTGTTCCTGA | 2525 |
| GSTM1.1 | 86 | AAGCTATGAGGAAAAGAAGTACACGATGGGGGACGCTCCTGATTATGACAGAAGCCAGTGG CTGAATGAAAAATTCAAGCTGGGCC | 2526 |
| GSTM3.2 | 76 | CAATGCCATCTTGCGCTACATCGCTCGCAAGCACAACATGTGTGGTGAGACTGAAGAAGAA AAGATTCGAGTGGAC | 2527 |
| GSTp.3 | 76 | GAGACCCTGCTGTCCCAGAACCAGGGAGGCAAGACCTTCATTGTGGGAGACCAGATCTCCT TCGCTGACTACAACC | 2528 |
| GSTT1.3 | 66 | CACCATCCCCACCCTGTCTTCCACAGCCGCCTGAAAGCCACAATGAGAATGATGCACACTG AGGCC | 2529 |
| GZMA.1 | 79 | GAAAGAGTTTCCCTATCCATGCTATGACCCAGCCACACGCGAAGGTGACCTTAAACTTTTA CAGCTGACGGAAAAAGCA | 2530 |
| HADH.1 | 66 | CCACCAGACAAGACCGATTCGCTGGCCTCCATTTCTTCAACCCAGTGCCTGTCATGAAACT TGTGG | 2531 |
| HAVCR1.1 | 76 | CCACCCAAGGTCACGACTACTCCAATTGTCACAACTGTTCCAACCGTCACGACTGTTCGAA CGAGCACCACTGTTC | 2532 |
| HADC1.1 | 74 | CAAGTACCACAGCGATGACTACATTAAATTCTTGCGCTCCATCCGTCCAGATAACATGTCG GAGTACAGCAAGC | 2533 |
| Hepsin.1 | 84 | AGGCTGCTGGAGGTCATCTCCGTGTGTGATTGCCCCAGAGGCCGTTTCTTGGCCGCCATCT GCCAAGACTGTGGCCGCAGGAAG | 2534 |
| HER2.3 | 70 | CGGTGTGAGAAGTGCAGCAAGCCCTGTGCCCGAGTGTGCTATGGTCTGGGCATGGAGCACT TGCGAGAGG | 2535 |
| HGD.1 | 76 | CTCAGGTCTGCCCCTACAATCTCTATGCTGAGCAGCTCTCAGGATCGGCTTTCACTTGTCC ACGGAGCACCAATAA | 2536 |
| HGF.4 | 65 | CCGAAATCCAGATGATGATGCTCATGGACCCTGGTGCTACACGGGAAATCCACTCATTCCT TGGG | 2537 |
| HGFAC.1 | 72 | CAGGACACAAGTGCCAGATTGCGGGCTGGGGCCACTTGGATGAGAACGTGAGCGGCTACTC CAGCTCCCTGC | 2538 |
| HIF1A.3 | 82 | TGAACATAAAGTCTGCAACATGGAAGGTATTGCACTGCACAGGCCACATTCACGTATATGA TACCAACAGTAACCAACCTCA | 2539 |
| HIF1AN.1 | 66 | TGTTGGCCAGGTCTCACTGCAGCCTGCCCGAGGCTAACTGGCTAGAGCCTCCAGGCCCTAT GATGC | 2540 |
| HIST1H1D.1 | 67 | AAAAAGGCGAAGAAGGCAGGCGCAACTGCTGGGAAACGCAAAGCATCCGGACCCCCAGTAT CTGAGC | 2541 |
| HLA-B.1 | 78 | CTTGTGAGGGACTGAGATGCAGGATTTCTTCACGCCTCCCCTTTGTGACTTCAAGAGCCTC TGGCATCTCTTTCTGCA | 2542 |
| HLA-DPA1.1 | 78 | CGCCCTGAAGACAGAATGTTCCATATCAGAGCTGTGATCTTGAGAGCCCTCTCCTTGGCTT TCCTGCTGAGTCTCCGA | 2543 |
| HLA-DPB1.1 | 73 | TCCATGATGGTTCTGCAGGTTTCTGCGGCCCCCCGGACAGTGGCTCTGACGGCGTTACTGA TGGTGCTGCTCA | 2544 |
| HLA-DQB1.1 | 67 | GGTCTGCTCGGTGACAGATTTCTATCCAGGCCAGATCAAAGTCCGGTGGTTTCGGAATGAT CAGGAG | 2545 |
| HLADQA1.2 | 76 | CATCTTTCCTCCTGTGGTCAACATCACATGGCTGAGCAATGGGCAGTCAGTCACAGAAGGT GTTTCTGAGACCAGC | 2546 |
| HMGB1.1 | 71 | TGGCCTGTCCATTGGTGATGTTGCGAAGAAACTGGGAGAGATGTGGAATAACACTGCTGCA GATGACAAGC | 2547 |

TABLE B-continued

| Gene | Target Sequence Length | Amplicon Sequence | SEQ ID NO. |
|---|---|---|---|
| HNRPAB.1 | 84 | AGCAGGAGCGACCAACTGATCGCACACATGCTTTGTTTGGATATGGAGTGAACACAATTAT GTACCAAATTTAACTTGGCAAAC | 2548 |
| HPCAL1.1 | 70 | CAGGCAGATGGACACCAACAATGACGGCAAACTGTCCTTGGAAGAATTCATCAGAGGTGCC AAGAGCGAC | 2549 |
| HPD.1 | 78 | AGCTGAAGACGGCCAAGATCAAGGTGAAGGAGAACATTGATGCCCTGGAGGAGCTGAAAAT CCTGGTGGACTACGACG | 2550 |
| HSD11B2.1 | 69 | CCAACCTGCCTCAAGAGCTGCTGCAGGCCTACGGCAAGGACTACATCGAGCACTTGCATGG GCAGTTCC | 2551 |
| HSP90AB1.1 | 66 | GCATTGTGACCAGCACCTACGGCTGGACAGCCAATATGGAGCGGATCATGAAAGCCCAGGC ACTTC | 2552 |
| HSPA1A.1 | 70 | CTGCTGCGACAGTCCACTACCTTTTTCGAGAGTGACTCCCGTTGTCCCAAGGCTTCCCAGA GCGAACCTG | 2553 |
| HSPA8.1 | 73 | CCTCCCTCTGGTGGTGCTTCCTCAGGGCCCACCATTGAAGAGGTTGATTAAGCCAACCAAG TGTAGATGTAGC | 2554 |
| HSPB1.1 | 84 | CCGACTGGAGGAGCATAAAAGCGCAGCCGAGCCCAGCGCCCCGCACTTTTCTGAGCAGACG TCCAGAGCAGAGTCAGCCAGCAT | 2555 |
| HSPG2.1 | 66 | GAGTACGTGTGCCGAGTGTTGGGCAGCTCCGTGCCTCTAGAGGCCTCTGTCCTGGTCACCA TTGAG | 2556 |
| HTATIP.1 | 66 | TCGAATTGTTTGGGCACTGATGAGGACTCCCAGGACAGCTCTGATGGAATACCGTCAGCAC CACGC | 2557 |
| HYAL1.1 | 78 | TGGCTGTGGAGTTCAAATGTCGATGCTACCCTGGCTGGCAGGCACCGTGGTGTGAGCGGAA GAGCATGTGGTGATTGG | 2558 |
| HYAL2.1 | 67 | CAACCATGCACTCCCAGTCTACGTCTTCACACGACCCACCTACAGCCGCAGGCTCACGGGG CTTAGT | 2559 |
| HYAL3.1 | 67 | TATGTCCGCCTCACACACCGGAGATCTGGGAGGTTCCTGTCCCAGGATGACCTTGTGCAGT CCATTG | 2560 |
| ICAM1.1 | 68 | GCAGACAGTGACCATCTACAGCTTTCCGGCGCCCAACGTGATTCTGACGAAGCCAGAGGTC TCAGAAG | 2561 |
| ICAM2.1 | 62 | GGTCATCCTGACACTGCAACCCACTTTGGTGGCTGTGGGCAAGTCCTTCACCATTGAGTGC A | 2562 |
| ICAM3.1 | 67 | GCCTTCAATCTCAGCAACGTGACTGGCAACAGTCGGATCCTCTGCTCAGTGTACTGCAATG GCTCTC | 2563 |
| ID1.1 | 70 | AGAACCGCAAGGTGAGCAAGGTGGAGATTCTCCAGCACGTCATCGACTACATCAGGGACCT TCAGTTGGA | 2564 |
| ID2.4 | 76 | AACGACTGCTACTCCAAGCTCAAGGAGCTGGTGCCCAGCATCCCCCAGAACAAGAAGGTGA GCAAGATGGAAATCC | 2565 |
| ID3.1 | 80 | CTTCACCAAATCCCTTCCTGGAGACTAAACCTGGTGCTCAGGAGCGAAGGACTGTGAACTT GTGGCCTGAAGAGCCAGAG | 2566 |
| IFI27.1 | 71 | CTCTCCGGATTGACCAAGTTCATCCTGGGCTCCATTGGGTCTGCCATTGCGGCTGTCATTG CGAGGTTCTA | 2567 |
| IGF1.2 | 76 | TCCGGAGCTGTGATCTAAGGAGGCTGGAGATGTATTGCGCACCCCTCAAGCCTGCCAAGTC AGCTCGCTCTGTCCG | 2568 |
| IGF1R.3 | 83 | GCATGGTAGCCGAAGATTTCACAGTCAAAATCGGAGATTTTGGTATGACGCGAGATATCTA TGAGACAGACTATTACCGGAAA | 2569 |
| IGF2.2 | 72 | CCGTGCTTCCGGACAACTTCCCCAGATACCCCGTGGGCAAGTTCTTCCAATATGACACCTG GAAGCAGTCCA | 2570 |
| IGFBP2.1 | 73 | GTGGACAGCACCATGAACATGTTGGGCGGGGGAGGCAGTGCTGGCCGGAAGCCCCTCAAGT CGGGTATGAAGG | 2571 |
| IGFBP3.1 | 66 | ACATCCCAACGCATGCTCCTGGAGCTCACAGCCTTCTGTGGTGTCATTTCTGAAACAAGGG CGTGG | 2572 |

TABLE B-continued

| Gene | Target Sequence Length | Amplicon Sequence | SEQ ID NO. |
|---|---|---|---|
| IGFBP5.1 | 69 | TGGACAAGTACGGGATGAAGCTGCCAGGCATGGAGTACGTTGACGGGGACTTTCAGTGCCA CACCTTCG | 2573 |
| IGFBP6.1 | 77 | TGAACCGCAGAGACCAACAGAGGAATCCAGGCACCTCTACCACGCCCTCCCAGCCCAATTC TGCGGGTGTCCAAGAC | 2574 |
| IL-7.1 | 71 | GCGGTGATTCGGAAATTCGCGAATTCCTCTGGTCCTCATCCAGGTGCGCGGGAAGCAGGTG CCCAGGAGAG | 2575 |
| IL-8.1 | 70 | AAGGAACCATCTCACTGTGTGTAAACATGACTTCCAAGCTGGCCGTGGCTCTCTTGGCAGC CTTCCTGAT | 2576 |
| IL10.3 | 79 | GGCGCTGTCATCGATTTCTTCCCTGTGAAAACAAGAGCAAGGCCGTGGAGCAGGTGAAGAA TGCCTTTAATAAGCTCCA | 2577 |
| IL11.2 | 66 | TGGAAGGTTCCACAAGTCACCCTGTGATCAACAGTACCCGTATGGGACAAAGCTGCAAGGT CAAGA | 2578 |
| IL15.1 | 79 | GGCTGGGTACCAATGCTGCAGGTCAACAGCTATGCTGGTAGGCTCCTGCCAGTGTGGAACC ACTGACTACTGGCTCTCA | 2579 |
| IL1B.1 | 67 | AGCTGAGGAAGATGCTGGTTCCCTGCCCACAGACCTTCCAGGAGAATGACCTGAGCACCTT CTTTCC | 2580 |
| IL6.3 | 72 | CCTGAACCTTCCAAAGATGGCTGAAAAAGATGGATGCTTCCAATCTGGATTCAATGAGGAG ACTTGCCTGGT | 2581 |
| IL6ST.3 | 74 | GGCCTAATGTTCCAGATCCTTCAAAGAGTCATATTGCCCAGTGGTCACCTCACACTCCTCC AAGGCACAATTTT | 2582 |
| ILT-2.2 | 63 | AGCCATCACTCTCAGTGCAGCCAGGTCCTATCGTGGCCCCTGAGGAGACCCTGACTCTGCA GT | 2583 |
| IMP3.1 | 72 | GTGGACTCGTCCAAGATCAAGCGGCACGTGCTAGAGTACAATGAGGAGCGCGATGACTTCG ATCTGGAAGCC | 2584 |
| INDO.1 | 66 | CGCCTTGCACGTCTAGTTCTGGGATGCATCACCATGGCATATGTGTGGGCAAAGGTCATG GAGAT | 2585 |
| INHBA.1 | 72 | GTGCCCGAGCCATATAGCAGGCACGTCCGGGTCCTCACTGTCCTTCCACTCAACAGTCATC AACCACTACCG | 2586 |
| INHBB.1 | 72 | AGCCTCCAGGATACCAGCAAATGGATGCGGTGACAAATGGCAGCTTAGCTACAAATGCCTG TCAGTCGGAGA | 2587 |
| INSR.1 | 67 | CAGTCTCCGAGAGCGGATTGAGTTCCTCAATGAGGCCTCGGTCATGAAGGGCTTCACCTGC CATCAC | 2588 |
| IQGAP2.1 | 66 | AGAGACACCAGCAACTGCGCAACAGGAGGTAGACCATGCCACGGACATGGTGAGCCGTGCA ATGAT | 2589 |
| ITGA3.2 | 77 | GTGTCAGACTGAAGCCCCATCCAGCCCGTTCCGCAGGGACTAGAGGCTTTCGGCTTTTTGG GACAGCAAC | 2590 |
| ITGA3.2 | 77 | CCATGATCCTCACTCTGCTGGTGGACTATACACTCCAGACCTCGCTTAGCATGGTAAATCA CCGGCTACAAAGCTTC | 2591 |
| ITGA4.2 | 66 | CAACGCTTCAGTGATCAATCCCGGGGCGATTTACAGATGCAGGATCGGAAAGAATCCCGGC CAGAC | 2592 |
| ITGA5.1 | 75 | AGGCCAGCCCTACATTATCAGAGCAAGAGCCGGATAGAGGACAAGGCTCAGATCTTGCTGG ACTGTGGAGAAGAC | 2593 |
| ITGA6.2 | 69 | CAGTGACAAACAGCCCTTCCAACCCAAGGAATCCCACAAAAGATGGCGATGACGCCCATGA GGCTAAAC | 2594 |
| ITGA7.1 | 79 | GATATGATTGGTCGCTGCTTTGTGCTCAGCCAGGACCTGGCCATCCGGGATGAGTTGGATG GTGGGAATGGAAGTTCT | 2595 |
| ITGAV.1 | 79 | ACTCGGACTGCACAAGCTATTTTTGATGACAGCTATTTGGGTTATTCTGTGGCTGTCGGAG ATTTCAATGGTGATGGCA | 2596 |
| ITGB1.1 | 74 | TCAGAATTGGATTTGGCTCATTTGTGGAAAAGACTGTGATGCCTTACATTAGCACAACACC AGCTAAGCTCAGG | 2597 |

TABLE B-continued

| Gene | Target Sequence Length | Amplicon Sequence | SEQ ID NO. |
|---|---|---|---|
| ITGB3.1 | 78 | ACCGGGGAGCCCTACATGACGAAAATACCTGCAACCGTTACTGCCGTGACGAGATTGAGTCAGTGAAAGAGCTTAAGG | 2598 |
| ITGB4.2 | 66 | CAAGGTGCCCTCAGTGGAGCTCACCAACCTGTACCCGTATTGCGACTATGAGATGAAGGTGTGCGC | 2599 |
| ITGB5.1 | 71 | TCGTGAAAGATGACCAGGAGGCTGTGCTATGTTTCTACAAAACCGCCAAGGACTGCGTCATGATGTTCACC | 2600 |
| JAG1.1 | 69 | TGGCTTACACTGGCAATGGTAGTTTCTGTGGTTGGCTGGGAAATCGAGTGCCGCATCTCACAGCTATGC | 2601 |
| K-ras.10 | 71 | GTCAAAATGGGGAGGGACTAGGGCAGTTTGGATAGCTCAACAAGATACAATCTCACTCTGTGGTGGTCCTG | 2602 |
| KCNJ15.1 | 67 | GGACGTTCTACCTGCCTTGAAGAAGACACCTGACCTGCGGAGTGAGTGACCAGTGTTTCCAGAGCCT | 2603 |
| KDR.6 | 68 | GAGGACGAAGGCCTCTACACCTGCCAGGCATGCAGTGTTCTTGGCTGTGCAAAAGTGGAGGCATTTTT | 2604 |
| Ki-67.2 | 80 | CGGACTTTGGGTGCGACTTGACGAGCGGTGGTTCGACAAGTGGCCTTGCGGGCCGGATCGTCCCAGTGGAAGAGTTGTAA | 2605 |
| KIAA1303 raptor.1 | 66 | ACTACAGCGGGAGCAGGAGCTGGAGGTAGCTGCAATCAACCCAAATCACCCTCTTGCTCAGATGCC | 2606 |
| KIF1A.1 | 66 | CTCCTACTGGTCGCACACCTCACCTGAGGACATCAACTACGCGTCGCAGAAGCAGGTGTACCGGGA | 2607 |
| Kiting.4 | 79 | GTCCCCGGGATGGATGTTTTGCCAAGTCATTGTTGGATAAGCGAGATGGTAGTACAATTGTCAGACAGCTTGACTGATC | 2608 |
| KL.1 | 72 | GAGGTCCTGTCTAAACCCTGTGTCCCTGAGGGATCTGTCTCACTGGCATCTTGTTGAGGGCCTTGCACATAG | 2609 |
| KLK3.1 | 66 | CCAAGCTTACCACCTGCACCCGGAGAGCTGTGTCACCATGTGGGTCCCGGTTGTCTTCCTCACCCT | 2610 |
| KLRK1.2 | 70 | TGAGAGCCAGGCTTCTTGTATGTCTCAAAATGCCAGCCTTCTGAAAGTATACAGCAAAGAGGACCAGGAT | 2611 |
| KRT19.3 | 77 | TGAGCGGCAGAATCAGGAGTACCAGCGGCTCATGGACATCAAGTCGCGGCTGGAGCAGGAGATTGCCACCTACCGCA | 2612 |
| KRT5.3 | 69 | TCAGTGGAGAAGGAGTTGGACCAGTCAACATCTCTGTTGTCACAAGCAGTGTTTCCTCTGGATATGGCA | 2613 |
| KRT7.1 | 71 | TTCAGAGATGAACCGGGCCATCCAGAGGCTGCAGGCTGAGATCGACAACATCAAGAACCAGCGTGCCAAGT | 2614 |
| L1CAM.1 | 66 | CTTGCTGGCCAATGCCTACATCTACGTTGTCCAGCTGCCAGCCAAGATCCTGACTGCGGACAATCA | 2615 |
| LAMA3.1 | 73 | CAGATGAGGCACATGGAGACCCAGGCCAAGGACCTGAGGAATCAGTTGCTCAACTACCGTTCTGCCATTTCAA | 2616 |
| LAMA4.1 | 67 | GATGCACTGCGGTTAGCAGCGCTCTCCATCGAGGAAGGCAAATCCGGGGTGCTGAGCGTATCCTCTG | 2617 |
| LAMB1.1 | 66 | CAAGGAGACTGGGAGGTGTCTCAAGTGCCTGTACCACACGGAAGGGGAACACTGTCAGTTCTGCCG | 2618 |
| LAMB3.1 | 67 | ACTGACCAAGCCTGAGACCTACTGCACCCAGTATGGCGAGTGGCAGATGAAATGCTGCAAGTGTGAC | 2619 |
| LAMC2.2 | 80 | ACTCAAGCGGAAATTGAAGCAGATAGGTCTTATCAGCACAGTCTCCGCCTCCTGGATTCAGTGTCTCGGCTTCAGGGAGT | 2620 |
| LAPTM5.1 | 66 | TGCTGGACTTCTGCCTGAGCATCCTGACCCTCTGCAGCTCCTACATGGAAGTGCCCACCTATCTCA | 2621 |
| LDB1.2 | 67 | AACACCCAGTTTGACGCAGCCAACGGCATTGACGACGAGGACAGCTTTAACAACTCCCCTGCACTGG | 2622 |

TABLE B-continued

| Gene | Target Sequence Length | Amplicon Sequence | SEQ ID NO. |
|---|---|---|---|
| LDB2.1 | 66 | ATCACGGTGGACTGCGACCAGTGTACCATGGTCACCCAGCACGGGAAGCCCATGTTTACCAAGGTA | 2623 |
| LDHA.2 | 74 | AGGCTACACATCCTGGGCTATTGGACTCTCTGTAGCAGATTTGGCAGAGAGTATAATGAAGAATCTTAGGCGGG | 2624 |
| LGALS1.1 | 72 | GGGTGGAGTCTTCTGACAGCTGGTGCGCCTGCCCGGGAACATCCTCCTGGACTCAATCATGGCTTGTGGTCT | 2625 |
| LGALS3.1 | 69 | AGCGGAAAATGGCAGACAATTTTTCGCTCCATGATGCGTTATCTGGGTCTGGAAACCCAAACCCTCAAG | 2626 |
| LGALS9.1 | 67 | AGTACTTCCACCGCGTGCCCTTCCACCGTGTGGACACCATCTCCGTCAATGGCTCTGTGCAGCTGTC | 2627 |
| LIMK1.1 | 67 | GCTTCAGGTGTTGTGACTGCAGTGCCTCCCTGTCGCACCAGTACATATGAGAAGGATGGGCAGCTCTT | 2628 |
| LMNB1.1 | 66 | TGCAAACGCTGGTGTCACAGCCAGCCCCCCAACTGACCTCATCTGGAAGAACCAGAACTCGTGGGG | 2629 |
| LMO2.1 | 74 | GGCTGCCAGCAGAACATCGGGGACCGCTACTTCCTGAAGGCCATCGACCAGTACTGGCACGAGGACTGCCTGAG | 2630 |
| LOX.1 | 66 | CCAATGGGAGAACAACGGGCAGGTGTTCAGCTTGCTGAGCCTGGGCTCACAGTACCAGCCTCAGCG | 2631 |
| LRP2.1 | 66 | GGCTGTAGACTGGGTTTCCAGAAAGCTCTACTGGTTGGATGCCCGCCTGGATGGCCTCTTTGTCTC | 2632 |
| LRRC2.1 | 71 | CCAGTGTCCCAATCTGTGTCCTGCGGATGTCGAATTTGCAGTGGTTGGATATCAGCAGCAATAACCTGACC | 2633 |
| LTF.1 | 68 | AACGGAAGCCTGTGACTGAGGCTAGAAGCTGCCATCTTGCCATGGCCCCGAATCATGCCGTGGTGTCT | 2634 |
| LYZ.1 | 80 | TTGCTGCAAGATAACATCGCTGATGCTGTAGCTTGTGCAAAGAGGGTTGTCCGTGATCCACAAGGCATTAGAGCATGGGT | 2635 |
| MADH2.1 | 70 | GCTGCCTTTGGTAAGAACATGTCGTCCATCTTGCCATTCACGCCGCCAGTTGTGAAGAGACTGCTGGGAT | 2636 |
| MADH4.1 | 76 | GGACATTACTGGCCTGTTCACAATGAGCTTGCATTCCAGCCTCCCATTTCCAATCATCCTGCTCCTGAGTATTGGT | 2637 |
| MAL.1 | 66 | GTTGGGAGCTTGCTGTGTCTAACCTCCAACTGCTGTGCTGTCTGCTAGGGTCACCTCCTGTTTGTG | 2638 |
| MAL2.1 | 67 | CCTTCGTCTGCCTGGAGATTCTGTTCGGGGGTCTTGTCTGGATTTTGGTTGCCTCCTCCAATGTTCC | 2639 |
| MAP2K1.1 | 76 | GCCTTTCTTACCCAGAAGCAGAAGGTGGGAGAACTGAAGGATGACGACTTTGAGAAGATCAGTGAGCTGGGGCTG | 2640 |
| MAP2K3.1 | 67 | GCCCTCCAATGTCCTTATCAACAAGGAGGGCCATGTGAAGATGTGTGACTTTGGCATCAGTGGCTAC | 2641 |
| MAP4.1 | 72 | GCCGGTCAGGCACACAAGGGGCCCTTGGAGCGTGGACTGGTTGGTTTTGCCATTTTGTTGTGTGTATGCTGC | 2642 |
| MARCKS.1 | 67 | CCCCTCTTGGATCTGTTGAGTTTCTTTGTTGAAGAAGCCAGCATGGGTGCCCAGTTCTCCAAGACCG | 2643 |
| Maspin.2 | 77 | CAGATGGCCACTTTGAGAACATTTTAGCTGACAACAGTGTGAACGACCAGACCAAAATCCTTGTGGTTAATGCTGCC | 2644 |
| MCAM.1 | 66 | CGAGTTCCAGTGGCTGAGAGAAGAGACAGGCCAGGTGCTGGAAAGGGGGCCTGTGCTTCAGTTGCA | 2645 |
| MCM2.2 | 75 | GACTTTTGCCCGCTACCTTTCATTCCGGCGTGACAACAATGAGCTGTTGCTCTTCATACTGAAGCAGTTAGTGGC | 2646 |
| MCM3.3 | 75 | GGAGAACAATCCCCTTGAGACAGAATATGGCCTTTCTGTCTACAAGGATCACCAGACCATCACCATCCAGGAGAT | 2647 |

TABLE B-continued

| Gene | Target Sequence Length | Amplicon Sequence | SEQ ID NO. |
|---|---|---|---|
| MCM6.3 | 82 | TGATGGTCCTATGTGTCACATTCATCACAGGTTTCATACCAACACAGGCTTCAGCACTTCCTTTGGTGTGTTTCCTGTCCCA | 2648 |
| MCP1.1 | 71 | CGCTCAGCCAGATGCAATCAATGCCCCAGTCACCTGCTGTTATAACTTCACCAATAGGAAGATCTCAGTGC | 2649 |
| MDH2.1 | 63 | CCAACACCTTTGTTGCAGAGCTGAAGGGTTTGGATCCAGCTCGAGTCAACGTCCCTGTCATTG | 2650 |
| MDK.1 | 66 | GGAGCCGACTGCAAGTACAAGTTTGAGAACTGGGGTGCGTGTGATGGGGGCACAGGCACCAAAGTC | 2651 |
| MDM2.1 | 68 | CTACAGGGACGCCATCGAATCCGGATCTTGATGCTGGTGTAAGTGAACATTCAGGTGATTGGTTGGAT | 2652 |
| MGMT.1 | 69 | GTGAAATGAAACGCACCACACTGGACAGCCCTTTGGGGAAGCTGGAGCTGTCTGGTTGTGAGCAGGGTC | 2653 |
| mGST1.2 | 79 | ACGGATCTACCACACCATTGCATATTTGACACCCCTTCCCCAGCCAAATAGAGCTTTGAGTTTTTTTGTTGGATATGGA | 2654 |
| MICA.1 | 68 | ATGGTGAATGTCACCCGCAGCGAGGCCTCAGAGGGCAACATTACCGTGACATGCAGGGCTTCTGGCTT | 2655 |
| MIF.2 | 66 | CCGGACAGGGTCTACATCAACTATTACGACATGAACGCGGCCAATGTGGGCTGGAACAACTCCACC | 2656 |
| MMP1.1 | 72 | GGGAGATCATCGGGACAACTCTCCTTTTGATGGACCTGGAGGAAATCTTGCTCATGCTTTTCAACCAGGCCC | 2657 |
| MMP10.1 | 66 | TGGAGGTGACAGGGAAGCTAGACACTGACACTCTGGAGGTGATGCGCAAGCCCAGGTGTGGAGTTC | 2658 |
| MMP14.1 | 66 | GCTGTGGAGCTCTCAGGAAGGGCCCTGAGGAAGGCACACTTGCTCCTGTTGGTCCCTGTCCTTGCT | 2659 |
| MMP2.2 | 86 | CCATGATGGAGAGGCAGACATCATGATCAACTTTGGCCGCTGGGAGCATGGCGATGGATACCCCTTTGACGGTAAGGACGGACTCC | 2660 |
| MMP7.1 | 79 | GGATGGTAGCAGTCTAGGGATTAACTTCCTGTATGCTGCAACTCATGAACTTGGCCATTCTTTGGGTATGGGACATTCC | 2661 |
| MMP9.1 | 67 | GAGAACCAATCTCACCGACAGGCAGCTGGCAGAGGAATACCTGTACCGCTATGGTTACACTCGGGTG | 2662 |
| MRP1.1 | 79 | TCATGGTGCCCGTCAATGCTGTGATGGCGATGAAGACCAAGACGTATCAGGTGGCCCACATGAAGAGCAAAGACAATCG | 2663 |
| MRP2.3 | 65 | AGGGGATGACTTGGACACATCTGCCATTCGACATGACTGCAATTTTGACAAAGCCATGCAGTTTT | 2664 |
| MRP3.1 | 91 | TCATCCTGGCGATCTACTTCCTCTGGCAGAACCTAGGTCCCTCTGTCCTGGCTGGAGTCGCTTTCATGGTCTTGCTGATTCCACTCAACGG | 2665 |
| MRP4.2 | 66 | AGCGCCTGGAATCTACAACTCGGAGTCCAGTGTTTTCCCACTTGTCATCTTCTCTCCAGGGGCTCT | 2666 |
| MSH2.3 | 73 | GATGCAGAATTGAGGCAGACTTTACAAGAAGATTTACTTCGTCGATTCCCAGATCTTAACCGACTTGCCAAGA | 2667 |
| MSH3.2 | 82 | TGATTACCATCATGGCTCAGATTGGCTCCTATGTTCCTGCAGAAGAAGCGACAATTGGGATTGTGGATGGCATTTTCACAAG | 2668 |
| MSH6.3 | 68 | TCTATTGGGGATTGGTAGGAACCGTTACCAGCTGGAAATTCCTGAGAATTTCACCACTCGCAATTTG | 2669 |
| MT1B.1 | 66 | GTGGGCTGTGCCAAGTGTGCCCAGGGCTGTGTCTGCAAAGGCTCATCAGAGAAGTGCCGCTGCTGT | 2670 |
| MT1G.1 | 74 | GTGCACCCACTGCCTCTTCCCTTCTCGCTTGGGAACTCTAGTCTCGCCTCGGGTTGCAATGGACCCCAACTGCT | 2671 |
| MT1H.1 | 74 | CGTGTTCCACTGCCTCTTCTCTTCTCGCTTGGGAACTCCAGTCTCACCTCGGCTTGCAATGGACCCCAACTGCT | 2672 |

TABLE B-continued

| Gene | Target Sequence Length | Amplicon Sequence | SEQ ID NO. |
|---|---|---|---|
| MT1X.1 | 80 | CTCCTGCAAATGCAAAGAGTGCAAATGCACCTCCTGCAAGAAGAGCTGCTGCTCCTGCTGC CCTGTGGGCTGTGCCAAGT | 2673 |
| MUC1.2 | 71 | GGCCAGGATCTGTGGTGGTACAATTGACTCTGGCCTTCCGAGAAGGTACCATCAATGTCCA CGACGTGGAG | 2674 |
| MVP.1 | 75 | ACGAGAACGAGGGCATCTATGTGCAGGATGTCAAGACCGGAAAGGTGCGCGCTGTGATTGG AAGCACCTACATGC | 2675 |
| MX1.1 | 78 | GAAGGAATGGGAATCAGTCATGAGCTAATCACCCTGGAGATCAGCTCCCGAGATGTCCCGG ATCTGACTCTAATAGAC | 2676 |
| MYBL2.1 | 74 | GCCGAGATCGCCAAGATGTTGCCAGGGAGGACAGACAATGCTGTGAAGAATCACTGGAACT CTACCATCAAAAG | 2677 |
| MYH11.1 | 85 | CGGTACTTCTCAGGGCTAATATATACGTACTCTGGCCTCTTCTGCGTGGTGGTCAACCCCT ATAAACACCTGCCCATCTACTCGG | 2678 |
| MYRIP.2 | 69 | CCTTCACCTTCCTCGTCAACACCAAGCGCCAGTGTGGAGATTGCAAATTCAATGTCTGCAA GAGCTGCT | 2679 |
| NBN.1 | 76 | GCATCTACTTGCCAGAACCAAATTAACTTACTTCCAAGTTCTGGCTGCTTGCAGGTGGAAC TCCAGCTGCAAGGGA | 2680 |
| NCF1.1 | 66 | GACACCTTCATCCGTCACATCGCCCTGCTGGGCTTTGAGAAGCGCTTCGTACCCAGCCAGC ACTAT | 2681 |
| NFAT5.1 | 70 | CTGAACCCCTCTCCTGGTCACCGAGAATCAGTCCCCGTGGAGTTCCCCCTCCACCTCGCCA TCGTTTCCT | 2682 |
| NFATC2.1 | 72 | CAGTCAAGGTCAGAGGCTGAGCCCGGGTTCCTACCCCACAGTCATTCAGCAGCAGAATGCC ACGAGCCAAAG | 2683 |
| NFKBp50.3 | 73 | CAGACCAAGGAGATGGACCTCAGCGTGGTGCGGCTCATGTTTACAGCTTTTCTTCCGGATA GCACTGGCAGCT | 2684 |
| NFKBp65.3 | 68 | CTGCCGGGATGGCTTCTATGAGGCTGAGCTCTGCCCGGACCGCTGCATCCACAGTTTCCAG AACCTGG | 2685 |
| NFX1.1 | 74 | CCCTGCCATACCAGCTCACCCTGCCCTGTGACTGCTTGTAAAGCTAAGGTAGAGCTACAGT GTGAATGTGGACG | 2686 |
| NME2.1 | 66 | ATGCTTGGGGAGACCAATCCAGCAGATTCAAAGCCAGGCACCATTCGTGGGGACTTCTGCA TTCAG | 2687 |
| NNMT.1 | 67 | CCTAGGGCAGGGATGGAGAGAGAGTCTGGGCATGAGGAGAGGGTCTCGGGATGTTTGGCTG GACTAG | 2688 |
| NOL3.1 | 72 | CAGCCTTGGGAAGTGAGACTAGAAGAGGGGAGCAGAAAGGGACCTTGAGTAGACAAAGGCC ACACACATCAT | 2689 |
| NOS2A.3 | 67 | GGGTCCATTATGACTCCCAAAAGTTTGACCAGAGGACCCAGGGACAAGCCTACCCCTCCAG ATGAGC | 2690 |
| NOS3.1 | 68 | ATCTCCGCCTCGCTCATGGGCACGGTGATGGCGAAGCGAGTGAAGGCGACAATCCTGTATG CCTCCGA | 2691 |
| NOTCH1.1 | 76 | CGGGTCCACCAGTTTGAATGGTCAATGCGAGTGGCTGTCCCGGCTGCAGAGCGGCATGGTG CCGAACCAATACAAC | 2692 |
| NOTCH2.1 | 75 | CACTTCCCTGCTGGGATTATATCAACAACCAGTGTGATGAGCTGTGCAACACGGTCGAGTG CCTGTTTGACAACT | 2693 |
| NOTCH3.1 | 67 | TGTGGACGAGTGTGCTGGCCCCGCACCCTGTGGCCCTCATGGTATCTGCACCAACCTGGCA GGGAGT | 2694 |
| NPD009 (ABAT offici | 73 | GGCTGTGGCTGAGGCTGTAGCATCTCTGCTGGAGGTGAGACACTCTGGGAACTGATTTGAC CTCGAATGCTCC | 2695 |
| NPM1.2 | 84 | AATGTTGTCCAGGTTCTATTGCCAAGAATGTGTTGTCCAAAATGCCTGTTTAGTTTTTAAA GATGGAACTCCACCCTTTGCTTG | 2696 |
| NPPB.1 | 66 | GACACCTGCTTCTGATTCCACAAGGGGCTTTTTCCTCAACCCTGTGGCCGCTTTGAAGTGA CTCA | 2697 |

TABLE B-continued

| Gene | Target Sequence Length | Amplicon Sequence | SEQ ID NO. |
|---|---|---|---|
| NPR1.1 | 66 | ACATCTGCAGCTCCCCTGATGCCTTCAGAACCCTCATGCTCCTGGCCCTGGAAGCTGGCTT GTGTG | 2698 |
| NPY1R.1 | 70 | GGATCTTCCCCACTCTGCTCCCTTCCATTCCCACCCTTCCTTCTTTAATAAGCAGGAGCGA AAAAGACAA | 2699 |
| NRG1.3 | 83 | CGAGACTCTCCTCATAGTGAAAGGTATGTGTCAGCCATGACCACCCCGGCTCGTATGTCAC CTGTAGATTTCCACACGCCAAG | 2700 |
| NUDT1.1 | 77 | ACTGGTTTCCACTCCTGCTTCAGAAGAAGAAATTCCACGGGTACTTCAAGTTCCAGGGTCA GGACACCATCCTGGAC | 2701 |
| OGG1.1 | 71 | ACCAAGGTGGCTGACTGCATCTGCCTGATGGCCCTAGACAAGCCCCAGGCTGTGCCCGTGG ATGTCCATAT | 2702 |
| OPN, osteopontin.3 | 80 | CAACCGAAGTTTTCACTCCAGTTGTCCCCACAGTAGACACATATGATGGCCGAGGTGATAG TGTGGTTTATGGACTGAGG | 2703 |
| p21.3 | 65 | TGGAGACTCTCAGGGTCGAAAACGGCGGCAGACCAGCATGACAGATTTCTACCACTCCAAA CGCC | 2704 |
| p27.3 | 66 | CGGTGGACCACGAAGAGTTAACCCGGGACTTGGAGAAGCACTGCAGAGACATGGAAGAGGC GAGCC | 2705 |
| P53.2 | 68 | CTTTGAACCCTTGCTTGCAATAGGTGTGCGTCAGAAGCACCCAGGACTTCCATTTGCTTTG TCCCGGG | 2706 |
| PAH.1 | 80 | TGGCTGATTCCATTAACAGTGAAATTGGAATCCTTTGCAGTGCCCTCCAGAAAATAAAGTA AAGCCATGGACAGAATGTG | 2707 |
| PAI1.3 | 81 | CCGCAACGTGGTTTTCTCACCCTATGGGGTGGCCTCGGTGTTGGCCATGCTCCAGCTGACA ACAGGAGGAGAAACCCAGCA | 2708 |
| Pak1.2 | 70 | GAGCTGTGGGTTGTTATGGAATACTTGGCTGGAGGCTCCTTGACAGATGTGGTGACAGAAA CTTGCATGG | 2709 |
| PARD6A.1 | 66 | GATCCTCGAGGTCAATGGCATTGAAGTAGCCGGGAAGACCTTGGACCAAGTGACGGACATG ATGGT | 2710 |
| PBOV1.1 | 72 | GCAAAGCCTTTCCAGAAAAATAAAAATGGTTGAAAAGGCAATTCTGCTACCAATGACTGTT TAAGCCCAGCC | 2711 |
| PCCA.1 | 68 | GGTGAAATCTGTGCACTGTCAAGCTGGAGACACAGTTGGAGAAGGGGATCTGCTCGTGGAG CTGGAAT | 2712 |
| PCK1.1 | 66 | CTTAGCATGGCCCAGCACCCAGCAGCCAAACTGCCCAAGATCTTCCATGTCAACTGGTTCC GGAAG | 2713 |
| PCNA.2 | 71 | GAAGGTGTTGGAGGCACTCAAGGACCTCATCAACGAGGCCTGCTGGGATATTAGCTCCAGC GGTGTAAACC | 2714 |
| PCSK6.1 | 67 | ACCTTGAGTAGCAGAGGCCCTCACACCTTCCTCAGAATGGACCCCCAGGTGAAATGGCTCC AGCAAC | 2715 |
| PDCD1.1 | 73 | GACAACGCCACCTTCACCTGCAGCTTCTCCAACACATCGGAGAGCTTCGTGCTAAACTGGT ACCGCATGAGCC | 2716 |
| PDE4DIP.1 | 73 | GCTTCGTCTTGCTGTGAGAGAGCGAGATCATGACTTAGAGAGACTGCGCGATGTCCTCTCC TCCAATGAAGCT | 2717 |
| PDGFA.3 | 67 | TTGTTGGTGTGCCCTGGTGCCGTGGTGGCGGTCACTCCCTCTGCTGCCAGTGTTTGGACAG AACCCA | 2718 |
| PDGFB.3 | 62 | ACTGAAGGAGACCCTTGGAGCCTAGGGGCATCGGCAGGAGAGTGTGTGGGCAGGGTTATTT A | 2719 |
| PDGFC.3 | 79 | AGTTACTAAAAAATACCACGAGGTCCTTCAGTTGAGACCAAAGACCGGTGTCAGGGGATTG CACAAATCACTCACCGAC | 2720 |
| PDGFD.2 | 74 | TATCGAGGCAGGTCATACCATGACCGGAAGTCAAAAGTTGACCTGGATAGGCTCAATGATG ATGCCAAGCGTTA | 2721 |
| PDGFRa.2 | 72 | GGGAGTTTCCAAGAGATGGACTAGTGCTTGGTCGGGTCTTGGGGTCTGGAGCGTTTGGGAA GGTGGTTGAAG | 2722 |

TABLE B-continued

| Gene | Target Sequence Length | Amplicon Sequence | SEQ ID NO. |
|---|---|---|---|
| PDGFRb.3 | 66 | CCAGCTCTCCTTCCAGCTACAGATCAATGTCCCTGTCCGAGTGCTGGAGCTAAGTGAGAGCCACCC | 2723 |
| PDZK1.1 | 75 | AATGACCTCCACCTTCAACCCCCGAGAATGTAAACTGTCCAAGCAAGAAGGGCAAAACTATGGCTTCTTCCTGCG | 2724 |
| PDZK3.1 | 68 | GAGCTGAGAGCCTTGAGCATGCCTGACCTTGACAAGCTCTGCAGCGAGGATTACTCAGCAGGGCCGAG | 2725 |
| PF4.1 | 73 | GCAGTGCCTGTGTGTGAAGACCACCTCCCAGGTCCGTCCCAGGCACATCACCAGCCTGGAGGTGATCAAGGCC | 2726 |
| PFKP.1 | 68 | AGCTGATGCCGCATACATTTTCGAAGAGCCCTTCGACATCAGGGATCTGCAGTCCAACGTGGAGCACC | 2727 |
| PFN2.1 | 82 | TCTATACGTCGATGGTGACTGCACAATGGACATCCGGACAAAGAGTCAAGGTGGGGAGCCAACATACAATGTGGCTGTCGGC | 2728 |
| PGF.1 | 71 | GTGGTTTTCCCTCGGAGCCCCCTGGCTCGGGACGTCTGAGAAGATGCCGGTCATGAGGCTGTTCCCTTGCT | 2729 |
| PI3K.2 | 98 | TGCTACCTGGACAGCCCGTTGGTGCGCTTCCTCCTGAAACGAGCTGTGTCTGACTTGAGAGTGACTCACTACTTCTTCTGGTTACTGAAGGACGGCCT | 2730 |
| PI3KC2A.1 | 83 | ATACCAATCACCGCACAAACCCAGGCTATTTGTTAAGTCCAGTCACAGCACAAAGAAACATATGCGGAGAAAATGCTAGTGTG | 2731 |
| PIK3CA.1 | 67 | GTGATTGAAGAGCATGCCAATTGGTCTGTATCCCGAGAAGCAGGATTTAGCTATTCCCACGCAGGAC | 2732 |
| PLA2G4C.1 | 68 | CCCTTTCCCCAAGTAGAAGAGGCTGAGCTGGATTTGTGGTCCAAGGCCCCCGCCAGCTGCTACATCCT | 2733 |
| PLAT.1 | 67 | GATTTGCTGGGAAGTGCTGTGAAATAGATACCAGGGCCACGTGCTACGAGGACCAGGGCATCAGCTA | 2734 |
| PLAUR.3 | 76 | CCCATGGATGCTCCTCTGAAGAGACTTTCCTCATTGACTGCCGAGGCCCCATGAATCAATGTCTGGTAGCCACCGG | 2735 |
| PLG.1 | 77 | GGCAAAATTTCCAAGACCATGTCTGGACTGGAATGCCAGGCCTGGGACTCTCAGAGCCCACACGCTCATGGATACAT | 2736 |
| PLN.1 | 84 | TGATGCTTCTCTGAAGTTCTGCTACAACCTCTAGATCTGCAGCTTGCCACATCAGCTTAAAATCTGTCATCCCATGCAGACAGG | 2737 |
| PLOD2.1 | 84 | CAGGGAGGTGGTTGCAAATTTCTAAGGTACAATTGCTCTATTGAGTCACCACGAAAAGGCTGGAGCTTCATGCATCCTGGGAGA | 2738 |
| PLP1.1 | 66 | AGAACAGACTGGCCTGAGGAGCAGCAGTTGCTGGTGGCTAATGGTGTAACCTGAGATGGCCCTCTG | 2739 |
| PMP22.1 | 66 | CCATCTACACGGTGAGGCACCCGGAGTGGCATCTCAACTCGGATTACTCCTACGGTTTCGCCTACA | 2740 |
| PPAP2B.1 | 77 | ACAAGCACCATCCCAGTGATGTTCTGGCAGGATTTGCTCAAGGAGCCCTGGTGGCCTGCTGCATAGTTTTCTTCGTG | 2741 |
| PPARG.3 | 72 | TGACTTTATGGAGCCCAAGTTTGAGTTTGCTGTGAAGTTCAATGCACTGGAATTAGATGACAGCGACTTGGC | 2742 |
| PPP1R3C.1 | 82 | TTCCTTCCCTCTCAATCCACTAGCTTTCATGTTGGGCAAGGAAAAGTTGAGGAAGGATGGCTGATGGTGATGGAAAGCTGTG | 2743 |
| PPP2CA.1 | 78 | GCAATCATGGAACTTGACGATACTCTAAAATACTCTTTCTTGCAGTTTGACCCAGCACCTCGTAGAGGCGAGCCACAT | 2744 |
| PRCC.1 | 67 | GAGGAAGAGGAGGCGGTGGCTCCTACATCTGGGCCCGCTTTAGGGGCTTGTTCGCTTCTCTCCCTG | 2745 |
| PRKCA.1 | 70 | CAAGCAATGCGTCATCAATGTCCCCAGCCTCTGCGGAATGGATCACACTGAGAAGAGGGGGCGGATTTAC | 2746 |
| PRKCB1.1 | 67 | GACCCAGCTCCACTCCTGCTTCCAGACCATGGACCGCCTGTACTTTGTGATGGAGTACGTGAATGGG | 2747 |

TABLE B-continued

| Gene | Target Sequence Length | Amplicon Sequence | SEQ ID NO. |
|---|---|---|---|
| PRKCD.2 | 68 | CTGACACTTGCCGCAGAGAATCCCTTTCTCACCCACCTCATCTGCACCTTCCAGACCAAGGACCACCT | 2748 |
| PRKCH.1 | 68 | CTCCACCTATGAGCGTCTGTCTCTGTGGGCTTGGGATGTTAACAGGAGCCAAAAGGAGGGAAAGTGTG | 2749 |
| PRO2000.3 | 79 | ATTGGAAAAACCTCGTCACCAGAGAAAGCCCAACATATTTTATAGTGGCCCAGCTTCTCCTGCAAGACCAAGATACCGA | 2750 |
| PROM1.1 | 74 | CTATGACAGGCATGCCACCCCGACCACCCGAGGCTGTGTCTCCAACACCGGAGGCGTCTTCCTCATGGTTGGAG | 2751 |
| PROM2.1 | 67 | CTTCAGCGCATCCACTACCCCGACTTCCTCGTTCAGATCCAGAGGCCCGTGGTGAAGACCAGCATGG | 2752 |
| PRPS2.1 | 69 | CACTGCACCAAGATTCAGGTCATTGACATTTCCATGATCTTGGCCGAAGCAATCCGAAGGACACACAAT | 2753 |
| PRSS8.1 | 68 | GTACACTCTGGCCTCCAGCTATGCCTCCTGGATCCAAAGCAAGGTGACAGAACTCCAGCCTCGTGTGG | 2754 |
| PSMA7.1 | 67 | GCCAAACTGCAGGATGAAAGAACAGTGCGGAAGATCTGTGCTTTGGATGACAACGTCTGCATGGCCT | 2755 |
| PSMB8.1 | 66 | CAGTGGCTATCGGCCTAATCTTAGCCCTGAAGAGGCCTATGACCTTGGCCGCAGGGCTATTGCTTA | 2756 |
| PSMB9.1 | 66 | GGGGTGTCATCTACCTGGTCACTATTACAGCTGCCGGTGTGGACCATCGAGTCATCTTGGGCAATG | 2757 |
| PTEN.2 | 81 | TGGCTAAGTGAAGATGACAATCATGTTGCAGCAATTCACTGTAAAGCTGGAAAGGGACGAACTGGTGTAATGATATGTGCA | 2758 |
| PTGIS.1 | 66 | CCACACTGGCATCTCCCTGACCTTCTCCAGGGACAGAAGCAGGAGTAAGTTTCTCATCCCATGGGC | 2759 |
| PTHR1.1 | 73 | CGAGGTACAAGCTGAGATCAAGAAATCTTGGAGCCGCTGGACACTGGCACTGGACTTCAAGCGAAAGGCACGC | 2760 |
| PTK2.1 | 68 | GACCGGTCGAATGATAAGGTGTACGAGAATGTGACGGGCCTGGTGAAAGCTGTCATCGAGATGTCCAG | 2761 |
| PTK2B.1 | 74 | CAAGCCCAGCCGACCTAAGTACAGACCCCCTCCGCAAACCAACCTCCTGGCTCCAAAGCTGCAGTTCCAGGTTC | 2762 |
| PTN.1 | 67 | CCTTCCAGTCCAAAAATCCCGCCAAGAGAGCCCCAGAGCAGAGGAAAATCCAAAGTGGAGAGAGGGG | 2763 |
| PTPNS1.1 | 77 | CTCCAGCTAGCACTAAGCAACATCTCGCTGTGGACGCCTGTAAATTACTGAGAAATGTGAAACGTGCAATCTTGAAA | 2764 |
| PTPRB.1 | 68 | GATATGCGGTGAGGAACAGCTTGATGCACACAGACTCATCCGCCACTTTCACTATACGGTGTGGCCAG | 2765 |
| PTPRC.1 | 74 | TGGCCGTCAATGGAAGAGGGCACTCGGGCTTTTGGAGATGTTGTTGTAAAGATCAACCAGCACAAAAGATGTCC | 2766 |
| PTPRG.1 | 71 | GGACAGCGACAAAGACTTGAAAGCCACCATTAGCCATGTCTCACCCGATAGCCTTTACCTGTTCCGAGTCC | 2767 |
| PTTG1.2 | 74 | GGCTACTCTGATCTATGTTGATAAGGAAAATGGAGAACCAGGCACCCGTGTGGTTGCTAAGGATGGGCTGAAGC | 2768 |
| PVALB.1 | 81 | AAACCAAGATGCTGATGGCTGCTGGAGACAAAGATGGGGACGGCAAAATTGGGGTTGACGAATTCTCCACTCTGGTGGCTG | 2769 |
| PXDN.1 | 67 | GCTGCTCAAGCTGAACCCGCACTGGGACGGCGACACCATCTACTATGAGACCAGGAAGATCGTGGGT | 2770 |
| RAC1.3 | 66 | TGTTGTAAATGTCTCAGCCCCTCGTTCTTGGTCCTGTCCCTTGGAACCTTTGTACGCTTTGCTCAA | 2771 |
| RAD51.1 | 66 | AGACTACTCGGGTCGAGGTGAGCTTTCAGCCAGGCAGATGCACTTGGCCAGGTTTCTGCGGATGCT | 2772 |

TABLE B-continued

| Gene | Target Sequence Length | Amplicon Sequence | SEQ ID NO. |
|---|---|---|---|
| RAF1.3 | 73 | CGTCGTATGCGAGAGTCTGTTTCCAGGATGCCTGTTAGTTCTCAGCACAGATATTCTACACCTCACGCCTTCA | 2773 |
| RALBP1.1 | 84 | GGTGTCAGATATAAATGTGCAAATGCCTTCTTGCTGTCCTGTCGGTCTCAGTACGTTCACTTTATAGCTGCTGGCAATATCGAA | 2774 |
| RARB.2 | 78 | TGCCTGGACATCCTGATTCTTAGAATTTGCACCAGGTATACCCCAGAACAAGACACCATGACTTTCTCAGACGGCCTT | 2775 |
| RASSF1.1 | 75 | AGGGCACGTGAAGTCATTGAGGCCCTGCTGCGAAAGTTCTTGGTGGTGGATGACCCCCGCAAGTTTGCACTCTTT | 2776 |
| RB1.1 | 77 | CGAAGCCCTTACAAGTTTCCTAGTTCACCCTTACGGATTCCTGGAGGGAACATCTATATTTCACCCCTGAAGAGTCC | 2777 |
| RBM35A.1 | 66 | TGGTTTTGAATCACCAGGGCCGCCCATCAGGAGATGCCTTTATCCAGATGAAGTCTGCGGACAGAG | 2778 |
| REG4.1 | 83 | TGCTAACTCCTGCACAGCCCCGTCCTCTTCCTTTCTGCTAGCCTGGCTAAATCTGCTCATTATTTCAGAGGGGAAACCTAGCA | 2779 |
| RET.1 | 71 | GCCTGTGCAGTTCTTGTGCCCCAACATCAGCGTGGCCTACAGGCTCCTGGAGGGTGAGGGTCTGCCCTTCC | 2780 |
| RGS1.1 | 84 | TGCCCTGTAAAGCAGAAGAGATATATAAAGCATTTGTGCATTCAGATGCTGCTAAACAAATCAATATTGACTTCCGCACTCGAG | 2781 |
| RGS5.1 | 79 | TTCAAACGGAGGCTCCTAAAGAGGTGAATATTGACCACTTCACTAAGGACATCACAATGAAGAACCTGGTGGAACCTTC | 2782 |
| RHEB.2 | 78 | GATGATTGAGAACAGCCTTGCCTGTCACTGTCCTAGAACACCCTGGAGTTTAGTGTTCTGTGTCAGAGTCTTGGGAGC | 2783 |
| RhoB.1 | 67 | AAGCATGAACAGGACTTGACCATCTTTCCAACCCCTGGGGAAGACATTTGCAACTGACTTGGGGAGG | 2784 |
| rhoC.1 | 68 | CCCGTTCGGTCTGAGGAAGGCCGGGACATGGCGAACCGGATCAGTGCCTTTGGCTACCTTGAGTGCTC | 2785 |
| RIPK1.1 | 67 | AGTACCTTCAAGCCGGTCAAATTCAGCCACAGAACAGCCTGGTTCACTGCACAGTTCCCAGGGACTT | 2786 |
| RND3.1 | 66 | TCGGAATTGGACTTGGGAGGCGCGGTGAGGAGTCAGGCTTAAAACTTGTTGGAGGGGAGTAACCAG | 2787 |
| ROCK1.1 | 73 | TGTGCACATAGGAATGAGCTTCAGATGCAGTTGGCCAGCAAAGAGAGTGATATTGAGCAATTGCGTGCTAAAC | 2788 |
| ROCK2.1 | 66 | GATCCGAGACCCTCGCTCCCCATCAACGTGGAGAGCTTGCTGGATGGCTTAAATTCCTTGGTCCT | 2789 |
| RPLP1.1 | 68 | CAAGGTGCTCGGTCCTTCCGAGGAAGCTAAGGCTGCGTTGGGGTGAGGCCCTCACTTCATCCGGCGAC | 2790 |
| RPS23.1 | 67 | GTTCTGGTTGCTGGATTTGGTCGCAAAGGTCATGCTGTTGGTGATATTCCTGGAGTCCGCTTTAAGG | 2791 |
| RPS27A.1 | 74 | CTTACGGGGAAGACCATCACCCTCGAGGTTGAACCCTCGGATACGATAGAAAATGTAAAGGCCAAGATCCAGGA | 2792 |
| RPS6KAI.1 | 70 | GCTCATGGAGCTAGTGCCTCTGGACCCGGAGAATGGACAGACCTCAGGGGAAGAAGCTGGACTTCAGCCG | 2793 |
| RPS6KB1.3 | 81 | GCTCATTATGAAAAACATCCCAAACTTTAAAATGCGAAATTATTGGTTGGTGTGAAGAAAGCCAGACAACTTCTGTTTCTT | 2794 |
| RRM1.2 | 66 | GGGCTACTGGCAGCTACATTGCTGGGACTAATGGCAATTCCAATGGCCTTGTACCGATGCTGAGAG | 2795 |
| RRM2.1 | 71 | CAGCGGGATTAAACAGTCCTTTAACCAGCACAGCCAGTTAAAAGATGCAGCCTCACTGCTTCAACGCAGAT | 2796 |
| RUNX1.1 | 70 | AACAGAGACATTGCCAACCATATTGGATCTGCTTGCTGTCCAAACCAGCAAACTTTCCTGGGCAAATCAC | 2797 |

TABLE B-continued

| Gene | Target Sequence Length | Amplicon Sequence | SEQ ID NO. |
|---|---|---|---|
| S100A1.1 | 70 | TGGACAAGGTGATGAAGGAGCTAGACGAGAATGGAGACGGGGAGGTGGACTTCCAGGAGTATGTGGTGCT | 2798 |
| S100A10.1 | 77 | ACACCAAAATGCCATCTCAAATGGAACACGCCATGGAAACCATGATGTTTACATTTCACAAATTCGCTGGGGATAAA | 2799 |
| S100A2.1 | 73 | TGGCTGTGCTGGTCACTACCTTCCACAAGTACTCCTGCCAAGAGGGCGACAAGTTCAAGCTGAGTAAGGGGGA | 2800 |
| SAA2.2 | 72 | CTACAGCACAGATCAGCACCATGAAGCTTCTCACGGGCCTGGTTTTCTGCTCCTTGGTCCTGAGTGTCAGCA | 2801 |
| SCN4B.1 | 67 | GCCTTCCTGGAGTACCCGAGTGCTCCCTATGCCTTTCCAAGCATTTCTACTTGGGGAATTGGGCCCAC | 2802 |
| SCNN1A.2 | 66 | ATCAACATCCTGTCGAGGCTGCCAGAGACTCTGCCATCCCTGGAGGAGGACACGCTGGGCAACTTC | 2803 |
| SDHA.1 | 67 | GCAGAACTGAAGATGGGAAGATTTATCAGCGTGCATTTGGTGGACAGAGCCTCAAGTTTGGAAAGGG | 2804 |
| SDPR.1 | 66 | ACCAGCACAAGATGGAGCAGCGACAGATCAGTTTGGAGGGCTCCGTGAAGGGCATCCAGAATGACC | 2805 |
| SELE.1 | 71 | ACACTGGTCTGGCCTGCTACCTACCTGTGAAGCTCCCACTGAGTCCAACATTCCCTTGGTAGCTGGACTTT | 2806 |
| SELENBP1.1 | 67 | GGTACCAGCCTCGACACAATGTCATGATCAGCACTGAGTGGGCAGCTCCCAATGTCTTACGAGATGG | 2807 |
| SELL.1 | 67 | TGCAACTGTGATGTGGGGTACTATGGGCCCCAGTGTCAGTTTGTGATTCAGTGTGAGCCTTTGGAGG | 2808 |
| SELPLG.1 | 83 | TGGCCACTATCTTCTTCGTGTGCACTGTGGTGCTGGCGGTCCGCCTCTCCCGCAAGGGCCACATGTACCCCGTGCGTAATTAC | 2809 |
| SEMA3B.1 | 71 | GCTCCAGGATGTGTTTCTGTTGTCCTCGCGGGACCACCGGACCCCGCTGCTCTATGCCGTCTTCTCCACGT | 2810 |
| SEMA3C.1 | 66 | ATGGCCATTCCTGTTCCAGATTCTACCCAACTGGGAAACGGAGGAGCCGAAGACAAGATGTGAGAC | 2811 |
| SEMA3F.3 | 86 | CGCGAGCCCCTCATTATACACTGGGCAGCCTCCCCACAGCGCATCGAGGAATGCGTGCTCTCAGGCAAGGATGTCAACGGCGAGTG | 2812 |
| SEMA5B.1 | 67 | CTCGAGGACAGCTCCAACATGAGCCTCTGGACCCAGAACATCACCGCCTGTCCTGTGCGGAATGTGA | 2813 |
| SERPINA5.1 | 66 | CAGCATGGTAGTGGCAAAGAGAGGTCCAGAGTCCTGGCCCTTGATGCCCAGCTCAGTGCCACAAAG | 2814 |
| SFN.1 | 70 | GAGAGAGCCAGTCTGATCCAGAAGGCCAAGCTGGCAGAGCAGGCCGAACGCTATGAGGACATGGCAGCCT | 2815 |
| SGK.1 | 73 | TCCGCAAGACACCTCCTGGAGGGCCTCCTGCAGAAGGACAGGACAAAGCGGCTCGGGGCCAAGGATGACTTCA | 2816 |
| SHANK3.1 | 68 | CTGTGCCCTCTACAACCAGGAGAGCTGTGCTCGTGTCCTGCTCTTCCGTGGAGCTAACAGGGATGTCC | 2817 |
| SHC1.1 | 71 | CCAACACCTTCTTGGCTTCTGGGACCTGTGTTCTTGCTGAGCACCCTCTCCGGTTTGGGTTGGGATAACAG | 2818 |
| SILV.1 | 66 | CCGCATCTTCTGCTCTTGTCCCATTGGTGAGAATAGCCCCCTCCTCAGTGGGCAGCAGGTCTGAGT | 2819 |
| SKIL.1 | 66 | AGAGGCTGAATATGCAGGACAGTTGGCAGAACTGAGGCAGAGATTGGACCATGCTGAGGCCGATAG | 2820 |
| SLC13A3.1 | 66 | CTTGCCCTCCAACAAGGTCTGCCCCCAGTACTTCCTCGACACCAACTTCCTCTTCCTCAGTGGGCT | 2821 |
| SLC16A3.1 | 68 | ATGCGACCCACGTCTACATGTACGTGTTCATCCTGGCGGGGGCCGAGGTGCTCACCTCCTCCCTGATT | 2822 |

TABLE B-continued

| Gene | Target Sequence Length | Amplicon Sequence | SEQ ID NO. |
|---|---|---|---|
| SLC22A3.1 | 66 | ATCGTCAGCGAGTTTGACCTTGTCTGTGTCAATGCGTGGATGCTGGACCTCACCCAAGCCATCCTG | 2823 |
| SLCC22A6.1 | 68 | TCCGCCACCTCTTCCTCTGCCTCTCCATGCTGTGGTTTGCCACTAGCTTTGCATACTATGGGCTGGTC | 2824 |
| SLC2A1.1 | 67 | GCCTGAGTCTCCTGTGCCCACATCCCAGGCTTCACCCTGAATGGTTCCATGCCTGAGGGTGGAGACT | 2825 |
| SLC23A1.1 | 66 | GCTGAGACCCACTGACCTGCAGACCTCATAGTGGGTGCCCAGGATGTTGTCCTACGGAGAGAGGCT | 2826 |
| SLC7A5.2 | 70 | GCGCAGAGGCCAGTTAAAGTAGATCACCTCCTCGAACCCACTCCGGTTCCCCGCAACCCACAGCTCAGCT | 2827 |
| SLC9A1.1 | 67 | CTTCGAGATCTCCCTCTGGATCCTTCTGGCCTGCCTCATGAAGATAGGTTTCCATGTGATCCCCACT | 2828 |
| SLIT2.2 | 67 | TTTACCGATGCACCTGTCCATATGGTTTCAAGGGGCAGGACTGTGATGTCCCAATTCATGCTGCAT | 2829 |
| SNAI1.1 | 69 | CCCAATCGGAAGCCTAACTACAGCGAGCTGCAGGACTCTAATCCAGAGTTTACCTTCCAGCAGCCCTAC | 2830 |
| SNRK.1 | 71 | GAGGAAAAGTCAGGGCCGGGGCTCCAGCTGCAGTAGTTCGGAGACCAGTGATGATGATTCTGAAAGCCGGC | 2831 |
| SOD1.1 | 70 | TGAAGAGAGGCATGTTGGAGACTTGGGCAATGTGACTGCTGACAAAGATGGTGTGGCCGATGTGTCTATT | 2832 |
| SP3.1 | 69 | TCAAGAGTCTCAGCAGCCAACCAGTCAAGCCCAAATTGTGCAAGGTATTACACCACAGACAATCCATGG | 2833 |
| SPARC.1 | 73 | TCTTCCCTGTACACTGGCAGTTCGGCCAGCTGGACCAGCACCCCATTGACGGGTACCTCTCCCACACCGAGCT | 2834 |
| SPARCL1.1 | 67 | GGCACAGTGCAAGTGATGACTACTTCATCCCAAGCCAGGCCTTTCTGGAGGCCGAGAGAGCTCAATC | 2835 |
| SPAST.1 | 66 | CCTGAGTTGTTCACAGGGCTTAGAGCTCCTGCCAGAGGGCTGTTACTCTTTGGTCCACCTGGGAAT | 2836 |
| SPHK1.1 | 67 | GGCAGCTTCCTTGAACCATTATGCTGGCTATGAGCAGGTCACCAATGAAGACCTCCTGACCAACTGC | 2837 |
| SPRY1.1 | 77 | CAGACCAGTCCCTGGTCATAGGTCTGAAAGGGCAATCCGGACCCAGCCCAAGCAACTGATTGTGGATGACTTGAAGG | 2838 |
| SQSTM1.1 | 69 | GGACCCGTCTACAGGTGAACTCCAGTCCCTACAGATGCCAGAATCCGAAGGGCCAAGCTCTCTGGACCC | 2839 |
| STAT1.3 | 81 | GGGCTCAGCTTTCAGAAGTGCTGAGTTGGCAGTTTTCTTCTGTCACCAAAAGAGGTCTCAATGTGGACCAGCTGAACATGT | 2840 |
| STAT3.1 | 70 | TCACATGCCACTTTGGTGTTTCATAATCTCCTGGGAGAGATTGACCAGCAGTATAGCCGCTTCCTGCAAG | 2841 |
| STAT5A.1 | 77 | GAGGCGCTCAACATGAAATTCAAGGCCGAAGTGCAGAGCAACCGGGGCCTGACCAAGGAGAACCTCGTGTTCCTGGC | 2842 |
| STAT5B.2 | 74 | CCAGTGGTGGTGATCGTTCATGGCAGCCAGGACAACAATGCGACGGCCACTGTTCTCTGGGACAATGCTTTTGC | 2843 |
| STC2.1 | 67 | AAGGAGGCCATCACCCACAGCGTGCAGGTTCAGTGTGAGCAGAACTGGGGAAGCCTGTGCTCCATCT | 2844 |
| STK11.1 | 66 | GGACTCGGAGACGCTGTGCAGGAGGGCCGTCAAGATCCTCAAGAAGAAGAAGTTGCGAAGGATCCC | 2845 |
| STK15.2 | 69 | CATCTTCCAGGAGGACCACTCTCTGTGGCACCCTGGACTACCTGCCCCCTGAAATGATTGAAGGTCGGA | 2846 |
| STK4.1 | 66 | GAGCCATCTTCCTGCAACTTTACCTCTTTCCCTCAGATGGGGAGCCATGACTGGGTTGCACCTCAG | 2847 |

TABLE B-continued

| Gene | Target Sequence Length | Amplicon Sequence | SEQ ID NO. |
|---|---|---|---|
| STMY3.3 | 90 | CCTGGAGGCTGCAACATACCTCAATCCTGTCCCAGGCCGGATCCTCCTGAAGCCCTTTTCG CAGCACTGCTATCCTCCAAAGCCATTGTA | 2848 |
| SUYCLG1.1 | 66 | CCAAGCCTGTAGTGTCCTTCATTGCTGGTTTAACTGCTCCTCCTGGGAGAAGAATGGGTCA TGCCG | 2849 |
| SULT1C2.1 | 67 | GGGACCCAAAGCATGAAATTCGGAAGGTGATGCAGTTCATGGGAAAGAAGGTGGATGAAAC AGTGCT | 2850 |
| SURV.2 | 80 | TGTTTTGATTCCCGGGCTTACCAGGTGAGAAGTGAGGGAGGAAGAAGGCAGTGTCCCTTTT GCTAGAGCTGACAGCTTTG | 2851 |
| TACSTD2.1 | 80 | ATCACCAACCGGAGAAAGTCGGGGAAGTACAAGAAGGTGGAGATCAAGGAACTGGGGGAGT TGAGAAAGGAACCGAGCTT | 2852 |
| TAGLN.1 | 73 | GATGGAGCAGGTGGCTCAGTTCCTGAAGGCGGCTGAGGACTATGGGGTCATCAAGACTGAC ATGTTCCAGACT | 2853 |
| TAP1.1 | 72 | GTATGCTGCTGAAAGTGGGAATCCTCTACATTGGTGGGCAGCTGGTGACCAGTGGGCTGT AAGCAGTGGGA | 2854 |
| TCF4.1 | 67 | CACACCCTGGAATGGGAGACGCATCGAATCACATGGGACAGATGTAAAAGGGTCCAAGTTG CCACAT | 2855 |
| TCOF1.2 | 66 | AGCGAGGATGAGGACGTGATCCCCGCTACACAGTGCTTGACTCCTGGCATCAGAACCAATG TGGTG | 2856 |
| TEK.1 | 76 | ACTTCGGTGCTACTTAACAACTTACATCCCAGGGAGCAGTACGTGGTCCGAGCTAGAGTCA ACACCAAGGCCCAGG | 2857 |
| TERT.1 | 85 | GACATGGAGAACAAGCTGTTTGCGGGGATTCGGCGGGACGGGCTGCTCCTGCGTTTGGTGG ATGATTTCTTGTTGGTGACACCTC | 2858 |
| TFAP2B.1 | 67 | CGTGTGACGTGCGAGAGACGCGATGGACGCGCCTTGCTCTTACTGTGCAGGTCCTGAGAGC GTGTGG | 2859 |
| TFAP2C.1 | 68 | CATGCCTCACCAGATGGACGAGGTGCAGAATGTCGACGACCAGCACCTGTTGCTGCACGAT CAGACAG | 2860 |
| TFPI.1 | 69 | CCGAATGGTTTCCAGGTGGATAATTATGGAACCCAGCTCAATGCTGTGAATAACTCCCTGA CTCCGCAA | 2861 |
| TGFA.2 | 83 | GGTGTGCCACAGACCTTCCTACTTGGCCTGTAATCACCTGTGCAGCCTTTTGTGGGCCTTC AAAACTCTGTCAAGAACTCCGT | 2862 |
| TGFb1.1 | 80 | CTGTATTTAAGGACACCCGTGCCCCAAGCCCACCTGGGGCCCCATTAAAGATGGAGAGAGG ACTGCGGATCTCTGTGTCA | 2863 |
| TGFB2.2 | 75 | ACCAGTCCCCCAGAAGACTATCCTGAGCCCGAGGAAGTCCCCCCGGAGGTGATTTCCATCT ACAACAGCACCAGG | 2864 |
| TGFBI.1 | 67 | GCTACGAGTGCTGTCCTGGATATGAAAAGGTCCCTGGGGAGAAGGGCTGTCCAGCAGCCCT ACCACT | 2865 |
| TGFBR1.1 | 67 | GTCATCACCTGGCCTTGGTCCTGTGGAACTGGCAGCTGTCATTGCTGGACCAGTGTGCTTC GTCTGC | 2866 |
| TGFBR2.3 | 66 | AACACCAATGGGTTCCATCTTTCTGGGCTCCTGATTGCTCAAGCACAGTTTGGCCTGATGA AGAGG | 2867 |
| THBD.1 | 68 | AGATCTGCGACGGACTGCGGGGCCACCTAATGACAGTGCGCTCCTCGGTGGCTGCCGATGT CATTTCC | 2868 |
| THBS1.1 | 85 | CATCCGCAAAGTGACTGAAGAGAACAAAGAGTTGGCCAATGAGCTGAGGCGGCCTCCCCTA TGCTATCACAACGGAGTTCAGTAC | 2869 |
| TIMP1.1 | 76 | TCCCTGCGGTCCCAGATAGCCTGAATCCTGCCCGGAGTGGAAGCTGAAGCCTGCACAGTGT CCACCCTGTTCCCAC | 2870 |
| TIMP2.1 | 69 | TCACCCTCTGTGACTTCATCGTGCCCTGGGACACCCTGAGCACCACCCAGAAGAAGAGCCT GAACCACA | 2871 |
| TIMP3.3 | 67 | CTACCTGCCTTGCTTTGTGACTTCCAAGAACGAGTGTCTCTGGACCGACATGCTCTCCAAT TTCGGT | 2872 |

TABLE B-continued

| Gene | Target Sequence Length | Amplicon Sequence | SEQ ID NO. |
|---|---|---|---|
| TK1.2 | 84 | GCCGGGAAGACCGTAATTGTGGCTGCACTGGATGGGACCTTCCAGAGGAAGCCATTTGGGG CCATCCTGAACCTGGTGCCGCTG | 2873 |
| TLR3.1 | 71 | GGTTGGGCCACCTAGAAGTACTTGACCTGGGCCTTAATGAAATTGGGCAAGAACTCACAGG CCAGGAATGG | 2874 |
| TMEM27.1 | 75 | CCCTGAAAGAATGTTGTGGCTGCTCTTTTTTCTGGTGACTGCCATTCATGCTGAACTCTGT CAACCAGGTGCAGA | 2875 |
| TMEM47.1 | 71 | GGATTCCACTGTTAGAGCCCTTACCGCCTGCTTATCCTACCCAATGACTACATTGGCTGTT GGTTATTTGC | 2876 |
| TMSB10.1 | 68 | GAAATCGCCAGCTTCGATAAGGCCAAGCTGAAGAAAACGGAGACGCAGGAGAAGAACACCC TGCCGAC | 2877 |
| TNF.1 | 69 | GGAGAAGGGTGACCGACTCAGCGCTGAGATCAATCGGCCCGACTATCTCGACTTTGCCGAG TCTGGGCA | 2878 |
| TNFAIP3.1 | 68 | ATCGTCTTGGCTGAGAAAGGGAAAAGACACACAAGTCGCGTGGGTTGGAGAAGCCAGAGCC ATTCCAC | 2879 |
| TNFAIP6.1 | 67 | AGGAGTGAAAGATGGGATGCCTATTGCTACAACCCACACGCAAAGGAGTGTGGTGGCGTCT TTACAG | 2880 |
| TNFRSF10C.3 | 67 | GGAGTTTGACCAGAGATGCAAGGGGTGAAGGAGCGCTTCCTACCGTTAGGGAACTCTGGGG ACAGAG | 2881 |
| TNFRSF10D.1 | 66 | CCTCTCGCTTCTGGTGGTCTGTGAACTGAGTCCCTGGGATGCCTTTTAGGGCAGAGATTCC TGAGC | 2882 |
| TNFRSF11B.1 | 67 | TGGCGACCAAGACACCTTGAAGGGCCTAATGCACGCACTAAAGCACTCAAAGACGTACCAC TTTCCC | 2883 |
| TNFRSF1A.1 | 71 | ACTGCCCTGAGCCCAAATGGGGAGTGAGAGGCCATAGCTGTCTGGCATGGGCCTCTCCAC CGTGCCTGAC | 2884 |
| TNFSF12.1 | 68 | TAGGCCAGGAGTTCCCAAATGTGAGGGGCGAGAAACAAGACAAGCTCCTCCCTTGAGAATT CCCTGTG | 2885 |
| TNFSF13B.1 | 80 | CCTACGCCATGGGACATCTAATTCAGAGGAAGAAGGTCCATGTCTTTGGGGATGAATTGAG TCTGGTGACTTTGTTTCGA | 2886 |
| TNFSF7.1 | 67 | CCAACCTCACTGGGACACTTTTGCCTTCCCGAAACACTGATGAGACCTTCTTTGGAGTGCA GTGGGT | 2887 |
| TNIP2.1 | 66 | CATGTCAGAAAGGGCCGATCGGGAACGGGCTCAAAGTAGGATTCAAGAACTGGAGGAAAAG GTCGC | 2888 |
| TOP2A.4 | 72 | AATCCAAGGGGGAGAGTGATGACTTCCATATGGACTTTGACTCAGCTGTGGCTCCTCGGGC AAAATCTGTAC | 2889 |
| TOP2B.2 | 66 | TGTGGACATCTTCCCCTCAGACTTCCCTACTGAGCCACCTTCTCTGCCACGAACCGGTCGG GCTAG | 2890 |
| TP.3 | 82 | CTATATGCAGCCAGAGATGTGACAGCCACCGTGGACAGCCTGCCACTCATCACAGCCTCCA TTCTCAGTAAGAAACTCGTGG | 2891 |
| TRAIL.1 | 73 | CTTCACAGTGCTCCTGCAGTCTCTCTGTGTGGCTGTAACTTACGTGTACTTTACCAACGAG CTGAAGCAGATG | 2892 |
| TS.1 | 65 | GCCTCGGTGTGCCTTTCAACATCGCCAGCTACGCCCTGCTCACGTACATGATTGCGCACAT CACG | 2893 |
| TSC1.1 | 66 | TCACCAAATCTCAGCCCGCTTTCCTCATCGTTCAGCCGATGTCACCACCAGCCCTTATGCT GACAC | 2894 |
| TSC2.1 | 69 | CACAGTGGCCTCTTTCTCCTCCCTGTACCAGTCCAGCTGCCAAGGACAGCTGCACAGGAGC GTTTCCTG | 2895 |
| TSPAN7.2 | 67 | ATCACTGGGGTGATCCTGCTGGCTGTTGGAGTCTGGGGCAAACTTACTCTGGGCACCTATA TCTCCC | 2896 |
| TSPAN8.1 | 83 | CAGAAATCTCTGCAGGCAAGTTGCTCCAGAGCATATTGCAGGACAAGCCTGTAACGAATAG TTAAATTCACGGCATCTGGATT | 2897 |

TABLE B-continued

| Gene | Target Sequence Length | Amplicon Sequence | SEQ ID NO. |
|---|---|---|---|
| TUBB.1 | 73 | CGAGGACGAGGCTTAAAAACTTCTCAGATCAATCGTGCATCCTTAGTGAACTTCTGTTGTCCTCAAGCATGGT | 2898 |
| TUSC2.1 | 68 | CACCAAGAACGGGCAGAAGCGGGCCAAGCTGAGGCGAGTGCATAAGAATCTGATTCCTCAGGGCATCG | 2899 |
| tusc4.2 | 68 | GGAGGAGCTAAATGCCTCAGGCCGGTGCACTCTGCCCATTGATGAGTCCAACACCATCCACTTGAAGG | 2900 |
| TXLNA.1 | 68 | GCCAGAACGGCTCAGTCTGGGGCCCTTCGTGATGTCTCTGAGGAGCTGAGCCGCCAACTGGAAGACAT | 2901 |
| UBB.1 | 522 | GAGTCGACCCTGCACCTGGTCCTGCGTCTGAGAGGTGGTATGCAGATCTTCGTGAAGACCCTGACCGGCAAGACCATCACCCTGGAAGTGGAGCCCAGTGACACCATCGAAAATGTGAAGGCCAAGATCCAGGATAAAGAAGGCATCCCTCCCGACCAGCAGAGGCTCATCTTTGCAGGCAAGCAGCTGGAAGATGGCCGCACTCTTTCTGACTACAACATCCAGAAGGAGTCGACCCTGCACCTGGTCCTGCGTCTGAGAGGTGGTATGCAGATCTTCGTGAAGACCCTGACCGGCAAGACCATCACTCTGGAAGTGGAGCCCAGTGACACCATCGAAAATGTGAAGGCCAAGATCCAAGATAAAGAAGGCATCCCTCCCGACCAGCAGAGGCTCATCTTTGCAGGCAAGCAGCTGGAAGATGGCCGCACTCTTTCTGACTACAACATCCAGAAGGAGTCGACCCTGCACCTGGTCCTGCGCCTGAGGGGTGGCTGTTAATTCTTCAGTCATGGCATTCGC | 2902 |
| UBE1C.1 | 76 | GAATGCACGCTGGAACTTTATCCACCACAGGTTAATTTTCCCATGTGCACCATTGCATCTATGCCCAGGCTACCAG | 2903 |
| UBE2C.1 | 67 | TGTCTGGCGATAAAGGGATTTCTGCCTTCCCTGAATCAGACAACCTTTTCAAATGGGTAGGGACCAT | 2904 |
| UBE2T.1 | 67 | TGTTCTCAAATTGCCACCAAAAGGTGCTTGGAGACCATCCCTCAACATCGCAACTGTGTTGACCTCT | 2905 |
| UGCG.1 | 73 | GGCAACTGACAAACAGCCTTATAGCAAGCTCCCAGGTGTCTCTCTTCTGAAACCACTGAAAGGGGTAGATCCT | 2906 |
| UMOD.1 | 66 | GCGTGGACCTGGATGAGTGCGCCATTCCTGGAGCTCACAACTGCTCCGCCAACAGCAGCTGCGTAA | 2907 |
| upa.3 | 70 | GTGGATGTGCCCTGAAGGACAAGCCAGGCGTCTACACGAGAGTCTCACACTTCTTACCCTGGATCCGCAG | 2908 |
| USP34.1 | 70 | AAGCTGTGATGGCCAAGCTTTGCCCTCCCAGGACCCTGAGGTTGCTTTATCTCTCAGTTGTGGCCATTCC | 2909 |
| VCAM1.1 | 89 | TGGCTTCAGGAGCTGAATACCCTCCCAGGCACACACAGGTGGGACACAAATAAGGGTTTTGGAACCACTATTTTCTCATCACGACAGCA | 2910 |
| VCAN.1 | 69 | CCTGCTACACAGCCAACAAGACCACCCACTGTGGAAGACAAAGAGGCCTTTGGACCTCAGGCGCTTTCT | 2911 |
| VDR.2 | 67 | GCCCTGGATTTCAGAAAGAGCCAAGTCTGGATCTGGGACCCTTTCCTTCCTTCCCTGGCTTGTAACT | 2912 |
| VEGF.1 | 71 | CTGCTGTCTTGGGTGCATTGGAGCCTTGCCTTGCTGCTCTACCTCCACCATGCCAAGTGGTCCCAGGCTGC | 2913 |
| BEGFB.1 | 71 | TGACGATGGCCTGGAGTGTGTGCCCACTGGGCAGCACCAAGTCCGGATGCAGATCCTCATGATCCGGTACC | 2914 |
| VHL.1 | 67 | CGGTTGGTGACTTGTCTGCCTCCTGCTTTGGGAAGACTGAGGCATCCGTGAGGCAGGGACAAGTCTT | 2915 |
| VIM.3 | 72 | TGCCCTTAAAGGAACCAATGAGTCCCTGGAACGCCAGATGCGTGAAATGGAAGAGAACTTTGCCGTTGAAGC | 2916 |
| VTCN1.1 | 70 | ACAGTGGTCTGGGCATCCCAAGTTGACCAGGGAGCCAACTTCTCGGAAGTCTCCAATACCAGCTTTGAGC | 2917 |
| VTN.1 | 67 | AGTCAATCTTCGCACACGGCGAGTGGACACTGTGGACCCTCCCTACCCACGCTCCATCGCTCAGTAC | 2918 |
| VWF.1 | 66 | TGAAGCACAGTGCCCTCTCCGTCGAGCTGCACAGTGACATGGAGGTGACGGTGAATGGGAGACTGG | 2919 |
| WIF.1 | 67 | AACAAGCTGAGTGCCCAGGCGGGTGCCGAAATGGAGGCTTTTGTAATGAAAGACGCATCTGCGAGTG | 2920 |

TABLE B-continued

| Gene | Target Sequence Length | Amplicon Sequence | SEQ ID NO. |
|---|---|---|---|
| WISP1.1 | 75 | AGAGGCATCCATGAACTTCACACTTGCGGGCTGCATCAGCACACGCTCCTATCAACCCAAGTACTGTGGAGTTTG | 2921 |
| WT1.1 | 66 | TGTACGGTCGGCATCTGAGACCAGTGAGAAACGCCCCTTCATGTGTGCTTACCCAGGCTGCAATAA | 2922 |
| WWOX.5 | 74 | ATCGCAGCTGGTGGGTGTACACACTGCTGTTTACCTTGGCGAGGCCTTTCACCAAGTCCATGCAACAGGGAGCT | 2923 |
| XDH.1 | 66 | TGGTGGCAGACATCCCTTCCTGGCCAGATACAAGGTTGGCTTCATGAAGACTGGGACAGTTGTGGC | 2924 |
| XIAP.1 | 77 | GCAGTTGGAAGACACAGGAAAGTATCCCCAAATTGCAGATTTATCAACGGCTTTTATCTTGAAAATAGTGCCACGCA | 2925 |
| SPNPEP2.2 | 72 | CACCCTGCACTGAACATACCCCAAGAGCCCCTGCTGGCCCATTGCCTAGAAACCTTTGCATTCATCCTCCTT | 2926 |
| YB-1.2 | 76 | AGACTGTGGAGTTTGATGTTGTTGAAGGAGAAAAGGGTGCGGAGGCAGCAAATGTTACAGGTCCTGGTGGTGTTCC | 2927 |
| ZHX2.1 | 67 | GAGTACGACCAGTTAGCGGCCAAGACTGGCCTGGTCCGAACTGAGATTGTGCGTTGGTTCAAGGAGA | 2928 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09551034B2). An electronic copy of the "Sequence Listing" will also be available from the USPTO upon request and payment of the fee set forth in 37 CFR 1.19(b)(3).

What is claimed is:

1. A method for determining a likelihood of recurrence of renal cell carcinoma for a human patient comprising:
   (a) measuring, in a renal cell carcinoma sample obtained from the human patient a level of an RNA transcript of PPAP2B, wherein the measuring is performed using polymerase chain reaction (PCR) with a polynucleotide comprising the sequence of SEQ ID NO: 545 and a polynucleotide comprising the sequence of SEQ ID NO: 1277 as PCR primers and a polynucleotide comprising the sequence of SEQ ID NO: 2009 as a probe to detect PPAP2B polynucleotides produced by PCR;
   (b) normalizing the level of the RNA transcript of PPAP2B against at least one reference RNA transcript from the sample to obtain a normalized PPAP2B expression level;
   (c) comparing the normalized PPAP2B expression level to a normalized PPAP2B expression level obtained from a renal cell carcinoma sample from a human patient with recurrent renal cell carcinoma; and
   (d) determining a decreased likelihood for recurrence of renal cell carcinoma for the human patient if the normalized PPAP2B expression level is increased compared to the normalized PPAP2B expression level obtained from the renal cancer sample from the human patient with recurrent renal cell carcinoma.

2. The method of claim 1, further comprising generating a report based on the normalized PPAP2B expression level.

3. The method of claim 1, further comprising calculating a score estimating the likelihood that the patient will have a recurrence of renal cell carcinoma based on the normalized PPAP2B expression level.

4. The method of claim 3, further comprising generating a report based on the score.

5. The method of claim 1, further comprising wherein the renal cell carcinoma sample is a paraffin-embedded sample.

6. The method of claim 1, wherein the renal cell carcinoma sample is a frozen sample.

7. A method for determining presence of necrosis in a renal cell carcinoma sample obtained from a human patient, comprising:
   (a) measuring, in a renal cell carcinoma sample obtained from the human patient a level of an RNA transcript of PPAP2B, wherein the measuring is performed using polymerase chain reaction (PCR) with a polynucleotide comprising the sequence of SEQ ID NO: 545 and a polynucleotide comprising the sequence of SEQ ID NO: 1277 as PCR primers and a polynucleotide comprising the sequence of SEQ ID NO: 2009 as a probe to detect PPAP2B polynucleotides produced by PCR;
   (b) normalizing the level of the RNA transcript of PPAP2B against at least one reference RNA transcript from the sample to obtain a normalized PPAP2B expression level;
   (c) comparing the normalized PPAP2B expression level to a normalized PPAP2B expression level obtained from a renal cell carcinoma sample without necrosis; and (d) determining the presence of necrosis in the renal cell carcinoma sample if the normalized PPAP2B expression level is decreased compared to the normalized PPAP2B expression level obtained from the renal cancer sample without necrosis.

8. The method of claim 7, wherein the renal cell carcinoma sample is a paraffin-embedded sample.

9. The method of claim 7, wherein the renal cell carcinoma sample is a frozen sample.

10. A method for determining a likelihood of recurrence of renal cell carcinoma for a human patient, comprising:
   extracting RNA from a renal cell carcinoma sample obtained from the human patient;
   reverse transcribing an RNA transcript of PPAP2B to produce a cDNA of PPAP2B;
   amplifying, using polymerase chain reaction (PCR), the cDNA of PPAP2B to produce an amplicon of the RNA transcript of PPAP2B, wherein the PCR uses a polynucleotide comprising the sequence of SEQ ID NO:545 and a polynucleotide comprising the sequence of SEQ ID NO: 1277 as primers;
   assaying a level of the amplicon of the RNA transcript of PPAP2B with a polynucleotide comprising the sequence of SEQ ID NO: 2009;
   normalizing the amplicon level of the RNA transcript of PPAP2B against an amplicon level of at least one reference RNA transcript in the renal cell carcinoma sample to provide normalized amplicon level of PPAP2B,
   comparing the normalized amplicon level of PPAP2B from the human patient to a normalized amplicon level of PPAP2B from a renal cell carcinoma sample from a human patient with recurrent renal cell carcinoma; and
   determining that the human patient has a decreased likelihood of recurrence of renal cell carcinoma if the normalized amplicon level of PPAP2B from the human patient is increased compared to the normalized PPAP2B expression level obtained from the renal cell carcinoma sample from the human patient with recurrent renal cell carcinoma.

11. The method of claim 10, further comprising wherein the renal cell carcinoma sample is a paraffin-embedded sample.

12. The method of claim 10, wherein the renal cell carcinoma sample is a frozen sample.

* * * * *

UNITED STATES PATENT AND TRADEMARK OFFICE
CERTIFICATE OF CORRECTION

| | | |
|---|---|---|
| PATENT NO. | : 9,551,034 B2 | Page 1 of 1 |
| APPLICATION NO. | : 12/987023 | |
| DATED | : January 24, 2017 | |
| INVENTOR(S) | : Cowens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 77 days.

Signed and Sealed this
Tenth Day of April, 2018

Andrei Iancu
*Director of the United States Patent and Trademark Office*